US009056866B2

(12) United States Patent
Adam et al.

(10) Patent No.: US 9,056,866 B2
(45) Date of Patent: Jun. 16, 2015

(54) [1,2,3]TRIAZOLO[4,5-D]PYRIMIDINE DERIVATIVES

(71) Applicant: HOFFMANN-LA ROCHE INC., Nutley, NJ (US)

(72) Inventors: Jean-Michel Adam, Village-Neuf (FR); Caterina Bissantz, Village-Neuf (FR); Uwe Grether, Efringen-Kirchen (DE); Atsushi Kimbara, Tokyo (JP); Matthias Nettekoven, Grenzach-Wyhlen (DE); Stephan Roever, Inzlingen (DE); Mark Rogers-Evans, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/250,781

(22) Filed: Apr. 11, 2014

(65) Prior Publication Data
US 2014/0288046 A1 Sep. 25, 2014

Related U.S. Application Data

(63) Continuation of application No. 13/669,610, filed on Nov. 6, 2012, now Pat. No. 8,741,906.

(30) Foreign Application Priority Data

Nov. 8, 2011 (EP) ..................................... 11188333

(51) Int. Cl.
*A01N 43/90* (2006.01)
*A61K 31/519* (2006.01)
*C07D 487/00* (2006.01)
*C07D 487/04* (2006.01)
*C07D 491/107* (2006.01)

(52) U.S. Cl.
CPC ............ *C07D 487/04* (2013.01); *A61K 31/519* (2013.01); *C07D 491/107* (2013.01)

(58) Field of Classification Search
None
See application file for complete search history.

(56) References Cited

FOREIGN PATENT DOCUMENTS

| WO | 2008076810 | 6/2008 |
|----|------------|--------|
| WO | 2009059264 | 5/2009 |
| WO | 2011123372 | 10/2011 |

OTHER PUBLICATIONS

The English translation of the letter of opposition in the corresponding Costa Rican Application No. 2014-0136, which was notified by the Costa Rican Patent Office on Sep. 24, 2014.
McAllister et al., "An Aromatic Microdomain at the Cannabinoid CB1 Receptor Constitutes an Agonist/Inverse Agonist Binding Region," Journal of Medicinal Chemistry, vol. 46, No. 24, 5139-5152 (2003).
Bai et al., "MBC94, a Conjugable Ligand for Cannabinoid CB2 Receptor Imaging," Bioconjugate Chem., 2008, 19 (5), pp. 988-992.
The English translation of the Colombian Office Action, issued on Mar. 17, 2015, in the corresponding Colombian Application No. 14-067.070.

*Primary Examiner* — Jeffrey H Murray

(57) ABSTRACT

The invention relates to a compound of formula (I)

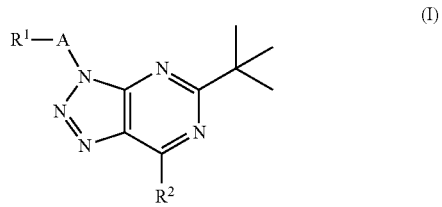

wherein A, $R^1$ and $R^2$ are defined as in the description and in the claims. The compound of formula (I) can be used as a medicament.

46 Claims, No Drawings

[1,2,3]TRIAZOLO[4,5-D]PYRIMIDINE DERIVATIVES

PRIORITY TO RELATED APPLICATION(S)

This application claims priority to and is a continuation of pending U.S. application Ser. No 13/669,610, filed Nov. 6, 2012, and claims the benefit of European Patent Application No. 11188333.6 filed Nov. 8, 2011, which is hereby incorporated by referenced it its entirety.

FIELD OF THE INVENTION

The present invention relates to organic compounds useful for therapy and/or prophylaxis in a mammal, and in particular to compounds that are preferential agonists of the Cannabinoid Receptor 2.

BACKGROUND OF THE INVENTION

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in pre-conditioning and contribute to prevent reperfusion injury by down regulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

SUMMARY OF THE INVENTION

The present invention relates to a compound of formula (I)

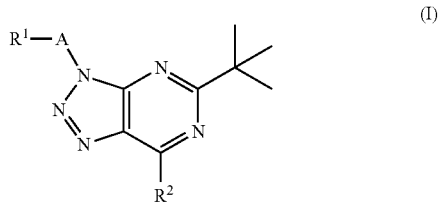

wherein

A is selected from the group consisting of alkyl, hydroxyalkyl, —CH$_2$C(O)—, —C(O)—, —SO$_2$— and a bond;

R$^1$ is selected from the group consisting of hydrogen, alkyl, haloalkyl, hydroxyl, alkoxy, haloalkoxy, phenyl, halophenyl, alkoxyphenyl, haloalkylphenyl, haloalkoxyphenyl, (halo)(haloalkyl)phenyl, cyanophenyl, hydroxyalkoxyphenyl, alkylsulfonylphenyl, alkylsulfonylaminophenyl, cyano, cycloalkyl, cycloalkylalkoxy, amino, (alkylsulfonyl)(alkyl)[1,2,4]triazolyl, (halo)(dialkylamino)pyridinyl, (alkyl)(oxy)pyridinyl, nitro-benzo[1,2,5]oxadiazolylaminopyridinyl, heterocyclyl, alkylheterocyclyl, hydroxyheterocyclyl, alkylheterocyclyl, heteroaryl, haloheteroaryl, alkylheteroaryl, cycloalkylheteroaryl and haloalkylheteroaryl, wherein said heterocyclyl is a three to eight membered carbocyclic ring comprising at least one nitrogen or oxygen atom, and wherein said heteroaryl is pyridinyl, pyrazolyl, oxadiazolyl, furazanyl, tetrazolyl or triazolyl;

R$^2$ is selected from the group consisting of halogen, —NR$^3$R$^4$ and —OR$^5$;

one of R$^3$ and R$^4$ is hydrogen or alkyl and the other one is alkyl or cycloalkyl;

or R$^3$ and R$^4$ together with the nitrogen atom to which they are attached form heterocyclyl or substituted heterocyclyl, wherein said heterocyclyl is morpholinyl, piperidinyl, piperazinyl, pyrrolidinyl, 2-oxa-6-azaspiro[3.3]heptyl, azetidinyl, thiazolidinyl, thiomorpholinyl, dioxothiomorpholinyl, oxazepanyl, 2-oxa-6-azaspiro[3.4]octyl, 6-oxa-1-azaspiro[3.3]heptyl, 2-oxa-5-aza-spiro[3.4]octyl, isoxazolidinyl, aziridinyl, dioxoisothiazolidinyl or oxopyrrolidinyl and wherein said substituted heterocyclyl is heterocyclyl substituted with one to four substituents independently selected from the group consisting of alkyl, halogen, hydroxyl, alkoxy, hydroxyalkyl, carboxyl, alkoxyalkyl, cyano, alkylamino, dialkylamino, alkylcarbonylamino, alkylcarbonyl(alkylamino), phenyl, alkoxycarbonyl, aminoalkyl, alkylpyrazolyl or alkylisoxazolyl; and R$^5$ is selected from the group consisting of alkyl, cycloalkyl, cycloalkylalkyl, haloalkyl and oxetanyl;

or a pharmaceutically acceptable salt or ester thereof;

with the proviso that said compound is not 3-[(2-chlorophenyl)methyl]-5-(1,1-dimethylethyl)-7-(4-morpholinyl)-3H-1,2,3-triazolo[4,5-d]pyrimidine or N-cyclopropyl-5-(1,1-dimethylethyl)-3-(phenylmethyl)-3H-1,2,3-triazolo[4,5-d]pyrimidin-7-amine.

The present invention also relates to a pharmaceutical composition comprising said compound and a therapeutically inert carrier.

The compounds of the invention bind to and modulate the CB2 receptor and have lower CB1 receptor activity.

The compound of formula (I) is particularly useful in the treatment or prophylaxis of e.g. pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

DETAILED DESCRIPTION OF THE INVENTION

The present invention relates to a compound of formula (I)

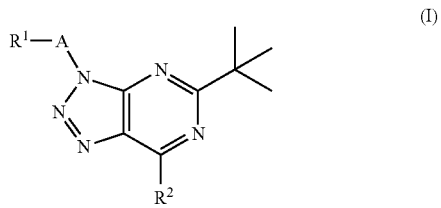

wherein

A is selected from the group consisting of alkyl, hydroxyalkyl, —CH$_2$C(O)—, —C(O)—, —SO$_2$— and a bond;

R$^1$ is selected from the group consisting of hydrogen, alkyl, haloalkyl, hydroxyl, alkoxy, haloalkoxy, phenyl, halophenyl, alkoxyphenyl, haloalkylphenyl, haloalkoxyphenyl, (halo)(haloalkyl)phenyl, cyanophenyl, hydroxyalkoxyphenyl, alkylsulfonylphenyl, alkylsulfonylaminophenyl, cyano, cycloalkyl, cycloalkylalkoxy, amino, (alkylsulfonyl)(alkyl)[1,2,4]triazolyl, (halo)(dialkylamino)pyridinyl, (alkyl)(oxy)pyridinyl, nitro-benzo[1,2,5]oxadiazolylaminopyridinyl, heterocyclyl, alkylheterocyclyl, hydroxyheterocyclyl, alkylheterocyclyl, heteroaryl, haloheteroaryl, alkylheteroaryl, cycloalkylheteroaryl and haloalkylheteroaryl, wherein said heterocyclyl is a three to eight membered carbocyclic ring comprising at least one nitrogen or oxygen atom, and wherein said heteroaryl is pyridinyl, pyrazolyl, oxadiazolyl, furazanyl, tetrazolyl or triazolyl;

R$^2$ is selected from the group consisting of halogen, —NR$^3$R$^4$ and —OR$^5$;

one of R$^3$ and R$^4$ is hydrogen or alkyl and the other one is alkyl or cycloalkyl;

or R$^3$ and R$^4$ together with the nitrogen atom to which they are attached form heterocyclyl or substituted heterocyclyl, wherein said heterocyclyl is morpholinyl, piperidinyl, piperazinyl, pyrrolidinyl, 2-oxa-6-azaspiro[3.3]heptyl, azetidinyl, thiazolidinyl, thiomorpholinyl, dioxothiomorpholinyl, oxazepanyl, 2-oxa-6-azaspiro[3.4]octyl, 6-oxa-1-azaspiro[3.3]heptyl, 2-oxa-5-aza-spiro[3.4]octyl, isoxazolidinyl, aziridinyl, dioxoisothiazolidinyl or oxopyrrolidinyl and wherein said substituted heterocyclyl is heterocyclyl substituted with one to four substituents independently selected from the group consisting of alkyl, halogen, hydroxyl, alkoxy, hydroxyalkyl, carboxyl, alkoxyalkyl, cyano, alkylamino, dialkylamino, alkylcarbonylamino, alkylcarbonyl(alkylamino), phenyl, alkoxycarbonyl, aminoalkyl, alkylpyrazolyl or alkylisoxazolyl; and R$^5$ is selected from the group consisting of alkyl, cycloalkyl, cycloalkylalkyl, haloalkyl and oxetanyl;

or a pharmaceutically acceptable salt or ester thereof;

with the proviso that said compound is not 3-[(2-chlorophenyl)methyl]-5-(1,1-dimethylethyl)-7-(4-morpholinyl)-3H-1,2,3-triazolo[4,5-d]pyrimidine or N-cyclopropyl-5-(1,1-dimethylethyl)-3-(phenylmethyl)-3H-1,2,3-triazolo[4,5-d]pyrimidin-7-amine.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C$_1$-C$_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl more particularly methyl, ethyl, propyl, isopropyl, isobutyl, tert.-butyl and isopentyl. Particular examples of alkyl are methyl, ethyl and pentyl, in particular methyl and ethyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. Particular "cycloalkyl" are cyclopropyl, cyclobutyl, cyclopentyl and cyclohexyl. A particular example of cycloalkyl is cyclohexyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy, particularly methoxy.

The term "oxy", alone or in combination, signifies the —O— group.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. Particular halogens are fluorine, bromine and chlorine, more particularly fluorine and chlorine.

The term "haloalkyl", alone or in combination, denotes an alkyl group substituted with at least one halogen, particularly substituted with one to five halogens, particularly one to three halogens. Particular "haloalkyl" are trifluoromethyl and trifluoropropyl. A particular "haloalkyl" is trifluoromethyl.

The term "haloalkoxy", alone or in combination, denotes an alkoxy group substituted with at least one halogen, particularly substituted with one to five halogens, particularly one to three halogens. A particular "haloalkoxy" is trifluoromethoxy.

The term "halophenyl", alone or in combination, denotes a phenyl group substituted with at least one halogen, particularly substituted with one to three halogens. Particular "halophenyl" are chlorophenyl, chlorofluorophenyl, dichlorophenyl, bromophenyl and chlorodifluorophenyl.

The terms "hydroxyl" and "hydroxy", alone or in combination, signify the —OH group.

The term "carbonyl", alone or in combination, signifies the —C(O)— group.

The term "amino", alone or in combination, signifies the primary amino group (—NH$_2$), the secondary amino group (—NH—), or the tertiary amino group (—N—).

The term "sulfonyl", alone or in combination, signifies the —SO$_2$— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

In the definition of $R^1$, examples of three to eight membered carbocyclic ring comprising at least one nitrogen or oxygen atom are morpholinyl, piperidinyl, piperazinyl, pyrrolidinyl, 2-oxa-6-azaspiro[3.3]heptyl, azetidinyl, 3,3-difluoroazetidinyl, 3-hydroxyazetindyl, 3-methoxyazetidinyl, thiazolidinyl, thiomorpholinyl, dioxothiomorpholinyl, oxazepanyl, 2-oxa-6-azaspiro[3.4]octyl, 6-oxa-1-azaspiro[3.3]heptyl, 2-oxa-5-aza-spiro[3.4]octyl, aziridinyl, dioxoisothiazolidinyl, oxetanyl, 3-alkyl-oxetanyl, 3-fluorooxetanyl, tetrahydrofuranyl, tetrahydropyranyl, azetidin-2-onyl, pyrrolidin-2-onyl, piperidin-2-onyl, dioxothiazetidinyl, dioxothiazetidinyl, dioxothiazinanyl, hydroxypyrrolidinyl and difluorpyrrolidinyl;

In the definition of $R^1$, particular examples of three to eight membered carbocyclic ring comprising at least one nitrogen or oxygen atom are morpholinyl, piperidinyl, piperazinyl, pyrrolidinyl, azetidinyl, 3,3-difluoroazetidinyl, 3-hydroxyazetindyl, 3-methoxyazetidinyl, thiomorpholinyl, dioxothiomorpholinyl, dioxoisothiazolidinyl, oxetanyl, 3-alkyl-oxetanyl, 3-fluorooxetanyl, tetrahydrofuranyl and pyrrolidin-2-onyl;

In the definition of $R^1$, particular examples of three to eight membered carbocyclic ring comprising at least one nitrogen or oxygen atom are morpholinyl, piperidinyl, azetidinyl, 3,3-difluoroazetidinyl, 3-methoxyazetidinyl, thiomorpholinyl, dioxothiomorpholinyl, oxetanyl, 3-alkyl-oxetanyl and pyrrolidin-2-onyl:

In the definition of $R^1$, further particular examples of three to eight membered carbocyclic ring comprising at least one nitrogen or oxygen atom are morpholinyl and 2-oxa-6-azaspiro[3.3]heptyl.

In the definition of $R^1$, heterocyclyl is advantageously oxetanyl, tetrahydrofuranyl, 1,1-dioxo-thietanyl or 1,1-dioxo-tetrahydrothiophenyl.

In the definition of $R^5$: alkyl is advantageously methyl, ethyl, isopropyl or pentyl; cycloalkyl is advantageously cyclopropyl, cyclobutyl or cyclopentyl, in particular cyclobutyl or cyclopentyl; cycloalkylalkyl is advantageously cyclopropylalkyl or cyclopropylethyl; haloalkyl is advantageously trifluoropropyl.

The invention relates in particular to a compound of formula (I) wherein:
A is selected from the group consisting of alkyl, hydroxyalkyl, —CH$_2$C(O)—, —C(O)—, —SO$_2$— and a bond;
$R^1$ is selected from the group consisting of hydrogen, alkyl, haloalkyl, hydroxyl, alkoxy, haloalkoxy, phenyl, halophenyl, alkoxyphenyl, haloalkylphenyl, haloalkoxyphenyl, cyanophenyl, hydroxyalkoxyphenyl, alkylsulfonylphenyl, alkylsulfonylaminophenyl, cyano, cycloalkyl, cycloalkylalkoxy, amino, heterocyclyl, alkylheterocyclyl, hydroxyheterocyclyl, alkylheterocyclyl, heteroaryl and haloheteroaryl, wherein said heterocyclyl is a three to eight membered carbocyclic ring comprising at least one nitrogen or oxygen atom, and wherein said heteroaryl is pyridinyl, pyrazolyl, oxadiazolyl or furazanyl;
$R^2$ is halogen or —NR$^3$R$^4$; and
one of $R^3$ and $R^4$ is hydrogen or alkyl and the other one is alkyl or cycloalkyl;
or $R^3$ and $R^4$ together with the nitrogen atom to which they are attached form heterocyclyl or substituted heterocyclyl, wherein said heterocyclyl is morpholinyl, piperidinyl, piperazinyl, pyrrolidinyl, 2-oxa-6-azaspiro[3.3]heptyl, azetidinyl, thiazolidinyl, thiomorpholinyl, dioxothiomorpholinyl, oxazepanyl, 2-oxa-6-azaspiro[3.4]octyl, 6-oxa-1-azaspiro[3.3]heptyl, 2-oxa-5-aza-spiro[3.4]octyl, isoxazolidinyl, aziridinyl or dioxoisothiazolidinyl and wherein said substituted heterocyclyl is heterocyclyl substituted with one to four substituents independently selected from the group consisting of alkyl, halogen, hydroxyl, alkoxy, hydroxyalkyl, carboxyl, alkoxyalkyl and cyano;
or a pharmaceutically acceptable salt or ester thereof;
with the proviso that said compound is not 3-[(2-chlorophenyl)methyl]-5-(1,1-dimethylethyl)-7-(4-morpholinyl)-3H-1,2,3-triazolo[4,5-d]pyrimidine or N-cyclopropyl-5-(1,1-dimethylethyl)-3-(phenylmethyl)-3H-1,2,3-triazolo[4,5-d]pyrimidin-7-amine.

Another embodiment of the present invention is a compound of formula (I) wherein A is selected from the group consisting of —CH$_2$—, —CH$_2$CH$_2$—, —CH(CH$_3$)—, —CH(OH)CH$_2$—, —CH$_2$C(O)—, —C(O)—, —SO$_2$— and a bond.

Another embodiment of the present invention is a compound of formula (I) wherein A is alkyl or hydroxyalkyl.

Another embodiment of the present invention is a compound of formula (I) wherein A is selected from the group consisting of —CH$_2$—, —CH$_2$CH$_2$—, —CH(CH$_3$)— and —CH(OH)CH$_2$—.

Another embodiment of the present invention is a compound of formula (I) wherein $R^1$ is selected from the group consisting of hydrogen, alkyl, haloalkyl, hydroxyl, alkoxy, phenyl, halophenyl, alkoxyphenyl, haloalkylphenyl, haloalkoxyphenyl, alkylsulfonylphenyl, cyanophenyl, cycloalkyl, alkylheterocyclyl, hydroxyheterocyclyl, heteroaryl, cycloalkylheteroaryl, haloheteroaryl and alkylheteroaryl, wherein said heterocyclyl is a carbocyclic ring containing at least one nitrogen atom and wherein said heteroaryl is pyridinyl, pyrazolyl, oxadiazolyl, tetrazolyl or furazanyl.

Another embodiment of the present invention is a compound of formula (I) wherein $R^1$ is selected from the group consisting of hydrogen, alkyl, haloalkyl, hydroxyl, alkoxy, phenyl, halophenyl, alkoxyphenyl, haloalkylphenyl, haloalkoxyphenyl, cyanophenyl, cycloalkyl, alkylheterocyclyl, hydroxyheterocyclyl, heteroaryl and haloheteroaryl, wherein said heterocyclyl is morpholinyl or 2-oxa-6-azaspiro[3.3]heptyl, and wherein said heteroaryl is pyridinyl, pyrazolyl or oxadiazolyl.

Another embodiment of the present invention is a compound of formula (I) wherein $R^1$ is selected from the group consisting of haloalkyl, phenyl, halophenyl, haloalkylphenyl, cyanophenyl, alkylsulfonylphenyl, cycloalkyl, heteroaryl, cycloalkylheteroaryl, haloheteroaryl and alkylheteroaryl, wherein said heteroaryl is pyridinyl, pyrazolyl, oxadiazolyl, tetrazolyl or furazanyl.

Another embodiment of the present invention is a compound of formula (I) wherein $R^1$ is selected from the group consisting of haloalkyl, phenyl, halophenyl, haloalkylphenyl, cyanophenyl, cycloalkyl and heteroaryl, wherein said heteroaryl is pyridinyl, pyrazolyl and oxadiazolyl.

Another embodiment of the present invention is a compound of formula (I) wherein $R^1$ is selected from the group consisting of hydrogen, methyl, methoxy, hydroxyl, chlorophenyl, bromophenyl, methoxyphenyl, trifluoromethoxyphenyl, chlorofluorophenyl, cyclohexyl, dichlorophenyl, trichlorophenyl, hydroxyethoxyphenyl, dichlorofluorophenyl, (chloro)(trifluoromethyl)phenyl, (dichloro)(trifluoromethyl)phenyl, methylsulfonylphenyl, methylsulfonylaminophenyl, pyridinyl, chloropyridinyl, dichloropyridinyl, methylpyrrolidinyl, oxetanyl, methyloxetanyl, (methylsulfonyl)(methyl)[1,2,4]triazolyl, (chloro)(dimethylamino)pyridinyl, (methyl)(oxy)pyridinyl, nitro-benzo[1,2,5]oxadiazolylaminopyridinyl, pyrazolyl, methylpiperidinyl, morpholinyl, 2-oxa-6-azaspiro[3.3]heptyl, hydroxypyrrolidinyl, trifluoromethyl, chlorodifluoromethyl, trifluoromethylphenyl, cyanophenyl, phenyl, tetrahydrofuranyl, methyl-[1,2,4]oxadiazolyl, furazanyl, methylfurazanyl, methyl-[1,3,4]oxadiazolyl, methyl-[1,3,4]oxadiazolyl, methyltetrazolyl, methyl-[1,2,4]triazolyl, dimethyl-[1,2,4]triazolyl, trifluoromethylpyrazolyl, dimethylpyrazolyl, methyl-[1,2,3]triazolyl, trifluoromethyl-[1,2,4]oxadiazolyl, cyclopropyltetrazoly and methylfurazanyl.

Another embodiment of the present invention is a compound of formula (I) wherein $R^1$ is selected from the group consisting of hydrogen, methyl, methoxy, hydroxyl, chlorophenyl, bromophenyl, methoxyphenyl, trifluoromethoxyphenyl, chlorofluorophenyl, cyclohexyl, dichlorophenyl, hydroxyethoxyphenyl, dichlorofluorophenyl, methylsulfonylphenyl, methylsulfonylaminophenyl, pyridinyl, chloropyridinyl, dichloropyridinyl, methylpyrrolidinyl, oxetanyl, methyloxetanyl, pyrazolyl, methylpiperidinyl, morpholinyl, 2-oxa-6-azaspiro[3.3]heptyl, hydroxypyrrolidinyl, trifluoromethyl, chlorodifluorophenyl, trifluoromethylphenyl, cyanophenyl, phenyl, tetrahydrofuranyl, methyl-[1,2,4]oxadiazolyl and furazanyl.

Another embodiment of the present invention is a compound of formula (I) wherein $R^1$ is selected from the group consisting of hydrogen, methyl, methoxy, hydroxyl, chlorophenyl, bromophenyl, methoxyphenyl, trifluoromethoxyphenyl, chlorofluorophenyl, cyclohexyl, dichlorophenyl, pyridinyl, chloropyridinyl, pyrazolyl, furazanyl, methylpiperidinyl, morpholinyl, 2-oxa-6-azaspiro[3.3]heptyl, hydroxypyrrolidinyl, trifluoromethyl, chlorodifluorophenyl, trifluoromethylphenyl, cyanophenyl and phenyl.

Another embodiment of the present invention is a compound of formula (I) wherein $R^1$ is selected from the group consisting of chlorophenyl, cyclohexyl, dichlorophenyl, pyridinyl, chloropyridinyl, dichloropyridinyl, trifluoromethyl, chlorodifluorophenyl, trifluoromethylphenyl, cyanophenyl, phenyl, methylsulfonylphenyl, methyltetrazolyl, methylfurazanyl and cyclopropyltetrazolyl.

Another embodiment of the present invention is a compound of formula (I) wherein $R^1$ is selected from the group consisting of chlorophenyl, cyclohexyl, dichlorophenyl, pyridinyl, trifluoromethyl, chlorodifluorophenyl, trifluoromethylphenyl, cyanophenyl and phenyl.

Another embodiment of the present invention is a compound of formula (I) wherein $R^1$ is selected from the group consisting of chlorophenyl, methylfurazanyl, chloropyridinyl, methylsulfonylphenyl and methyltetrazolyl.

Another embodiment of the present invention is a compound of formula (I) wherein $R^2$ is —$NR^3R^4$.

Another embodiment of the present invention is a compound of formula (I) wherein one of $R^3$ and $R^4$ is hydrogen or ethyl and the other one is ethyl or cyclohexyl.

Another embodiment of the present invention is a compound of formula (I) wherein $R^3$ and $R^4$ together with the nitrogen atom to which they are attached form heterocyclyl or substituted heterocyclyl, wherein said heterocyclyl is piperidinyl, piperazinyl, pyrrolidinyl, morpholinyl, thiazolidinyl, thiomorpholinyl, dioxo-thiomorpholinyl, oxazepanyl, 2-azetidinyl, 2-oxa-6-azaspiro[3.3]heptyl, oxopyrrolidinyl, 2-oxa-6-azaspiro[3.4]octyl, 6-oxa-1-azaspiro[3.3]heptyl, isoxazolidinyl, aziridinyl, dioxoisothiazolidinyl, 2-oxa-5-or azaspiro[3.4]octyl, and wherein said substituted heterocyclyl is heterocyclyl substituted with one to four substituents independently selected from alkyl, halogen, hydroxyl, hydroxyalkyl, alkoxy, alkoxyalkyl, cyano, alkylamino, dialkylamino, alkylcarbonylamino, alkylcarbonyl(alkylamino), phenyl, aminoalkyl, methylpyrazolyl and methylisoxazolyl.

A compound of formula (I) wherein $R^3$ and $R^4$ together with the nitrogen atom to which they are attached form heterocyclyl or substituted heterocyclyl, wherein said heterocyclyl is piperidinyl, pyrrolidinyl or azetidinyl, and wherein said substituted heterocyclyl is heterocyclyl substituted with one to four substituents independently selected from the group consisting of alkyl, halogen, hydroxyl, hydroxyalkyl and alkoxyalkyl;

Another embodiment of the present invention is a compound of formula (I) wherein $R^3$ and $R^4$ together with the nitrogen atom to which they are attached form piperidinyl, pyrrolidinyl, difluoropiperidinyl, difluoropyrrolidinyl, difluoroazetidinyl, (methyl)(hydroxyl)azetidinyl, hydroxypyrrolidinyl, hydroxymethylpyrrolidinyl, (hydroxymethyl)(difluoro)pyrrolidinyl, (hydroxyl)(difluoro)pyrrolidinyl, (hydroxyl)(hydroxymethyl)pyrrolidinyl, tetrafluoropyrrolidinyl, 2-oxa-6-azaspiro[3.3]heptyl, methoxymethylpyrrolidinyl, methylpiperazinyl, morpholinyl, azetidinyl, hydroxyazetidinyl, methoxyazetidinyl, dimethylmorpholinyl, methylmorpholinyl, hydroxymethylmorpholinyl, thiazolidinyl, thiomorpholinyl, dioxothiomorpholinyl, oxazepanyl, dimethylpyrrolidinyl, methoxypyrrolidinyl, methylpyrrolidinyl, hydroxypiperidinyl, (hydroxyl)(hydroxymethyl)pyrrolidinyl, (methyl)(hydroxyl)pyrrolidinyl, 2-oxa-6-azaspiro[3.4]octyl, 6-oxa-1-azaspiro[3.3]heptyl, fluoropyrrolidinyl, isoxazolidinyl, aziridinyl, (cyano)(fluoro)pyrrolidinyl, dioxo-isothiazolidinyl, cyanopyrrolidinyl, 2-oxa-5-azaspiro[3.4]octyl, dihydroxypyrrolidinyl, oxopyrrolidinyl, methylaminopyrrolidinyl, dimethylaminopyrrolidinyl, methylcarbonylaminopyrrolidinyl, methylcarbonyl(methylaminopyrrolidinyl), phenylpyrrolidinyl, methylcarbonyl(ethylaminopyrrolidinyl), methoxycarbonylazetidinyl, aminomethylpyrrolidinyl, methylpyrazolyl-pyrrolidinyl, methylisoxazolyl-pyrrolidinyl or methyl[1,2,4]oxadiazolyl-pyrrolidinyl.

Another embodiment of the present invention is a compound of formula (I) wherein $R^3$ and $R^4$ together with the nitrogen atom to which they are attached form piperidinyl, pyrrolidinyl, difluoropiperidinyl, difluoropyrrolidinyl, difluoroazetidinyl, (methyl)(hydroxyl)azetidinyl, hydroxypyrrolidinyl, hydroxymethylpyrrolidinyl, (hydroxymethyl)(difluoro)pyrrolidinyl, (hydroxyl)(difluoro)pyrrolidinyl, (hydroxyl)(hydroxymethyl)pyrrolidinyl, tetrafluoropyrrolidinyl, 2-oxa-6-azaspiro[3.3]heptyl, methoxymethylpyrrolidinyl, methylpiperazinyl, morpholinyl, azetidinyl, hydroxyazetidinyl, methoxyazetidinyl, dimethylmorpholinyl, methylmorpholinyl, hydroxymethylmorpholinyl, thiazolidinyl, thiomorpholinyl, dioxothiomorpholinyl, oxazepanyl, dimethylpyrrolidinyl, methoxypyrrolidinyl, methylpyrrolidinyl, hydroxypiperidinyl, (hydroxyl)(hydroxymethyl)pyrrolidinyl, (methyl)(hydroxyl)pyrrolidinyl, 2-oxa-6-azaspiro[3.4]octyl, 6-oxa-1-azaspiro[3.3]heptyl, fluoropyrrolidinyl, isoxazolidinyl, aziridinyl, (cyano)(fluoro)pyrrolidinyl, dioxo-isothiazolidinyl, cyanopyrrolidinyl, 2-oxa-5-azaspiro[3.4]octyl or dihydroxypyrrolidinyl.

Another embodiment of the present invention is a compound of formula (I) wherein $R^3$ and $R^4$ together with the nitrogen atom to which they are attached form piperidinyl, pyrrolidinyl, difluoropiperidinyl, difluoropyrrolidinyl, difluoroazetidinyl, (methyl)(hydroxyl)azetidinyl, hydroxypyrrolidinyl, hydroxymethylpyrrolidinyl, tetrafluoropyrrolidinyl, 2-oxa-6-azaspiro[3.3]heptyl, methoxymethylpyrrolidinyl, methylpiperazinyl, morpholinyl, azetidinyl, hydroxyazetidinyl, methoxyazetidinyl, dimethylmorpholinyl, methylmorpholinyl, hydroxymethylmorpholinyl, thiazolidinyl, thiomorpholinyl, dioxothiomorpholinyl, oxazepanyl, dimethylpyrrolidinyl, methoxypyrrolidinyl, methylpyrrolidinyl, hydroxypiperidinyl, (hydroxyl)(hydroxymethyl)pyrrolidinyl, (methyl)(hydroxyl)pyrrolidinyl, 2-oxa-6-azaspiro[3.4]octyl, 6-oxa-1-azaspiro[3.3]heptyl, fluoropyrrolidinyl, isoxazolidinyl, aziridinyl, (cyano)(fluoro)pyrrolidinyl, dioxo-isothiazolidinyl, cyanopyrrolidinyl, (hydroxyl)(hydroxymethyl)pyrrolidinyl, 2-oxa-5-azaspiro[3.4]octyl or dihydroxypyrrolidinyl.

Another embodiment of the present invention is a compound of formula (I) wherein $R^3$ and $R^4$ together with the nitrogen atom to which they are attached form difluoropiperidinyl, difluoropyrrolidinyl, difluoroazetidinyl, (methyl)(hydroxyl)azetidinyl, hydroxypyrrolidinyl, hydroxymethylpyrrolidinyl, tetrafluoropyrrolidinyl, methoxymethylpyrrolidinyl, (hydroxyl)(hydroxymethyl)pyrrolidinyl or (methyl)(hydroxyl)pyrrolidinyl.

Another embodiment of the present invention is a compound of formula (I) wherein $R^3$ and $R^4$ together with the nitrogen atom to which they are attached form heterocyclyl or substituted heterocyclyl, wherein said heterocyclyl is piperidinyl, pyrrolidinyl, azetidinyl or 2-oxa-6-azaspiro[3.3] heptyl, and wherein said substituted heterocyclyl is heterocyclyl substituted with one to four substituents independently selected from the group consisting of alkyl, halogen, hydroxyl, hydroxyalkyl and alkoxyalkyl.

Another embodiment of the present invention is a compound of formula (I) wherein $R^3$ and $R^4$ together with the nitrogen atom to which they are attached form difluoropiperidinyl, difluoropyrrolidinyl, difluoroazetidinyl, (methyl)(hydroxyl)azetidinyl, hydroxypyrrolidinyl, hydroxymethylpyrrolidinyl, tetrafluoropyrrolidinyl, methoxymethylpyrrolidinyl, (hydroxyl)(hydroxymethyl)pyrrolidinyl, (methyl)(hydroxyl)pyrrolidinyl or 2-oxa-6-azaspiro[3.3]heptyl.

Another embodiment of the present invention is a compound of formula (I) wherein $R^2$ is hydroxypyrrolidinyl or methylhydroxypyrrolidinyl, in particular hydroxypyrrolidinyl.

Another embodiment of the present invention is a compound of formula (I) wherein $R^5$ is selected from the group consisting of methyl, ethyl, isopropyl, pentyl, cyclobutyl, cyclopentyl, cyclopropylmethyl, cyclopropylethyl, trifluoropropyl and oxetanyl.

In the definition of $R^1$, halophenyl, alkylfurazanyl, halopyridinyl, alkylsulfonylphenyl and alkyltetrazolyl are particularly advantageous, and halophenyl and alkyltetrazolyl are more particularly advantageous.

In the definition of $R^1$, chlorophenyl, methylfurazanyl, chloropyridinyl, methylsulfonylphenyl and methyltetrazolyl are particularly advantageous, and chlorophenyl and methyltetrazolyl are more particularly advantageous.

It is particularly advantageous that $R^2$ is —$NR^3R^4$ and that $R^3$ and $R^4$ together with the nitrogen atom to which they are attached form hydroxypyrrolidinyl.

It is particularly advantageous that A is alkyl, more particularly —$CH_2$—.

The invention therefore also relates to the following advantageous embodiment:

Another embodiment of the present invention is a compound of formula (I) wherein:
A is alkyl;
$R^1$ is selected from the group consisting of halophenyl, alkylfurazanyl, halopyridinyl, alkylsulfonylphenyl and alkyltetrazolyl; and
$R^2$ is —$NR^3R^4$ and $R^3$ and $R^4$ together with the nitrogen atom to which they are attached form hydroxypyrrolidinyl.

The invention further relates to the following advantageous embodiment:
A compound of formula (I) wherein:
A is —$CH_2$—;
$R^1$ is selected from the group consisting of chlorophenyl, methylfurazanyl, chloropyridinyl, methylsulfonylphenyl and methyltetrazolyl; and
$R^2$ is —$NR^3R^4$ and $R^3$ and $R^4$ together with the nitrogen atom to which they are attached form hydroxypyrrolidinyl.

The invention further relates to the following advantageous embodiment:
A compound of formula (I) wherein:
A is alkyl;
$R^1$ is halophenyl or alkyltetrazolyl; and
$R^2$ is —$NR^3R^4$ and $R^3$ and $R^4$ together with the nitrogen atom to which they are attached form hydroxypyrrolidinyl.

The invention further relates to the following advantageous embodiment:
A compound of formula (I) wherein:
A is —$CH_2$—;
$R^1$ is chlorophenyl or methyltetrazolyl; and
$R^2$ is —$NR^3R^4$ and $R^3$ and $R^4$ together with the nitrogen atom to which they are attached form hydroxypyrrolidinyl.

The invention further relates in particular to a compound of formula (I) selected from the group consisting of:
5-tert-butyl-3-(2-chloro-benzyl)-7-morpholin-4-yl-3H-[1,2,3]triazolo[4,5-d]pyrimidine;
5-tert-butyl-3-(2-chlorobenzyl)-7-(piperidin-1-yl)-3H-[1,2,3]triazolo[4,5-d]pyrimidine;
5-tert-butyl-3-(2-chlorobenzyl)-7-(4,4-difluoropiperidin-1-yl)-3H-[1,2,3]triazolo[4,5-d]pyrimidine;
5-tert-butyl-3-(2-chlorobenzyl)-7-(4-methylpiperazin-1-yl)-3H-[1,2,3]triazolo[4,5-d]pyrimidine;
5-tert-butyl-3-(2-chlorobenzyl)-7-(pyrrolidin-1-yl)-3H-[1,2,3]triazolo[4,5-d]pyrimidine;
5-tert-butyl-3-(2-chlorobenzyl)-7-(3,3-difluoropyrrolidin-1-yl)-3H-[1,2,3]triazolo[4,5-d]pyrimidine;
5-tert-butyl-3-(2-chlorobenzyl)-N-ethyl-3H-[1,2,3]triazolo[4,5-d]pyrimidin-7-amine;
5-tert-butyl-3-(2-chlorobenzyl)-N-cyclohexyl-3H-[1,2,3]triazolo[4,5-d]pyrimidin-7-amine;
5-tert-butyl-3-(2-chlorobenzyl)-N,N-diethyl-3H-[1,2,3]triazolo[4,5-d]pyrimidin-7-amine;
6-(5-tert-butyl-3-(2-chlorobenzyl)-3H-[1,2,3]triazolo[4,5-d]pyrimidin-7-yl)-2-oxa-6-azaspiro[3.3]heptane;
7-(azetidin-1-yl)-5-tert-butyl-3-(2-chlorobenzyl)-3H-[1,2,3]triazolo[4,5-d]pyrimidine;
5-tert-butyl-3-(2-chlorobenzyl)-7-(3,3-difluoroazetidin-1-yl)-3H-[1,2,3]triazolo[4,5-d]pyrimidine;
1-(5-tert-butyl-3-(2-chlorobenzyl)-3H-[1,2,3]triazolo[4,5-d]pyrimidin-7-yl)azetidin-3-ol;
1-(5-tert-butyl-3-(2-chlorobenzyl)-3H-[1,2,3]triazolo[4,5-d]pyrimidin-7-yl)-3-methylazetidin-3-ol;
5-tert-butyl-3-(2-chlorobenzyl)-7-(3-methoxyazetidin-1-yl)-3H-[1,2,3]triazolo[4,5-d]pyrimidine;
(2S,6R)-4-(5-tert-butyl-3-(2-chlorobenzyl)-3H-[1,2,3]triazolo[4,5-d]pyrimidin-7-yl)-2,6-dimethylmorpholine;
4-(5-tert-butyl-3-(2-chlorobenzyl)-3H-[1,2,3]triazolo[4,5-d]pyrimidin-7-yl)-3-methylmorpholine;
(4-(5-tert-butyl-3-(2-chlorobenzyl)-3H-[1,2,3]triazolo[4,5-d]pyrimidin-7-yl)morpholin-2-yl)methanol;
3-(5-tert-butyl-3-(2-chlorobenzyl)-3H-[1,2,3]triazolo[4,5-d]pyrimidin-7-yl)thiazolidine;
4-(5-tert-butyl-3-(2-chlorobenzyl)-3H-[1,2,3]triazolo[4,5-d]pyrimidin-7-yl)thiomorpholine;
5-tert-butyl-3-(2-chloro-benzyl)-7-(1,1-dioxo-1λ6-thiomorpholin-4-yl)-3H-[1,2,3]triazolo[4,5-d]pyrimidine;
4-(5-tert-butyl-3-(2-chlorobenzyl)-3H-[1,2,3]triazolo[4,5-d]pyrimidin-7-yl)-1,4-oxazepane;
4-(5-tert-butyl-3-(2-chlorobenzyl)-3H-[1,2,3]triazolo[4,5-d]pyrimidin-7-yl)-2,2-dimethylmorpholine;
4-(5-tert-butyl-3-(2-chlorobenzyl)-3H-[1,2,3]triazolo[4,5-d]pyrimidin-7-yl)-3,3-dimethylmorpholine;
5-tert-butyl-3-(2-chlorobenzyl)-7-((2R,5R)-2,5-dimethylpyrrolidin-1-yl)-3H-[1,2,3]triazolo[4,5-d]pyrimidine;
(S)-1-(5-tert-butyl-3-(2-chlorobenzyl)-3H-[1,2,3]triazolo[4,5-d]pyrimidin-7-yl)pyrrolidin-3-ol;
(R)-1-(5-tert-butyl-3-(2-chlorobenzyl)-3H-[1,2,3]triazolo[4,5-d]pyrimidin-7-yl)pyrrolidin-3-ol;
5-tert-butyl-3-(2-chlorobenzyl)-7-(3-methoxypyrrolidin-1-yl)-3H-[1,2,3]triazolo[4,5-d]pyrimidine;
5-tert-butyl-3-(2-chlorobenzyl)-7-(2,2-dimethylpyrrolidin-1-yl)-3H-[1,2,3]triazolo[4,5-d]pyrimidine;
5-tert-butyl-3-(2-chlorobenzyl)-7-(2-methylpyrrolidin-1-yl)-3H-[1,2,3]triazolo[4,5-d]pyrimidine;
6-(5-tert-butyl-3-(2-chlorobenzyl)-3H-[1,2,3]triazolo[4,5-d]pyrimidin-7-yl)-2-oxa-6-azaspiro[3.4]octane;

1-(5-tert-butyl-3-(2-chlorobenzyl)-3H-[1,2,3]triazolo[4,5-d]pyrimidin-7-yl)piperidin-4-ol;
(S)-1-(5-tert-butyl-3-(2-chlorobenzyl)-3H-[1,2,3]triazolo[4,5-d]pyrimidin-7-yl)piperidin-3-ol;
(R)-1-(5-tert-butyl-3-(2-chlorobenzyl)-3H-[1,2,3]triazolo[4,5-d]pyrimidin-7-yl)piperidin-3-ol;
1-(5-tert-butyl-3-(2-chlorobenzyl)-3H-[1,2,3]triazolo[4,5-d]pyrimidin-7-yl)-6-oxa-1-azaspiro[3.3]heptane;
(S)-5-tert-butyl-3-(2-chlorobenzyl)-7-(3-fluoropyrrolidin-1-yl)-3H-[1,2,3]triazolo[4,5-d]pyrimidine;
(R)-(1-(5-tert-butyl-3-(2-chlorobenzyl)-3H-[1,2,3]triazolo[4,5-d]pyrimidin-7-yl)pyrrolidin-2-yl)methanol;
(S)-(1-(5-tert-butyl-3-(2-chlorobenzyl)-3H-[1,2,3]triazolo[4,5-d]pyrimidin-7-yl)pyrrolidin-2-yl)methanol;
2-(5-tert-butyl-3-(2-chlorobenzyl)-3H-[1,2,3]triazolo[4,5-d]pyrimidin-7-yl)morpholine;
2-(5-tert-butyl-3-(2-chlorobenzyl)-3H-[1,2,3]triazlo[4,5-d]pyrimidin-7-yl)isoxazolidine;
7-(aziridin-1-yl)-5-tert-butyl-3-(2-chlorobenzyl)-3H-[1,2,3]triazolo[4,5-d]pyrimidine;
(R)-5-tert-butyl-3-(2-chlorobenzyl)-7-(3-fluoropyrrolidin-1-yl)-3H-[1,2,3]triazolo[4,5-d]pyrimidine;
5-tert-butyl-3-(2-chlorobenzyl)-7-(3,3,4,4-tetrafluoropyrrolidin-1-yl)-3H-[1,2,3]triazolo[4,5-d]pyrimidine;
(R)-5-tert-butyl-3-(2-chlorobenzyl)-7-(2-(methoxymethyl)pyrrolidin-1-yl)-3H-[1,2,3]triazolo[4,5-d]pyrimidine;
(S)-5-tert-butyl-3-(2-chlorobenzyl)-7-(2-(methoxymethyl)pyrrolidin-1-yl)-3H-[1,2,3]triazolo[4,5-d]pyrimidine;
(2S,4S)-1-(5-tert-butyl-3-(2-chlorobenzyl)-3H-[1,2,3]triazolo[4,5-d]pyrimidin-7-yl)-4-fluoropyrrolidine-2-carbonitrile;
5-tert-butyl-3-(2-chloro-benzyl)-7-(1,1-dioxo-1λ6-isothiazolidin-2-yl)-3H-[1,2,3]triazolo[4,5-d]pyrimidine;
(4-(5-tert-butyl-3-(2-chlorobenzyl)-3H-[1,2,3]triazolo[4,5-d]pyrimidin-7-yl)morpholin-3-yl)methanol;
(R)-1-(5-tert-butyl-3-(2-chlorobenzyl)-3H-[1,2,3]triazolo[4,5-d]pyrimidin-7-yl)pyrrolidine-2-carbonitrile;
(S)-1-(5-tert-butyl-3-(2-chlorobenzyl)-3H-[1,2,3]triazolo[4,5-d]pyrimidin-7-yl)pyrrolidine-2-carbonitrile;
(2S,3S)-1-(5-tert-butyl-3-(2-chlorobenzyl)-3H-[1,2,3]triazolo[4,5-d]pyrimidin-7-yl)-2-(hydroxymethyl)pyrrolidin-3-ol;
(2S,3R)-1-(5-tert-butyl-3-(2-chlorobenzyl)-3H-[1,2,3]triazolo[4,5-d]pyrimidin-7-yl)-2-(hydroxymethyl)pyrrolidin-3-ol;
5-tert-Butyl-3-(2-chloro-benzyl)-7-(2-oxa-5-aza-spiro[3.4]oct-5-yl)-3H-[1,2,3]triazolo[4,5-d]pyrimidine;
1-[5-tert-Butyl-3-(2-chloro-benzyl)-3H-[1,2,3]triazolo[4,5-d]pyrimidin-7-yl]-3-methyl-pyrrolidin-3-ol;
(3R,4R)-1-[5-tert-Butyl-3-(2-chloro-benzyl)-3H-[1,2,3]triazolo[4,5-d]pyrimidin-7-yl]-pyrrolidine-3,4-diol;
(3S,4R)-1-[5-tert-Butyl-3-(2-chloro-benzyl)-3H-[1,2,3]triazolo[4,5-d]pyrimidin-7-yl]-pyrrolidine-3,4-diol;
4-(5-tert-butyl-3-(4-methoxybenzyl)-3H-[1,2,3]triazolo[4,5-d]pyrimidin-7-yl)morpholine;
4-(5-tert-butyl-3H-[1,2,3]triazolo[4,5-d]pyrimidin-7-yl)morpholine;
5-tert-Butyl-3-(2-chloro-4-fluoro-benzyl)-7-morpholin-4-yl-3H-[1,2,3]triazolo[4,5-d]pyrimidine;
5-tert-Butyl-7-(3,3-difluoro-pyrrolidin-1-yl)-3-(4-methoxybenzyl)-3H-[1,2,3]triazolo[4,5-d]pyrimidine;
5-tert-Butyl-7-(3,3-difluoro-pyrrolidin-1-yl)-3-ethyl-3H-[1,2,3]triazolo[4,5-d]pyrimidine;
5-tert-Butyl-7-(3,3-difluoro-pyrrolidin-1-yl)-3-(2-methoxyethyl)-3H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-3-yl]-ethanol;
5-tert-Butyl-3-cyclohexylmethyl-7-(3,3-difluoro-pyrrolidin-1-yl)-3H-[1,2,3]triazolo[4,5-d]pyrimidine;
5-tert-Butyl-3-(3-chloro-benzyl)-7-(3,3-difluoro-pyrrolidin-1-yl)-3H-[1,2,3]triazolo[4,5-d]pyrimidine;
5-tert-Butyl-3-(4-chloro-benzyl)-7-(3,3-difluoro-pyrrolidin-1-yl)-3H-[1,2,3]triazolo[4,5-d]pyrimidine;
5-tert-Butyl-3-(2,3-dichloro-benzyl)-7-(3,3-difluoro-pyrrolidin-1-yl)-3H-[1,2,3]triazolo[4,5-d]pyrimidine;
5-tert-Butyl-3-(2,4-dichloro-benzyl)-7-(3,3-difluoro-pyrrolidin-1-yl)-3H-[1,2,3]triazolo[4,5-d]pyrimidine;
5-tert-Butyl-3-(2,5-dichloro-benzyl)-7-(3,3-difluoro-pyrrolidin-1-yl)-3H-[1,2,3]triazolo[4,5-d]pyrimidine;
5-tert-Butyl-3-(2,6-dichloro-benzyl)-7-(3,3-difluoro-pyrrolidin-1-yl)-3H-[1,2,3]triazolo[4,5-d]pyrimidine;
5-tert-Butyl-3-(2-chloro-4-fluoro-benzyl)-7-(3,3-difluoro-pyrrolidin-1-yl)-3H-[1,2,3]triazolo[4,5-d]pyrimidine;
5-tert-Butyl-3-(2-chloro-6-fluoro-benzyl)-7-(3,3-difluoro-pyrrolidin-1-yl)-3H-[1,2,3]triazolo[4,5-d]pyrimidine;
5-tert-Butyl-7-(3,3-difluoro-pyrrolidin-1-yl)-3-pyridin-2-ylmethyl-3H-[1,2,3]triazolo[4,5-d]pyrimidine;
5-tert-Butyl-7-(3,3-difluoro-pyrrolidin-1-yl)-3-pyridin-3-ylmethyl-3H-[1,2,3]triazolo[4,5-d]pyrimidine;
5-tert-Butyl-7-(3,3-difluoro-pyrrolidin-1-yl)-3-pyridin-4-ylmethyl-3H-[1,2,3]triazolo[4,5-d]pyrimidine;
5-tert-Butyl-7-(3,3-difluoro-pyrrolidin-1-yl)-3-(2,2,2-trifluoro-ethyl)-3H-[1,2,3]triazolo[4,5-d]pyrimidine;
5-tert-Butyl-3-(2-chloro-4,5-difluoro-benzyl)-7-(3,3-difluoro-pyrrolidin-1-yl)-3H-[1,2,3]triazolo[4,5-d]pyrimidine;
5-tert-Butyl-3-(2-chloro-3,6-difluoro-benzyl)-7-(3,3-difluoro-pyrrolidin-1-yl)-3H-[1,2,3]triazolo[4,5-d]pyrimidine;
3-(2-Bromo-benzyl)-5-tert-butyl-7-(3,3-difluoro-pyrrolidin-1-yl)-3H-[1,2,3]triazolo[4,5-d]pyrimidine;
5-tert-Butyl-7-(3,3-difluoro-pyrrolidin-1-yl)-3-(2-trifluoromethyl-benzyl)-3H-[1,2,3]triazolo[4,5-d]pyrimidine;
5-tert-Butyl-7-(3,3-difluoro-pyrrolidin-1-yl)-3-(2-methoxy-benzyl)-3H-[1,2,3]triazolo[4,5-d]pyrimidine;
5-tert-Butyl-7-(3,3-difluoro-pyrrolidin-1-yl)-3-(2-trifluoromethoxy-benzyl)-3H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-3-ylmethyl]-benzonitrile;
5-tert-Butyl-7-(3,3-difluoro-pyrrolidin-1-yl)-3-phenethyl-3H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-3-yl]-1-phenyl-ethanone;
5-tert-Butyl-3-[(R)-1-(2-chloro-phenyl)-ethyl]-7-(3,3-difluoro-pyrrolidin-1-yl)-3H-[1,2,3]triazolo[4,5-d]pyrimidine;
5-tert-Butyl-3-[(S)-1-(2-chloro-phenyl)-ethyl]-7-(3,3-difluoro-pyrrolidin-1-yl)-3H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-3-yl]-1-phenyl-ethanol;
5-tert-Butyl-3-(2-chloro-3-fluoro-benzyl)-7-(3,3-difluoro-pyrrolidin-1-yl)-3H-[1,2,3]triazolo[4,5-d]pyrimidine;
5-tert-Butyl-3-(2-chloro-5-fluoro-benzyl)-7-(3,3-difluoro-pyrrolidin-1-yl)-3H-[1,2,3]triazolo[4,5-d]pyrimidine;
5-tert-Butyl-7-(3,3-difluoro-pyrrolidin-1-yl)-3-oxetan-3-yl-3H-[1,2,3]triazolo[4,5-d]pyrimidine; and
[5-tert-Butyl-7-(3,3-difluoro-pyrrolidin-1-yl)-[1,2,3]triazolo[4,5-d]pyrimidin-3-yl]-(2-chloro-phenyl)-methanone.

The invention further relates in particular to a compound of formula (I) selected from (3S,5R)-1-[5-tert-Butyl-3-(2-chloro-benzyl)-3H-[1,2,3]triazolo[4,5-d]pyrimidin-7-yl]-5-hydroxymethyl-pyrrolidin-3-ol;
{(R)-1-[5-tert-Butyl-3-(2-chloro-benzyl)-3H-[1,2,3]triazolo[4,5-d]pyrimidin-7-yl]-4,4-difluoro-pyrrolidin-2-yl}-methanol;
(R)-1-[5-tert-Butyl-3-(2-chloro-benzyl)-3H-[1,2,3]triazolo[4,5-d]pyrimidin-7-yl]-4,4-difluoro-pyrrolidin-3-ol;
5-tert-Butyl-3-(2,6-dichloro-3-fluoro-benzyl)-7-(3,3-difluoro-pyrrolidin-1-yl)-3H-[1,2,3]triazolo[4,5-d]pyrimidine;
5-tert-Butyl-3-(2-chloro-pyridin-3-ylmethyl)-7-(3,3-difluoro-pyrrolidin-1-yl)-3H-[1,2,3]triazolo[4,5-d]pyrimidine;
5-tert-Butyl-3-(3-chloro-pyridin-2-ylmethyl)-7-(3,3-difluoro-pyrrolidin-1-yl)-3H-[1,2,3]triazolo[4,5-d]pyrimidine;
5-tert-Butyl-3-(2,5-dichloro-pyridin-3-ylmethyl)-7-(3,3-difluoro-pyrrolidin-1-yl)-3H-[1,2,3]triazolo[4,5-d]pyrimidine;
5-tert-Butyl-3-(3,6-dichloro-pyridin-2-ylmethyl)-7-(3,3-difluoro-pyrrolidin-1-yl)-3H-[1,2,3]triazolo[4,5-d]pyrimidine;
5-tert-Butyl-7-(3,3-difluoro-pyrrolidin-1-yl)-3-(4-methyl-furazan-3-ylmethyl)-3H-[1,2,3]triazolo[4,5-d]pyrimidine;
5-tert-Butyl-7-(3,3-difluoro-pyrrolidin-1-yl)-3-(3-methyl-[1,2,4]oxadiazol-5-ylmethyl)-3H-[1,2,3]triazolo[4,5-d]pyrimidine;
5-tert-Butyl-3-[2-(2-chloro-phenyl)-ethyl]-7-(3,3-difluoro-pyrrolidin-1-yl)-3H-[1,2,3]triazolo[4,5-d]pyrimidine;
5-tert-Butyl-3-[2-(3-chloro-phenyl)-ethyl]-7-(3,3-difluoro-pyrrolidin-1-yl)-3H-[1,2,3]triazolo[4,5-d]pyrimidine;
5-tert-Butyl-3-[2-(4-chloro-phenyl)-ethyl]-7-(3,3-difluoro-pyrrolidin-1-yl)-3H-[1,2,3]triazolo[4,5-d]pyrimidine;
(S)-1-[5-tert-Butyl-3-(4-methoxy-benzyl)-3H-[1,2,3]triazolo[4,5-d]pyrimidin-7-yl]-pyrrolidin-3-ol;
5-tert-Butyl-3-(2-chloro-benzenesulfonyl)-7-(3,3-difluoro-pyrrolidin-1-yl)-3H-[1,2,3]triazolo[4,5-d]pyrimidine;
5-tert-Butyl-7-(3,3-difluoro-pyrrolidin-1-yl)-3-(R)-tetrahydro-furan-3-yl-3H-[1,2,3]triazolo[4,5-d]pyrimidine;
5-tert-Butyl-7-(3,3-difluoro-pyrrolidin-1-yl)-3-(S)-tetrahydro-furan-3-yl-3H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-3-yl]-1-(2-chloro-phenyl)-ethanone;
5-tert-Butyl-3-(2,3-dichloro-6-fluoro-benzyl)-7-(3,3-difluoro-pyrrolidin-1-yl)-3H-[1,2,3]triazolo[4,5-d]pyrimidine;
5-tert-Butyl-7-(3,3-difluoro-pyrrolidin-1-yl)-3-(2-methanesulfonyl-benzyl)-3H-[1,2,3]triazolo[4,5-d]pyrimidine;
5-tert-Butyl-7-(3,3-difluoro-pyrrolidin-1-yl)-3-(2-pyridin-2-yl-ethyl)-3H-[1,2,3]triazolo[4,5-d]pyrimidine;
5-tert-Butyl-7-(3,3-difluoro-pyrrolidin-1-yl)-3-(3-methyl-oxetan-3-ylmethyl)-3H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-3-yl]-1-(3-chloro-phenyl)-ethanone;
2-[5-tert-Butyl-7-(3,3-difluoro-pyrrolidin-1-yl)-[1,2,3]triazolo[4,5-d]pyrimidin-3-yl]-1-(4-chloro-phenyl)-ethanone;
2-[5-tert-Butyl-7-(3,3-difluoro-pyrrolidin-1-yl)-[1,2,3]triazolo[4,5-d]pyrimidin-3-yl]-1-pyridin-3-yl-ethanone;
2-[5-tert-Butyl-7-(3,3-difluoro-pyrrolidin-1-yl)-[1,2,3]triazolo[4,5-d]pyrimidin-3-yl]-1-pyridin-4-yl-ethanone;
5-tert-Butyl-7-(3,3-difluoro-pyrrolidin-1-yl)-3-(2,3,6-trichloro-benzyl)-3H-[1,2,3]triazolo[4,5-d]pyrimidine;
5-tert-Butyl-3-(2-chloro-3-trifluoromethyl-benzyl)-7-(3,3-difluoro-pyrrolidin-1-yl)-3H-[1,2,3]triazolo[4,5-d]pyrimidine;
5-tert-Butyl-7-(3,3-difluoro-pyrrolidin-1-yl)-3-(2-pyridin-3-yl-ethyl)-3H-[1,2,3]triazolo[4,5-d]pyrimidine;
5-tert-Butyl-7-(3,3-difluoro-pyrrolidin-1-yl)-3-(2-pyridin-4-yl-ethyl)-3H-[1,2,3]triazolo[4,5-d]pyrimidine;
5-tert-Butyl-3-(2,3-dichloro-6-trifluoromethyl-benzyl)-7-(3,3-difluoro-pyrrolidin-1-yl)-3H-[1,2,3]triazolo[4,5-d]pyrimidine;
5-tert-Butyl-3-(3,4-dichloro-pyridin-2-ylmethyl)-7-(3,3-difluoro-pyrrolidin-1-yl)-3H-[1,2,3]triazolo[4,5-d]pyrimidine;
5-tert-Butyl-7-(3,3-difluoro-pyrrolidin-1-yl)-3-(1,1-dioxo-1λ6-thietan-3-yl)-3H-[1,2,3]triazolo[4,5-d]pyrimidine;
5-tert-Butyl-7-(3,3-difluoro-pyrrolidin-1-yl)-3-(1,1-dioxo-tetrahydro-1λ6-thiophen-3-yl)-3H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-3-yl]-1-pyridin-2-yl-ethanone;
5-tert-Butyl-7-(3,3-difluoro-pyrrolidin-1-yl)-3-(5-methyl-[1,3,4]oxadiazol-2-ylmethyl)-3H-[1,2,3]triazolo[4,5-d]pyrimidine;
5-tert-Butyl-3-(3-chloro-pyridin-4-ylmethyl)-7-(3,3-difluoro-pyrrolidin-1-yl)-3H-[1,2,3]triazolo[4,5-d]pyrimidine;
5-tert-Butyl-7-(3,3-difluoro-pyrrolidin-1-yl)-3-(5-methyl-[1,2,4]oxadiazol-3-ylmethyl)-3H-[1,2,3]triazolo[4,5-d]pyrimidine;
5-tert-Butyl-7-(3,3-difluoro-pyrrolidin-1-yl)-3-(1-methyl-1H-tetrazol-5-ylmethyl)-3H-[1,2,3]triazolo[4,5-d]pyrimidine;
5-tert-Butyl-7-(3,3-difluoro-pyrrolidin-1-yl)-3-(2-methyl-2H-[1,2,4]triazol-3-ylmethyl)-3H-[1,2,3]triazolo[4,5-d]pyrimidine;
5-tert-Butyl-7-(3,3-difluoro-pyrrolidin-1-yl)-3-(5-methanesulfonyl-4-methyl-4H-[1,2,4]triazol-3-ylmethyl)-3H-[1,2,3]triazolo[4,5-d]pyrimidine;
{3-[5-tert-Butyl-7-(3,3-difluoro-pyrrolidin-1-yl)-[1,2,3]triazolo[4,5-d]pyrimidin-3-ylmethyl]-5-chloro-pyridin-4-yl}-dimethyl-amine;
5-tert-Butyl-7-(3,3-difluoro-pyrrolidin-1-yl)-3-(3-trifluoromethyl-1H-pyrazol-4-ylmethyl)-3H-[1,2,3]triazolo[4,5-d]pyrimidine;
(S)-1-[5-tert-Butyl-3-(4-methyl-furazan-3-ylmethyl)-3H-[1,2,3]triazolo[4,5-d]pyrimidin-7-yl]-pyrrolidin-3-ol;
(S)-1-[5-tert-Butyl-3-(3-methyl-[1,2,4]oxadiazol-5-ylmethyl)-3H-[1,2,3]triazolo[4,5-d]pyrimidin-7-yl]-pyrrolidin-3-ol;
(S)-1-[5-tert-Butyl-3-(3-chloro-pyridin-2-ylmethyl)-3H-[1,2,3]triazolo[4,5-d]pyrimidin-7-yl]-pyrrolidin-3-ol;
(S)-1-[5-tert-Butyl-3-(3,6-dichloro-pyridin-2-ylmethyl)-3H-[1,2,3]triazolo[4,5-d]pyrimidin-7-yl]-pyrrolidin-3-ol;
(S)-1-[5-tert-Butyl-3-(2-chloro-pyridin-3-ylmethyl)-3H-[1,2,3]triazolo[4,5-d]pyrimidin-7-yl]-pyrrolidin-3-ol;
(S)-1-[5-tert-Butyl-3-(2,3-dichloro-benzyl)-3H-[1,2,3]triazolo[4,5-d]pyrimidin-7-yl]-pyrrolidin-3-ol;
(S)-1-[5-tert-Butyl-3-(2-trifluoromethyl-benzyl)-3H-[1,2,3]triazolo[4,5-d]pyrimidin-7-yl]-pyrrolidin-3-ol;
(S)-1-[5-tert-Butyl-3-(2-methanesulfonyl-benzyl)-3H-[1,2,3]triazolo[4,5-d]pyrimidin-7-yl]-pyrrolidin-3-ol;
5-tert-Butyl-7-(3,3-difluoro-pyrrolidin-1-yl)-3-(2,5-dimethyl-2H-pyrazol-3-ylmethyl)-3H-[1,2,3]triazolo[4,5-d]pyrimidine;

5-tert-Butyl-7-(3,3-difluoro-pyrrolidin-1-yl)-3-(3-methyl-3H-[1,2,3]triazol-4-ylmethyl)-3H-[1,2,3]triazolo[4,5-d]pyrimidine;

5-tert-Butyl-7-(3,3-difluoro-pyrrolidin-1-yl)-3-(4,5-dimethyl-4H-[1,2,4]triazol-3-ylmethyl)-3H-[1,2,3]triazolo[4,5-d]pyrimidine;

5-tert-Butyl-7-(3,3-difluoro-pyrrolidin-1-yl)-3-(2-methyl-1-oxy-pyridin-3-ylmethyl)-3H-[1,2,3]triazolo[4,5-d]pyrimidine;

(S)-1-[5-tert-Butyl-3-(3,4-dichloro-pyridin-2-ylmethyl)-3H-[1,2,3]triazolo[4,5-d]pyrimidin-7-yl]-pyrrolidin-3-ol;

(S)-1-[5-tert-Butyl-3-(5-methyl-[1,2,4]oxadiazol-3-ylmethyl)-3H-[1,2,3]triazolo[4,5-d]pyrimidin-7-yl]-pyrrolidin-3-ol;

(S)-1-[5-tert-Butyl-3-(5-methyl-[1,3,4]oxadiazol-2-ylmethyl)-3H-[1,2,3]triazolo[4,5-d]pyrimidin-7-yl]-pyrrolidin-3-ol;

(S)-1-[5-tert-Butyl-3-(1-methyl-1H-tetrazol-5-ylmethyl)-3H-[1,2,3]triazolo[4,5-d]pyrimidin-7-yl]-pyrrolidin-3-ol;

(S)-1-[5-tert-Butyl-3-(2-methyl-2H-[1,2,4]triazol-3-ylmethyl)-3H-[1,2,3]triazolo[4,5-d]pyrimidin-7-yl]-pyrrolidin-3-ol;

(S)-1-[5-tert-Butyl-3-(4,5-dimethyl-4H-[1,2,4]triazol-3-ylmethyl)-3H-[1,2,3]triazolo[4,5-d]pyrimidin-7-yl]-pyrrolidin-3-ol;

(S)-1-[5-tert-Butyl-3-(3-methyl-3H-[1,2,3]triazol-4-ylmethyl)-3H-[1,2,3]triazolo[4,5-d]pyrimidin-7-yl]-pyrrolidin-3-ol;

(S)-1-[5-tert-Butyl-3-(2,5-dimethyl-2H-pyrazol-3-ylmethyl)-3H-[1,2,3]triazolo[4,5-d]pyrimidin-7-yl]-pyrrolidin-3-ol;

5-tert-Butyl-7-(3,3-difluoro-pyrrolidin-1-yl)-3-(3-trifluoromethyl-[1,2,4]oxadiazol-5-ylmethyl)-3H-[1,2,3]triazolo[4,5-d]pyrimidine;

5-tert-Butyl-3-(1-cyclopropyl-1H-tetrazol-5-ylmethyl)-7-(3,3-difluoro-pyrrolidin-1-yl)-3H-[1,2,3]triazolo[4,5-d]pyrimidine;

(S)-1-{5-tert-Butyl-3-[2-(7-nitro-benzo[1,2,5]oxadiazol-4-ylamino)-pyridin-3-ylmethyl]-3H-[1,2,3]triazolo[4,5-d]pyrimidin-7-yl}-pyrrolidin-3-ol;

(2S,3S)-1-[5-tert-Butyl-3-(4-methoxy-benzyl)-3H-[1,2,3]triazolo[4,5-d]pyrimidin-7-yl]-2-hydroxymethyl-pyrrolidin-3-ol;

(S)-1-[5-tert-Butyl-3-(1-cyclopropyl-1H-tetrazol-5-ylmethyl)-3H-[1,2,3]triazolo[4,5-d]pyrimidin-7-yl]-pyrrolidin-3-ol;

(S)-1-[5-tert-Butyl-3-(2,5-dimethyl-2H-[1,2,4]triazol-3-ylmethyl)-3H-[1,2,3]triazolo[4,5-d]pyrimidin-7-yl]-pyrrolidin-3-ol;

(S)-1-[5-tert-Butyl-3-(2-methyl-1-oxy-pyridin-3-ylmethyl)-3H-[1,2,3]triazolo[4,5-d]pyrimidin-7-yl]-pyrrolidin-3-ol;

5-tert-Butyl-7-(3,3-difluoro-pyrrolidin-1-yl)-3-(2,5-dimethyl-2H-[1,2,4]triazol-3-ylmethyl)-3H-[1,2,3]triazolo[4,5-d]pyrimidine;

(2S,3S)-1-[5-tert-Butyl-3-(4-methyl-furazan-3-ylmethyl)-3H-[1,2,3]triazolo[4,5-d]pyrimidin-7-yl]-2-hydroxymethyl-pyrrolidin-3-ol;

(2S,3S)-1-[5-tert-Butyl-3-(1-methyl-1H-tetrazol-5-ylmethyl)-3H-[1,2,3]triazolo[4,5-d]pyrimidin-7-yl]-2-hydroxymethyl-pyrrolidin-3-ol;

(2S,3S)-1-[5-tert-Butyl-3-(1-cyclopropyl-1H-tetrazol-5-ylmethyl)-3H-[1,2,3]triazolo[4,5-d]pyrimidin-7-yl]-2-hydroxymethyl-pyrrolidin-3-ol;

(2S,3S)-1-[5-tert-Butyl-3-(3-chloro-pyridin-2-ylmethyl)-3H-[1,2,3]triazolo[4,5-d]pyrimidin-7-yl]-2-hydroxymethyl-pyrrolidin-3-ol;

(2S,3S)-1-[5-tert-Butyl-3-(2-methanesulfonyl-benzyl)-3H-[1,2,3]triazolo[4,5-d]pyrimidin-7-yl]-2-hydroxymethyl-pyrrolidin-3-ol;

(2S,3S)-1-[5-tert-Butyl-3-(2-methyl-2H-[1,2,4]triazol-3-ylmethyl)-3H-[1,2,3]triazolo[4,5-d]pyrimidin-7-yl]-2-hydroxymethyl-pyrrolidin-3-ol;

(2S,3S)-1-[5-tert-Butyl-3-(4,5-dimethyl-4H-[1,2,4]triazol-3-ylmethyl)-3H-[1,2,3]triazlo[4,5-d]pyrimidin-7-yl]-2-hydroxymethyl-pyrrolidin-3-ol;

(2S,3S)-1-[5-tert-Butyl-3-(3-methyl-3H-[1,2,3]triazolo-4-ylmethyl)-3H-[1,2,3]triazolo[4,5-d]pyrimidin-7-yl]-2-hydroxymethyl-pyrrolidin-3-ol;

(2S,3S)-1-[5-tert-Butyl-3-(2-chloro-pyridin-3-ylmethyl)-3H-[1,2,3]triazolo[4,5-d]pyrimidin-7-yl]-2-hydroxymethyl-pyrrolidin-3-ol;

5-tert-Butyl-3-(4-methyl-furazan-3-ylmethyl)-7-(3,3,4,4-tetrafluoro-pyrrolidin-1-yl)-3H-[1,2,3]triazolo[4,5-d]pyrimidine;

5-tert-Butyl-3-(3-methyl-[1,2,4]oxadiazol-5-ylmethyl)-7-(3,3,4,4-tetrafluoro-pyrrolidin-1-yl)-3H-[1,2,3]triazolo[4,5-d]pyrimidine;

5-tert-Butyl-3-(5-methyl-[1,3,4]oxadiazol-2-ylmethyl)-7-(3,3,4,4-tetrafluoro-pyrrolidin-1-yl)-3H-[1,2,3]triazolo[4,5-d]pyrimidine;

5-tert-Butyl-3-(1-methyl-1H-tetrazol-5-ylmethyl)-7-(3,3,4,4-tetrafluoro-pyrrolidin-1-yl)-3H-[1,2,3]triazolo[4,5-d]pyrimidine;

5-tert-Butyl-3-(4,5-dimethyl-4H-[1,2,4]triazol-3-ylmethyl)-7-(3,3,4,4-tetrafluoro-pyrrolidin-1-yl)-3H-[1,2,3]triazolo[4,5-d]pyrimidine;

5-tert-Butyl-3-(3-methyl-3H-[1,2,3]triazol-4-ylmethyl)-7-(3,3,4,4-tetrafluoro-pyrrolidin-1-yl)-3H-[1,2,3]triazolo[4,5-d]pyrimidine;

5-tert-Butyl-3-(4-methyl-furazan-3-ylmethyl)-7-(2-oxa-6-aza-spiro[3.3]hept-6-yl)-3H-[1,2,3]triazolo[4,5-d]pyrimidine;

5-tert-Butyl-3-(3-methyl-[1,2,4]oxadiazol-5-ylmethyl)-7-(2-oxa-6-aza-spiro[3.3]hept-6-yl)-3H-[1,2,3]triazolo[4,5-d]pyrimidine;

5-tert-Butyl-3-(5-methyl-[1,3,4]oxadiazol-2-ylmethyl)-7-(2-oxa-6-aza-spiro[3.3]hept-6-yl)-3H-[1,2,3]triazolo[4,5-d]pyrimidine;

5-tert-Butyl-3-(1-methyl-1H-tetrazol-5-ylmethyl)-7-(2-oxa-6-aza-spiro[3.3]hept-6-yl)-3H-[1,2,3]triazolo[4,5-d]pyrimidine;

5-tert-Butyl-3-(1-cyclopropyl-1H-tetrazol-5-ylmethyl)-7-(2-oxa-6-aza-spiro[3.3]hept-6-yl)-3H-[1,2,3]triazolo[4,5-d]pyrimidine;

5-tert-Butyl-3-(4,5-dimethyl-4H-[1,2,4]triazol-3-ylmethyl)-7-(2-oxa-6-aza-spiro[3.3]hept-6-yl)-3H-[1,2,3]triazolo[4,5-d]pyrimidine;

5-tert-Butyl-3-(3-methyl-3H-[1,2,3]triazol-4-ylmethyl)-7-(2-oxa-6-aza-spiro[3.3]hept-6-yl)-3H-[1,2,3]triazolo[4,5-d]pyrimidine;

5-tert-Butyl-3-(2-methanesulfonyl-benzyl)-7-(2-oxa-6-aza-spiro[3.3]hept-6-yl)-3H-[1,2,3]triazolo[4,5-d]pyrimidine;

5-tert-Butyl-3-(3-chloro-pyridin-2-ylmethyl)-7-(2-oxa-6-aza-spiro[3.3]hept-6-yl)-3H-[1,2,3]triazolo[4,5-d]pyrimidine;

1-[5-tert-Butyl-3-(2-chloro-benzyl)-3H-[1,2,3]triazolo[4,5-d]pyrimidin-7-yl]-pyrrolidin-3-one;

5-tert-Butyl-3-(2-chloro-benzyl)-7-(3,3-dimethyl-pyrrolidin-1-yl)-3H-[1,2,3]triazolo[4,5-d]pyrimidine;

{1-[5-tert-Butyl-3-(2-chloro-benzyl)-3H-[1,2,3]triazolo[4,5-d]pyrimidin-7-yl]-pyrrolidin-3-yl}-methyl-amine;

{1-[5-tert-Butyl-3-(2-chloro-benzyl)-3H-[1,2,3]triazolo[4,5-d]pyrimidin-7-yl]-pyrrolidin-3-yl}-dimethyl-amine;

N-{(S)-1-[5-tert-Butyl-3-(2-chloro-benzyl)-3H-[1,2,3]triazolo[4,5-d]pyrimidin-7-yl]-pyrrolidin-3-yl}-acetamide;
N-{(R)-1-[5-tert-Butyl-3-(2-chloro-benzyl)-3H-[1,2,3]triazolo[4,5-d]pyrimidin-7-yl]-pyrrolidin-3-yl}-acetamide;
N-{1-[5-tert-Butyl-3-(2-chloro-benzyl)-3H-[1,2,3]triazolo[4,5-d]pyrimidin-7-yl]-pyrrolidin-3-yl}-N-methyl-acetamide;
5-tert-Butyl-3-(2-chloro-benzyl)-7-(3-phenyl-pyrrolidin-1-yl)-3H-[1,2,3]triazolo[4,5-d]pyrimidine;
N-(1-[5-tert-Butyl-3-(2-chloro-benzyl)-3H-[1,2,3]triazolo[4,5-d]pyrimidin-7-yl]-pyrrolidin-3-yl)-N-ethyl-acetamide;
1-[5-tert-Butyl-3-(2-chloro-benzyl)-3H-[1,2,3]triazolo[4,5-d]pyrimidin-7-yl]-azetidine-3-carboxylic acid methyl ester;
5-tert-Butyl-3-(2-chloro-benzyl)-7-(3-methyl-pyrrolidin-1-yl)-3H-[1,2,3]triazolo[4,5-d]pyrimidine;
C-{(S)-1-[5-tert-Butyl-3-(2-chloro-benzyl)-3H-[1,2,3]triazolo[4,5-d]pyrimidin-7-yl]-pyrrolidin-2-yl}-methylamine;
5-tert-Butyl-3-(2-chloro-benzyl)-7-[2-(1-methyl-1H-pyrazol-3-yl)-pyrrolidin-1-yl]-3H-[1,2,3]triazolo[4,5-d]pyrimidine;
5-tert-Butyl-3-(2-chloro-benzyl)-7-[2-(2-methyl-2H-pyrazol-3-yl)-pyrrolidin-1-yl]-3H-[1,2,3]triazolo[4,5-d]pyrimidine;
5-tert-Butyl-3-(2-chloro-benzyl)-7-[2-(3-methyl-isoxazol-5-yl)-pyrrolidin-1-yl]-3H-[1,2,3]triazolo[4,5-d]pyrimidine;
5-tert-Butyl-3-(2-chloro-benzyl)-7-[2-(3-methyl-[1,2,4]oxadiazol-5-yl)-pyrrolidin-1-yl]-3H-[1,2,3]triazolo[4,5-d]pyrimidine;
1-[5-tert-Butyl-3-(2-chloro-benzyl)-3H-[1,2,3]triazolo[4,5-d]pyrimidin-7-yl]-pyrrolidin-3-ol;
5-tert-Butyl-3-(2-chloro-benzyl)-7-cyclobutoxy-3H-[1,2,3]triazolo[4,5-d]pyrimidine;
5-tert-Butyl-3-(2-chloro-benzyl)-7-(oxetan-3-yloxy)-3H-[1,2,3]triazolo[4,5-d]pyrimidine;
5-tert-Butyl-3-(2-chloro-benzyl)-7-methoxy-3H-[1,2,3]triazolo[4,5-d]pyrimidine;
5-tert-Butyl-3-(2-chloro-benzyl)-7-ethoxy-3H-[1,2,3]triazolo[4,5-d]pyrimidine;
5-tert-Butyl-3-(2-chloro-benzyl)-7-isopropoxy-3H-[1,2,3]triazolo[4,5-d]pyrimidine;
5-tert-Butyl-3-(2-chloro-benzyl)-7-cyclopropylmethoxy-3H-[1,2,3]triazolo[4,5-d]pyrimidine;
5-tert-Butyl-3-(2-chloro-benzyl)-7-(1-cyclopropyl-ethoxy)-3H-[1,2,3]triazolo[4,5-d]pyrimidine;
5-tert-Butyl-3-(2-chloro-benzyl)-7-cyclopentyloxy-3H-[1,2,3]triazolo[4,5-d]pyrimidine;
5-tert-Butyl-3-(2-chloro-benzyl)-7-(2,2-dimethyl-propoxy)-3H-[1,2,3]triazolo[4,5-d]pyrimidine;
5-tert-Butyl-3-(2-chloro-benzyl)-7-(2,2,2-trifluoro-1-methyl-ethoxy)-3H-[1,2,3]triazolo[4,5-d]pyrimidine;
5-tert-Butyl-3-(2-chloro-benzyl)-7-((S)-2,2,2-trifluoro-1-methyl-ethoxy)-3H-[1,2,3]triazolo[4,5-d]pyrimidine;
5-tert-Butyl-3-(2-chloro-benzyl)-7-((R)-2,2,2-trifluoro-1-methyl-ethoxy)-3H-[1,2,3]triazolo[4,5-d]pyrimidine;
(3S)-1-(3-benzyl-5-tert-butyl-triazolo[4,5-d]pyrimidin-7-yl)pyrrolidin-3-ol;
1-(5-tert-butyl-3-(2-chlorobenzyl)-3H-[1,2,3]triazolo[4,5-d]pyrimidin-7-yl)pyrrolidin-3-ol;
(R)-1-(5-tert-butyl-3-((1-methyl-1H-tetrazol-5-yl)methyl)-3H-[1,2,3]triazolo[4,5-d]pyrimidin-7-yl)pyrrolidin-3-ol;
1-(5-tert-butyl-3-((1-methyl-1H-tetrazol-5-yl)methyl)-3H-[1,2,3]triazolo[4,5-d]pyrimidin-7-yl)pyrrolidin-3-ol;
(S)-1-(5-tert-butyl-3-(2-chlorobenzyl)-3H-[1,2,3]triazolo[4,5-d]pyrimidin-7-yl)-3-methylpyrrolidin-3-ol;
(R)-1-(5-tert-butyl-3-(2-chlorobenzyl)-3H-[1,2,3]triazolo[4,5-d]pyrimidin-7-yl)-3-methylpyrrolidin-3-ol;
(S)-1-(5-tert-butyl-3-(2-(trifluoromethyl)benzyl)-3H-[1,2,3]triazolo[4,5-d]pyrimidin-7-yl)-3-methylpyrrolidin-3-ol;
(R)-1-(5-tert-butyl-3-(2-(trifluoromethyl)benzyl)-3H-[1,2,3]triazolo[4,5-d]pyrimidin-7-yl)-3-methylpyrrolidin-3-ol;
(S)-1-(5-tert-butyl-3-(2-(methylsulfonyl)benzyl)-3H-[1,2,3]triazolo[4,5-d]pyrimidin-7-yl)-3-methylpyrrolidin-3-ol;
(R)-1-(5-tert-butyl-3-(2-(methylsulfonyl)benzyl)-3H-[1,2,3]triazolo[4,5-d]pyrimidin-7-yl)-3-methylpyrrolidin-3-ol;
(S)-1-(5-tert-butyl-3-((3-chloropyridin-2-yl)methyl)-3H-[1,2,3]triazolo[4,5-d]pyrimidin-7-yl)-3-methylpyrrolidin-3-ol;
(R)-1-(5-tert-butyl-3-((3-chloropyridin-2-yl)methyl)-3H-[1,2,3]triazolo[4,5-d]pyrimidin-7-yl)-3-methylpyrrolidin-3-ol;
(S)-1-(5-tert-butyl-3-((5-methyl-1,3,4-oxadiazol-2-yl)methyl)-3H-[1,2,3]triazolo[4,5-d]pyrimidin-7-yl)-3-methylpyrrolidin-3-ol;
(R)-1-(5-tert-butyl-3-((5-methyl-1,3,4-oxadiazol-2-yl)methyl)-3H-[1,2,3]triazolo[4,5-d]pyrimidin-7-yl)-3-methylpyrrolidin-3-ol;
(S)-1-(5-tert-butyl-3-((3-methyl-1,2,4-oxadiazol-5-yl)methyl)-3H-[1,2,3]triazolo[4,5-d]pyrimidin-7-yl)-3-methylpyrrolidin-3-ol;
(R)-1-(5-tert-butyl-3-((3-methyl-1,2,4-oxadiazol-5-yl)methyl)-3H-[1,2,3]triazolo[4,5-d]pyrimidin-7-yl)-3-methylpyrrolidin-3-ol;
(S)-1-(5-tert-butyl-3-((1-methyl-1H-tetrazol-5-yl)methyl)-3H-[1,2,3]triazolo[4,5-d]pyrimidin-7-yl)-3-methylpyrrolidin-3-ol;
(R)-1-(5-tert-butyl-3-((1-methyl-1H-tetrazol-5-yl)methyl)-3H-[1,2,3]triazolo[4,5-d]pyrimidin-7-yl)-3-methylpyrrolidin-3-ol;
(S)-1-(5-tert-butyl-3-((4-methyl-1,2,5-oxadiazol-3-yl)methyl)-3H-[1,2,3]triazolo[4,5-d]pyrimidin-7-yl)-3-methylpyrrolidin-3-ol;
(R)-1-(5-tert-butyl-3-((4-methyl-1,2,5-oxadiazol-1,2,5-oxadiazol-3-yl)methyl)-3H-[1,2,3]triazolo[4,5-d]pyrimidin-7-yl)-3-methylpyrrolidin-3-ol;
(S)-1-(5-tert-butyl-3-(3,3,3-trifluoropropyl)-3H-[1,2,3]triazolo[4,5-d]pyrimidin-7-yl)-3-methylpyrrolidin-3-ol;
(R)-1-(5-tert-butyl-3-(3,3,3-trifluoropropyl)-3H-[1,2,3]triazolo[4,5-d]pyrimidin-7-yl)-3-methylpyrrolidin-3-ol;
(S)-1-(5-tert-butyl-3-((1-cyclopropyl-1H-tetrazol-5-yl)methyl)-3H-[1,2,3]triazolo[4,5-d]pyrimidin-7-yl)-3-methylpyrrolidin-3-ol; and
(R)-1-(5-tert-butyl-3-((1-cyclopropyl-1H-tetrazol-5-yl)methyl)-3H-[1,2,3]triazolo[4,5-d]pyrimidin-7-yl)-3-methylpyrrolidin-3-ol.

The invention relates in particular to a compound of formula (I) selected from
5-tert-Butyl-3-(2-chlorobenzyl)-7-(4,4-difluoropiperidin-1-yl)-3H-[1,2,3]triazolo[4,5-d]pyrimidine;
5-tert-Butyl-3-(2-chlorobenzyl)-7-(3,3-difluoropyrrolidin-1-yl)-3H-[1,2,3]triazolo[4,5-d]pyrimidine;
5-tert-Butyl-3-(2-chlorobenzyl)-7-(3,3-difluoroazetidin-1-yl)-3H-[1,2,3]triazolo[4,5-d]pyrimidine;
1-(5-tert-Butyl-3-(2-chlorobenzyl)-3H-[1,2,3]triazolo[4,5-d]pyrimidin-7-yl)-3-methylazetidin-3-ol;
(S)-1-(5-tert-Butyl-3-(2-chlorobenzyl)-3H-[1,2,3]triazolo[4,5-d]pyrimidin-7-yl)pyrrolidin-3-ol;
(R)-(1-(5-tert-Butyl-3-(2-chlorobenzyl)-3H-[1,2,3]triazolo[4,5-d]pyrimidin-7-yl)pyrrolidin-2-yl)methanol;

5-tert-Butyl-3-(2-chlorobenzyl)-7-(3,3,4,4-tetrafluoropyrrolidin-1-yl)-3H-[1,2,3]triazolo[4,5-d]pyrimidine;
(R)-5-tert-Butyl-3-(2-chlorobenzyl)-7-(2-(methoxymethyl)pyrrolidin-1-yl)-3H-[1,2,3]triazolo[4,5-d]pyrimidine;
(2S,3S)-1-(5-tert-Butyl-3-(2-chlorobenzyl)-3H-[1,2,3]triazolo[4,5-d]pyrimidin-7-yl)-2-(hydroxymethyl)pyrrolidin-3-ol;
1-[5-tert-Butyl-3-(2-chloro-benzyl)-3H-[1,2,3]triazolo[4,5-d]pyrimidin-7-yl]-3-methyl-pyrrolidin-3-ol;
5-tert-Butyl-3-cyclohexylmethyl-7-(3,3-difluoro-pyrrolidin-1-yl)-3H-[1,2,3]triazolo[4,5-d]pyrimidine;
5-tert-Butyl-3-(2,6-dichloro-benzyl)-7-(3,3-difluoro-pyrrolidin-1-yl)-3H-[1,2,3]triazolo[4,5-d]pyrimidine;
5-tert-Butyl-7-(3,3-difluoro-pyrrolidin-1-yl)-3-pyridin-2-ylmethyl-3H-[1,2,3]triazolo[4,5-d]pyrimidine;
5-tert-Butyl-7-(3,3-difluoro-pyrrolidin-1-yl)-3-pyridin-3-ylmethyl-3H-[1,2,3]triazolo[4,5-d]pyrimidine;
5-tert-Butyl-7-(3,3-difluoro-pyrrolidin-1-yl)-3-(2,2,2-trifluoro-ethyl)-3H-[1,2,3]triazolo[4,5-d]pyrimidine;
5-tert-Butyl-3-(2-chloro-3,6-difluoro-benzyl)-7-(3,3-difluoro-pyrrolidin-1-yl)-3H-[1,2,3]triazolo[4,5-d]pyrimidine;
5-tert-Butyl-7-(3,3-difluoro-pyrrolidin-1-yl)-3-(2-trifluoromethyl-benzyl)-3H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-3-ylmethyl]-benzonitrile;
5-tert-Butyl-7-(3,3-difluoro-pyrrolidin-1-yl)-3-phenethyl-3H-[1,2,3]triazolo[4,5-d]pyrimidine;
5-tert-Butyl-3-[(R)-1-(2-chloro-phenyl)-ethyl]-7-(3,3-difluoro-pyrrolidin-1-yl)-3H-[1,2,3]triazolo[4,5-d]pyrimidine; and
2-[5-tert-Butyl-7-(3,3-difluoro-pyrrolidin-1-yl)-[1,2,3]triazolo[4,5-d]pyrimidin-3-yl]-1-phenyl-ethanol.

The invention relates in particular to a compound of formula (I) selected from the group consisting of:
5-tert-Butyl-3-(3-chloro-pyridin-2-ylmethyl)-7-(3,3-difluoro-pyrrolidin-1-yl)-3H-[1,2,3]triazolo[4,5-d]pyrimidine;
5-tert-Butyl-3-(3,6-dichloro-pyridin-2-ylmethyl)-7-(3,3-difluoro-pyrrolidin-1-yl)-3H-[1,2,3]triazolo[4,5-d]pyrimidine;
5-tert-Butyl-7-(3,3-difluoro-pyrrolidin-1-yl)-3-(1-methyl-1H-tetrazol-5-ylmethyl)-3H-[1,2,3]triazolo[4,5-d]pyrimidine;
5-tert-Butyl-7-(3,3-difluoro-pyrrolidin-1-yl)-3-(2-methyl-2H-[1,2,4]triazol-3-ylmethyl)-3H-[1,2,3]triazolo[4,5-d]pyrimidine;
(S)-1-[5-tert-Butyl-3-(4-methyl-furazan-3-ylmethyl)-3H-[1,2,3]triazolo[4,5-d]pyrimidin-7-yl]-pyrrolidin-3-ol;
(S)-1-[5-tert-Butyl-3-(3-chloro-pyridin-2-ylmethyl)-3H-[1,2,3]triazolo[4,5-d]pyrimidin-7-yl]-pyrrolidin-3-ol;
(S)-1-[5-tert-Butyl-3-(2-chloro-pyridin-3-ylmethyl)-3H-[1,2,3]triazolo[4,5-d]pyrimidin-7-yl]-pyrrolidin-3-ol;
(S)-1-[5-tert-Butyl-3-(2-methanesulfonyl-benzyl)-3H-[1,2,3]triazolo[4,5-d]pyrimidin-7-yl]-pyrrolidin-3-ol;
(S)-1-[5-tert-Butyl-3-(1-methyl-1H-tetrazol-5-ylmethyl)-3H-[1,2,3]triazlo[4,5-d]pyrimidin-7-yl]-pyrrolidin-3-ol;
(S)-1-[5-tert-Butyl-3-(1-cyclopropyl-1H-tetrazol-5-ylmethyl)-3H-[1,2,3]triazolo[4,5-d]pyrimidin-7-yl]-pyrrolidin-3-ol;
5-tert-Butyl-3-(4-methyl-furazan-3-ylmethyl)-7-(3,3,4,4-tetrafluoro-pyrrolidin-1-yl)-3H-[1,2,3]triazolo[4,5-d]pyrimidine;
5-tert-Butyl-3-(3-chloro-pyridin-2-ylmethyl)-7-(2-oxa-6-aza-spiro[3.3]hept-6-yl)-3H-[1,2,3]triazolo[4,5-d]pyrimidine;
5-tert-Butyl-3-(2-chloro-benzyl)-7-((R)-2,2,2-trifluoro-1-methyl-ethoxy)-3H-[1,2,3]triazolo[4,5-d]pyrimidine;
(S)-1-(5-tert-butyl-3-(2-chlorobenzyl)-3H-[1,2,3]triazolo[4,5-d]pyrimidin-7-yl)-3-methylpyrrolidin-3-ol;
(R)-1-(5-tert-butyl-3-(2-chlorobenzyl)-3H-[1,2,3]triazolo[4,5-d]pyrimidin-7-yl)-3-methylpyrrolidin-3-ol;
(S)-1-(5-tert-butyl-3-(2-(trifluoromethyl)benzyl)-3H-[1,2,3]triazolo[4,5-d]pyrimidin-7-yl)-3-methylpyrrolidin-3-ol;
(R)-1-(5-tert-butyl-3-(2-(trifluoromethyl)benzyl)-3H-[1,2,3]triazolo[4,5-d]pyrimidin-7-yl)-3-methylpyrrolidin-3-ol;
(S)-1-(5-tert-butyl-3-(2-(methylsulfonyl)benzyl)-3H-[1,2,3]triazolo[4,5-d]pyrimidin-7-yl)-3-methylpyrrolidin-3-ol; and
(R)-1-(5-tert-butyl-3-(2-(methylsulfonyl)benzyl)-3H-[1,2,3]triazolo[4,5-d]pyrimidin-7-yl)-3-methylpyrrolidin-3-ol.

The following compounds of formula (I) are particularly advantageous:
(S)-1-(5-tert-butyl-3-(2-chlorobenzyl)-3H-[1,2,3]triazolo[4,5-d]pyrimidin-7-yl)pyrrolidin-3-ol;
(S)-1-[5-tert-Butyl-3-(4-methyl-furazan-3-ylmethyl)-3H-[1,2,3]triazolo[4,5-d]pyrimidin-7-yl]-pyrrolidin-3-ol;
(S)-1-[5-tert-Butyl-3-(3-chloro-pyridin-2-ylmethyl)-3H-[1,2,3]triazolo[4,5-d]pyrimidin-7-yl]-pyrrolidin-3-ol;
(S)-1-[5-tert-Butyl-3-(2-methanesulfonyl-benzyl)-3H-[1,2,3]triazolo[4,5-d]pyrimidin-7-yl]-pyrrolidin-3-ol; and
(S)-1-[5-tert-Butyl-3-(1-methyl-1H-tetrazol-5-ylmethyl)-3H-[1,2,3]triazolo[4,5-d]pyrimidin-7-yl]-pyrrolidin-3-ol.
(S)-1-(5-tert-butyl-3-(2-chlorobenzyl)-3H-[1,2,3]triazolo[4,5-d]pyrimidin-7-yl)pyrrolidin-3-ol is a particularly advantageous compound.

The preparation of compounds of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations, 2nd Edition*, Richard C. Larock. John Wiley & Sons, New York, N.Y. 1999). We found it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

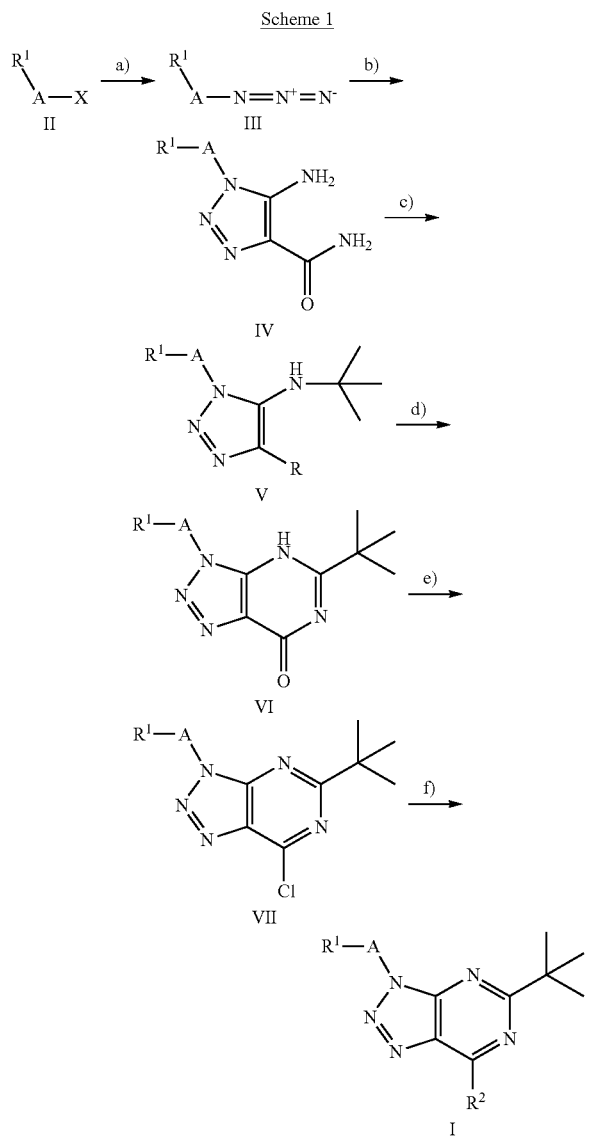

X = Br or Cl
R = CONH$_2$, CN

A) Halides II are either commercially available or can be synthesized according to methods known in the art. These halides II are conveniently reacted with sodium azide in a suitable solvent such as acetonitrile, ethanol or DMF to afford azide derivatives III. Alternative preferred conditions involve the use of solvents like DMA, NMP or DMSO, even more preferred are NMP and DMSO. In polar aprotic solvents like NMP and DMSO, the alkylations can usually be conducted at lower temperature than for example in acetonitrile, often at room temperature to 40° C. (this is the case for example for BnCl, 1-chloro-2-(chloromethyl)benzene or PMB-Cl; this depends of course on the reactivity of the Halides II) and hence provide a better process safety window (caution organic azides are of course know to be potentially dangerous and process safety has always to be carefully assessed). The addition of water can be beneficial as it increases the solubility of sodium azide and provided more robust kinetic profiles as it helps to dissolves hard clumps of NaN3. It can also lead to a better filterability of the final azide reaction mixture. Filtration of the reaction mixture might be required for example when the following cycloaddition is performed in a continuous mode in small channels reactors. The azide is not isolated and its solution is best introduced in the next step. This also avoids its isolation which can also lead to safety issues.

b) Triazole derivatives IV can be prepared by a [3+2]cycloaddition of azide derivatives III with 2-cyanoacetamide in the presence of an appropriate base such as sodium methoxide or sodium ethoxide in a suitable solvent such as methanol, ethanol or DMF. Alternative preferred conditions involve reacting the azide with 2-cyanoacetamide in solvents like NMP or DMSO, in the presence of sodium hydroxide. The batch process is usually performed at room temperature to 50° C., preferably between room temperature and 40° C. (caution, process safety has always to be carefully assessed). The cycloaddition process is also amendable to continuous mode (for a relevant literature example, see Org. Process Res. Dev., 2009, 13 (6), pp 1401-1406) and in this case the reaction temperature can be increased above 50° C., for example (but not limited to) between 50° C. and 90° C., preferably between 60° C. and 70° C.

c) Triazole derivatives V can be obtained by acylation of IV with an acyl-halide in the presence of a base such as DIEA, DMAP, pyridine and the like. Double acylation and the formation of nitrile side products have been observed. These can be significant when working for example in pyridine as solvent. However, these can be minimized when using DMA or NMP, preferably DMA as solvent instead of pyridine. Preferred conditions involves the use of 1.0-2 equiv. of pyridine and pivaloyl chloride, preferably 1.0 to 1.5 equiv, preferably around 1.5 equiv at 50-100° C., preferably between 75-85° C. These high boiling polar solvents also allow telescoping the following cyclization step which greatly simplifies the process.

d) Triazolopyrimidine derivatives VI can be prepared by intramolecular cyclization of triazole derivative V in the presence of a base such as KHCO$_3$, Na$_2$CO$_3$ and water either with or without a solvent such as methanol, ethanol, dioxane and toluene. Alternative preferred conditions involve the use of DMA or NMP as solvents, preferably DMA. The reaction can be performed in the presence of KHCO$_3$ at 130-170° C., preferably between 140 and 160° C. Compound VI may exist as a tautomer or a mixture of tautomers, for example:

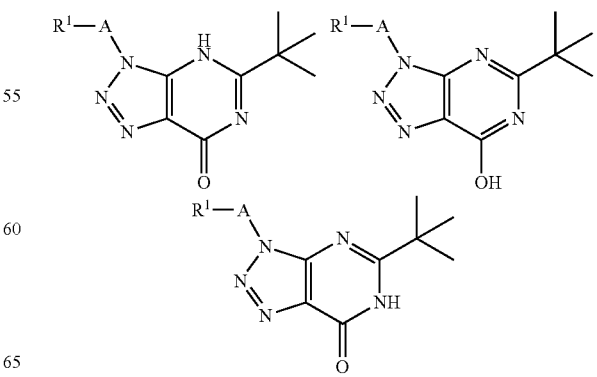

e) Chlorides VII can be obtained by reaction of VI with a chlorination reagent such as $POCl_3$, $SOCl_2$ or $(COCl)_2$ in the presence of an appropriate base such as N,N-diethyl aniline, lutidine, or pyridine. Alternative preferred conditions involve the use of the Vislmeier reagent as chlorinating agent. It can also be generated in situ by reacting oxalyl chloride with DMF. The chlorination can be performed for example in acetonitrile, DCM or AcOEt, preferably in DCM. These conditions allow for mild reaction temperature and for example, avoid the quench of excess $POCl_3$ upon work-up. The crude product can be introduced in the next step.

f) VII are conveniently reacted with various nucleophiles, particularly amines, in the presence of an appropriate base such as triethylamine, DIEA or DBU in a suitable solvent such as acetonitrile, methanol, toluene or DMF to yield triazolo-pyrimidine derivatives I. If the nucleophile is an alcohol, the reaction can be performed using a base such as sodium hydride in a solvent such as DMF preferentially at temperatures between 0° C. and 50° C. or by applying other conditions known to a person skilled in the art, to arrive at ethers I.

These derivatives can be the final compounds, however preferably when $R^1$-A=substituted benzyl group such as p-methoxy benzyl, these groups can be cleaved with TFA, CAN, hydrogenation and the like to access derivatives I ($R^1$-A=H). $R^1$-A=benzyl represents a suitable alternative protecting group. It avoids the use of PMB-Cl (for the preparation of the corresponding azide intermediate III) which is known to have some thermal stability issues (see for example *Organic Process Research & Development* 2005, 9, 1009-1012) and varying quality depending on the supplier. The benzyl group can be cleaved under standard hydrogenolysis conditions also for example in the presence of acids. When HCl is used, the derivatives I ($R^1$-A=H) can potentially be isolated as salts.

The triazole derivatives I ($R^1$-A=H) is conveniently reacted either with a halide (or sulfonate) in the presence of suitable base such as DIEA, DBU, $K_2CO_3$, or $Cs_2CO_3$ in a solvent such as DMF, dioxane or toluene, or alternatively with an alcohol under Mitsunobu reaction conditions using suitable diazodicarboxylate (DEAD, DIAD and the like) and phosphine such as $PBu_3$ or $PPh_3$ in an appropriate solvent such as THF, DCM, toluene to afford final triazolo-pyrimidine derivatives I.

The invention also relates to a process for the preparation of a compound of formula (I) comprising one of the following reaction:

(a) the reaction of a compound of formula (A), a tautomer thereof or a mixture of tautomers thereof, in particular as defined above

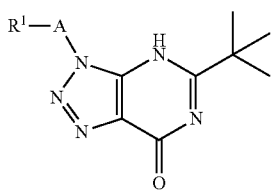

(A)

in the presence of a halogenation reagent and optionally with a base; or (b) the reaction of a compound of formula (B)

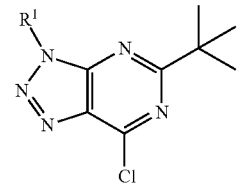

(B)

in the presence of $NHR^3R^4$ and optionally with a base; wherein A, $R^1$, $R^3$ and $R^4$ are as defined above.

In step (a), the base is for example N,N-diethyl aniline, lutidine or pyridine. Halogenation reagents are well known to those skilled in the art. Particular halogenation reagents are chlorination reagents. Examples of halogenation reagent are $POCl_3$, $SOCl_2$, $(COCl)_2$ or Vilsmeier reagent. $POCl_3$ and the Vilsmeier reagent are particular halogenation reagents useful in the process of the invention.

In step (b), the base is for example triethylamine, DIEA or DBU.

In step (b), a solvent can be used, which can be selected for example from acetonitrile, methanol, toluene and DMF.

A compound of formula (I) when manufactured according to a process of the invention is also an object of the invention.

The invention further relates to a compound of formula (I) for use as therapeutically active substance.

The invention further relates to a pharmaceutical composition comprising a compound of formula (I) and a therapeutically inert carrier.

The use of a compound of formula (I) for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors is another object of the invention.

The use of a compound of formula (I) for the preparation of a medicament for the treatment or prophylaxis of chronic pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors is a further object of the invention.

The invention also relates to a compound of formula (I) for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors.

The use of 3-[(2-chlorophenyl)methyl]-5-(1,1-dimethylethyl)-7-(4-morpholinyl)-3H-1,2,3-triazolo[4,5-d]pyrimidine or N-cyclopropyl-5-(1,1-dimethylethyl)-3-(phenylmethyl)-3H-1,2,3-triazolo[4,5-d]pyrimidin-7-amine, in particular 3-[(2-chlorophenyl)methyl]-5-(1,1-dimethylethyl)-7-(4-morpholinyl)-3H-1,2,3-triazolo[4,5-d]pyrimidine, for the preparation of a medicament for the treatment or prophylaxis of chronic pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors is a further object of the invention.

The invention also relates to 3-[(2-chlorophenyl)methyl]-5-(1,1-dimethylethyl)-7-(4-morpholinyl)-3H-1,2,3-triazolo[4,5-d]pyrimidine or N-cyclopropyl-5-(1,1-dimethylethyl)-3-(phenylmethyl)-3H-1,2,3-triazolo[4,5-d]pyrimidin-7-amine, in particular 3-[(2-chlorophenyl)methyl]-5-(1,1-dimethylethyl)-7-(4-morpholinyl)-3H-1,2,3-triazolo[4,5-d]pyrimidine for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors.

Another embodiment of the present invention is the use of a compound of formula (I) for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

Another embodiment of the present invention is the use of a compound according of formula (I) for the preparation of a medicament for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

Another embodiment of the present invention is the compound of formula (I) for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

Another embodiment of the present invention is a method for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention is further directed to a compound of formula (I), when manufactured according to a process according to the invention.

A method for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors, which method comprises administering an effective amount of a compound of formula (I) to a patient in need thereof is also an object of the invention.

Another embodiment of the invention provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Abbreviations

MS=mass spectrometry; CAN=ceric ammonium nitrate; Ac=acetyl; DIEA=N,N-diisopropylethylamine; DBU=1,8-Diazabicyclo[5.4.0]undec-7-ene; DMF=dimethylformamide; HPLC=LC=high performance liquid chromatography; THF=tetrahydrofurane; TFA=trifluoroacetic acid; Ph=phenyl; DCM=dichloromethane. BnN3=benzyl azide; CSTR=continuous stirred tank reactor.

Chiral separation of 1-(3-Benzyl-5-tert-butyl-3H-[1,2,3]triazolo[4,5-d]pyrimidin-7-yl)-3-methyl-pyrrolidin-3-ol (example 221, step a) yielded the respective enantiopure R and S derivatives. However, the unequivocal stereochemical assignment is pending. Therefore, the stereochemical assignment for enantiopure examples 221-230 has not been made.

Example 1

5-tert-Butyl-3-(2-chloro-benzyl)-7-morpholin-4-yl-3H-[1,2,3]triazolo[4,5-d]pyrimidine

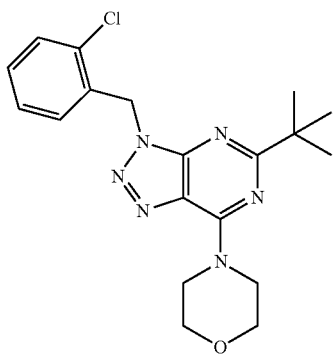

a) 5-Amino-1-(2-chlorobenzyl)-1H-1,2,3-triazole-4-carboxamide

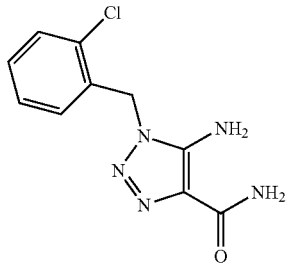 [SMILES: NC(=O)c1nnn(Cc2ccccc2Cl)c1N]

A mixture of 1-(bromomethyl)-2-chlorobenzene (5 g, 24.3 mmol) and sodium azide (2.37 g, 36.5 mmol) in acetonitrile (48.7 mL) was refluxed for 3 h under $N_2$ atmosphere. Then, the mixture was filtered and concentrated in vacuo. The residue was diluted in DCM, washed with $H_2O$ and brine, dried over $Na_2SO_4$ and concentrated in vacuo to afford crude 1-(azidomethyl)-2-chlorobenzene. The residue was used for the next reaction without further purification. A mixture of the above crude residue, 2-cyanoacetamide (1.82 g, 21.7 mmol) and sodium ethanolate (1.47 g, 21.7 mmol) in ethanol (43.3 mL) was refluxed for 3 h under $N_2$ atmosphere. The mixture was concentrated in vacuo, diluted with 4M AcOH aq. and filtered. The residue was washed with $H_2O$ and dried in vacuo to afford 5-amino-1-(2-chlorobenzyl)-1H-1,2,3-triazole-4-carboxamide as pale-orange solid (5.10 g, 94% for 2 steps). MS(m/e): 252.1 ($MH^+$).

b) 5-tert-Butyl-3-(2-chlorobenzyl)-3H-[1,2,3]triazolo[4,5-d]pyrimidin-7(4H)-one

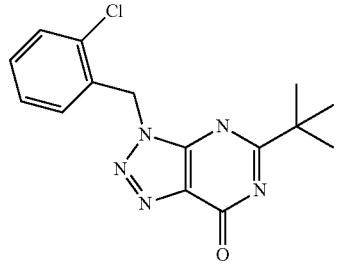 [SMILES: CC(C)(C)c1nc(=O)c2nnn(Cc3ccccc3Cl)c2[nH]1]

A mixture of 5-amino-1-(2-chlorobenzyl)-1H-1,2,3-triazole-4-carboxamide (2 g, 7.95 mmol) and pivaloyl chloride (1.47 mL, 11.9 mmol) in pyridine (3.98 mL) was stirred at 80° C. for 2 h under $N_2$ atmosphere. Then, to the reaction mixture was added 8M sodium hydroxide aq. (2.98 mL, 23.8 mmol) and methanol (3.98 mL). After being stirred at 80° C. for 2 h, the reaction mixture was poured into 1M HCl aq., extracted with diethyl ether, washed with 2M HCl, water and brine, dried over $Na_2SO_4$ and concentrated in vacuo to afford the mixture of crude 1-(2-chlorobenzyl)-5-pivalamido-1H-1,2,3-triazole-4-carboxamide and N-(1-(2-chlorobenzyl)-4-cyano-1H-1,2,3-triazol-5-yl)pivalamide. The residue was used for the next reaction without further purification.

A mixture of the above crude residue and $KHCO_3$ (3.00 g, 30.0 mmol) in $H_2O$ (60.0 mL) was refluxed for 18 h. The reaction mixture was poured into 1M HCl aq., extracted with EtOAc, washed with brine, dried over $Na_2SO_4$ and concentrated in vacuo. The crude residue was purified by flash chromatography (silica gel, 10% to 70% EtOAc in heptane) to afford 5-tert-butyl-3-(2-chlorobenzyl)-3H-[1,2,3]triazolo[4,5-d]pyrimidin-7(4H)-one as white solid (1.03 g, 41% for 2 steps). MS(m/e): 318.2 ($MH^+$).

c) 5-tert-Butyl-3-(2-chloro-benzyl)-7-morpholin-4-yl-3H-[1,2,3]triazolo[4,5-d]pyrimidine A mixture of 5-tert-butyl-3-(2-chlorobenzyl)-3H-[1,2,3]triazolo[4,5-d]pyrimidin-7(4H)-one (12.3 mg, 38.7 µmol) and N,N-diethylaniline (12.3 µL, 77.4 µmol) in POCl$_3$ (250 µL, 2.73 mmol) was refluxed for 3 h under N$_2$ atmosphere. The reaction mixture was concentrated in vacuo, diluted with EtOAc, washed with cold H$_2$O and brine, dried over Na$_2$SO$_4$ and concentrated in vacuo to afford crude 5-tert-butyl-7-chloro-3-(2-chlorobenzyl)-3H-[1,2,3]triazolo[4,5-d]pyrimidine. The residue was used for the next reaction without further purification.

A mixture of the above crude residue, morpholine (6.77 µL, 77.4 µmol) and DIEA (13.5 µL, 77.4 µmol) in acetonitrile (200 µL) was stirred at the room temperature overnight. The reaction mixture was directly purified by preparative HPLC (column: Gemini 5 um C18 110A 75×30 mm. mobile phase: water (0.05% Et$_3$N): acetonitrile 50:50% to 5:95%. WL: 254 nm Flow: 30 mL/min.) to afford the title compound as light-yellow solid (5.8 mg, 39% for 2 steps). MS(m/e): 387.3 (MH$^+$).

Example 2

5-tert-Butyl-3-(2-chloro-benzyl)-7-piperidin-1-yl-3H-[1,2,3]triazolo[4,5-d]pyrimidine

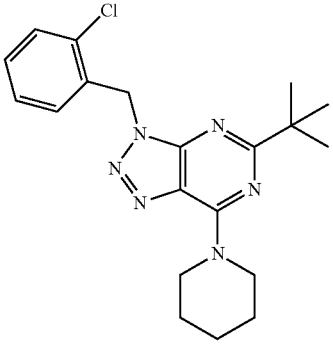 [SMILES: CC(C)(C)c1nc(N2CCCCC2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and piperidine and isolated as light-yellow solid (10.0 mg, 55%). MS(m/e): 385.4 (MH$^+$).

Example 3

5-tert-Butyl-3-(2-chloro-benzyl)-7-(4,4-difluoro-piperidin-1-yl)-3H-[1,2,3]triazolo[4,5-d]pyrimidine

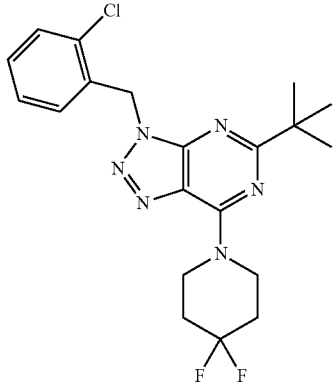 [SMILES: CC(C)(C)c1nc(N2CCC(F)(F)CC2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 4,4-difluoropiperidine hydrochloride and isolated as light-yellow gum (10.9 mg, 55%). MS(m/e): 421.4 (MH$^+$).

Example 4

5-tert-Butyl-3-(2-chloro-benzyl)-7-(4-methyl-piperazin-1-yl)-3H-[1,2,3]triazolo[4,5-d]pyrimidine

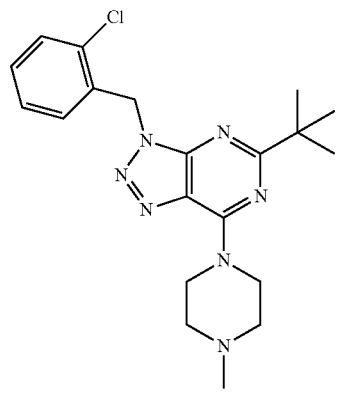 [SMILES: CN1CCN(c2nc(C(C)(C)C)nc3c2nnn3Cc2ccccc2Cl)CC1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 1-methylpiperazine and isolated as light-yellow solid (13.4 mg, 71%). MS(m/e): 400.4 (MH$^+$).

Example 5

5-tert-Butyl-3-(2-chloro-benzyl)-7-pyrrolidin-1-yl-3H-[1,2,3]triazolo[4,5-d]pyrimidine

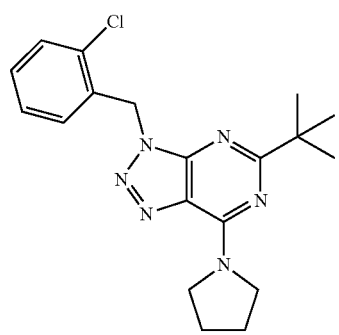 [SMILES: CC(C)(C)c1nc(N2CCCC2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and pyrrolidine and isolated as white solid (12.4 mg, 71%). MS(m/e): 371.4 (MH⁺).

Example 6

5-tert-Butyl-3-(2-chloro-benzyl)-7-(3,3-difluoro-pyrrolidin-1-yl)-3H-[1,2,3]triazolo[4,5-d]pyrimidine

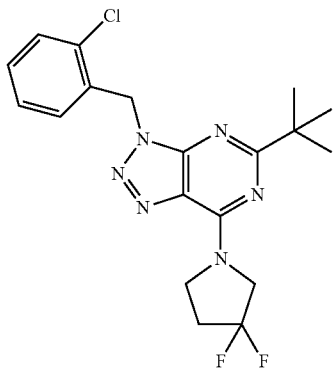 [SMILES: CC(C)(C)c1nc(N2CCC(F)(F)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3,3-difluoropyrrolidine hydrochloride and isolated as colorless gum (13.3 mg, 69%). MS(m/e): 407.4 (MH⁺).

Example 7

[5-tert-Butyl-3-(2-chloro-benzyl)-3H-[1,2,3]triazolo[4,5-d]pyrimidin-7-yl]-ethyl-amine

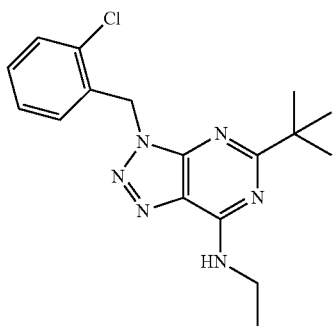 [SMILES: CCNc1nc(C(C)(C)C)nc2c1nnn2Cc1ccccc1Cl]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and ethanamine hydrochloride and isolated as white solid (1.1 mg, 7%). MS(m/e): 345.3 (MH⁺).

Example 8

[5-tert-Butyl-3-(2-chloro-benzyl)-3H-[1,2,3]triazolo[4,5-d]pyrimidin-7-yl]-cyclohexyl-amine

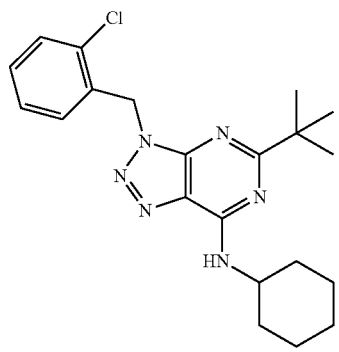 [SMILES: CC(C)(C)c1nc(NC2CCCCC2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and cyclohexane-amine and isolated as light-yellow solid (3.8 mg, 20%). MS(m/e): 399.4 (MH⁺).

Example 9

[5-tert-Butyl-3-(2-chloro-benzyl)-3H-[1,2,3]triazolo[4,5-d]pyrimidin-7-yl]-diethyl-amine

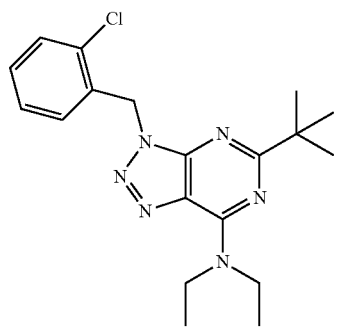 [SMILES: CCN(CC)c1nc(C(C)(C)C)nc2c1nnn2Cc1ccccc1Cl]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and diethylamine and isolated as colorless gum (11.5 mg, 65%). MS(m/e): 373.4 (MH⁺).

Example 10

5-tert-Butyl-3-(2-chloro-benzyl)-7-(2-oxa-6-aza-spiro[3.3]hept-6-yl)-3H-[1,2,3]triazolo[4,5-d]pyrimidine

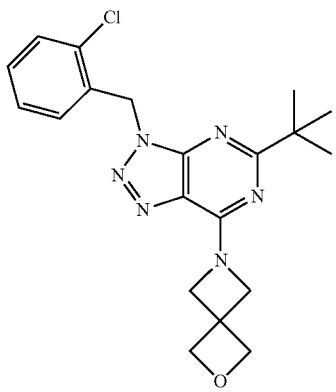 [SMILES: CC(C)(C)c1nc(N2CC3(COC3)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 2-oxa-6-azaspiro[3.3]heptane oxalate and isolated as white solid (10.8 mg, 57%). MS(m/e): 399.4 (MH⁺).

Example 11

7-Azetidin-1-yl-5-tert-butyl-3-(2-chloro-benzyl)-3H-[1,2,3]triazolo[4,5-d]pyrimidine

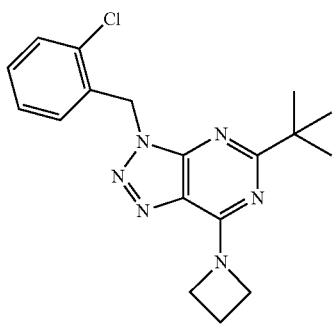 [SMILES: CC(C)(C)c1nc(N2CCC2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and azetidine and isolated as white solid (9.8 mg, 52%). MS(m/e): 357.3 (MH⁺).

Example 12

5-tert-Butyl-3-(2-chloro-benzyl)-7-(3,3-difluoro-azetidin-1-yl)-3H-[1,2,3]triazolo[4,5-d]pyrimidine

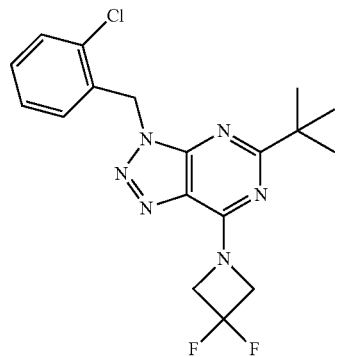 [SMILES: CC(C)(C)c1nc(N2CC(F)(F)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3,3-difluoroazetidine hydrochloride and isolated as light-yellow gum (11.9 mg, 64%). MS(m/e): 393.4 (MH⁺).

Example 13

1-[5-tert-Butyl-3-(2-chloro-benzyl)-3H-[1,2,3]triazolo[4,5-d]pyrimidin-7-yl]-3-methyl-azetidin-3-ol

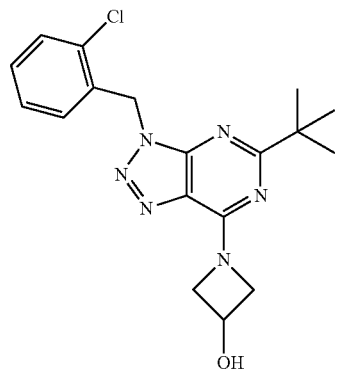 [SMILES: CC(C)(C)c1nc(N2CC(O)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and azetidin- 3-ol hydrochloride and isolated as light-yellow solid (8.0 mg, 46%). MS(m/e): 373.4 (MH⁺).

Example 14

1-[5-tert-Butyl-3-(2-chloro-benzyl)-3H-[1,2,3]triazolo[4,5-d]pyrimidin-7-yl]-3-methyl-azetidin-3-ol

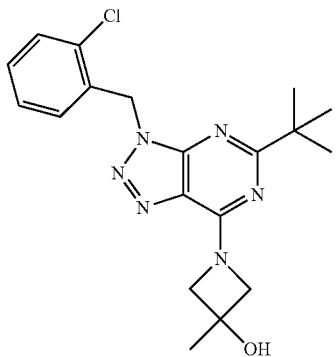 [SMILES: CC1(O)CN(c2nc(C(C)(C)C)nc3c2nnn3Cc2ccccc2Cl)C1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and azetidin-3-ol hydrochloride and isolated as white solid (10.3 mg, 56%). MS(m/e): 387.4 (MH⁺).

Example 15

5-tert-Butyl-3-(2-chloro-benzyl)-7-(3-methoxy-azetidin-1-yl)-3H-[1,2,3]triazolo[4,5-d]pyrimidine

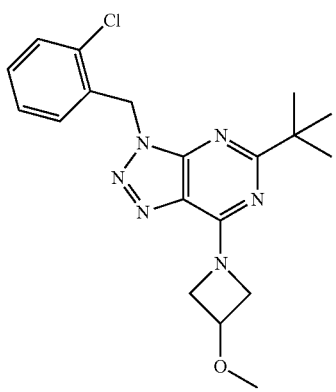 [SMILES: COC1CN(c2nc(C(C)(C)C)nc3c2nnn3Cc2ccccc2Cl)C1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3-methoxyazetidine hydrochloride and isolated as white solid (11.0 mg, 60%). MS(m/e): 387.4 (MH⁺).

Example 16

5-tert-Butyl-3-(2-chloro-benzyl)-7-((2R,6S)-2,6-dimethyl-morpholin-4-yl)-3H-[1,2,3]triazolo[4,5-d]pyrimidine

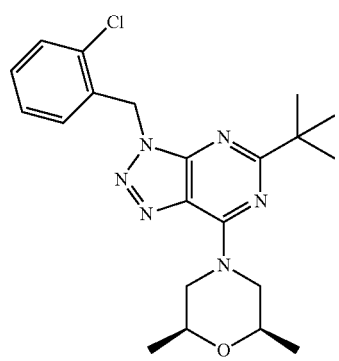 [SMILES: C[C@@H]1CN(c2nc(C(C)(C)C)nc3c2nnn3Cc2ccccc2Cl)C[C@H](C)O1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (2S,6R)-2,6-dimethylmorpholine and isolated as white solid (13.1 mg, 67%). MS(m/e): 415.5 (MH⁺).

Example 17

5-tert-Butyl-3-(2-chloro-benzyl)-7-(3-methyl-morpholin-4-yl)-3H-[1,2,3]triazolo[4,5-d]pyrimidine

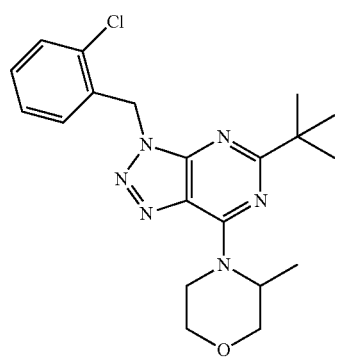 [SMILES: CC1COCCN1c1nc(C(C)(C)C)nc2c1nnn2Cc1ccccc1Cl]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3-methylmorpholine and isolated as light-yellow gum (12.7 mg, 67%). MS(m/e): 401.5 (MH⁺).

Example 18

{4-[5-tert-Butyl-3-(2-chloro-benzyl)-3H-[1,2,3]triazolo[4,5-d]pyrimidin-7-yl]-morpholin-2-yl}-methanol

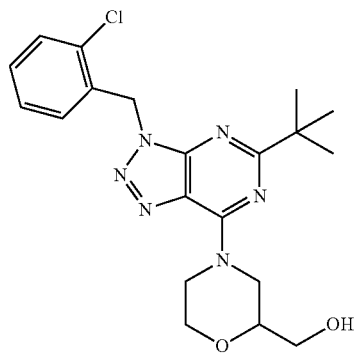 [SMILES: CC(C)(C)c1nc(N2CCOC(CO)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and morpholin-2-ylmethanol and isolated as light-yellow gum (11.8 mg, 60%). MS(m/e): 417.5 (MH⁺).

Example 19

5-tert-Butyl-3-(2-chloro-benzyl)-7-thiazolidin-3-yl-3H-[1,2,3]triazolo[4,5-d]pyrimidine

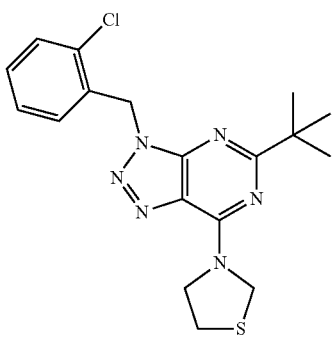 [SMILES: CC(C)(C)c1nc(N2CCSC2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and thiazolidine and isolated as light-yellow gum (10.6 mg, 58%). MS(m/e): 389.4 (MH⁺).

Example 20

5-tert-Butyl-3-(2-chloro-benzyl)-7-thiomorpholin-4-yl-3H-[1,2,3]triazolo[4,5-d]pyrimidine

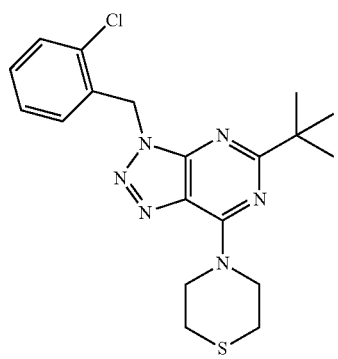 [SMILES: CC(C)(C)c1nc(N2CCSCC2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and thiomorpholine and isolated as light-yellow gum (10.2 mg, 54%). MS(m/e): 403.4 (MH⁺).

Example 21

5-tert-Butyl-3-(2-chloro-benzyl)-7-(1,1-dioxo-1λ6-thiomorpholin-4-yl)-3H-[1,2,3]triazolo[4,5-d]pyrimidine

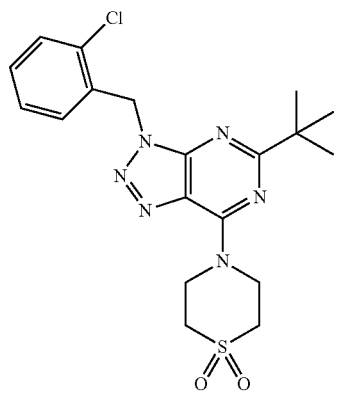 [SMILES: CC(C)(C)c1nc(N2CCS(=O)(=O)CC2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and thiomorpholine 1,1-dioxide and isolated as white solid (13.5 mg, 66%). MS(m/e): 435.4 (MH⁺).

Example 22

5-tert-Butyl-3-(2-chloro-benzyl)-7-[1,4]oxazepan-4-yl-3H-[1,2,3]triazolo[4,5-d]pyrimidine

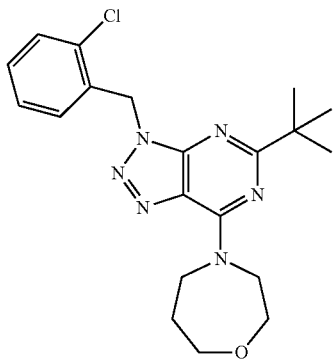 [SMILES: CC(C)(C)c1nc(N2CCCOCC2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 1,4-oxazepane hydrochloride and isolated as white gum (12.0 mg, 63%). MS(m/e): 401.5 (MH⁺).

Example 23

5-tert-Butyl-3-(2-chloro-benzyl)-7-(2,2-dimethyl-morpholin-4-yl)-3H-[1,2,3]triazolo[4,5-d]pyrimidine

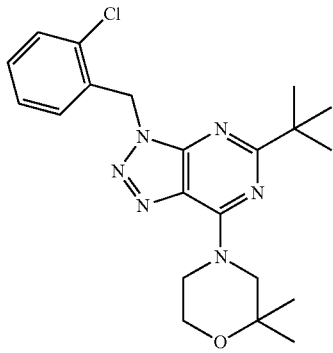 [SMILES: CC1(C)CN(c2nc(C(C)(C)C)nc3c2nnn3Cc2ccccc2Cl)CCO1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 2,2-dimethylmorpholine and isolated as colorless gum (13.7 mg, 70%). MS(m/e): 415.4 (MH⁺).

Example 24

5-tert-Butyl-3-(2-chloro-benzyl)-7-(3,3-dimethyl-morpholin-4-yl)-3H-[1,2,3]triazolo[4,5-d]pyrimidine

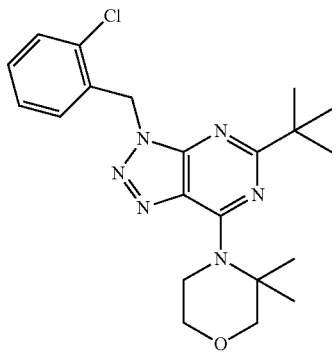 [SMILES: CC(C)(C)c1nc(N2CCOCC2(C)C)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3,3-dimethylmorpholine and isolated as colorless gum (12.5 mg, 64%). MS(m/e): 415.4 (MH⁺).

Example 25

5-tert-Butyl-3-(2-chloro-benzyl)-7-((2R,5R)-2,5-dimethyl-pyrrolidin-1-yl)-3H-[1,2,3]triazolo[4,5-d]pyrimidine

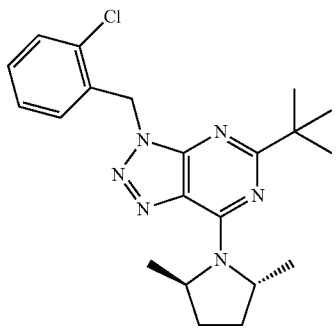 [SMILES: C[C@@H]1CC[C@@H](C)N1c1nc(C(C)(C)C)nc2c1nnn2Cc1ccccc1Cl]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (2R,5R)-

2,5-dimethylpyrrolidine and isolated as colorless gum (11.2 mg, 60%). MS(m/e): 399.4 (MH⁺).

Example 26

(S)-1-[5-tert-Butyl-3-(2-chloro-benzyl)-3H-[1,2,3]triazolo[4,5-d]pyrimidin-7-yl]-pyrrolidin-3-ol

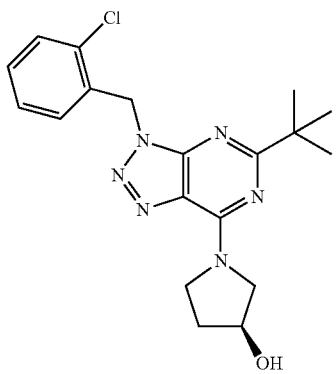 [SMILES: CC(C)(C)c1nc(N2CC[C@H](O)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (S)-pyrrolidin-3-ol and isolated as colorless gum (12.5 mg, 69%). MS(m/e): 387.3 (MH⁺).

Alternative Conditions

Step 1: 5-amino-1-[(2-chlorophenyl)methyl]triazole-4-carboxamide

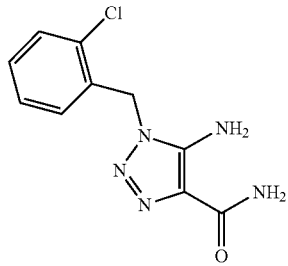 [SMILES: NC(=O)c1nnn(Cc2ccccc2Cl)c1N]

Sodium azide (3.36 g, 51.1 mmol, Eq: 1.05) was charged in the reactor followed by DMSO (35.2 g, 32.0 ml) and Hunig's base (642 mg, 868 µl, 4.87 mmol, Eq: 0.1). The suspension was stirred for 10 Min. at 25° C. Then 1-chloro-2-(chloromethyl)benzene (8 g, 6.29 ml, 48.7 mmol, Eq: 1.00) was added dropwise over 60 min. (Tr=25° C.) and stirred at 25° C. until reaction completion (<2 h). The resulting white suspension was treated with water (1.6 g, 1.6 ml) and stirred for 45 Min. at R.T. The suspension was filtered and the filter cake was washed with DMSO (17.6 g, 16.0 ml) to give a colorless solution of 1-(azidomethyl)-2-chloro-benzene solution.

In a separate reactor, DMSO (17.6 g, 16.0 ml) was charged followed by 32% aqueous NaOH (6.09 g, 4.51 ml, 48.7 mmol, Eq: 1.0) and water (5.00 g, 5.00 ml). A solution consisting of 2-cyanoacetamide (6.2 g, 73.0 mmol, Eq: 1.50) and DMSO (17.6 g, 16.0 ml) was added dropwise over 15 min. at 25° C.

The previously prepared azide solution was added dropwise at 25° C. within 4 h. After an additional 15 h reaction, water (120 g, 120 ml) was added dropwise over 10 min (exothermic). The resulting suspension was cooled to 0° C. After 1 h30 at 0° C. the suspension was filtered. The filter cake was washed with water (40.0 g, 40.0 ml) and dried under reduced pressure 50° C./5 mbar until constant weight to give 10.87 g of the title compound as a white powder. MS(m/e): 251.9 (MH+).

Step 2: 5-tert-butyl-3-[(2-chlorophenyl)methyl]-4H-triazolo[4,5-d]pyrimidin-7-one

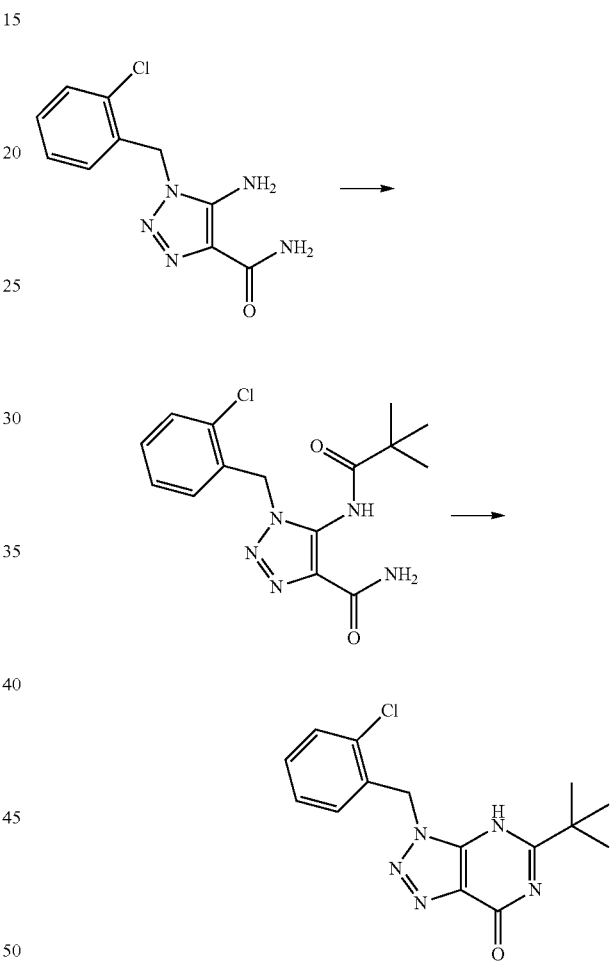

5-amino-1-(2-chlorobenzyl)-1H-1,2,3-triazole-4-carboxamide (10.80 g, 42.9 mmol, Eq: 1.00) was suspended in N,N-dimethylacetamide (50.2 g, 54.0 ml). Pyridine (5.1 g, 5.19 ml, 64.4 mmol, Eq: 1.5) was added followed by pivaloyl chloride (7.84 g, 8.00 ml, 64.4 mmol, Eq: 1.5) and the reaction mixture was heated to ca 80° C. After 3 h reaction (and complete conversion of the starting material to the intermediate), KHCO₃ (21.6 g, 215 mmol, Eq: 5.00) was added and the suspension was heated to Tj=155° C. for 24 h to convert the 1-[(2-chlorophenyl)methyl]-5-(2,2-dimethylpropanoylamino)triazole-4-carboxamide intermediate to the product. The reaction mixture was cooled to RT and water (254 g, 254 ml) was added dropwise over 30 min. The brown suspension was cooled to 0° C., stirred for 1 h30 min and was filtered. The filter cake was washed with water (43.2 g, 43.2 ml) and dried at 500° C./5 mbar to give 11 g of the title compound as an off-white powder. MS(m/e): 318.0 (MH+).

Step 3: 5-tert-butyl-7-chloro-3-[(2-chlorophenyl) methyl]triazolo[4,5-d]pyrimidine

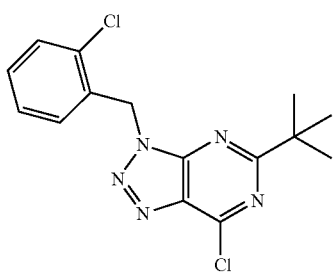 [SMILES: CC(C)(C)c1nc(Cl)c2nnn(Cc3ccccc3Cl)c2n1]

DMF (10.1 g, 10.7 ml, 139 mmol, Eq: 4.14) and dichlormethane (113 g, 85.6 ml) were charged in the reactor and the solution was heated to 35° C. Oxalylchloride (8.66 g, 5.86 ml, 66.9 mmol, Eq: 2) was added over 1 h at 35° C. After 45 min at 35° C., a light turbid solution of 5-tert-butyl-3-(2-chlorobenzyl)-3H-[1,2,3]triazolo[4,5-d]pyrimidin-7(4H)-one (10.7 g, 33.4 mmol, Eq: 1.00) in Dichlormethane (32 ml) and DMF (2 ml) was added over 15 min at 35° C.

After 4 h at 35° C., the reaction mixture was cooled to RT and was slowly added onto cold (0-5° C.) half saturated aqueous NaHCO₃ (160 ml). The organic phase was separated and washed with water (119 g, 119 ml) and half saturated aqueous NaCl (119 ml). The organic phase was dried over MgSO4, rotavaped and dried at 50° C./10 mbar to give 10.89 g of the title compound as an oil which solidifies on standing to provide a light yellow solid. MS(m/e): 335.9 (MH+).

Step 4 (3S)-1-[5-tert-butyl-3-[(2-chlorophenyl)methyl]triazolo[4,5-d]pyrimidin-7-yl]pyrrolidin-3-ol 5-tert-butyl-7-chloro-3-(2-chlorobenzyl)-3H-[1,2,3]triazolo[4,5-d]pyrimidine (10 g, 29.7 mmol, Eq: 1.00) was dissolved in Acetonitrile (54.6 g, 70.0 ml). N-Ethyldiisopropylamin (7.84 g, 10.3 ml, 59.5 mmol, Eq: 2) was added dropwise over 5-10 min. After 10 min at RT, a solution of (S)-pyrrolidin-3-ol (2.94 g, 2.8 ml, 32.7 mmol, Eq: 1.1) in Acetonitrile (2.27 g, 2.91 ml) added dropwise over 30 min at 20° C. After 2 h30 reaction, toluene (86.5 g, 100 ml) was added and the reaction mixture was concentrated under reduced pressure to remove most of the acetonitrile. A 10% aqueous citric acid solution (100 ml) was added. The aqueous phase was separated and extracted with toluene (86.5 g, 100 ml). The organic phases were washed sequentially with half saturated aqueous NaHCO3 (50 ml) and half saturated aqueous NaCl (50 ml). The organic phases were combined dried over MgSO4 and rotavaped at 45° C./10 mbar. The crude product was taken up in ethanol (150 ml) and concentrated under reduced pressure. This was repeated twice in order to remove toluene and gave 11.1 g of the crude title compound as a light yellow solid/foam.

The product can be crystallized, for example, from toluene/heptane or acetone/water. Crystallization from Toluene/n-Heptane 1.0 g of the crude product was dissolved at room temperature in 4 ml of Toluene. Then 8 ml of n-Heptane was added in one portion. The clear, light yellow solution was seeded (the seed crystals were obtained from a test tube crystallization in Toluene/n-heptane). The crystallization started slowly. After 1 h at R.T., the white suspension was filtered. The filter cake was washed with n-Heptane and dried under reduced pressure (5-10 mbar) at 50° C. overnight then at 80° C. for 8 h to give 0.9 g of the title compound.

Crystallization from Acetone/Water 5.5 g of the crude product was dissolved at room temperature in 30 ml of Acetone. Then 13.6 ml of water was added in one portion. The clear, light yellow solution was seeded (the seed crystals were obtained from a test tube crystallization in acetone/water). The crystallization started slowly. After stirring overnight at RT, the white suspension was cooled down to 0° C., stirred for 2 h at 0° C. and filtered. The filter cake was washed with cold acetone/water 1:1 and dried at 80° C. under reduced pressure to give 4.9 g of the title compound.

Example 27

(R)-1-[5-tert-Butyl-3-(2-chloro-benzyl)-3H-[1,2,3] triazolo[4,5-d]pyrimidin-7-yl]-pyrrolidin-3-ol

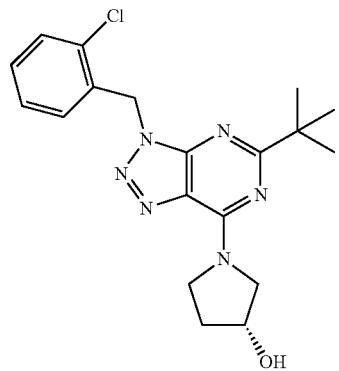 [SMILES: CC(C)(C)c1nc(N2CC[C@@H](O)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2, 3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (R)-pyrrolidin-3-ol and isolated as colorless gum (11.6 mg, 64%). MS(m/e): 387.3 (MH⁺).

Example 28

5-tert-Butyl-3-(2-chloro-benzyl)-7-(3-methoxy-pyrrolidin-1-yl)-3H-[1,2,3]triazolo[4,5-d]pyrimidine

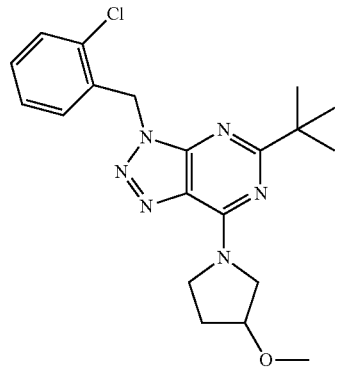 [SMILES: COC1CCN(c2nc(C(C)(C)C)nc3c2nnn3Cc2ccccc2Cl)C1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3-methoxypyrrolidine hydrochloride and isolated as colorless gum (13.2 mg, 70%), MS(m/e): 401.4 (MH$^+$).

Example 29

5-tert-Butyl-3-(2-chloro-benzyl)-7-(2,2-dimethyl-pyrrolidin-1-yl)-3H-[1,2,3]triazolo[4,5-d]pyrimidine

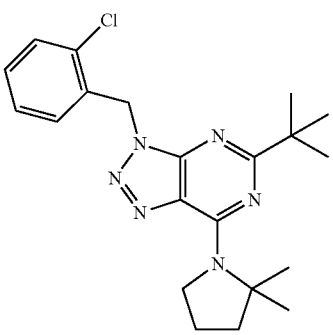 [SMILES: CC(C)(C)c1nc(N2CCCC2(C)C)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 2-methylpyrrolidine and isolated as white solid (13.2 mg, 70%). MS(m/e): 399.4 (MH$^+$).

Example 30

5-tert-Butyl-3-(2-chloro-benzyl)-7-(2-methyl-pyrrolidin-1-yl)-3H-[1,2,3]triazolo[4,5-d]pyrimidine

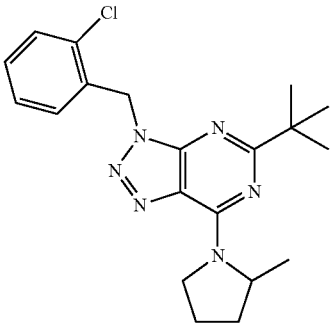 [SMILES: CC1CCCN1c1nc(C(C)(C)C)nc2c1nnn2Cc1ccccc1Cl]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 2-methylpyrrolidine and isolated as white solid (13.0 mg, 70%). MS(m/e): 385.4 (MH$^+$).

Example 31

5-tert-Butyl-3-(2-chloro-benzyl)-7-(2-oxa-6-aza-spiro[3.4]oct-6-yl)-3H-[1,2,3]triazolo[4,5-d]pyrimidine

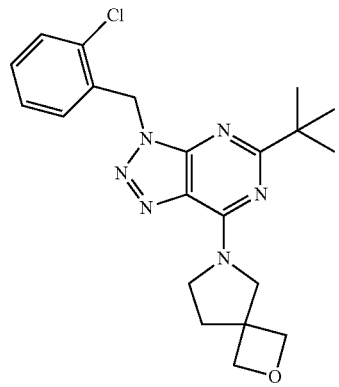 [SMILES: CC(C)(C)c1nc(N2CCC3(COC3)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 2-oxa-6-azaspiro[3.4]octane oxalate and isolated as colorless gum (2.6 mg, 13%). MS(m/e): 413.4 (MH$^+$).

Example 32

1-[5-tert-Butyl-3-(2-chloro-benzyl)-3H-[1,2,3]triazolo[4,5-d]pyrimidin-7-yl]-piperidin-4-ol

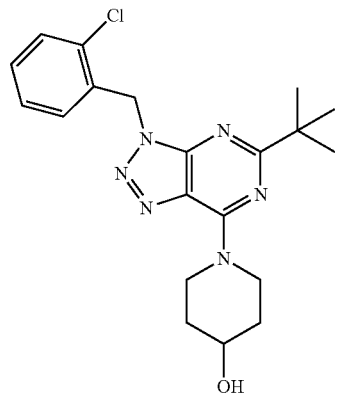 [SMILES: CC(C)(C)c1nc(N2CCC(O)CC2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and piperidin-4-ol and isolated as light-yellow gum (12.6 mg, 67%). MS(m/e): 401.4 (MH⁺).

Example 33

(S)-1-[5-tert-Butyl-3-(2-chloro-benzyl)-3H-[1,2,3]triazolo[4,5-d]pyrimidin-7-yl]-piperidin-3-ol

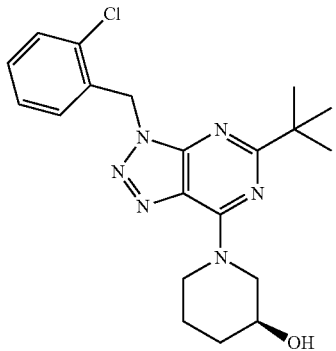 [SMILES: CC(C)(C)c1nc(N2CCC[C@H](O)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (S)-piperidin-3-ol hydrochloride and isolated as light-yellow gum (13.3 mg, 70%). MS(m/e): 401.4 (MH⁺).

Example 34

(R)-1-[5-tert-Butyl-3-(2-chloro-benzyl)-3H-[1,2,3]triazolo[4,5-d]pyrimidin-7-yl]-piperidin-3-ol

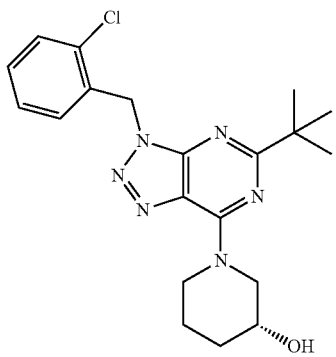 [SMILES: CC(C)(C)c1nc(N2CCC[C@@H](O)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (R)-piperidin-3-ol hydrochloride and isolated as colorless gum (8.3 mg, 44%). MS(m/e): 401.4 (MH⁺).

Example 35

5-tert-Butyl-3-(2-chloro-benzyl)-7-(6-oxa-1-azaspiro[3.3]hept-1-yl)-3H-[1,2,3]triazolo[4,5-d]pyrimidine

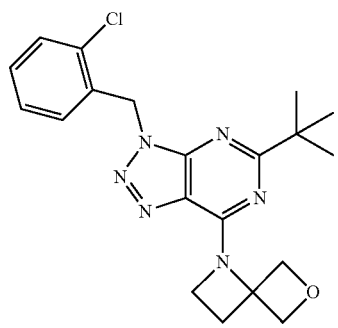 [SMILES: CC(C)(C)c1nc(N2CCC23COC3)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 6-oxa-1-azaspiro[3.3]heptane oxalate and isolated as light-yellow gum (12.5 mg, 65%). MS(m/e): 399.4 (MH⁺).

Example 36

5-tert-Butyl-3-(2-chloro-benzyl)-7-((S)-3-fluoro-pyrrolidin-1-yl)-3H-[1,2,3]triazolo[4,5-d]pyrimidine

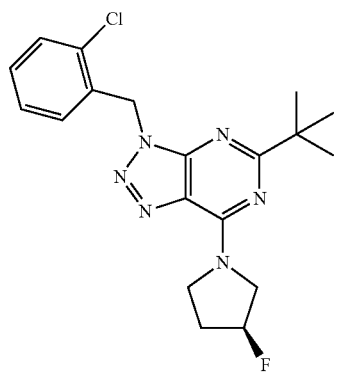 [SMILES: CC(C)(C)c1nc(N2CC[C@H](F)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (S)-3- fluoropyrrolidine hydrochloride and isolated as light-yellow solid (16.5 mg, 90%). MS(m/e): 389.4 (MH⁺).

Example 37

{(R)-1-[5-tert-Butyl-3-(2-chloro-benzyl)-3H-[1,2,3]triazolo[4,5-d]pyrimidin-7-yl]-pyrrolidin-2-yl}-methanol

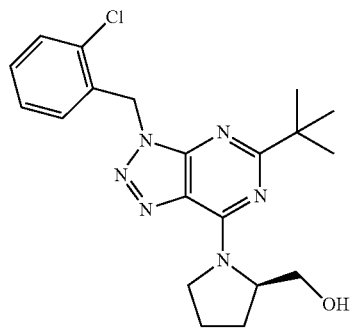 [SMILES: CC(C)(C)c1nc(N2CCC[C@@H]2CO)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (R)-pyrrolidin-2-ylmethanol and isolated as light-yellow gum (14.2 mg, 75%). MS(m/e): 401.4 (MH⁺).

Example 38

{(S)-1-[5-tert-Butyl-3-(2-chloro-benzyl)-3H-[1,2,3]triazlo[4,5-d]pyrimidin-7-yl]-pyrrolidin-2-yl}-methanol

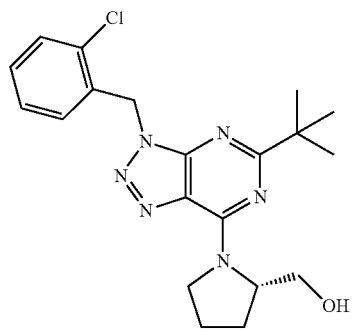 [SMILES: CC(C)(C)c1nc(N2CCC[C@H]2CO)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (S)-pyrrolidin-2-ylmethanol and isolated as light-yellow gum (14.6 mg, 77%). MS(m/e): 401.4 (MH⁺).

Example 39

5-tert-Butyl-3-(2-chloro-benzyl)-7-[1,2]oxazinan-2-yl-3H-[1,2,3]triazolo[4,5-d]pyrimidine

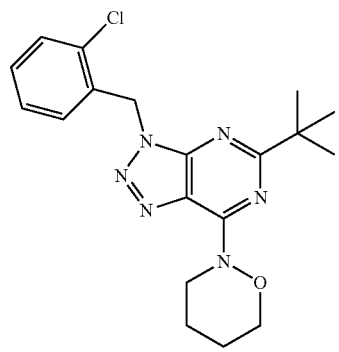 [SMILES: CC(C)(C)c1nc(N2CCCCO2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and [1,2]oxazinane and isolated as light-yellow gum (13.6 mg, 75%). MS(m/c): 387.4 (MH⁺).

Example 40

5-tert-Butyl-3-(2-chloro-benzyl)-7-isoxazolidin-2-yl-3H-[1,2,3]triazolo[4,5-d]pyrimidine

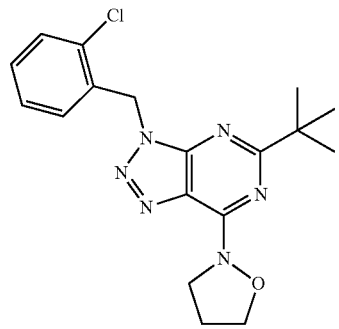

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and isoxazolidine hydrochloride and isolated as white solid (13.1 mg, 74%). MS(m/e): 373.4 (MH+).

Example 41

7-Aziridin-1-yl-5-tert-butyl-3-(2-chloro-benzyl)-3H-[1,2,3]triazolo[4,5-d]pyrimidine

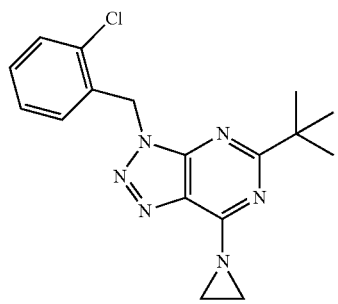 [SMILES: CC(C)(C)c1nc(N2CC2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and aziridine and isolated as white solid (4.9 mg, 30%). MS(m/e): 343.3 (MH+).

Example 42

5-tert-Butyl-3-(2-chloro-benzyl)-7-((R)-3-fluoro-pyrrolidin-1-yl)-3H-[1,2,3]triazolo[4,5-d]pyrimidine

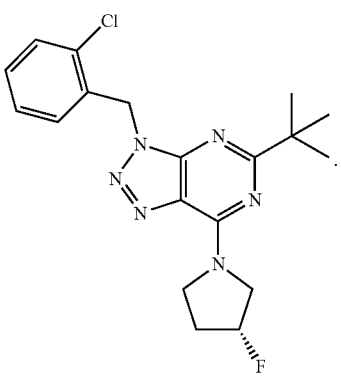 [SMILES: CC(C)(C)c1nc(N2CC[C@@H](F)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (R)-3- fluoropyrrolidine hydrochloride and isolated as light-yellow gum (9.8 mg, 54%). MS(m/e): 389.4 (MH+).

Example 43

5-tert-Butyl-3-(2-chloro-benzyl)-7-(3,3,4,4-tetrafluoro-pyrrolidin-1-yl)-3H-[1,2,3]triazolo[4,5-d]pyrimidine

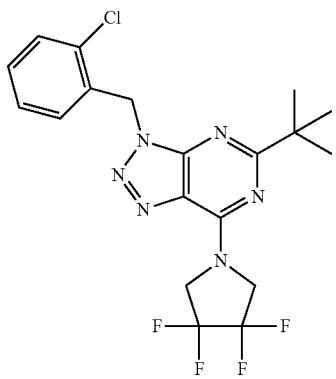 [SMILES: CC(C)(C)c1nc(N2CC(F)(F)C(F)(F)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3,3,4,4-tetrafluoropyrrolidine hydrochloride and isolated as light-yellow gum (12.6 mg, 60%). MS(m/e): 443.4 (MH+).

Example 44

5-tert-Butyl-3-(2-chloro-benzyl)-7-((R)-2-methoxymethyl-pyrrolidin-1-yl)-3H-[1,2,3]triazolo[4,5-d]pyrimidine

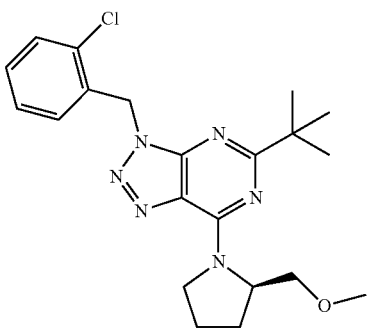 [SMILES: COC[C@H]1CCCN1c1nc(C(C)(C)C)nc2c1nnn2Cc1ccccc1Cl]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (R)-2-

(methoxymethyl)pyrrolidine and isolated as colorless gum (12.4 mg, 64%). MS(m/e): 415.4 (MH+).

Example 45

5-tert-Butyl-3-(2-chloro-benzyl)-7-((S)-2-methoxymethyl-pyrrolidin-1-yl)-3H-[1,2,3]triazolo[4,5-d]pyrimidine

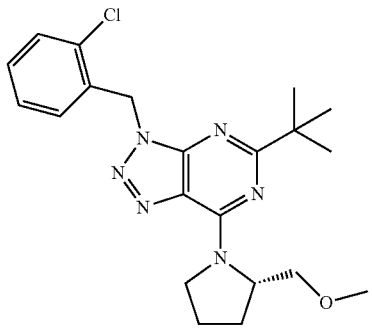 [SMILES: COC[C@@H]1CCCN1c1nc(C(C)(C)C)nc2c1nnn2Cc1ccccc1Cl]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (S)-2-(methoxymethyl)pyrrolidine and isolated as light-yellow gum (12.0 mg, 61%). MS(m/e): 415.4 (MH+).

Example 46

(2S,4S)-1-[5-tert-Butyl-3-(2-chloro-benzyl)-3H-[1,2,3]triazolo[4,5-d]pyrimidin-7-yl]-4-fluoro-pyrrolidine-2-carbonitrile

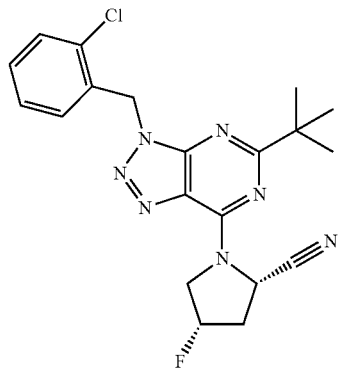 [SMILES: CC(C)(C)c1nc(N2C[C@@H](F)C[C@H]2C#N)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (2S,4S)-4-fluoropyrrolidine-2-carbonitrile and isolated as light-yellow gum (10.6 mg, 54%). MS(m/e): 414.4 (MH+).

Example 47

5-tert-Butyl-3-(2-chloro-benzyl)-7-(1,1-dioxo-1λ6-isothiazolidin-2-yl)-3H-[1,2,3]triazolo[4,5-d]pyrimidine

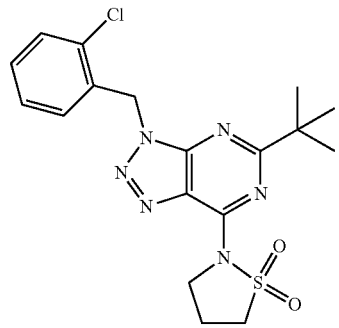 [SMILES: CC(C)(C)c1nc(N2CCCS2(=O)=O)c2nnn(Cc3ccccc3Cl)c2n1]

A mixture of 5-tert-butyl-7-chloro-3-(2-chlorobenzyl)-3H-[1,2,3]triazolo[4,5-d]pyrimidine (15.9 mg, 47.2 µmol), 1,1-dioxo-isothiazolidine (11.4 mg, 94.4 µmol) and DBU (14.2 µL, 94.4 mmol) in DMF (250 µL) was stirred at the room temperature overnight. The reaction mixture was directly purified by preparative HPLC (column: Gemini 5 um C18 110A 75×30 mm. mobile phase: water (0.05% Et$_3$N): acetonitrile 75:25% to 5:95%. WL: 230 nm Flow: 30 mL/min.) to afford the title compound as white solid (3.10 mg, 16%). MS(m/e): 387.3 (MH+).

Example 48

{4-[5-tert-Butyl-3-(2-chloro-benzyl)-3H-[1,2,3]triazolo[4,5-d]pyrimidin-7-yl]-morpholin-3-yl}-methanol

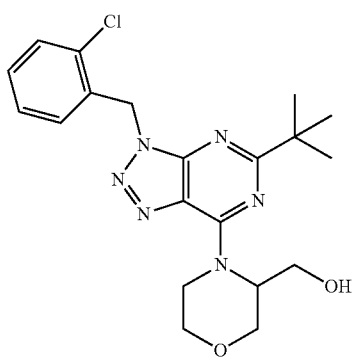 [SMILES: CC(C)(C)c1nc(N2CCOCC2CO)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and morpholin-3-ylmethanol and isolated as light-yellow gum (13.3 mg, 68%). MS(m/e): 417.4 (MH+).

Example 49

(R)-1-[5-tert-Butyl-3-(2-chloro-benzyl)-3H-[1,2,3]triazolo[4,5-d]pyrimidin-7-yl]-pyrrolidine-2-carbonitrile

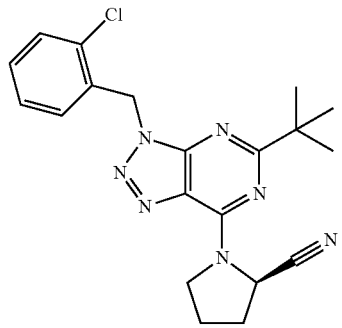 [SMILES: CC(C)(C)c1nc(N2CCC[C@@H]2C#N)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (R)-pyrrolidine-2-carbonitrile hydrochloride and isolated as light-yellow solid (9.7 mg, 52%). MS(m/e): 396.4 (MH+).

Example 50

(S)-1-[5-tert-Butyl-3-(2-chloro-benzyl)-3H-[1,2,3]triazolo[4,5-d]pyrimidin-7-yl]-pyrrolidine-2-carbonitrile

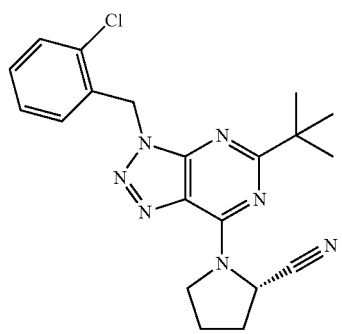 [SMILES: CC(C)(C)c1nc(N2CCC[C@H]2C#N)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (S)-pyrrolidine-2-carbonitrile hydrochloride and isolated as light-yellow solid (11.5 mg, 65%). MS(m/e): 396.4 (MH+).

Example 51

(2S,3S)-1-[5-tert-Butyl-3-(2-chloro-benzyl)-3H-[1,2,3]triazolo[4,5-d]pyrimidin-7-yl]-2-hydroxymethyl-pyrrolidin-3-ol

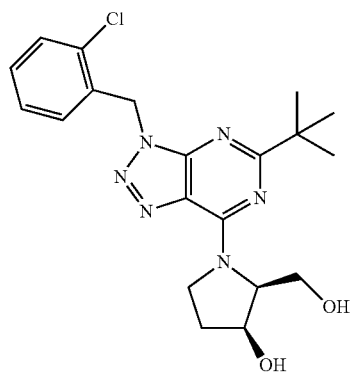 [SMILES: CC(C)(C)c1nc(N2CC[C@H](O)[C@@H]2CO)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (2S,3S)-2-(hydroxymethyl)pyrrolidin-3-ol and isolated as light-yellow gum (10.3 mg, 52%). MS(m/e): 417.4 (MH+).

Example 52

(2S,3R)-1-[5-tert-Butyl-3-(2-chloro-benzyl)-3H-[1,2,3]triazolo[4,5-d]pyrimidin-7-yl]-2-hydroxymethyl-pyrrolidin-3-ol

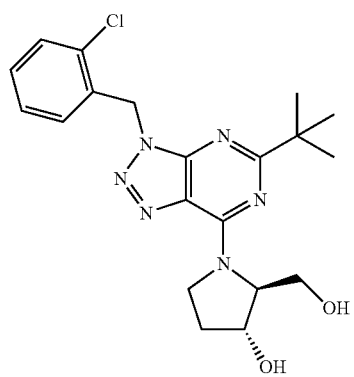 [SMILES: CC(C)(C)c1nc(N2CC[C@@H](O)[C@@H]2CO)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (2S,3R)-

2-(hydroxymethyl)pyrrolidin-3-ol and isolated as light-yellow gum (9.6 mg, 49%). MS(m/e): 417.4 (MH⁺).

Example 53

5-tert-Butyl-3-(2-chloro-benzyl)-7-(2-oxa-5-aza-spiro[3.4]oct-5-yl)-3H-[1,2,3]triazolo[4,5-d]pyrimidine

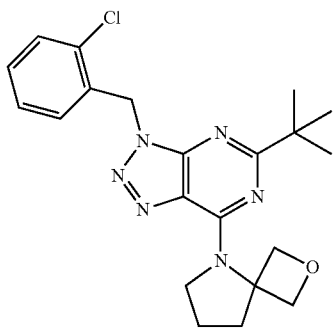 [SMILES: CC(C)(C)c1nc(N2CCCC23COC3)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 2-oxa-5-azaspiro[3.4]octane oxalate and isolated as white solid (8.4 mg, 43%). MS(m/e): 413.4 (MH⁺).

Example 54

1-[5-tert-Butyl-3-(2-chloro-benzyl)-3H-[1,2,3]triazolo[4,5-d]pyrimidin-7-yl]-3-methyl-pyrrolidin-3-ol

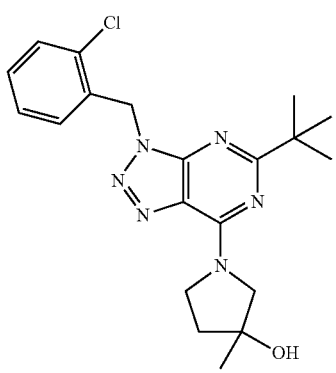 [SMILES: CC1(O)CCN(c2nc(C(C)(C)C)nc3c2nnn3Cc2ccccc2Cl)C1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3-methylpyrrolidin-3-ol hydrochloride and isolated as white solid (14.1 mg, 75%). MS(m/e): 401.4 (MH⁺).

Example 55

1-[5-tert-Butyl-3-(2-chloro-benzyl)-3H-[1,2,3]triazolo[4,5-d]pyrimidin-7-yl]-pyrrolidine-3,4-trans-diol

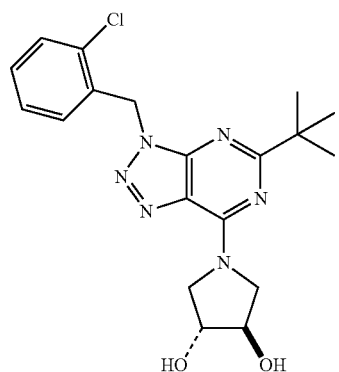 [SMILES: CC(C)(C)c1nc(N2C[C@@H](O)[C@H](O)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and pyrrolidine-3,4-trans-diol and isolated as white solid (9.1 mg, 48%). MS(m/e): 403.4 (MH⁺).

Example 56

(3S,4R)-1-[5-tert-Butyl-3-(2-chloro-benzyl)-3H-[1,2,3]triazolo[4,5-d]pyrimidin-7-yl]-pyrrolidine-3,4-diol

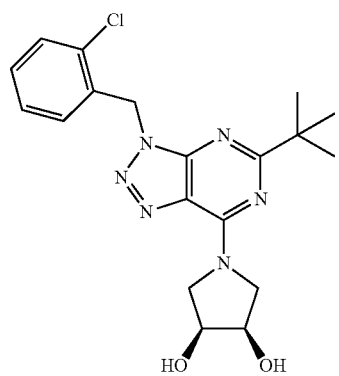 [SMILES: CC(C)(C)c1nc(N2C[C@@H](O)[C@@H](O)C2)c2nnn(Cc3ccccc3Cl)c2n1]

In analogy to the procedure described for the synthesis of 5-tert-butyl-3-(2-chloro-benzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (3R,4S)-pyrrolidine-3,4-diol and isolated as light-yellow gum (10.3 mg, 54%). MS(m/e): 403.4 (MH⁺).

Example 57

5-tert-Butyl-3-(4-methoxy-benzyl)-7-morpholin-4-yl-3H-[1,2,3]triazolo[4,5-d]pyrimidine

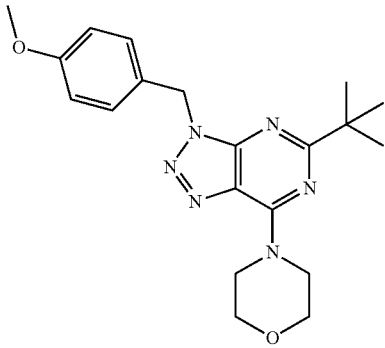 [SMILES: COc1ccc(Cn2nnc3c(N4CCOCC4)nc(C(C)(C)C)nc32)cc1]

a) 5-Amino-1-(4-methoxybenzyl)-1H-1,2,3-triazole-4-carboxamide

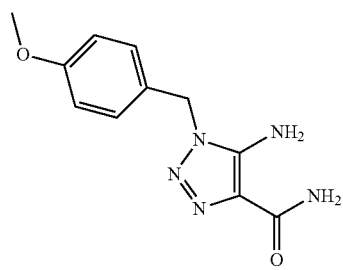 [SMILES: COc1ccc(Cn2nnc(C(N)=O)c2N)cc1]

A mixture of 1-(chloromethyl)-4-methoxybenzene (20 g, 128 mmol) and sodium azide (12.5 g, 192 mmol) in acetonitrile (255 mL) was refluxed for 5 h under $N_2$ atmosphere. The mixture was filtered and concentrated in vacuo. The residue was diluted with DCM, washed with $H_2O$ and brine, dried over $Na_2SO_4$ and concentrated in vacuo to afford crude 1-(azidomethyl)-4-methoxybenzene. The residue was used for the next reaction without further purification.

A mixture of the above crude residue, 2-cyanoacetamide (10.8 g, 128 mmol) and sodium ethanolate (8.71 g, 128 mmol) in ethanol (256 mL) was refluxed for 21 h under $N_2$ atmosphere. The mixture was concentrated in vacuo, diluted with 4M AcOH aq. and filtered. The residue was washed with $H_2O$ and dried in vacuo to afford 5-amino-1-(4-methoxybenzyl)-1H-1,2,3-triazole-4-carboxamide as pale-orange solid (26.5 g, 84% for 2 steps). MS(m/e): 248.1 (MH+).

b) 5-tert-Butyl-3-(4-methoxybenzyl)-3H-[1,2,3]triazolo[4,5-d]pyrimidin-7(4H)-one

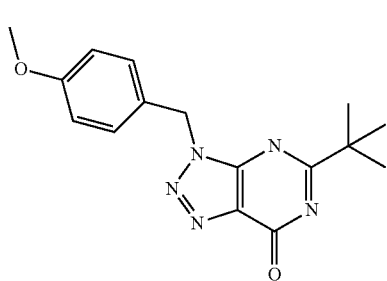 [SMILES: COc1ccc(Cn2nnc3c(=O)nc(C(C)(C)C)[nH]c32)cc1]

A mixture of 5-amino-1-(4-methoxybenzyl)-1H-1,2,3-triazole-4-carboxamide (10.0 g, 40.4 mmol) and pivaloyl chloride (7.47 mL, 60.7 mmol) in pyridine (20.2 mL) was stirred at 80° C. for 2 h under $N_2$ atmosphere. Then, to the reaction mixture was added 8 M sodium hydroxide aq. (15.2 mL, 121 mmol) and methanol (20.2 mL). After being stirred at 80° C. for 1 h, the reaction mixture was poured into 1M HCl aq., extracted with diethyl ether, washed with 2M HCl aq., water and brine, dried over $Na_2SO_4$ and concentrated in vacuo to afford the mixture of crude 1-(4-methoxybenzyl)-5-pivalamido-1H-1,2,3-triazole-4-carboxamide and N-(4-cyano-1-(4-methoxybenzyl)-1H-1,2,3-triazol-5-yl)pivalamide. The residue was used for the next reaction without further purification.

A mixture of the above crude residue and $KHCO_3$ (12.1 g, 121 mmol) in $H_2O$ (242 mL) was refluxed for 18 h. The reaction mixture was poured into 1M HCl aq., extracted with EtOAc, washed with brine, dried over $Na_2SO_4$ and concentrated in vacuo. The crude residue was purified by flash chromatography (silica gel, 10% to 70% EtOAc in heptane) to afford 5-tert-butyl-3-(4-methoxybenzyl)-3H-[1,2,3]triazolo[4,5-d]pyrimidin-7(4H)-one (4.44 g, 35% for 2 steps). MS(m/e): 314.2 (MH+).

c) 4-(5-tert-Butyl-3-(4-methoxybenzyl)-3H-[1,2,3]triazolo[4,5-d]pyrimidin-7-yl)morpholine A mixture of 5-tert-butyl-3-(4-methoxybenzyl)-3H-[1,2,3]triazolo[4,5-d]pyrimidin-7(4H)-one (50.0 mg, 160 μmol) and N,N-diethylaniline (50.8 μL, 319 μmol) in $POCl_3$ (1000 μL, 10.9 mmol) was refluxed for 4 h under $N_2$ atmosphere. The reaction mixture was concentrated in vacuo, diluted with EtOAc, washed with cold $H_2O$ and brine, dried over $Na_2SO_4$ and concentrated in vacuo to afford crude 5-tert-butyl-7-chloro-3-(4-methoxybenzyl)-3H-[1,2,3]triazolo[4,5-d]pyrimidine. The residue was used for the next reaction without further purification.

A mixture of the above crude residue, morpholine (28.0 μL, 320 mol) and DIEA (55.9 μL, 320 μmol) in acetonitrile (250 μL) was stirred at the room temperature overnight. The reaction mixture was directly purified by preparative HPLC (column: Gemini 5 um C18 110A 75×30 mm. mobile phase: water (0.05% $Et_3N$): acetonitrile 45:55% to 5:95%. WL: 280 nm Flow: 30 mL/min.) to afford the title compound as white solid (47.7 mg, 78% for 2 steps). MS(m/e): 383.4 (MH+).

Example 58

5-tert-Butyl-7-morpholin-4-yl-3H-[1,2,3]triazolo[4,5-d]pyrimidine

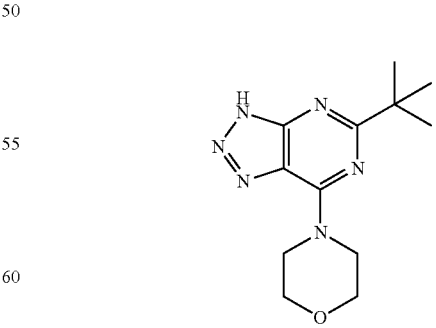

A mixture of 4-(5-tert-butyl-3-(4-methoxybenzyl)-3H-[1,2,3]triazolo[4,5-d]pyrimidin-7-yl)morpholine (10.0 mg, 26.1 μmol) and TFA (250 μL) was refluxed for 5 h under $N_2$ atmosphere. Then, the reaction mixture was concentrated in vacuo and purified by preparative HPLC (column: Gemini 5 um C18 110A 75×30 mm. mobile phase: water (0.05% Et₃N): acetonitrile 85:15% to 5:95%. WL: 300 nm Flow: 30 mL/min.) to afford the title compound as white solid (0.9 mg, 13%). MS(m/c): 263.3 (MH⁺).

Example 59

5-tert-Butyl-3-(2-chloro-4-fluoro-benzyl)-7-morpholin-4-yl-3H-[1,2,3]triazolo[4,5-d]pyrimidine

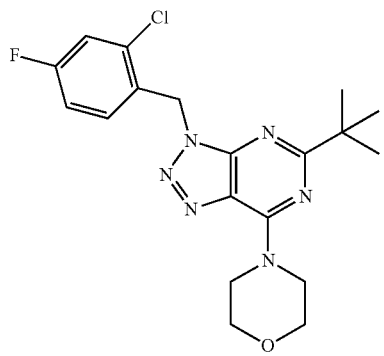 [SMILES: CC(C)(C)c1nc(N2CCOCC2)c2nnn(Cc3ccc(F)cc3Cl)c2n1]

A mixture of 4-(5-tert-butyl-3-(4-methoxybenzyl)-3H-[1,2,3]triazolo[4,5-d]pyrimidin-7-yl)morpholine (49.0 mg, 128 μmol) and TFA (1000 μL) was refluxed for 8 h under N₂ atmosphere. The reaction mixture was concentrated in vacuo to afford crude to 5-tert-butyl-7-morpholin-4-yl-3H-[1,2,3]triazolo[4,5-d]pyrimidine. The residue was used for the next reaction without further purification.

A mixture of the portion of above residue (42.0 μmol), and 1-(bromomethyl)-2-chloro-4-fluorobenzene (18.8 mg, 84.0 μmol) and DBU (12.7 μL, 84.0 μmol) in DMF (250 μL) was stirred at the room temperature overnight. The reaction mixture was directly purified by preparative HPLC (column: Gemini 5 um C18 110A 75×30 mm. mobile phase: water (0.05% Et₃N): acetonitrile 70:30% to 5:95%. WL: 300 nm Flow: 30 mL/min.) to afford the title compound as light-yellow solid (8.3 mg, 49%). MS(m/e): 405.4 (MH⁺).

Example 60

5-tert-Butyl-7-(3,3-difluoro-pyrrolidin-1-yl)-3-(4-methoxy-benzyl)-3H-[1,2,3]triazolo[4,5-d]pyrimidine

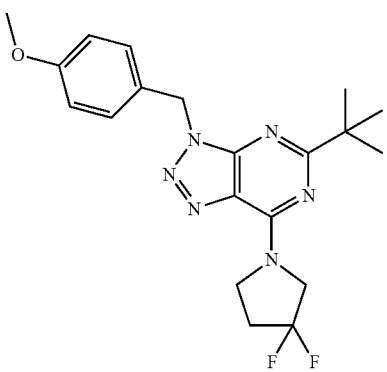 [SMILES: COc1ccc(Cn2nnc3c(N4CCC(F)(F)C4)nc(C(C)(C)C)nc32)cc1]

In analogy to the procedure described for the synthesis of 4-(5-tert-butyl-3-(4-methoxy benzyl)-3H-[1,2,3]triazolo[4,5-d]pyrimidin-7-yl)morpholine (example 58, step c), the title compound was prepared from 5-tert-butyl-7-chloro-3-(4-methoxybenzyl)-3H-[1,2,3]triazolo [4,5-d]pyrimidine and 3,3-difluoropyrrolidine hydrochloride and isolated as white solid (271 mg, 83%). MS(m/e): 403.4 (MH⁺).

Example 61

5-tert-Butyl-7-(3,3-difluoro-pyrrolidin-1-yl)-3-ethyl-3H-[1,2,3]triazolo[4,5-d]pyrimidine

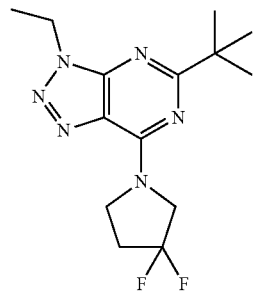 [SMILES: CCn1nnc2c(N3CCC(F)(F)C3)nc(C(C)(C)C)nc21]

A mixture of 5-tert-butyl-7-(3,3-difluoro-pyrrolidin-1-yl)-3-(4-methoxy-benzyl)-3H-[1,2,3]triazolo[4,5-d]pyrimidine (264 mg, 656 μmol) and TFA (5.0 mL) was refluxed for 8 h under N₂ atmosphere. The reaction mixture was concentrated in vacuo to afford crude to 5-tert-butyl-7-(3,3-difluoropyrrolidin-1-yl)-3H-[1,2,3]triazolo[4,5-d]pyrimidine. The residue was used for the next reaction without further purification.

A mixture of the portion of above residue (41.0 μmol), and iodoethane (6.63 μL, 82.0 μmol) and DBU (12.4 μL, 82.0 μmol) in DMF (250 μL) was stirred at the room temperature overnight. The reaction mixture was directly purified by preparative HPLC (column: Gemini 5 um C18 110A 75×30 mm. mobile phase: water (0.05% Et₃N): acetonitrile 60:40% to 5:95%. WL: 300 nm Flow: 30 mL/min.) to afford the title compound as light-yellow gum (0.6 mg, 4%). MS(m/e): 311.3 (MH⁺).

Example 62

5-tert-Butyl-7-(3,3-difluoro-pyrrolidin-1-yl)-3-(2-methoxy-ethyl)-3H-[1,2,3]triazolo[4,5-d]pyrimidine

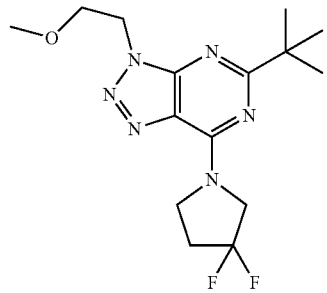 [SMILES: COCCn1nnc2c(N3CCC(F)(F)C3)nc(C(C)(C)C)nc21]

In analogy to the procedure described for the synthesis of 5-tert-butyl-7-(3,3-difluoro-pyrrolidin-1-yl)-3-ethyl-3H-[1, 2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-bromo-2-methoxyethane and isolated as light-yellow gum (2.5 mg, 18%). MS(m/e): 341.3 (MH⁺).

Example 63

2-[5-tert-Butyl-7-(3,3-difluoro-pyrrolidin-1-yl)-[1,2,3]triazolo[4,5-d]pyrimidin-3-yl]-ethanol

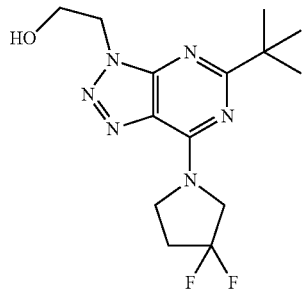 [SMILES: CC(C)(C)c1nc(N2CCC(F)(F)C2)c2nnn(CCO)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-bromoethanol and isolated as white solid (5.8 mg, 43%). MS(m/e): 327.3 (MH⁺).

Example 64

5-tert-Butyl-3-cyclohexylmethyl-7-(3,3-difluoro-pyrrolidin-1-yl)-3H-[1,2,3]triazolo[4,5-d]pyrimidine

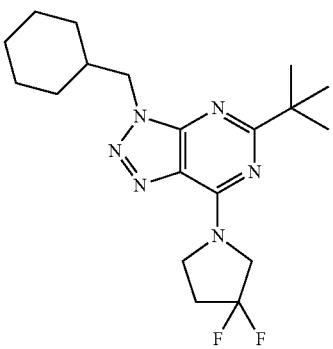 [SMILES: CC(C)(C)c1nc(N2CCC(F)(F)C2)c2nnn(CC3CCCCC3)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and (bromomethyl)cyclohexane and isolated as white solid (4.2 mg, 27%). MS(m/e): 379.5 (MH⁺).

Example 65

5-tert-Butyl-3-(3-chloro-benzyl)-7-(3,3-difluoro-pyrrolidin-1-yl)-3H-[1,2,3]triazolo[4,5-d]pyrimidine

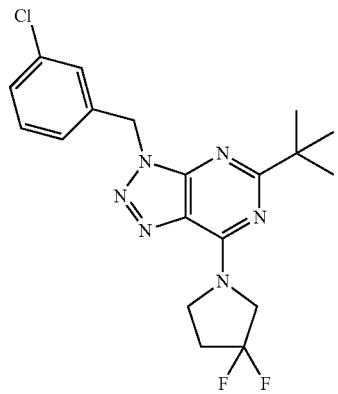 [SMILES: CC(C)(C)c1nc(N2CCC(F)(F)C2)c2nnn(Cc3cccc(Cl)c3)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(bromomethyl)-3-chlorobenzene and isolated as light-yellow gum (7.0 mg, 42%). MS(m/e): 407.4 (MH⁺).

Example 66

5-tert-Butyl-3-(4-chloro-benzyl)-7-(3,3-difluoro-pyrrolidin-1-yl)-3H-[1,2,3]triazolo[4,5-d]pyrimidine

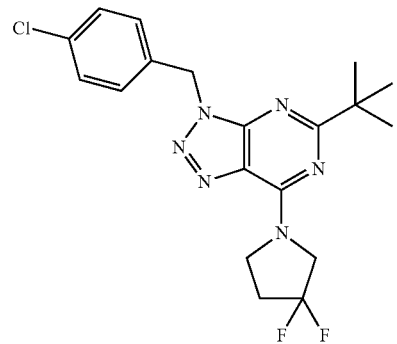 [SMILES: CC(C)(C)c1nc(N2CCC(F)(F)C2)c2nnn(Cc3ccc(Cl)cc3)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(bromomethyl)-4-chlorobenzene and isolated as white solid (5.8 mg, 35%). MS(m/e): 407.4 (MH+).

Example 67

5-tert-Butyl-3-(2,3-dichloro-benzyl)-7-(3,3-difluoro-pyrrolidin-1-yl)-3H-[1,2,3]triazolo[4,5-d]pyrimidine

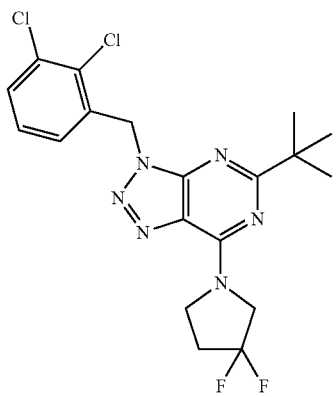 [SMILES: CC(C)(C)c1nc(N2CCC(F)(F)C2)c2nnn(Cc3cccc(Cl)c3Cl)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(bromomethyl)-2,3-dichlorobenzene and isolated as colorless gum (6.7 mg, 37%). MS(m/e): 441.3 (MH+).

Example 68

5-tert-Butyl-3-(2,4-dichloro-benzyl)-7-(3,3-difluoro-pyrrolidin-1-yl)-3H-[1,2,3]triazolo[4,5-d]pyrimidine

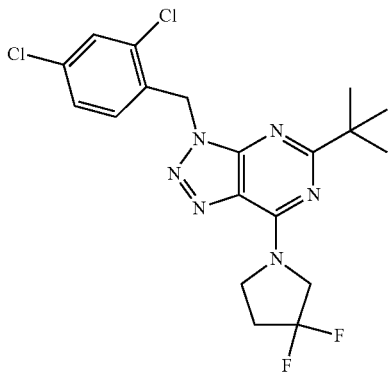 [SMILES: CC(C)(C)c1nc(N2CCC(F)(F)C2)c2nnn(Cc3ccc(Cl)cc3Cl)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(bromomethyl)-2,4-dichlorobenzene and isolated as colorless gum (6.5 mg, 36%). MS(m/e): 441.3 (MH+).

Example 69

5-tert-Butyl-3-(2,5-dichloro-benzyl)-7-(3,3-difluoro-pyrrolidin-1-yl)-3H-[1,2,3]triazolo[4,5-d]pyrimidine

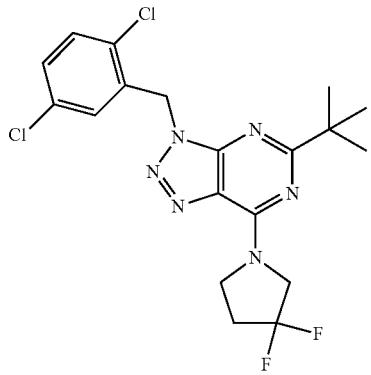 [SMILES: CC(C)(C)c1nc(N2CCC(F)(F)C2)c2nnn(Cc3cc(Cl)ccc3Cl)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(bromomethyl)-1,4-dichlorobenzene and isolated as white solid (6.6 mg, 37%). MS(m/e): 441.4 (MH+).

Example 70

5-tert-Butyl-3-(2,6-dichloro-benzyl)-7-(3,3-difluoro-pyrrolidin-1-yl)-3H-[1,2,3]triazolo[4,5-d]pyrimidine

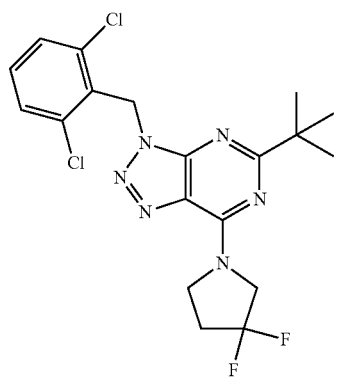 [SMILES: CC(C)(C)c1nc(N2CCC(F)(F)C2)c2nnn(Cc3c(Cl)cccc3Cl)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(bromomethyl)-1,3-dichlorobenzene and isolated as white solid (5.2 mg, 29%). MS(m/e): 441.3 (MH+).

Example 71

5-tert-Butyl-3-(2-chloro-4-fluoro-benzyl)-7-(3,3-difluoro-pyrrolidin-1-yl)-3H-[1,2,3]1 triazolo[4,5-d]pyrimidine

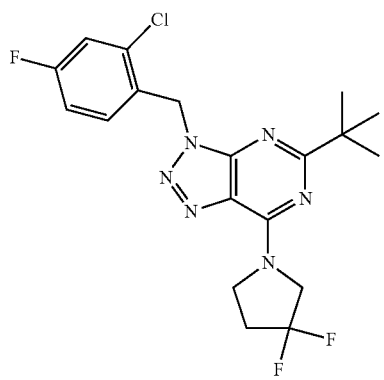 [SMILES: CC(C)(C)c1nc(N2CCC(F)(F)C2)c2nnn(Cc3ccc(F)cc3Cl)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(bromomethyl)-2-chloro-4-fluorobenzene and isolated as colorless gum (5.8 mg, 33%). MS(m/e): 425.4 (MH+).

Example 72

5-tert-Butyl-3-(2-chloro-6-fluoro-benzyl)-7-(3,3-difluoro-pyrrolidin-1-yl)-3H-[1,2,3]triazolo[4,5-d]pyrimidine

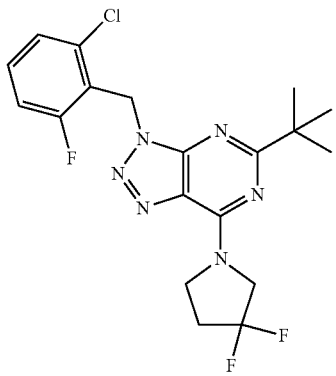 [SMILES: CC(C)(C)c1nc(N2CCC(F)(F)C2)c2nnn(Cc3c(F)cccc3Cl)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-chloro-2-(chloromethyl)-3-fluorobenzene and isolated as white solid (6.8 mg, 39%). MS(m/e): 425.4 (MH+).

Example 73

5-tert-Butyl-7-(3,3-difluoro-pyrrolidin-1-yl)-3-pyridin-2-ylmethyl-3H-[1,2,3]triazolo[4,5-d]pyrimidine

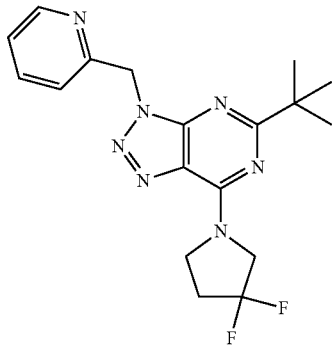 [SMILES: CC(C)(C)c1nc(N2CCC(F)(F)C2)c2nnn(Cc3ccccn3)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(bromomethyl)pyridine hydrobromide and isolated as light-yellow solid (4.2 mg, 27%). MS(m/e): 374.4 (MH+).

Example 74

5-tert-Butyl-7-(3,3-difluoro-pyrrolidin-1-yl)-3-pyridin-3-ylmethyl-3H-[1,2,3]triazol[4,5-d]pyrimidine

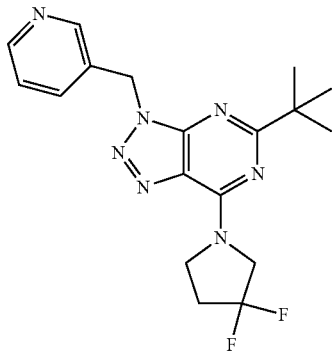 [SMILES: CC(C)(C)c1nc(N2CCC(F)(F)C2)c2nnn(Cc3cccnc3)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-(chloromethyl)pyridine hydrochloride and isolated as light-yellow gum (2.5 mg, 16%). MS(m/e): 374.4 (MH⁺).

Example 75

5-tert-Butyl-7-(3,3-difluoro-pyrrolidin-1-yl)-3-pyridin-4-ylmethyl-3H-[1,2,3]triazolo[4,5-d]pyrimidine

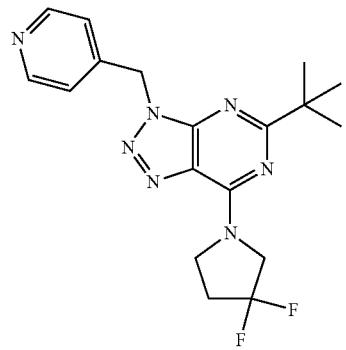 [SMILES: CC(C)(C)c1nc(N2CCC(F)(F)C2)c2nnn(Cc3ccncc3)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 4-(bromomethyl)pyridine hydrobromide and isolated as orange solid (5.4 mg, 35%). MS(m/e): 374.4 (MH⁺).

Example 76

5-tert-Butyl-7-(3,3-difluoro-pyrrolidin-1-yl)-3-(2,2,2-trifluoro-ethyl)-3H-[1,2,3]triazolo[4,5-d]pyrimidine

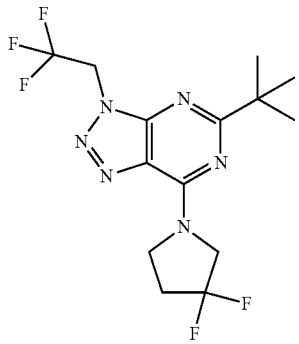 [SMILES: CC(C)(C)c1nc(N2CCC(F)(F)C2)c2nnn(CC(F)(F)F)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2,2,2-trifluoroethyl trifluoromethanesulfonate and isolated as light-yellow gum (0.9 mg, 6%). MS(m/e): 365.3 (MH⁺).

Example 77

5-tert-Butyl-3-(2-chloro-4,5-difluoro-benzyl)-7-(3,3-difluoro-pyrrolidin-1-yl)-3H-[1,2,3]triazolo[4,5-d]pyrimidine

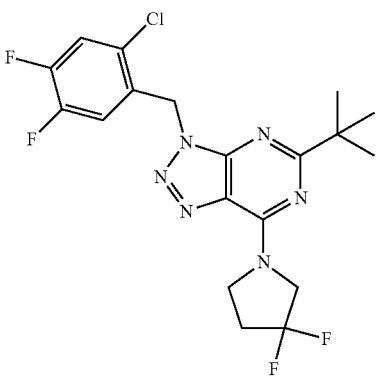 [SMILES: CC(C)(C)c1nc(N2CCC(F)(F)C2)c2nnn(Cc3cc(F)c(F)cc3Cl)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(bromomethyl)-2-chloro-4,5-difluorobenzene and isolated as colorless gum (8.3 mg, 45%). MS(m/e): 443.4 (MH⁺).

Example 78

5-tert-Butyl-3-(2-chloro-3,6-difluoro-benzyl)-7-(3,3-difluoro-pyrrolidin-1-yl)-3H-[1,2,3]triazolo[4,5-d]pyrimidine

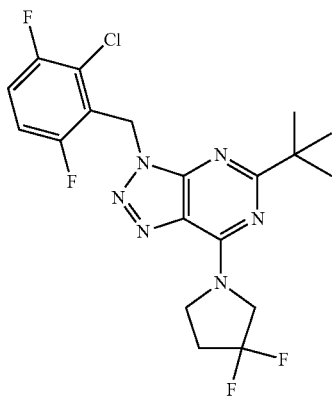 [SMILES: CC(C)(C)c1nc(N2CCC(F)(F)C2)c2nnn(Cc3c(F)ccc(F)c3Cl)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(bromomethyl)-3-chloro-1,4-difluorobenzene and isolated as white solid (8.0 mg, 44%). MS(m/e): 443.4 (MH+).

Example 79

3-(2-Bromo-benzyl)-5-tert-butyl-7-(3,3-difluoro-pyrrolidin-1-yl)-3H-[1,2,3]triazolo[4,5-d]pyrimidine

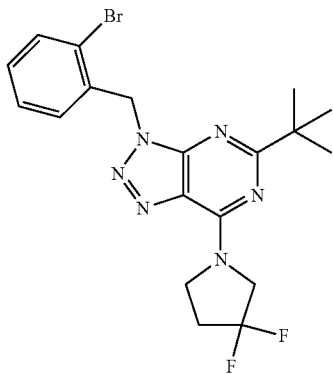 [SMILES: CC(C)(C)c1nc(N2CCC(F)(F)C2)c2nnn(Cc3ccccc3Br)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-bromo-2-(bromomethyl)benzene and isolated as colorless gum (6.6 mg, 35%). MS(m/e): 451.3 (MH+).

Example 80

5-tert-Butyl-7-(3,3-difluoro-pyrrolidin-1-yl)-3-(2-trifluoromethyl-benzyl)-3H-[1,2,3]triazolo[4,5-d]pyrimidine

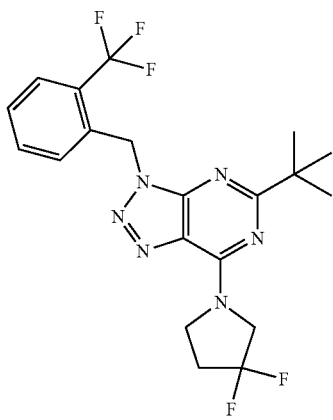 [SMILES: CC(C)(C)c1nc(N2CCC(F)(F)C2)c2nnn(Cc3ccccc3C(F)(F)F)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(bromomethyl)-2-(trifluoromethyl)benzene and isolated as light-yellow gum (7.8 mg, 43%). MS(m/e): 441.4 (MH+).

Example 81

5-tert-Butyl-7-(3,3-difluoro-pyrrolidin-1-yl)-3-(2-methoxy-benzyl)-3H-[1,2,3]triazolo[4,5-d]pyrimidine

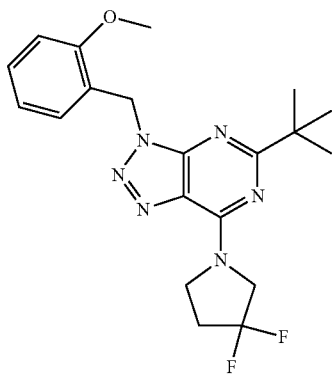 [SMILES: COc1ccccc1Cn1nnc2c(N3CCC(F)(F)C3)nc(C(C)(C)C)nc21]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(chloromethyl)-2-methoxybenzene and isolated as light-yellow gum (5.7 mg, 34%). MS(m/e): 403.4 (MH+).

Example 82

5-tert-Butyl-7-(3,3-difluoro-pyrrolidin-1-yl)-3-(2-trifluoromethoxy-benzyl)-3H-[1,2,3]triazolo[4,5-d]pyrimidine

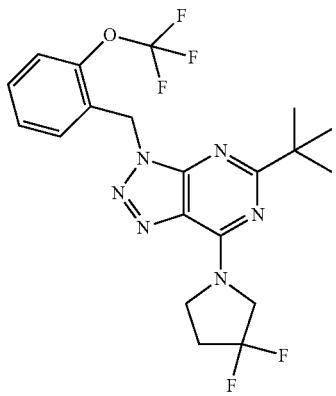 [SMILES: CC(C)(C)c1nc(N2CCC(F)(F)C2)c2nnn(Cc3ccccc3OC(F)(F)F)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(bromomethyl)-2-(trifluoromethoxy)benzene and isolated as light-yellow gum (7.3 mg, 39%). MS(m/e): 457.4 (MH⁺).

Example 83

2-[5-tert-Butyl-7-(3,3-difluoro-pyrrolidin-1-yl)-[1,2,3]triazolo[4,5-d]pyrimidin-3-ylmethyl]-benzonitrile

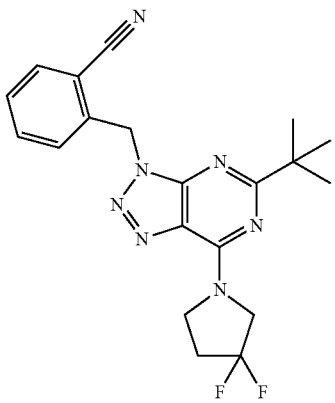 [SMILES: CC(C)(C)c1nc(N2CCC(F)(F)C2)c2nnn(Cc3ccccc3C#N)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(bromomethyl)benzonitrile and isolated as white solid (6.8 mg, 41%). MS(m/e): 398.3 (MH⁺).

Example 84

5-tert-Butyl-7-(3,3-difluoro-pyrrolidin-1-yl)-3-phenethyl-3H-[1,2,3]triazolo[4,5-d]pyrimidine

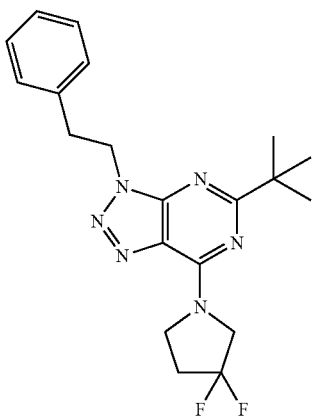 [SMILES: CC(C)(C)c1nc(N2CCC(F)(F)C2)c2nnn(CCc3ccccc3)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and (2-bromoethyl)benzene and isolated as light-yellow gum (4.8 mg, 30%). MS(m/e): 387.4 (MH⁺).

Example 85

2-[5-tert-Butyl-7-(3,3-difluoro-pyrrolidin-1-yl)-[1,2,3]triazolo[4,5-d]pyrimidin-2-yl]-1-phenyl-ethanone

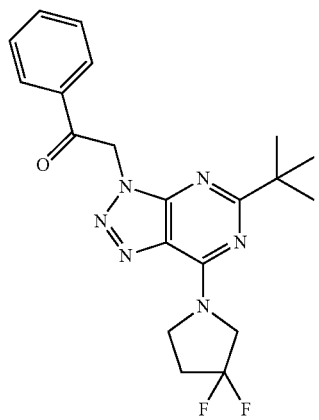 [SMILES: CC(C)(C)c1nc(N2CCC(F)(F)C2)c2nnn(CC(=O)c3ccccc3)c2n1]

In analogy to the procedure described for the synthesis of 5-tert-butyl-7-(3,3-difluoro-pyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-bromo-1-phenylethanone and isolated as light-green solid (9.5 mg, 55%). MS(m/e): 401.4 (MH⁺).

Example 86

5-tert-Butyl-2-[(R)-1-(2-chloro-phenyl)-ethyl]-7-(3,3-difluoro-pyrrolidin-1-yl)-3H-[1,2,3]triazolo[4,5-d]pyrimidine

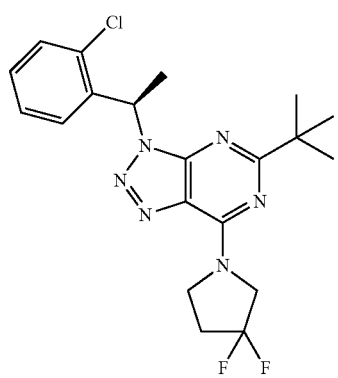 [SMILES: C[C@H](c1ccccc1Cl)n1nnc2c(N3CCC(F)(F)C3)nc(C(C)(C)C)nc21]

To a solution of 5-tert-butyl-7-(3,3-difluoropyrrolidin-1-yl)-3H-[1,2,3]triazolo[4,5-d]pyrimidine (41.3 µmol), (S)-1-(2-chlorophenyl)ethanol (12.9 mg, 82.6 µmol) and PPh₃ (21.7 mg, 82.6 µmol) in THF (250 µL) was added DEAD (13.1 µL, 82.6 µmol) at 0° C. After being stirred at the room temperature for 2 h, the reaction mixture was directly purified by preparative HPLC (column: Gemini 5 um C18 110A 75×30 mm. mobile phase: water (0.05% Et₃N): acetonitrile 50:50% to 5:95%. WL: 300 nm Flow: 30 mL/min.) to afford the title compound as light-yellow gum (3.1 mg, 17%). MS(m/e): 421.4 (MH+).

Example 87

5-tert-Butyl-3-[(S)-1-(2-chloro-phenyl)-ethyl]-7-(3,3-difluoro-pyrrolidin-1-yl)-3H-[1,2,3]triazolo[4,5-d]pyrimidine

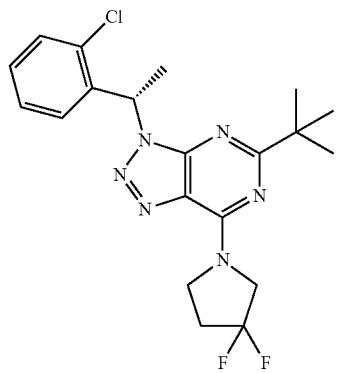 [SMILES: C[C@@H](c1ccccc1Cl)n1nnc2c(N3CCC(F)(F)C3)nc(C(C)(C)C)nc21]

In analogy to the procedure described for the synthesis of 5-tert-butyl-2-[(R)-1-(2-chloro-phenyl)-ethyl]-7-(3,3-difluoro-pyrrolidin-1-yl)-3H-[1,2,3]triazolo[4,5-d]pyrimidine (example 87), the title compound was prepared from 5-tert-butyl-7-(3,3-difluoropyrrolidin-1-yl)-3H-[1,2,3]triazolo[4,5-d]pyrimidine and (R)-1-(2-chlorophenyl)ethanol and isolated as light-yellow gum (3.8 mg, 21%). MS(m/e): 421.4 (MH+).

Example 88

2-[5-tert-Butyl-7-(3,3-difluoro-pyrrolidin-1-yl)-[1,2,3]triazolo[4,5-d]pyrimidin-3-yl]-1-phenyl-ethanol

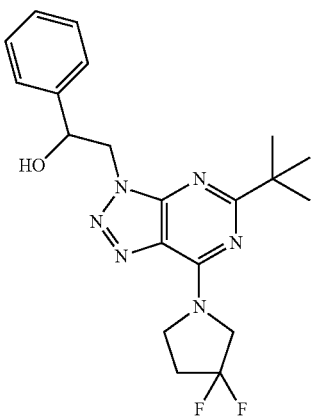 [SMILES: CC(C)(C)c1nc(N2CCC(F)(F)C2)c2nnn(CC(O)c3ccccc3)c2n1]

A mixture of 2-(5-tert-butyl-7-(3,3-difluoropyrrolidin-1-yl)-3H-[1,2,3]triazolo[4,5-d]pyrimidin-3-yl)-1-phenylethanone (6.0 mg, 15.0 μmol) and NaBH4 (1.7 mg, 45.0 μmol) in methanol (250 μL) was stirred at the room temperature for 1 h. The reaction mixture was directly purified by preparative HPLC (column: Gemini 5 um C18 110A 75×30 mm. mobile phase: water (0.05% Et3N): acetonitrile 72:25% to 5:95%. WL: 230 nm Flow: 30 mL/min.) to afford the title compound as white solid (2.3 mg, 38%). MS(m/e): 403.4 (MH+).

Example 89

5-tert-Butyl-3-(2-chloro-3-fluoro-benzyl)-7-(3,3-difluoro-pyrrolidin-1-yl)-3H-[1,2,3]triazolo[4,5-d]pyrimidine

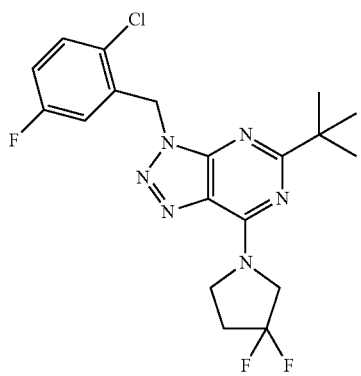 [SMILES: CC(C)(C)c1nc(N2CCC(F)(F)C2)c2nnn(Cc3cc(F)ccc3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(bromomethyl)-2-chloro-3-fluorobenzene and isolated as light-yellow gum. MS(m/e): 425.3 (MH+).

Example 90

5-tert-Butyl-3-(2-chloro-5-fluoro-benzyl)-7-(3,3-difluoro-pyrrolidin-1-yl)-3H-[1,2,3]triazolo[4,5-d]pyrimidine In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(bromomethyl)-1-chloro-4-fluorobenzene and isolated as light-yellow gum. MS(m/e): 425.3 (MH⁺).

Example 91

5-tert-Butyl-7-(3,3-difluoro-pyrrolidin-1-yl)-3-oxetan-3-yl-3H-[1,2,3]triazolo[4,5-d]pyrimidine

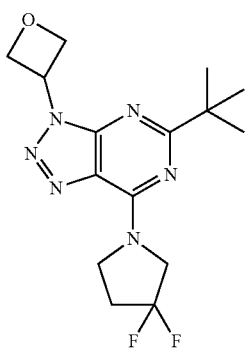 [SMILES: CC(C)(C)c1nc(N2CCC(F)(F)C2)c2nnn(C3COC3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-bromooxetane and isolated as light-yellow gum. MS(m/e): 339.3 (MH⁺).

Example 92

[5-tert-Butyl-7-(3,3-difluoro-pyrrolidin-1-yl)-[1,2,3]triazolo[4,5-d]pyrimidin-3-yl]-(2-chloro-phenyl)-methanone

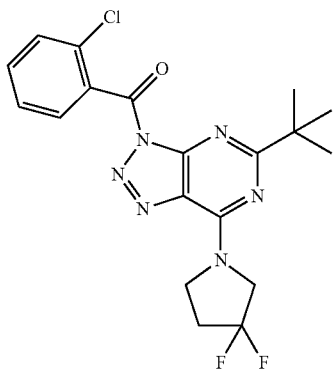 [SMILES: CC(C)(C)c1nc(N2CCC(F)(F)C2)c2nnn(C(=O)c3ccccc3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-chlorobenzoyl chloride and isolated as light-yellow solid. MS(m/e): 421.3 (MH⁺).

Example 93

(3S,5R)-1-[5-tert-Butyl-3-(2-chloro-benzyl)-3H-[1,2,3]triazolo[4,5-d]pyrimidin-7-yl]-5-hydroxymethyl-pyrrolidin-3-ol

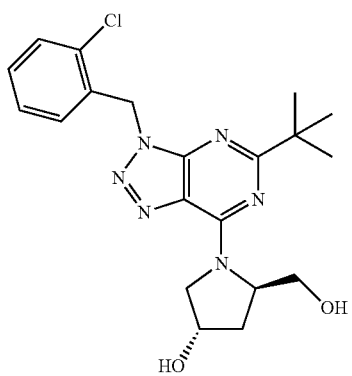 [SMILES: CC(C)(C)c1nc(N2C[C@@H](O)C[C@@H]2CO)c2nnn(Cc3ccccc3Cl)c2n1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (3S,5R)-5-(hydroxymethyl)pyrrolidin-3-ol hydrochloride and isolated as white solid. MS(m/e): 417.3 (MH⁺).

Example 94

{(R)-1-[5-tert-Butyl-3-(2-chloro-benzyl)-3H-[1,2,3]triazolo[4,5-d]pyrimidin-7-yl]-4,4-difluoro-pyrrolidin-2-yl}-methanol

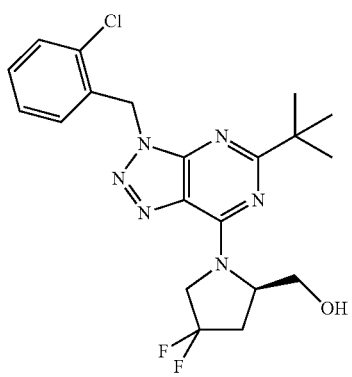 [SMILES: CC(C)(C)c1nc(N2CC(F)(F)C[C@@H]2CO)c2nnn(Cc3ccccc3Cl)c2n1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (R)-(4,4- difluoropyrrolidin-2-yl)methanol hydrochloride and isolated as white solid. MS(m/e): 437.3 (MH+).

Example 95

(R)-1-[5-tert-Butyl-3-(2-chloro-benzyl)-3H-[1,2,3]triazolo[4,5-d]pyrimidin-7-yl]-4,4-difluoro-pyrrolidin-3-ol

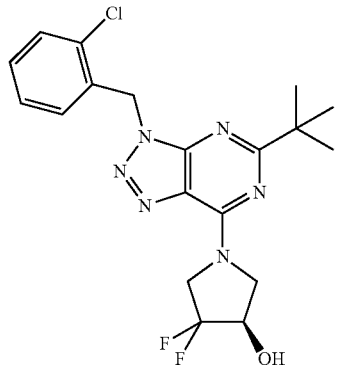 [SMILES: CC(C)(C)c1nc(N2C[C@@H](O)C(F)(F)C2)c2nnn(Cc3ccccc3Cl)c2n1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (R)-4,4-difluoropyrrolidin-3-ol hydrochloride and isolated as white solid. MS(m/e): 423.3 (MH+).

Example 96

5-tert-Butyl-3-(2,6-dichloro-3-fluoro-benzyl)-7-(3,3-difluoro-pyrrolidin-1-yl)-3H-[1,2,3]triazolo[4,5-d]pyrimidine

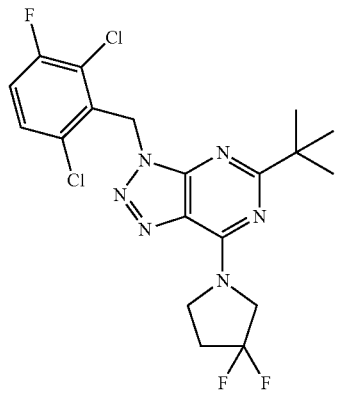 [SMILES: CC(C)(C)c1nc(N2CCC(F)(F)C2)c2nnn(Cc3c(Cl)ccc(F)c3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(bromomethyl)-1,3-dichloro-4-fluorobenzene and isolated as white solid. MS(m/e): 459.2 (MH+).

Example 97

5-tert-Butyl-3-(2-chloro-pyridin-3-ylmethyl)-7-(3,3-difluoro-pyrrolidin-1-yl)-3H-[1,2,3]triazolo[4,5-d]pyrimidine

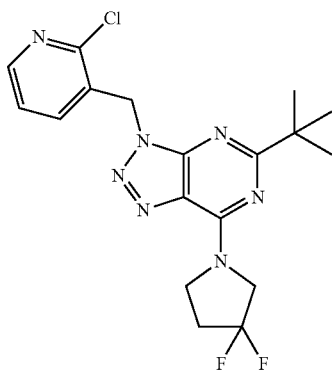 [SMILES: CC(C)(C)c1nc(N2CCC(F)(F)C2)c2nnn(Cc3cccnc3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-(bromomethyl)-2-chloropyridine hydrobromide and isolated as light-yellow gum. MS(m/e): 408.3 (MH+).

Example 98

5-tert-Butyl-3-(3-chloro-pyridin-2-ylmethyl)-7-(3,3-difluoro-pyrrolidin-1-yl)-3H-[1,2,3]triazolo[4,5-d]pyrimidine

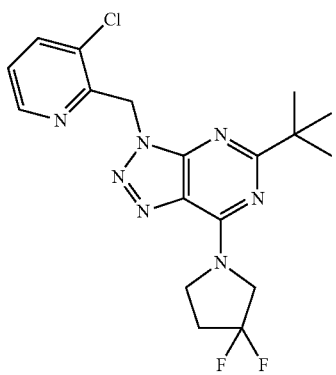 [SMILES: CC(C)(C)c1nc(N2CCC(F)(F)C2)c2nnn(Cc3ncccc3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 4-chloro-3-(chloromethyl)pyridine and isolated as light-yellow gum. MS(m/e): 408.3 (MH⁺).

Example 99

5-tert-Butyl-3-(2,5-dichloro-pyridin-3-ylmethyl)-7-(3,3-difluoro-pyrrolidin-1-yl)-3H-[1,2,3]triazolo[4,5-d]pyrimidine

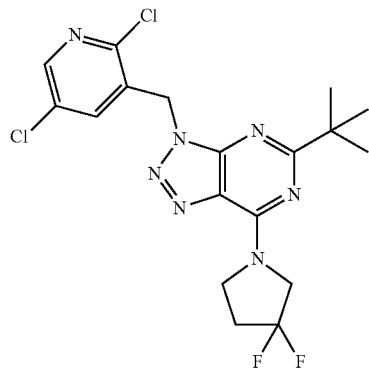 [SMILES: CC(C)(C)c1nc(N2CCC(F)(F)C2)c2nnn(Cc3cc(Cl)cnc3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2,5-dichloro-3-(chloromethyl)pyridine and isolated as light-yellow gum. MS(m/e): 442.3 (MH⁺).

Example 100

5-tert-Butyl-3-(3,6-dichloro-pyridin-2-ylmethyl)-7-(3,3-difluoro-pyrrolidin-1-yl)-3H-[1,2,3]triazolo[4,5-d]pyrimidine

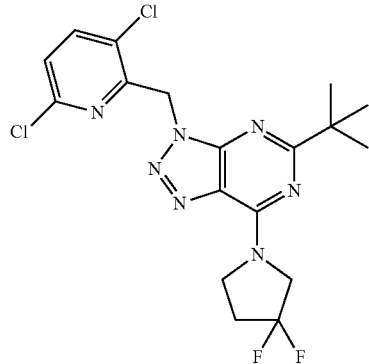 [SMILES: CC(C)(C)c1nc(N2CCC(F)(F)C2)c2nnn(Cc3nc(Cl)ccc3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3,6-dichloro-2-(chloromethyl)pyridine and isolated as light-yellow gum. MS(m/c): 442.3 (MH⁺).

Example 101

5-tert-Butyl-7-(3,3-difluoro-pyrrolidin-1-yl)-3-(4-methyl-furazan-3-ylmethyl)-3H-[1,2,3]triazolo[4,5-d]pyrimidine

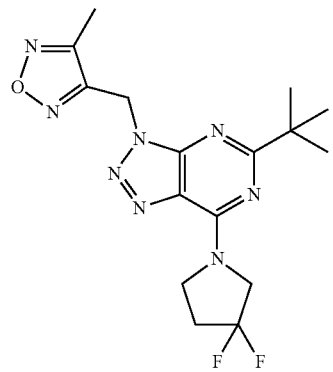 [SMILES: Cc1nonc1Cn1nnc2c(N3CCC(F)(F)C3)nc(C(C)(C)C)nc21]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-(bromomethyl)-4-methyl-1,2,5-oxadiazole and isolated as light-yellow gum. MS(m/e): 379.3 (MH⁺).

Example 102

5-tert-Butyl-7-(3,3-difluoro-pyrrolidin-1-yl)-3-(3-methyl-[1,2,4]oxadiazol-5-ylmethyl)-3H-[1,2,3]triazolo[4,5-d]pyrimidine

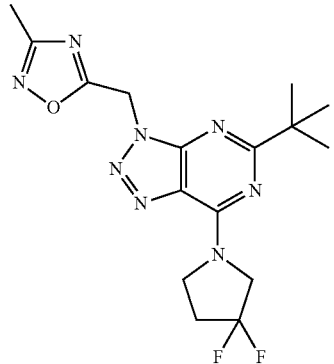 [SMILES: Cc1noc(Cn2nnc3c(N4CCC(F)(F)C4)nc(C(C)(C)C)nc32)n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and

85

5-(chloromethyl)-3-methyl-1,2,4-oxadiazole and isolated as light-yellow gum. MS(m/e): 379.3 (MH⁺).

Example 103

5-tert-Butyl-3-[2-(2-chloro-phenyl)-ethyl]-7-(3,3-difluoro-pyrrolidin-1-yl)-3H-[1,2,3]triazolo[4,5-d]pyrimidine

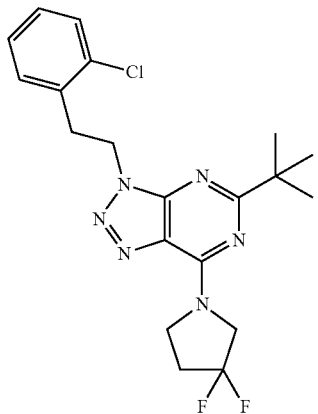 [SMILES: CC(C)(C)c1nc(N2CCC(F)(F)C2)c2nnn(CCc3ccccc3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(2-bromoethyl)-2-chlorobenzene and isolated as light-yellow gum. MS(m/e): 421.3 (MH⁺).

Example 104

5-tert-Butyl-3-[2-(3-chloro-phenyl)-ethyl]-7-(3,3-difluoro-pyrrolidin-1-yl)-3H-[1,2,3]triazolo[4,5-d]pyrimidine

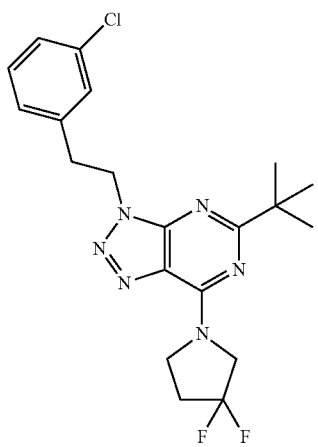 [SMILES: CC(C)(C)c1nc(N2CCC(F)(F)C2)c2nnn(CCc3cccc(Cl)c3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(2-bromoethyl)-3-chlorobenzene and isolated as light-yellow gum. MS(m/e): 421.3 (MH⁺).

Example 105

5-tert-Butyl-3-[2-(4-chloro-phenyl)-ethyl]-7-(3,3-difluoro-pyrrolidin-1-yl)-3H-[1,2,3]triazolo[4,5-d]pyrimidine

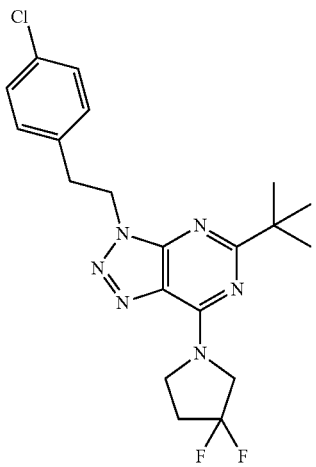 [SMILES: CC(C)(C)c1nc(N2CCC(F)(F)C2)c2nnn(CCc3ccc(Cl)cc3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(2-bromoethyl)-4-chlorobenzene and isolated as light-yellow gum. MS(m/e): 421.3 (MH⁺).

Example 106

(S)-1-[5-tert-Butyl-3-(4-methoxy-benzyl)-3H-[1,2,3]triazolo[4,5-d]pyrimidin-7-yl]-pyrrolidin-3-ol

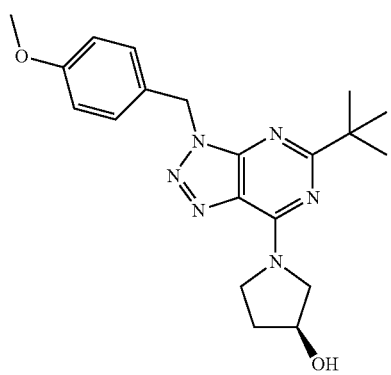 [SMILES: COc1ccc(Cn2nnc3c(N4CC[C@H](O)C4)nc(C(C)(C)C)nc32)cc1]

In analogy to the procedure described for the synthesis of 4-(5-tert-butyl-3-(4-methoxybenzyl)-3H-[1,2,3]triazolo[4,5-d]pyrimidin-7-yl)morpholine (example 58, step c), the title compound was prepared from 5-tert-butyl-7-chloro-3-(4- methoxybenzyl)-3H-[1,2,3]triazolo[4,5-d]pyrimidine and (S)-pyrrolidin-3-ol and isolated as light-yellow solid. MS(m/e): 383.3 (MH⁺).

Example 107

5-tert-Butyl-3-(2-chloro-benzenesulfonyl)-7-(3,3-difluoro-pyrrolidin-1-yl)-3H-[1,2,3]triazolo[4,5-d]pyrimidine

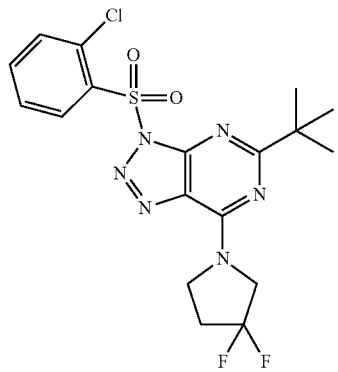 [SMILES: CC(C)(C)c1nc(N2CCC(F)(F)C2)c2nnn(S(=O)(=O)c3ccccc3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-chlorobenzene-1-sulfonyl chloride and isolated as brown solid. MS(m/e): 457.3 (MH⁺).

Example 108

5-tert-Butyl-7-(3,3-difluoro-pyrrolidin-1-yl)-3-(R)-tetrahydro-furan-3-yl-3H-[1,2,3]triazolo[4,5-d]pyrimidine

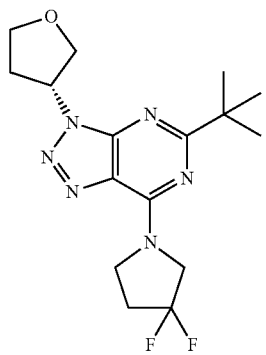 [SMILES: CC(C)(C)c1nc(N2CCC(F)(F)C2)c2nnn([C@@H]3CCOC3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrro-lidin-1-yl)-3H-[1,2,3]triazolo[4,5-d]pyrimidine and (S)-tetrahydrofuran-3-ol and isolated as colorless gum. MS(m/e): 353.3 (MH⁺).

Example 109

5-tert-Butyl-7-(3,3-difluoro-pyrrolidin-1-yl)-3-(S)-tetrahydro-furan-3-yl-3H-[1,2,3]triazolo[4,5-d]pyrimidine

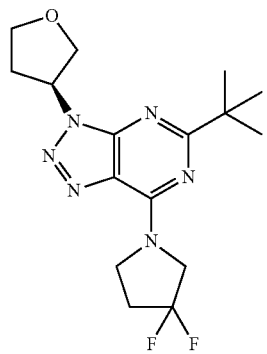 [SMILES: CC(C)(C)c1nc(N2CCC(F)(F)C2)c2nnn([C@H]3CCOC3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrro-lidin-1-yl)-3H-[1,2,3]triazolo[4,5-d]pyrimidine and (R)-tetrahydrofuran-3-ol and isolated as colorless gum. MS(m/e): 353.3 (MH⁺).

Example 110

2-[5-tert-Butyl-7-(3,3-difluoro-pyrrolidin-1-yl)-[1,2,3]triazolo[4,5-d]pyrimidin-3-yl]-1-(2-chloro-phenyl)-ethanone

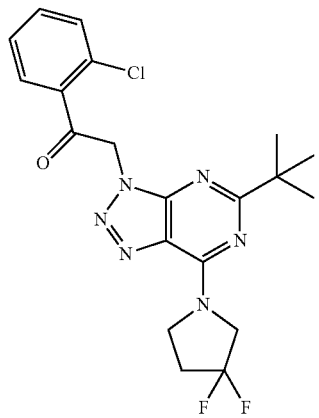 [SMILES: CC(C)(C)c1nc(N2CCC(F)(F)C2)c2nnn(CC(=O)c3ccccc3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-bromo-1-(2-chlorophenyl)ethanone and isolated as yellow gum. MS(m/e): 435.3 (MH+).

Example 111

5-tert-Butyl-3-(2,3-dichloro-6-fluoro-benzyl)-7-(3,3-difluoro-pyrrolidin-1-yl)-3H-[1,2,3]triazolo[4,5-d]pyrimidine

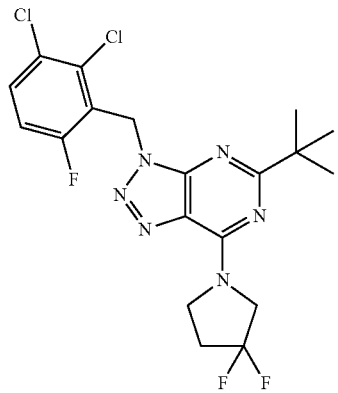 [SMILES: CC(C)(C)c1nc(N2CCC(F)(F)C2)c2nnn(Cc3c(F)ccc(Cl)c3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(bromomethyl)-3,4-dichloro-1-fluorobenzene and isolated as white solid. MS(m/e): 459.3 (MH+).

Example 112

5-tert-Butyl-7-(3,3-difluoro-pyrrolidin-1-yl)-3-(2-methanesulfonyl-benzyl)-3H-[1,2,3]triazolo[4,5-d]pyrimidine

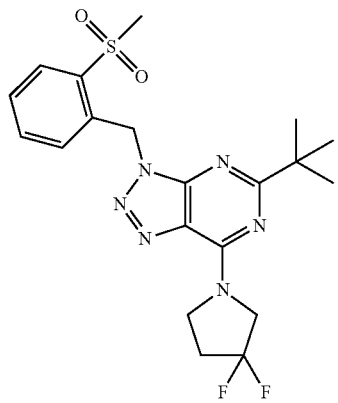 [SMILES: CC(C)(C)c1nc(N2CCC(F)(F)C2)c2nnn(Cc3ccccc3S(C)(=O)=O)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 1-(bromomethyl)-2-(methylsulfonyl)benzene and isolated as white solid. MS(m/e): 451.3 (MH+).

Example 113

5-tert-Butyl-7-(3,3-difluoro-pyrrolidin-1-yl)-3-(2-pyridin-2-yl-ethyl)-3H-[1,2,3]triazolo[4,5-d]pyrimidine

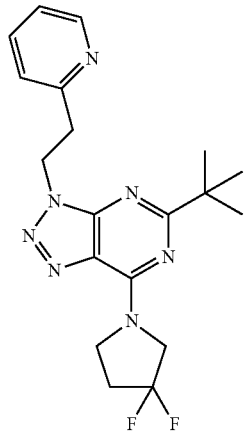 [SMILES: CC(C)(C)c1nc(N2CCC(F)(F)C2)c2nnn(CCc3ccccn3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(2-bromoethyl)pyridine hydrobromide and isolated as colorless gum. MS(m/e): 387.4 (MH+).

Example 114

5-tert-Butyl-7-(3,3-difluoro-pyrrolidin-1-yl)-3-(3-methyl-oxetan-3-ylmethyl)-3H-[1,2,3]triazolo[4,5-d]pyrimidine

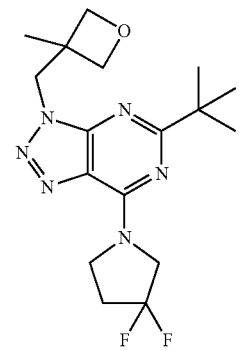 [SMILES: CC1(Cn2nnc3c(N4CCC(F)(F)C4)nc(C(C)(C)C)nc32)COC1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-(iodomethyl)-3-methyloxetane and isolated as white solid. MS(m/e): 367.3 (MH⁺).

Example 115

2-[5-tert-Butyl-7-(3,3-difluoro-pyrrolidin-1-yl)-[1,2,3]triazolo[4,5-d]pyrimidin-3-yl]-1-(3-chloro-phenyl)-ethanone

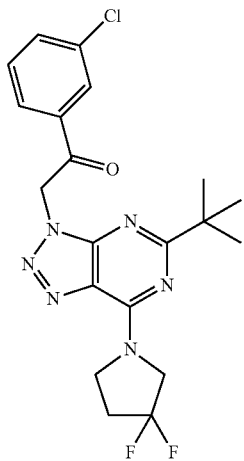 [SMILES: CC(C)(C)c1nc(N2CCC(F)(F)C2)c2nnn(CC(=O)c3cccc(Cl)c3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-bromo-1-(3-chlorophenyl)ethanone and isolated as white solid. MS(m/e): 435.3 (MH⁺).

Example 116

2-[5-tert-Butyl-7-(3,3-difluoro-pyrrolidin-1-yl)-[1,2,3]triazolo[4,5-d]pyrimidin-3-yl]-1-(4-chloro-phenyl)-ethanone

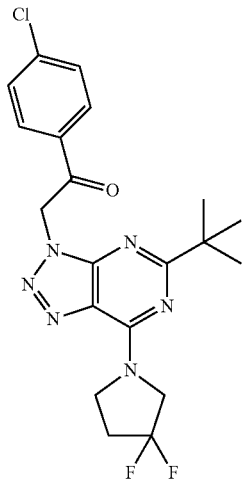 [SMILES: CC(C)(C)c1nc(N2CCC(F)(F)C2)c2nnn(CC(=O)c3ccc(Cl)cc3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-bromo-1-(4-chlorophenyl)ethanone and isolated as light-yellow solid. MS(m/e): 435.3 (MH⁺).

Example 117

2-[5-tert-Butyl-7-(3,3-difluoro-pyrrolidin-1-yl)-[1,2,3]triazolo[4,5-d]pyrimidin-3-yl]-1-pyridin-3-yl-ethanone

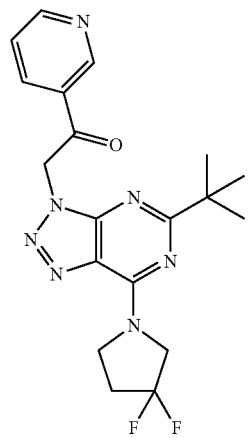 [SMILES: CC(C)(C)c1nc(N2CCC(F)(F)C2)c2nnn(CC(=O)c3cccnc3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-bromo-1-(pyridin-3-yl)ethanone hydrobromide and isolated as light-yellow solid. MS(m/e): 402.3 (MH⁺).

Example 118

2-[5-tert-Butyl-7-(3,3-difluoro-pyrrolidin-1-yl)-[1,2,3]triazolo[4,5-d]pyrimidin-3-yl]-1-pyridin-4-yl-ethanone

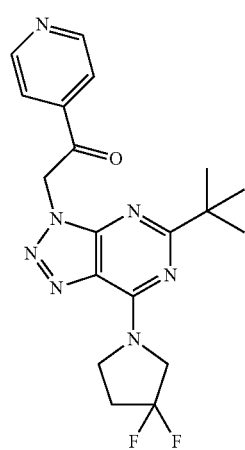 [SMILES: CC(C)(C)c1nc(N2CCC(F)(F)C2)c2nnn(CC(=O)c3ccncc3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-bromo-1-(pyridin-4-yl)ethanone hydrobromide and isolated as light-red solid. MS(m/e): 402.3 (MH$^+$).

Example 119

5-tert-Butyl-7-(3,3-difluoro-pyrrolidin-1-yl)-3-(2,36-trichloro-benzyl)-3H-[1,2,3]triazolo[4,5-d]pyrimidine

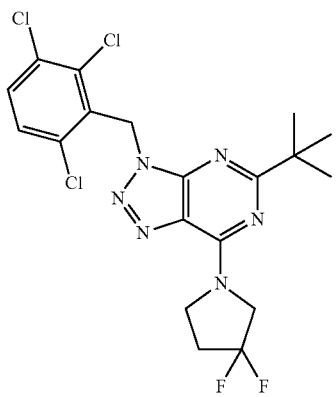 [SMILES: CC(C)(C)c1nc(N2CCC(F)(F)C2)c2nnn(Cc3c(Cl)ccc(Cl)c3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(bromomethyl)-1,3,4-trichlorobenzene and isolated as white solid. MS(m/e): 475.3 (MH$^+$).

Example 120

5-tert-Butyl-3-(2-chloro-3-trifluoromethyl-benzyl)-7-(3,3-difluoro-pyrrolidin-1-yl)-3H-[1,2,3]triazolo[4,5-d]pyrimidine

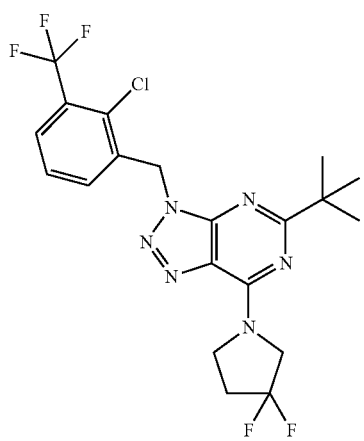 [SMILES: CC(C)(C)c1nc(N2CCC(F)(F)C2)c2nnn(Cc3cccc(C(F)(F)F)c3Cl)c2n1]

In analogy to the procedure described for the synthesis of 5-tert-butyl-7-(3,3-difluoropyrrolidin-1-yl)-3-ethyl-3H-[1,2, 3]triazolo[4,5-d]pyrimidine (example 61), the title compound was prepared from 5-tert-butyl-7-(3,3-difluoropyrrolidin-1-yl)-3H-[1,2,3]triazolo [4,5-d]pyrimidine and 1-(bromomethyl)-2-chloro-3-(trifluoromethyl)benzene and isolated as light-yellow solid. MS(nm/e): 475.2 (MH$^+$).

Example 121

5-tert-Butyl-7-(3,3-difluoro-pyrrolidin-1-yl)-3-(2-pyridin-3-yl-ethyl)-3H-[1,2,3]triazolo[4,5-d]pyrimidine

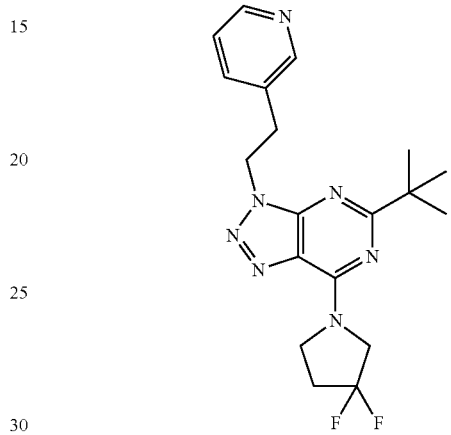

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-(2-bromoethyl)pyridine hydrobromide and isolated as white solid. MS(m/e): 388.3 (MH$^+$).

Example 122

5-tert-Butyl-7-(3,3-difluoro-pyrrolidin-1-yl)-3-(2-pyridin-4-yl-ethyl)-3H-[1,2,3]triazolo[4,5-d]pyrimidine

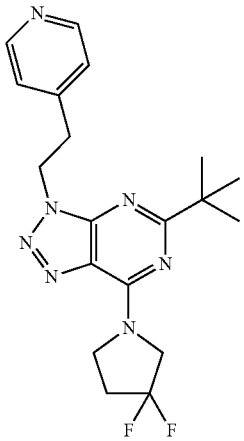 [SMILES: CC(C)(C)c1nc(N2CCC(F)(F)C2)c2nnn(CCc3ccncc3)c2n1]

In analogy to the procedure described for the synthesis of 5-tert-butyl-7-(3,3-difluoropyrrolidin-1-yl)-3-ethyl-3H-[1,2, 3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 4-(2-bromoethyl)pyridine hydrobromide and isolated as brown solid. MS(m/e): 388.3 (MH⁺).

Example 123

5-tert-Butyl-3-(2,3-dichloro-6-trifluoromethyl-benzyl)-7-(3,3-difluoro-pyrrolidin-1-yl)-3H-[1,2,3]triazolo[4,5-d]pyrimidine

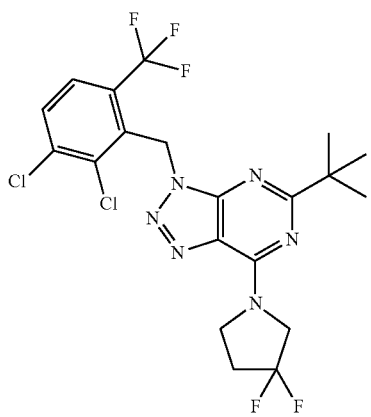 [SMILES: CC(C)(C)c1nc(N2CCC(F)(F)C2)c2nnn(Cc3c(C(F)(F)F)ccc(Cl)c3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(bromomethyl)-3,4-dichloro-1-(trifluoromethyl)benzene and isolated as white solid. MS(m/e): 509.3 (MH⁺).

Example 124

5-tert-Butyl-3-(3,4-dichloro-pyridin-2-ylmethyl)-7-(3,3-difluoro-pyrrolidin-1-yl)-3H-[1,2,3]triazolo[4,5-d]pyrimidine

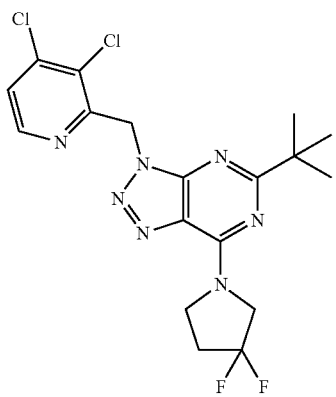 [SMILES: CC(C)(C)c1nc(N2CCC(F)(F)C2)c2nnn(Cc3nccc(Cl)c3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(bromomethyl)-3,4-dichloropyridine hydrobromide and isolated as white solid. MS(m/e): 442.2 (MH⁺).

Example 125

5-tert-Butyl-7-(3,3-difluoro-pyrrolidin-1-yl)-3-(1,1-dioxo-1λ⁶-thietan-3-yl)-3H-[1,2,3]triazolo[4,5-d]pyrimidine

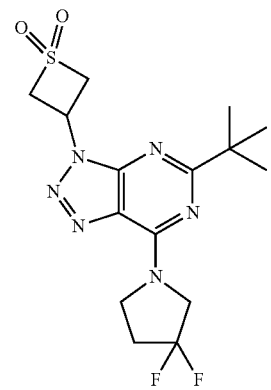 [SMILES: CC(C)(C)c1nc(N2CCC(F)(F)C2)c2nnn(C3CS(=O)(=O)C3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-bromo-thietane 1,1-dioxide and isolated as white solid. MS(m/e): 387.3 (MH⁺).

Example 126

5-tert-Butyl-7-(3,3-difluoro-pyrrolidin-1-yl)-3-(1,1-dioxo-tetrahydro-1λ⁶-thiophen-3-yl)-3H-[1,2,3]triazolo[4,5-d]pyrimidine

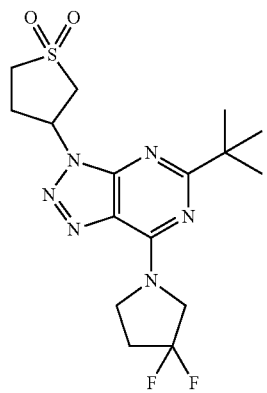 [SMILES: CC(C)(C)c1nc(N2CCC(F)(F)C2)c2nnn(C3CCS(=O)(=O)C3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-bromo-tetrahydro-thiophene 1,1-dioxide and isolated as white solid. MS(m/e): 401.3 (MH+).

Example 127

2-[5-tert-Butyl-7-(3,3-difluoro-pyrrolidin-1-yl)-[1,2,3]triazolo[4,5-d]pyrimidin-3-yl]-1-pyridin-2-yl-ethanone

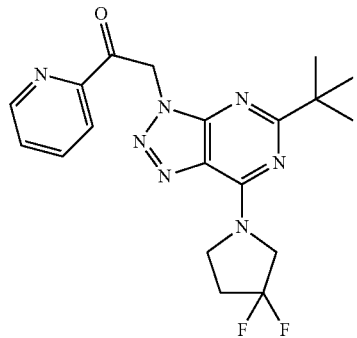 [SMILES: CC(C)(C)c1nc(N2CCC(F)(F)C2)c2nnn(CC(=O)c3ccccn3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-bromo-1-(pyridin-2-yl)ethanone hydrobromide and isolated as dark-brown solid. MS(m/e): 402.3 (MH+).

Example 128

5-tert-Butyl-7-(3,3-difluoro-pyrrolidin-1-yl)-3-(5-methyl-[1,3,4]oxadiazol-2-ylmethyl)-3H-[1,2,3]triazolo[4,5-d]pyrimidine

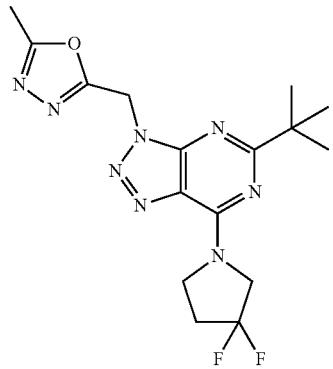 [SMILES: Cc1nnc(Cn2nnc3c(N4CCC(F)(F)C4)nc(C(C)(C)C)nc32)o1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 2-(chloromethyl)-5-methyl-1,3,4-oxadiazole and isolated as colorless gum. MS(m/e): 379.3 (MH+).

Example 129

5-tert-Butyl-3-(3-chloro-pyridin-4-ylmethyl)-7-(3,3-difluoro-pyrrolidin-1-yl)-3H-[1,2,3]triazolo[4,5-d]pyrimidine

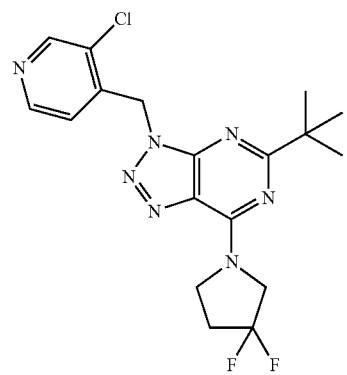 [SMILES: CC(C)(C)c1nc(N2CCC(F)(F)C2)c2nnn(Cc3ccncc3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 4-(bromomethyl)-3-chloropyridine hydrobromide and isolated as yellow gum. MS(m/e): 408.3 (MH+).

Example 130

5-tert-Butyl-7-(3,3-difluoro-pyrrolidin-1-yl)-3-(5-methyl-[1,2,4]oxadiazol-3-ylmethyl)-3H-[1,2,3]triazolo[4,5-d]pyrimidine

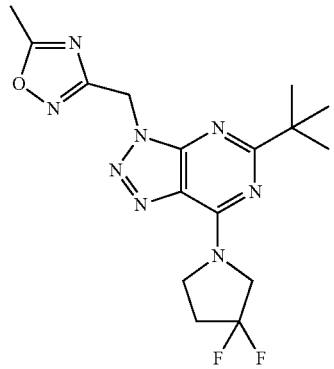 [SMILES: Cc1nc(Cn2nnc3c(N4CCC(F)(F)C4)nc(C(C)(C)C)nc32)no1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-(chloromethyl)-5-methyl-1,2,4-oxadiazole and isolated as yellow gum. MS(m/e): 379.3 (MH+).

Example 131

5-tert-Butyl-7-(3,3-difluoro-pyrrolidin-1-yl)-3-(1-methyl-1H-tetrazol-5-ylmethyl)-3H-[1,2,3]triazolo[4,5-d]pyrimidine

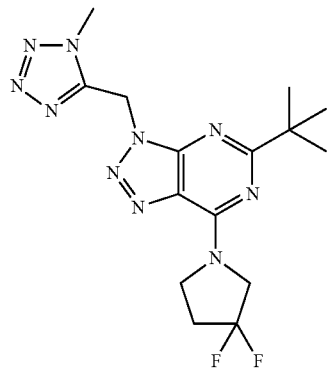 [SMILES: Cn1nnnc1Cn1nnc2c(N3CCC(F)(F)C3)nc(C(C)(C)C)nc21]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 5-(chloromethyl)-1-methyl-1H-tetrazole and isolated as white solid. MS(m/e): 379.3 (MH+).

Example 132

5-tert-Butyl-7-(3,3-difluoro-pyrrolidin-1-yl)-3-(2-methyl-2H-[1,2,4]triazol-3-ylmethyl)-3H-[1,2,3]triazolo[4,5-d]pyrimidine

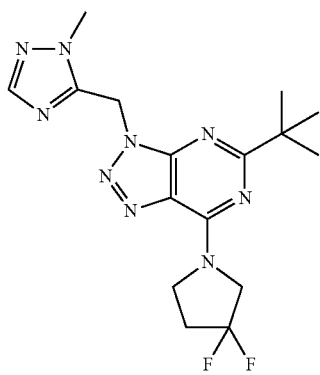 [SMILES: Cn1ncnc1Cn1nnc2c(N3CCC(F)(F)C3)nc(C(C)(C)C)nc21]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 5-(chloromethyl)-1-methyl-1H-1,2,4-triazole hydrochloride and isolated as colorless gum. MS(m/e): 378.3 (MH+).

Example 133

5-tert-Butyl-7-(3,3-difluoro-pyrrolidin-1-yl)-3-(5-methanesulfonyl-4-methyl-4H-[1,2,4]triazol-3-ylmethyl)-3H-[1,2,3]triazolo[4,5-d]pyrimidine

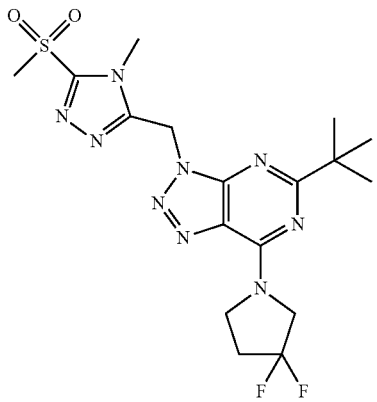 [SMILES: Cn1c(Cn2nnc3c(N4CCC(F)(F)C4)nc(C(C)(C)C)nc32)nnc1S(C)(=O)=O]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-(iodomethyl)-4-methyl-5-(methylsulfonyl)-4H-1,2,4-triazole and isolated as white solid. MS(m/e): 456.3 (MH+).

Example 134

{3-[5-tert-Butyl-7-(3,3-difluoro-pyrrolidin-1-yl)-[1,2,3]triazolo[4,5-d]pyrimidin-3-ylmethyl]-5-chloro-pyridin-4-yl}-dimethyl-amine

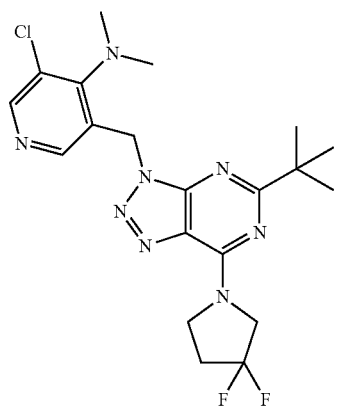 [SMILES: CN(C)c1c(Cl)cncc1Cn1nnc2c(N3CCC(F)(F)C3)nc(C(C)(C)C)nc21]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-(bromomethyl)-5-chloro-N,N-dimethylpyridin-4-amine hydrobromide and isolated as light-yellow gum. MS(m/e): 451.4 (MH+).

Example 135

5-tert-Butyl-7-(3,3-difluoro-pyrrolidin-1-yl)-3-(3-trifluoromethyl-1H-pyrazol-4-ylmethyl)-3H-[1,2,3]triazolo[4,5-d]pyrimidine

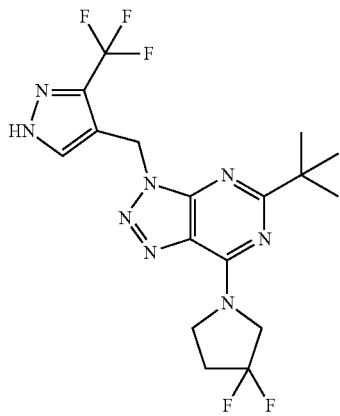 [SMILES: CC(C)(C)c1nc(N2CCC(F)(F)C2)c2nnn(Cc3c[nH]nc3C(F)(F)F)c2n1]

Step 1

5-tert-Butyl-7-(3,3-difluoro-pyrrolidin-1-yl)-3-(3-trifluoromethyl-1-trityl-1H-pyrazol-4-ylmethyl)-3H-[1,2,3]triazolo[4,5-d]pyrimidine

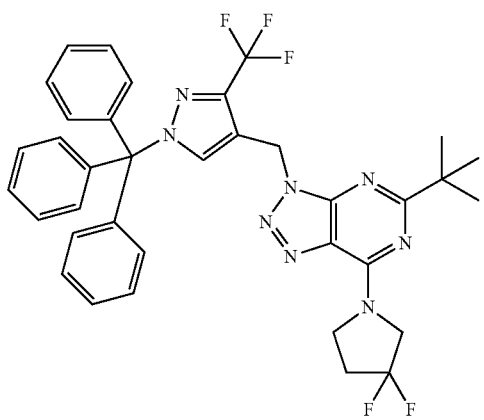 [SMILES: CC(C)(C)c1nc(N2CCC(F)(F)C2)c2nnn(Cc3cn(C(c4ccccc4)(c4ccccc4)c4ccccc4)nc3C(F)(F)F)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 4-(bromomethyl)-3-(trifluoromethyl)-1-trityl-1H-pyrazole and used in the next step without further purification.

Step 2

A mixture of crude 5-tert-Butyl-7-(3,3-difluoro-pyrrolidin-1-yl)-3-(3-trifluoromethyl-1-trityl-1H-pyrazol-4-ylmethyl)-3H-[1,2,3]triazolo[4,5-d]pyrimidine, triethylsilane in TFA was stirred at room temperature for 3 h, concentrated and subjected to purification with preparative HPLC on reversed phase eluting with a gradient formed from acetonitrile, water and NEt3. After evaporation of the product containing fractions the title compound was isolated as white solid. MS(m/e): 431.3 (MH+).

Example 136

(S)-1-[5-tert-Butyl-3-(4-methyl-furazan-3-ylmethyl)-3H-[1,2,3]triazolo[4,5-d]pyrimidin-7-yl]-pyrrolidin-3-ol

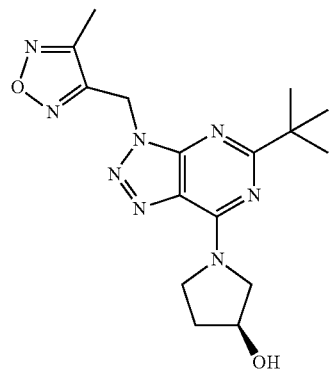 [SMILES: Cc1nonc1Cn1nnc2c(N3CC[C@H](O)C3)nc(C(C)(C)C)nc21]

Step 1

Trifluoro-acetic acid (S)-1-(5-tert-butyl-3H-[1,2,3]triazolo[4,5-d]pyrimidin-7-yl)-pyrrolidin-3-yl-ester

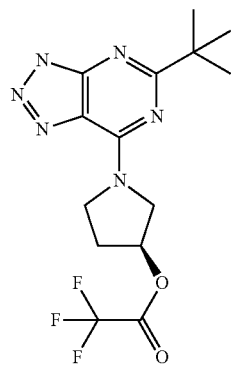 [SMILES: CC(C)(C)c1nc(N2CC[C@H](OC(=O)C(F)(F)F)C2)c2nn[nH]c2n1]

A mixture of (S)-1-[5-tert-Butyl-3-(4-methoxy-benzyl)-3H-[1,2,3]triazolo[4,5-d]pyrimidin-7-yl]-pyrrolidin-3-ol (example 106) and triethylsilane in TFA was heated to 70° C. for 22 h and evaporated to dryness. The residue was used without further purification in the consecutive step.

Step 2

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-(bromomethyl)-4-methyl-1,2,5-oxadiazole. After completion of the substitution reaction methanol was added and the mixture was stirred for 1 h at room temperature and subsequently subjected to purification with preparative HPLC on reversed phase eluting with a gradient formed from acetonitrile, water and NEt3. After evaporation of the product containing fractions the title compound was isolated as light-yellow gum. MS(m/e): 359.3 (MH⁺).

Alternative Conditions:

Step 1: (3S)-1-(5-tert-butyl-3H-triazolo[4,5-d]pyrimidin-7-yl)pyrrolidin-3-ol. n HCl

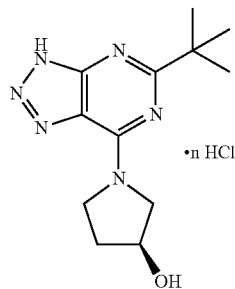 [SMILES: CC(C)(C)c1nc(N2CC[C@H](O)C2)c2nn[nH]c2n1]

(S)-1-(3-benzyl-5-tert-butyl-3H-[1,2,3]triazolo[4,5-d]pyrimidin-7-yl)pyrrolidin-3-ol (176 g, 494 mmol, Eq: 1.00) was dissolved in Methanol (2.09 kg, 2.64 l). 1.25 M HCl in Methanol (396 ml, 494 mmol, Eq: 1.00) was added followed by 10% Pd/C (34.7 g, 32.6 mmol, Eq: 0.066). The reaction mixture hydrogenated >20 h at 60° C./1 bar. The reaction mixture was cooled evacuated, purged and filtered. The light yellow solution was concentrated at 50° C. to ca 1 L. Toluene (1.3 kg, 1.5 l) was added and the solution was concentrated at 50° C./150 mbar to ca 1.2 kg to remove most of the methanol upon which the product started to crystallize. The white suspension was cooled to RT, stirred for 1 h and filtered. The filter cake was washed with Toluene and dried at 50° C./5 mbar to give 140.5 g of the title compound as a white solid. From microanalysis data, the structure would be consistent with a hemi hydrochloride.

Step 2(3S)-1-[5-tert-butyl-3-[(4-methyl-1,2,5-oxadiazol-3-yl)methyl]triazolo[4,5-d]pyrimidin-7-yl]pyrrolidin-3-ol

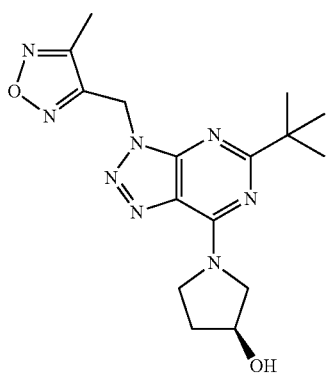 [SMILES: Cc1nonc1Cn1nnc2c(N3CC[C@H](O)C3)nc(C(C)(C)C)nc21]

(S)-1-(5-tert-butyl-3H-[1,2,3]triazolo[4,5-d]pyrimidin-7-yl)pyrrolidin-3-ol. n HCl (4.25 g) was dissolved in DMF (20.1 g, 21.2 ml). DBU (5.47 g, 5.41 ml) was added dropwise over 5-10 min. A solution of 3-(bromomethyl)-4-methyl-1,2,5-oxadiazole (3.78 g) in DMF (20.1 g, 21.2 ml) was added dropwise over 30 min. After 1 h, the reaction mixture was added to 25% aqueous NH4Cl (85.0 ml). MTBE (126 g, 170 ml) was added. The aqueous phase was separated and extracted with organic phase was separated and extracted with (126 g, 170 ml). The org phase was washed sequentially with water (85.0 g, 85.0 ml) and half saturated aqueous NaCl (85.0 ml). The organic phases were combined, dried over MgSO4 and concentrated at 45° C./10 mbar to give 5.67 g of crude product a light yellow oil (mixture of isomers ca 2:1 by HPLC at 220 nm desired:undesired). The crude product was purified by preparative SFC, column: Viridis 2-Ethyl-Pyridine, 5 um, 3×25 cm, 40° C., 15% EtOH/85% CO2sc, UV detection 260 nm, to give 2.16 g of the title compound.

Example 137

(S)-1-[5-tert-Butyl-3-(3-methyl-[1,2,4]oxadiazol-5-ylmethyl)-3H-[1,2,3]triazolo[4,5-d]pyrimidin-7-yl]-pyrrolidin-3-ol

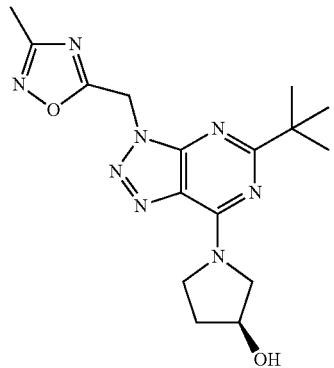 [SMILES: Cc1noc(Cn2nnc3c(N4CC[C@H](O)C4)nc(C(C)(C)C)nc32)n1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 5-(chloromethyl)-3-methyl-1,2,4-oxadiazole and isolated as brown gum. MS(m/e): 359.3 (MH⁺).

Example 138

(S)-1-[5-tert-Butyl-3-(3-chloro-pyridin-2-ylmethyl)-3H-[1,2,3]triazolo[4,5-d]pyrimidin-7-yl]-pyrrolidin-3-ol

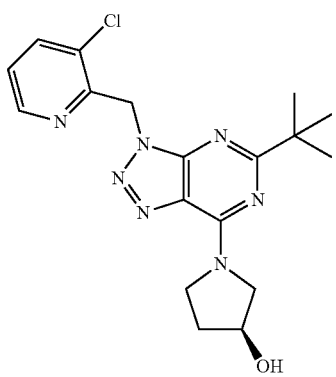 [SMILES: CC(C)(C)c1nc(N2CC[C@H](O)C2)c2nnn(Cc3ncccc3Cl)c2n1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 3-chloro-2-(chloromethyl)pyridine and isolated as brown gum. MS(m/e): 388.3 (MH+).

Example 139

(S)-1-[5-tert-Butyl-3-(3,6-dichloro-pyridin-2-ylmethyl)-3H-[1,2,3]triazolo[4,5-d]pyrimidin-7-yl]-pyrrolidin-3-ol

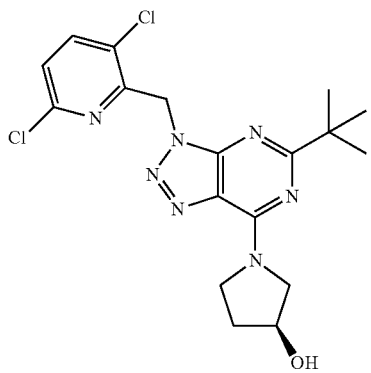 [SMILES: CC(C)(C)c1nc(N2CC[C@H](O)C2)c2nnn(Cc3nc(Cl)ccc3Cl)c2n1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 3,6-dichloro-2-(chloromethyl)pyridine as light-yellow gum. MS(m/e): 422.3 (MH+).

Example 140

(S)-1-[5-tert-Butyl-3-(2-chloro-pyridin-3-ylmethyl)-3H-[1,2,3]triazolo[4,5-d]pyrimidin-7-yl]-pyrrolidin-3-ol

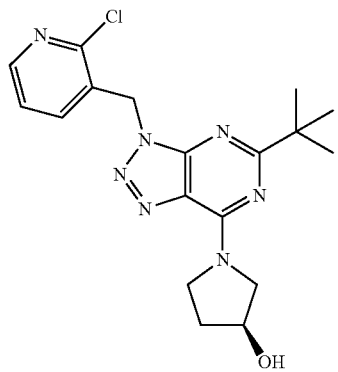 [SMILES: CC(C)(C)c1nc(N2CC[C@H](O)C2)c2nnn(Cc3cccnc3Cl)c2n1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 3-(bromomethyl)-2-chloropyridine hydrobromide as light-brown gum. MS(m/e): 388.3 (MH+).

Example 141

(S)-1-[5-tert-Butyl-3-(2,3-dichloro-benzyl)-3H-[1,2,3]triazolo[4,5-d]pyrimidin-7-yl]-pyrrolidin-3-ol

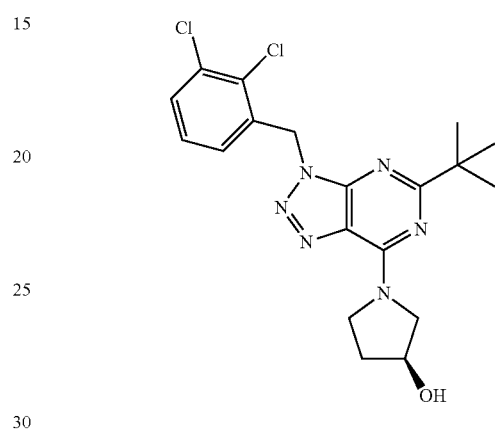

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,23]triazolo[4,5-d]pyrimidin-7-yl)-pyrrolidin-3-yl-ester (example 136, step 1) and 1-(bromomethyl)-2,3-dichlorobenzene as colorless gum. MS(m/e): 421.3 (MH+).

Example 142

(S)-1-[5-tert-Butyl-3-(2-trifluoromethyl-benzyl)-3H-[1,2,3]triazolo[4,5-d]pyrimidin-7-yl]-pyrrolidin-3-ol

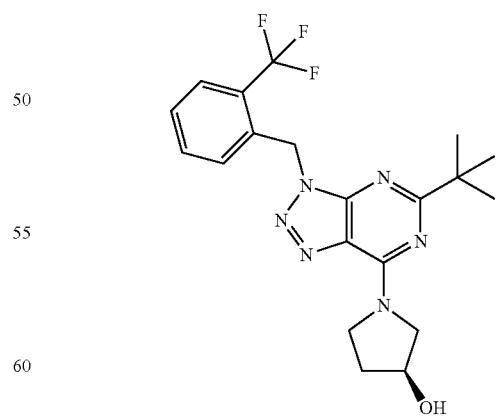

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 1-(bromomethyl)-2-(trifluoromethyl)benzene as light-yellow gum. MS(m/e): 421.3 (MH+).

Example 143

(S)-1-[5-tert-Butyl-3-(2-methanesulfonyl-benzyl)-3H-[1,2,3]triazolo[4,5-d]pyrimidin-7-yl]-pyrrolidin-3-ol

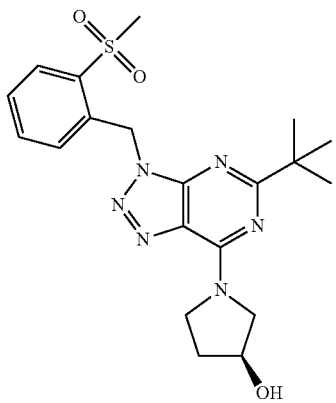 [SMILES: CC(C)(C)c1nc(N2CC[C@H](O)C2)c2nnn(Cc3ccccc3S(C)(=O)=O)c2n1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoroacetic acid (S)-1-(5-tert-butyl-3H-[1,2,3]triazolo[4,5-d]pyrimidin-7-yl)-pyrrolidin-3-yl-ester (example 136, step 1) and 1-(bromomethyl)-2-(methylsulfonyl)benzene as colorless gum. MS(m/e): 431.3 (MH+).

Example 144

5-tert-Butyl-7-(3,3-difluoro-pyrrolidin-1-yl)-3-(2,5-dimethyl-2H-pyrazol-3-ylmethyl)-3H-[1,2,3]triazolo[4,5-d]pyrimidine

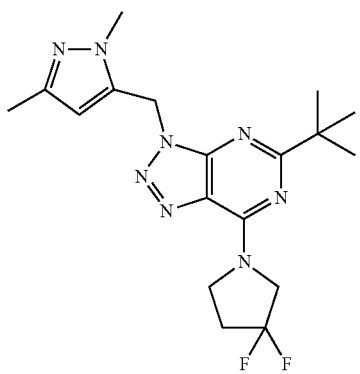

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 5-(chloromethyl)-1,3-dimethyl-1H-pyrazole and isolated as light-yellow gum. MS(m/e): 391.3 (MH+).

Example 145

5-tert-Butyl-7-(3,3-difluoro-pyrrolidin-1-yl)-3-(3-methyl-3H-[1,2,3]triazol-4-ylmethyl)-3H-[1,2,3]triazolo[4,5-d]pyrimidine

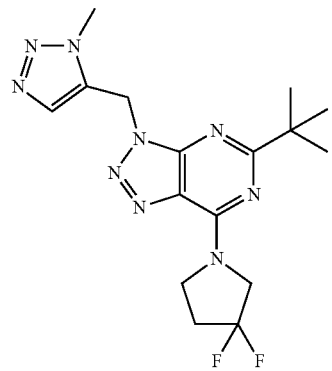 [SMILES: Cn1nncc1Cn1nnc2c(N3CCC(F)(F)C3)nc(C(C)(C)C)nc21]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 5-(chloromethyl)-1-methyl-1H-1,2,3-triazole hydrochloride and isolated as light-yellow gum. MS(m/e): 378.3 (MH+).

Example 146

5-tert-Butyl-7-(3,3-difluoro-pyrrolidin-1-yl)-3-(4,5-dimethyl-4H-[1,2,4]triazol-3-ylmethyl)-3H-[1,2,3]triazolo[4,5-d]pyrimidine

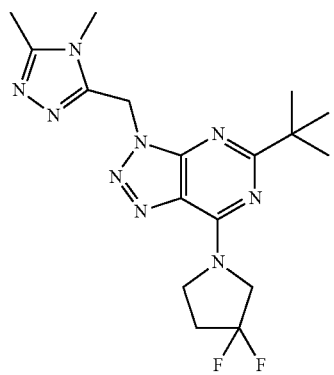 [SMILES: Cc1nnc(Cn2nnc3c(N4CCC(F)(F)C4)nc(C(C)(C)C)nc32)n1C]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-(chloromethyl)-4,5-dimethyl-4H-1,2,4-triazole and isolated as light-yellow solid. MS(m/e): 392.3 (MH+).

Example 147

5-tert-Butyl-7-(3,3-difluoro-pyrrolidin-1-yl)-3-(2-methyl-1-oxy-pyridin-3-ylmethyl)-3H-[1,2,3]triazolo[4,5-d]pyrimidine

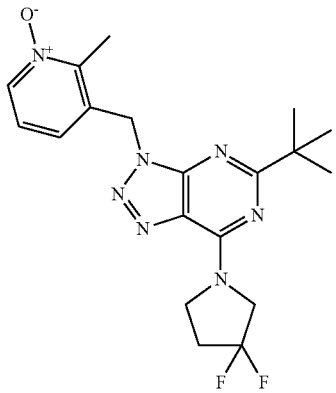 [SMILES: Cc1c(Cn2nnc3c(N4CCC(F)(F)C4)nc(C(C)(C)C)nc32)ccc[n+]1[O-]]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 3-(chloromethyl)-2-methylpyridine 1-oxide and isolated as light-yellow gum. MS(m/e): 404.2 (MH+).

Example 148

(S)-1-[5-tert-Butyl-3-(3,4-dichloro-pyridin-2-ylmethyl)-3H-[1,2,3]triazolo[4,5-d]pyrimidin-7-yl]-pyrrolidin-3-ol

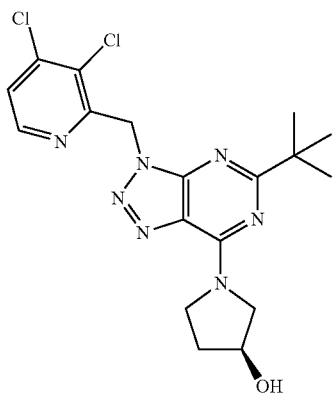 [SMILES: CC(C)(C)c1nc(N2CC[C@H](O)C2)c2nnn(Cc3nccc(Cl)c3Cl)c2n1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 2-(bromomethyl)-3,4-dichloropyridine hydrobromide as white solid. MS(m/e): 422.3 (MH+).

Example 149

(S)-1-[5-tert-Butyl-3-(5-methyl-[1,2,4]oxadiazol-3-ylmethyl)-3H-[1,2,3]triazolo[4,5-d]pyrimidin-7-yl]-pyrrolidin-3-ol

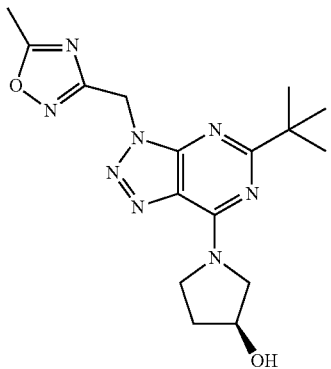 [SMILES: Cc1nc(Cn2nnc3c(N4CC[C@H](O)C4)nc(C(C)(C)C)nc32)no1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 3-(chloromethyl)-5-methyl-1,2,4-oxadiazole as light-yellow gum. MS(m/e): 359.3 (MH+).

Example 150

(S)-1-[5-tert-Butyl-3-(5-methyl-[1,3,4]oxadiazol-2-ylmethyl)-3H-[1,2,3]triazolo[4,5-d]pyrimidin-7-yl]-pyrrolidin-3-ol

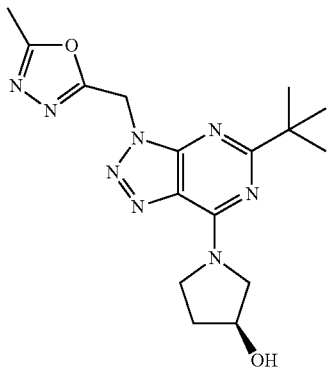 [SMILES: Cc1nnc(Cn2nnc3c(N4CC[C@H](O)C4)nc(C(C)(C)C)nc32)o1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin- 7-yl)-pyrrolidin-3-yl-ester (example 136, step 1) and 2-(chloromethyl)-5-methyl-1,3,4-oxadiazole as light-yellow gum. MS(m/e): 359.5 (MH⁺).

Example 151

(S)-1-[5-tert-Butyl-3-(1-methyl-1H-tetrazol-5-ylmethyl)-3H-[1,2,3]triazolo[4,5-d]pyrimidin-7-yl]-pyrrolidin-3-ol

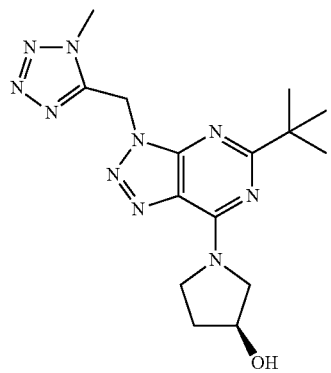 [SMILES: Cn1nnnc1Cn1nnc2c(N3CC[C@H](O)C3)nc(C(C)(C)C)nc21]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 5-(chloromethyl)-1-methyl-1H-tetrazole as light-yellow gum. MS(m/e): 359.2 (MH⁺).

Alternative Conditions:

(S)-1-(5-tert-butyl-3H-[1,2,3]triazolo[4,5-d]pyrimidin-7-yl)pyrrolidin-3-ol. n HCl (5 g) was dissolved in DMF (23.7 g, 25.0 ml). DBU (6.43 g, 6.37 ml) was added dropwise over 5-10 min. A solution of 5-(chloromethyl)-1-methyl-1H-tetrazole (3.33 g) in DMF (23.7 g, 25.0 ml) was added dropwise over 35 min at RT. The orange solution was stirred for 2 h. The reaction mixture was added to 25% aqueous NH4Cl (100 ml). MTBE (148 g, 200 ml) was added. The aqueous phase was separated and extracted with MTBE (148 g, 200 ml). The organic phases were washed sequentially with water (100 g, 100 ml) and half saturated NaCl (100 ml). Then the organic phases were combined dried over MgSO4 and evaporated at 45° C./down to 10 mbar to give 5.75 g of crude product as a white foam.

3.6 g of the crude product was purified by preparative SFC, column: Kromasil 60 SIL, 5 um, 21.2×250 mm, 80% CO2/ 20% MeOH, 40° C. to give 1.98 g of the product. Crystallization: 1.3 g of the product was crystallized from iPrOAc/ Heptane (ca 1:1) to give 1.2 g of product as a white powder (seed crystals were obtained from test tube cryst. tests in iPrOAc/Heptane and tAmOH/heptane mixture).

Example 152

(S)-1-[5-tert-Butyl-3-(2-methyl-2H-[1,2,4]triazol-3-ylmethyl)-3H-[1,2,3]triazolo[4,5-d]pyrimidin-7-yl]-pyrrolidin-3-ol

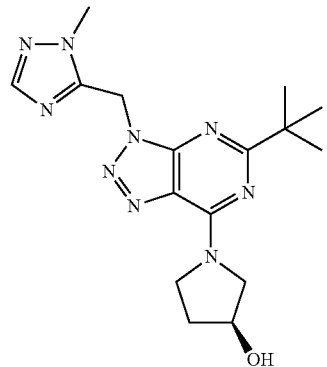 [SMILES: Cn1ncnc1Cn1nnc2c(N3CC[C@H](O)C3)nc(C(C)(C)C)nc21]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 5-(chloromethyl)-1-methyl-1H-1,2,4-triazole hydrochloride as colorless gum. MS(m/e): 358.2 (MH⁺).

Example 153

(S)-1-[5-tert-Butyl-3-(4,5-dimethyl-4H-[1,2,4]triazol-3-ylmethyl)-3H-[1,2,3]triazolo[4,5-d]pyrimidin-7-yl]-pyrrolidin-3-ol

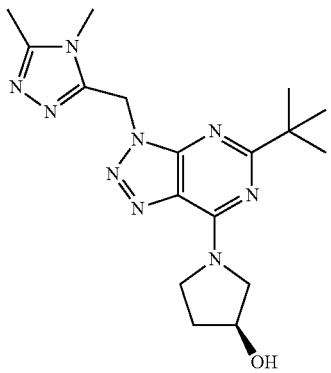 [SMILES: Cc1nnc(Cn2nnc3c(N4CC[C@H](O)C4)nc(C(C)(C)C)nc32)n1C]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 3-(chloromethyl)-4,5-dimethyl-4H-1,2,4-triazole hydrochloride as white solid. MS(m/e): 372.4 (MH+).

Example 154

(S)-1-[5-tert-Butyl-3-(3-methyl-3H-[1,2,3]triazol-4-ylmethyl)-3H-[1,2,3]triazolo[4,5-d]pyrimidin-7-yl]-pyrrolidin-3-ol

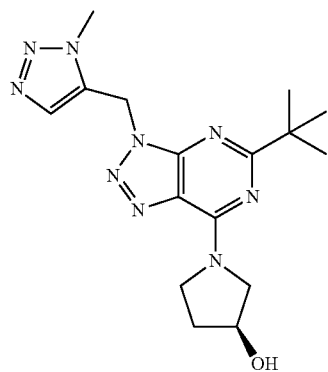 [SMILES: Cn1nncc1Cn1nnc2c(N3CC[C@H](O)C3)nc(C(C)(C)C)nc21]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 5-(chloromethyl)-1-methyl-1H-1,2,3-triazole hydrochloride as light-yellow gum. MS(m/e): 358.2 (MH+).

Example 155

(S)-1-[5-tert-Butyl-3-(2,5-dimethyl-2H-pyrazol-3-ylmethyl)-3H-[1,2,3]triazolo[4,5-d]pyrimidin-7-yl]-pyrrolidin-3-ol

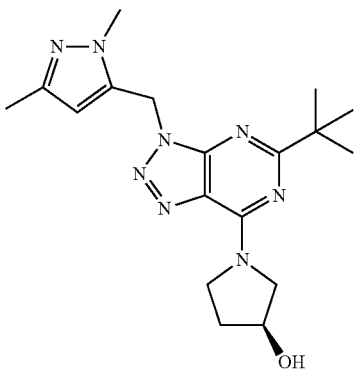 [SMILES: Cc1cc(Cn2nnc3c(N4CC[C@H](O)C4)nc(C(C)(C)C)nc32)n(C)n1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 5-(chloromethyl)-1,3-dimethyl-1H-pyrazole as white solid. MS(m/e): 371.3 (MH+).

Example 156

5-tert-Butyl-7-(3,3-difluoro-pyrrolidin-1-yl)-3-(3-trifluoromethyl-[1,2,4]oxadiazol-5-ylmethyl)-3H-[1,2,3]triazolo[4,5-d]pyrimidine

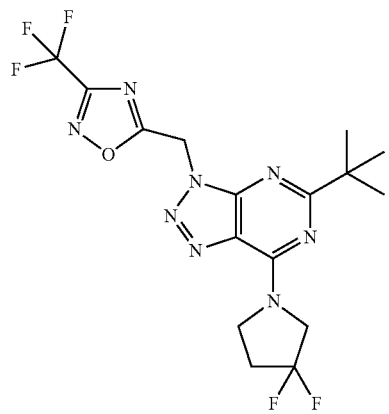 [SMILES: CC(C)(C)c1nc(N2CCC(F)(F)C2)c2nnn(Cc3nc(C(F)(F)F)no3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 5-(chloromethyl)-3-(trifluoromethyl)-1,2,4-oxadiazole and isolated as brown gum. MS(m/e): 433.3 (MH+).

Example 157

5-tert-Butyl-3-(1-cyclopropyl-1H-tetrazol-5-ylmethyl)-7-(3,3-difluoro-pyrrolidin-1-yl)-3H-[1,2,3]triazolo[4,5-d]pyrimidine

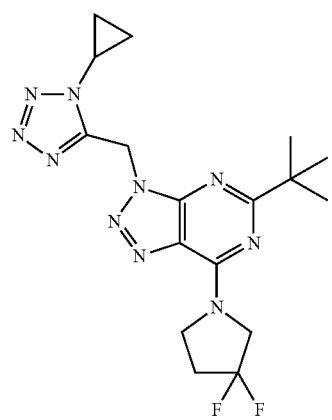 [SMILES: CC(C)(C)c1nc(N2CCC(F)(F)C2)c2nnn(Cc3nnnn3C3CC3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo[4,5-d]pyrimidine and 5-(chloromethyl)-1-cyclopropyl-1H-tetrazole and isolated as red gum. MS(m/e): 405.3 (MH+).

Example 158

(S)-1-{5-tert-Butyl-3-[2-(7-nitro-benzo[1,2,5]oxa-diazol-4-ylamino)-pyridin-3-ylmethyl]-3H-[1,2,3]triazolo[4,5-d]pyrimidin-7-yl}-pyrrolidin-3-ol

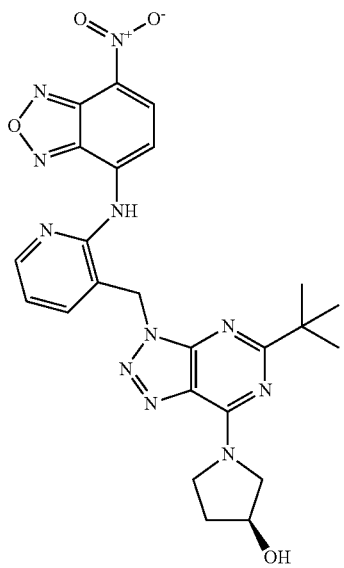 [SMILES: CC(C)(C)c1nc(N2CC[C@H](O)C2)c2nnn(Cc3cccnc3Nc3ccc([N+](=O)[O-])c4nonc34)c2n1]

A mixture of (S)-1-[5-tert-Butyl-3-(2-chloro-pyridin-3-ylmethyl)-3H-[1,2,3]triazolo[4,5-d]pyrimidin-7-yl]-pyrrolidin-3-ol (example 140) (5.30 mg, 13.7 µmol), 7-nitrobenzo[c][1,2,5]oxadiazol-4-amine (2.95 mg, 16.4 µmol), Pd$_2$(dba)$_3$ (1.25 mg, 1.37 µmol), xantphos (2.15 mg, 3.71 µmol) and Cs$_2$CO$_3$ (8.06 mg, 24.8 µmol) in dioxane (500 µl) was heated to 120° C. and stirred for 20 min. The crude material was filtered (celite), concentrated and purified by preparative HPLC eluting with a gradient formed from acetonitrile, water and NEt$_3$. The product containing fractions were evaporated to yield 1.2 mg (16%) of the title compound as red solid. MS(m/e): 532.4 (MH$^+$).

Example 159

(2S,3S)-1-[5-tert-Buty-3-(4-methoxy-benzyl)-3H-[1,2,3]triazolo[4,5-d]pyrimidin-7-yl]-2-hydroxymethyl-pyrrolidin-3-ol

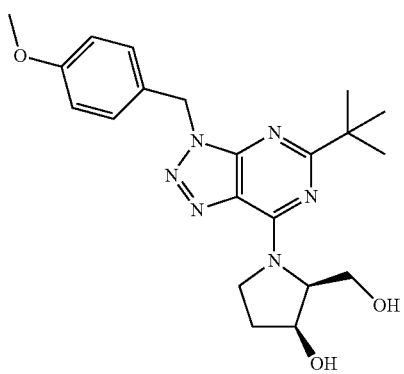 [SMILES: COc1ccc(Cn2nnc3c(N4CC[C@H](O)[C@@H]4CO)nc(C(C)(C)C)nc32)cc1]

In analogy to the procedure described for the synthesis of 4-(5-tert-butyl-3-(4-methoxybenzyl)-3H-[1,2,3]triazolo[4,5-d]pyrimidin-7-yl)morpholine (example 58, step c), the title compound was prepared from 5-tert-butyl-7-chloro-3-(4-methoxybenzyl)-3H-[1,2,3]triazolo[4,5-d]pyrimidine and (2S,3S)-2-(hydroxymethyl)pyrrolidin-3-ol hydrochloride and isolated as light-yellow gum. MS(m/e): 413.4 (MH$^+$).

Example 160

(S)-1-[5-tert-Butyl-3-(1-cyclopropyl-1H-tetrazol-5-ylmethyl)-3H-[1,2,3]triazolo[4,5-d]pyrimidin-7-yl]-pyrrolidin-3-ol

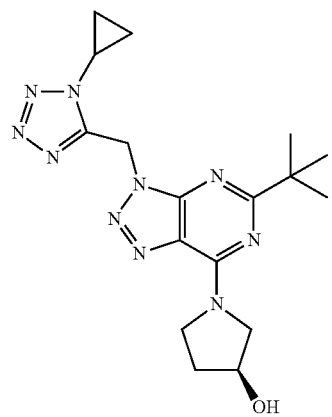 [SMILES: CC(C)(C)c1nc(N2CC[C@H](O)C2)c2nnn(Cc3nnnn3C3CC3)c2n1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoroacetic acid (S)-1-(5-tert-butyl-3H-[1,2,3]triazolo[4,5-d]pyrimidin-7-yl)-pyrrolidin-3-yl-ester (example 136, step 1) and 5-(chloromethyl)-1-cyclopropyl-1H-tetrazole as light-yellow gum. MS(m/e): 385.3 (MH$^+$).

Example 161

(S)-1-[5-tert-Butyl-3-(2,5-dimethyl-2H-[1,2,4]triazol-3-ylmethyl)-3H-[1,2,3]triazolo[4,5-d]pyrimidin-7-yl]-pyrrolidin-3-ol

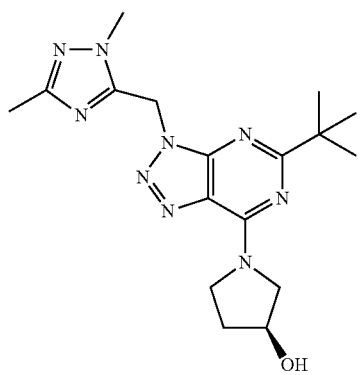 [SMILES: Cc1nc(Cn2nnc3c(N4CC[C@H](O)C4)nc(C(C)(C)C)nc32)n(C)n1]

In analogy to the procedure described for the synthesis of (S)-1-[5-tert-Butyl-3-(4-methyl-furazan-3-ylmethyl)-3H-[1, 2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 5-(chloromethyl)-1,3-dimethyl-1H-1,2,4-triazole as colorless gum. MS(m/e): 372.3 (MH⁺).

Example 162

(S)-1-[5-tert-Butyl-3-(2-methyl-1-oxy-pyridin-3-ylmethyl)-3H-[1,2,3]triazolo[4,5-d]pyrimidin-7-yl]-pyrrolidin-3-ol

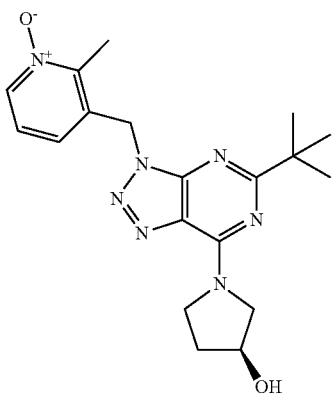 [SMILES: Cc1c(Cn2nnc3c(N4CC[C@H](O)C4)nc(C(C)(C)C)nc32)ccc[n+]1[O-]]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (S)-1-(5-tert-butyl-3H-[1,2,3]triazolo[4,5-d]pyrimidin-7-yl)-pyrrolidin-3-yl-ester (example 136, step 1) and 3-(chloromethyl)-2-methylpyridine 1-oxide as light yellow solid. MS(m/e): 384.3 (MH⁺).

Example 163

5-tert-Butyl-7-(3,3-difluoro-pyrrolidin-1-yl)-3-(2,5-dimethyl-2H-[1,2,4]triazol-3-ylmethyl)-3H-[1,2,3]triazolo[4,5-d]pyrimidine

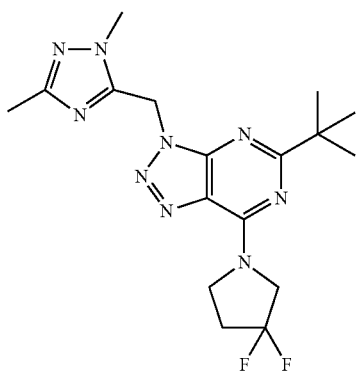 [SMILES: Cc1nc(Cn2nnc3c(N4CCC(F)(F)C4)nc(C(C)(C)C)nc32)n(C)n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-butyl-7-(3,3-difluoropyrrolidin-1-yl)-3H-[1,2,3]triazolo [4,5-d]pyrimidine and 5-(chloromethyl)-1,3-dimethyl-1H-1,2,4-triazole and isolated as light-yellow gum. MS(m/e): 392.3 (MH⁺).

Example 164

(2S,3S)-1-[5-tert-Butyl-3-(4-methyl-furazan-3-ylmethyl)-3H-[1,2,3]triazolo[4,5-d]pyrimidin-7-yl]-2-hydroxymethyl-pyrrolidin-3-ol

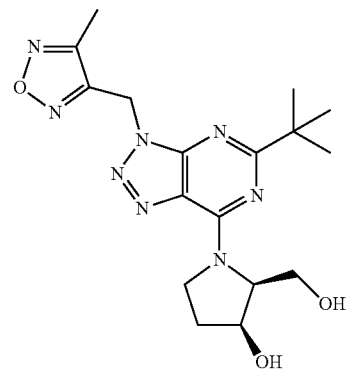 [SMILES: Cc1nonc1Cn1nnc2c(N3CC[C@H](O)[C@@H]3CO)nc(C(C)(C)C)nc21]

Step 1: Trifluoro-acetic acid (2S,3S)-1-(5-tert-butyl-3H-[1,2,3]triazolo[4,5-d]pyrimidin-7-yl)-2-(2,2,2-trifluoro-acetoxymethyl)-pyrrolidin-3-yl ester

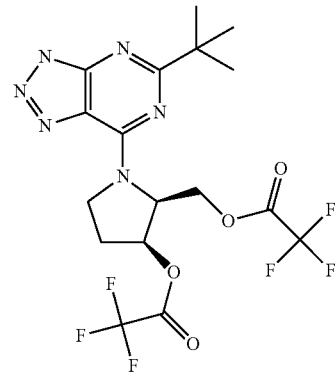 [SMILES: CC(C)(C)c1nc(N2CC[C@H](OC(=O)C(F)(F)F)[C@@H]2COC(=O)C(F)(F)F)c2nn[nH]c2n1]

A mixture of (2S,3S)-1-(5-tert-butyl-3-(4-methoxybenzyl)-3H-[1,2,3]triazolo[4,5-d]pyrimidin-7-yl)-2-(hydroxymethyl)pyrrolidin-3-ol (example 159) (9.0 mg, 21.8 mol) and triethylsilane (7.61 mg, 10.5 µl, 65.5 µmol) in TFA (200 µl) heated to 70° C. and stirred for 21 h. The reaction mixture was concentrated in vacuo and used without further purification in the consecutive step.

Step 2

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (2S,3S)-1-(5-tert-butyl-3H-[1,2,3]triazolo[4,5-d]pyrimidin-7-yl)-2- (2,2,2-trifluoro-acetoxymethyl)-pyrrolidin-3- yl ester (example 164, step 1) and 3-(bromomethyl)-4-methyl-1,2,5-oxadiazole as light yellow gum, MS(m/e): 389.3 (MH⁺).

Example 165

(2S,3S)-1-[5-tert-Butyl-3-(1-methyl-1H-tetrazol-5-ylmethyl)-3H-[1,2,3]triazolo[4,5-d]pyrimidin-7-yl]-2-hydroxymethyl-pyrrolidin-3-ol

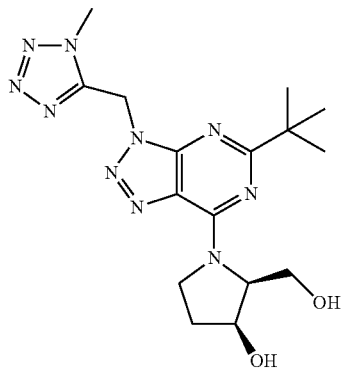 [SMILES: Cn1nnnc1Cn1nnc2c(N3CC[C@H](O)[C@@H]3CO)nc(C(C)(C)C)nc21]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (2S,3S)-1-(5-tert-butyl-3H-[1,2,3]triazolo[4,5-d]pyrimidin-7-yl)-2-(2,2,2-trifluoro-acetoxymethyl)-pyrrolidin-3-yl ester (example 164, step 1) and 5-(chloromethyl)-1-methyl-1H-tetrazole as white solid. MS(m/e): 389.3 (MH⁺).

Example 166

(2S,3S)-1-[5-tert-Butyl-3-(1-cyclopropyl-1H-tetrazol-5-ylmethyl)-3H-[1,2,3]triazolo[4,5-d]pyrimidin-7-yl]-2-hydroxymethyl-pyrrolidin-3-ol

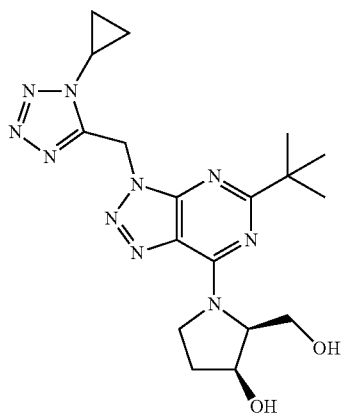 [SMILES: CC(C)(C)c1nc(N2CC[C@H](O)[C@@H]2CO)c2nnn(Cc3nnnn3C3CC3)c2n1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (2S,3S)-1-(5-tert-butyl-3H-[1,2,3]triazolo[4,5-d]pyrimidin-7-yl)-2-(2,2,2- trifluoro-acetoxymethyl)-pyrrolidin-3-yl ester (example 164, step 1) and 5-(chloromethyl)-1-cyclopropyl-1H-tetrazole as light-yellow solid. MS(m/e): 415.4 (MH⁺).

Example 167

(2S,3S)-1-[5-tert-Butyl-3-(3-chloro-pyridin-2-ylmethyl)-3H-[1,2,3]triazolo[4,5-d]pyrimidin-7-yl]-2-hydroxymethyl-pyrrolidin-3-ol

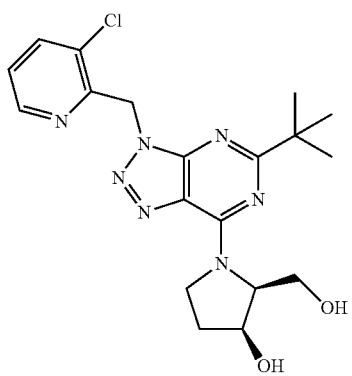

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (2S,3S)-1-(5-tert-butyl-3H-[1,2,3]triazolo[4,5-d]pyrimidin-7-yl)-2-(2,2,2-trifluoro-acetoxymethyl)-pyrrolidin-3-yl ester (example 164, step 1) and 3-chloro-2-(chloromethyl) pyridine as red gum. MS(m/e): 418.3 (MH⁺).

Example 168

(2S,3S)-1-[5-tert-Butyl-3-(2-methanesulfonyl-benzyl)-3H-[1,2,3]triazolo[4,5-d]pyrimidin-7-yl]-2-hydroxymethyl-pyrrolidin-3-ol

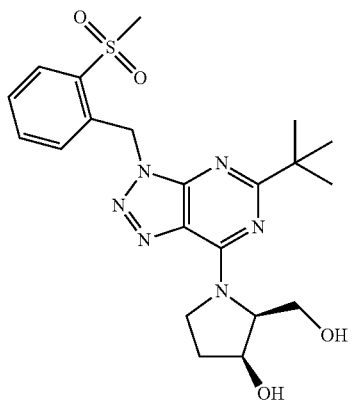 [SMILES: CC(C)(C)c1nc(N2CC[C@H](O)[C@@H]2CO)c2nnn(Cc3ccccc3S(C)(=O)=O)c2n1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (2S,3S)-1-(5-tert-butyl-3H-[1,2,3]triazolo[4,5-d]pyrimidin-7-yl)-2-(2,2,2- trifluoro-acetoxymethyl)-pyrrolidin-3- yl ester (example 164, step 1) and 1-(bromomethyl)-2-(methylsulfonyl)benzene as white solid. MS(m/e): 461.3 (MH⁺).

Example 169

(2S,3S)-1-[5-tert-Butyl-3-(2-methyl-2H-[1,2,4]triazol-3-ylmethyl)-3H-[1,2,3]triazolo[4,5-d]pyrimidin-7-yl]-2-hydroxymethyl-pyrrolidin-3-ol

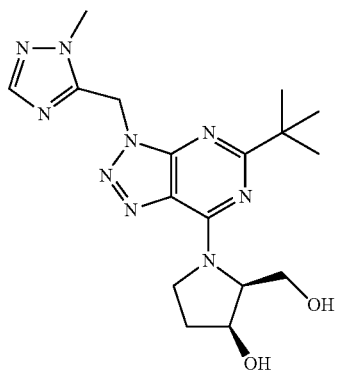 [SMILES: Cn1ncnc1Cn1nnc2c(N3CC[C@H](O)[C@@H]3CO)nc(C(C)(C)C)nc21]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (2S,3S)-1-(5-tert-butyl-3H-[1,2,3]triazolo[4,5-d]pyrimidin-7-yl)-2-(2,2,2-trifluoro-acetoxymethyl)-pyrrolidin-3-yl ester (example 164, step 1) and 5-(chloromethyl)-1-methyl-1H-1,2,4-triazole hydrochloride as white solid. MS(m/e): 388.3 (MH⁺).

Example 170

(2S,3S)-1-[5-tert-Butyl-3-(4,5-dimethyl-4H-[1,2,4]triazol-3-ylmethyl)-3H-[1,2,3]triazolo[4,5-d]pyrimidin-7-yl]-2-hydroxymethyl-pyrrolidin-3-ol

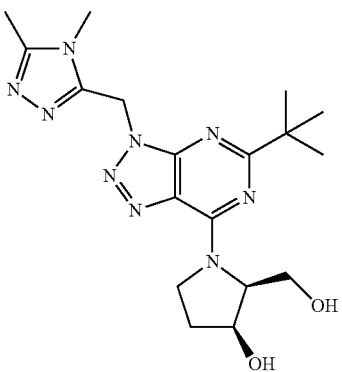 [SMILES: Cc1nnc(Cn2nnc3c(N4CC[C@H](O)[C@@H]4CO)nc(C(C)(C)C)nc32)n1C]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (2S,3S)-1-(5-tert-butyl-3H-[1,2,3]triazolo[4,5-d]pyrimidin-7-yl)-2-(2,2,2-trifluoro-acetoxymethyl)-pyrrolidin-3-yl ester (example 164, step 1) and 3-(chloromethyl)-4,5-dimethyl-4H-1,2,4-triazole hydrochloride as white solid. MS(m/e): 402.4 (MH⁺).

Example 171

(2S,3S)-1-[5-tert-Butyl-3-(3-methyl-3H-[1,2,3]triazol-4-ylmethyl)-3H-[1,2,3]triazolo[4,5-d]pyrimidin-7-yl]-2-hydroxymethyl-pyrrolidin-3-ol

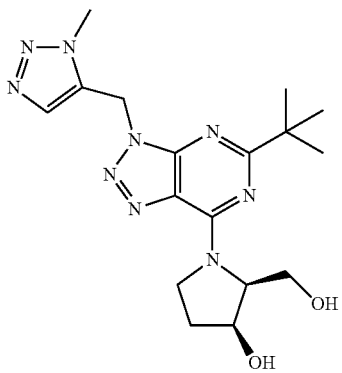 [SMILES: Cn1nncc1Cn1nnc2c(N3CC[C@H](O)[C@@H]3CO)nc(C(C)(C)C)nc21]

In analogy to the procedure described for the synthesis of(S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (2S,3S)-1-(5-tert-butyl-3H-[1,2,3]triazolo[4,5-d]pyrimidin-7-yl)-2-(2,2,2-trifluoro-acetoxymethyl)-pyrrolidin-3-yl ester (example 164, step 1) and 5-(chloromethyl)-1-methyl-1H-1,2,3-triazole hydrochloride as light-yellow solid. MS(m/e): 388.3 (MH⁺).

Example 172

(2S,3S)-1-[5-tert-Butyl-3-(2-chloro-pyridin-3-ylmethyl)-3H-[1,2,3]triazolo[4,5-d]pyrimidin-7-yl]-2-hydroxymethyl-pyrrolidin-3-ol

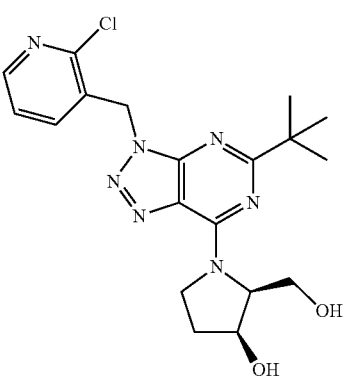 [SMILES: CC(C)(C)c1nc(N2CC[C@H](O)[C@@H]2CO)c2nnn(Cc3cccnc3Cl)c2n1]

In analogy to the procedure described for the synthesis of (S)-1-[5-tert-Butyl-3-(4-methyl-furazan-3-ylmethyl)-3H-[1,2,3]triazolo[4,5-d]pyrimidin-7-yl]-pyrrolidin-3-ol (example 136) the title compound was prepared from trifluoro-acetic acid (2S,3S)-1-(5-tert-butyl-3H-[1,2,3]triazolo[4,5-d]pyrimidin-7-yl)-2-(2,2,2-trifluoro-acetoxymethyl)-pyrrolidin-3- yl ester (example 164, step 1) and 3-(bromomethyl)-2-chloropyridine hydrobromide as white solid. MS(m/e): 418.3 (MH⁺).

Example 173

5-tert-Butyl-3-(4-methyl-furazan-3-ylmethyl)-7-(3,3,4,4-tetrafluoro-pyrrolidin-1-yl)-3H-[1,2,3]triazolo[4,5-d]pyrimidine

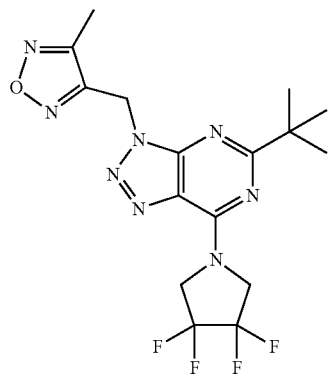 [SMILES: Cc1nonc1Cn1nnc2c(N3CC(F)(F)C(F)(F)C3)nc(C(C)(C)C)nc21]

Step 1

5-tert-Butyl-3-(4-methoxy-benzyl)-7-(3,3,4,4-tetrafluoro-pyrrolidin-1-yl)-3H-[1,2,3]triazolo[4,5-d]pyrimidine

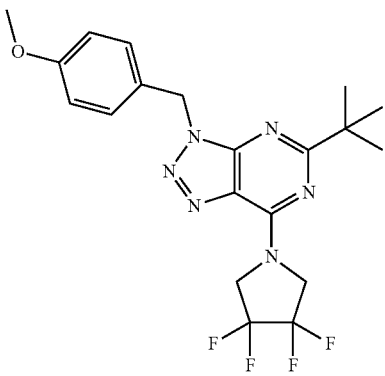 [SMILES: COc1ccc(Cn2nnc3c(N4CC(F)(F)C(F)(F)C4)nc(C(C)(C)C)nc32)cc1]

In analogy to the procedure described for the synthesis of 4-(5-tert-butyl-3-(4-methoxybenzyl)-3H-[1,2,3]triazolo[4,5-d]pyrimidin-7-yl)morpholine (example 58, step c), the title compound was prepared from 5-tert-butyl-7-chloro-3-(4-methoxybenzyl)-3H-[1,2,3]triazolo[4,5-d]pyrimidine and 3,3,4,4-tetrafluoropyrrolidine hydrochloride and used without further purification in the consecutive step.

Step 2

5-tert-Butyl-7-(3,3,4,4-tetrafluoro-pyrrolidin-1-yl)-3H-[1,2,3]triazolo[4,5-d]pyrimidine

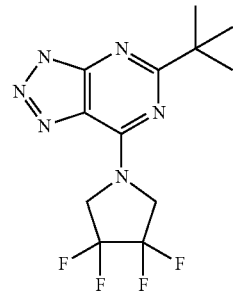 [SMILES: CC(C)(C)c1nc(N2CC(F)(F)C(F)(F)C2)c2nn[nH]c2n1]

The crude 5-tert-Butyl-3-(4-methoxy-benzyl)-7-(3,3,4,4-tetrafluoro-pyrrolidin-1-yl)-3H-[1,2,3]triazolo[4,5-d]pyrimidine was treated with triethylsilane in TFA and heated to 70° C. for 20 h and evaporated. The crude material was used without further purification in the consecutive step.

Step 3

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(3,3,4,4-tetrafluoro-pyrrolidin-1-yl)-3H-[1,2,3]triazolo[4,5-d]pyrimidine and 3-(bromomethyl)-4-methyl-1,2,5-oxadiazole and isolated as light-yellow gum. MS(m/e): 415.3 (MH⁺).

Example 174

5-tert-Butyl-3-(3-methyl-[1,2,4]oxadiazol-5-ylmethyl)-7-(3,3,4,4-tetrafluoro-pyrrolidin-1-yl)-3H-[1,2,3]triazolo[4,5-d]pyrimidine

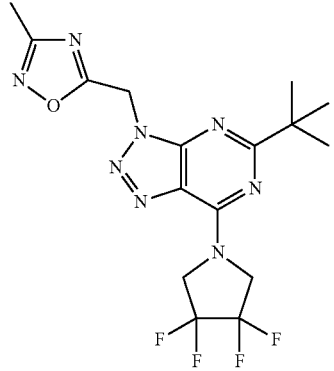 [SMILES: Cc1noc(Cn2nnc3c(N4CC(F)(F)C(F)(F)C4)nc(C(C)(C)C)nc32)n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(3,3,4,4-tetrafluoro-pyrrolidin-1-yl)-3H-[1,2,3]triazolo[4,5-d]pyrimidine and 5-(chloromethyl)-3-methyl-1,2,4-oxadiazole and isolated as light-yellow gum. MS(m/e): 415.3 (MH⁺).

Example 175

5-tert-Butyl-3-(5-methyl-[1,3,4]oxadiazol-2-ylmethyl)-7-(3,3,4,4-tetrafluoro-pyrrolidin-1-yl)-3H-[1,2,3]triazolo[4,5-d]pyrimidine

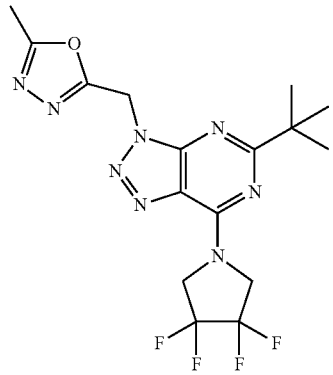 [SMILES: Cc1nnc(Cn2nnc3c(N4CC(F)(F)C(F)(F)C4)nc(C(C)(C)C)nc32)o1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(3,3,4,4-tetrafluoro-pyrrolidin-1-yl)-3H-[1,2,3]triazolo[4,5-d]pyrimidine and 2-(chloromethyl)-5-methyl-1,3,4-oxadiazole and isolated as light-yellow gum. MS(m/e): 415.3 (MH⁺).

Example 176

5-tert-Butyl-3-(1-methyl-1H-tetrazol-5-ylmethyl)-7-(3,3,4,4-tetrafluoro-pyrrolidin-1-yl)-3H-[1,2,3]triazolo[4,5-d]pyrimidine

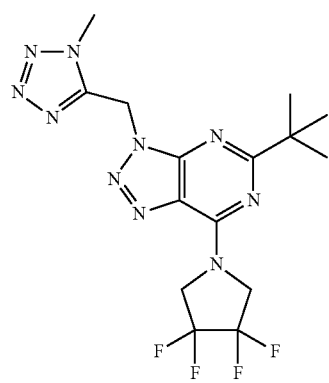 [SMILES: Cn1nnnc1Cn1nnc2c(N3CC(F)(F)C(F)(F)C3)nc(C(C)(C)C)nc21]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(3,3,4,4-tetrafluoro-pyrrolidin-1-yl)-3H-[1,2,3]triazolo[4,5-d]pyrimidine and 5-(chloromethyl)-1-methyl-1H-tetrazole and isolated as yellow solid. MS(m/e): 415.3 (MH⁺).

Example 177

5-tert-Butyl-3-(4,5-dimethyl-4H-[1,2,4]triazol-3-ylmethyl)-7-(3,3,4,4-tetrafluoro-pyrrolidin-1-yl)-3H-[1,2,3]triazolo[4,5-d]pyrimidine

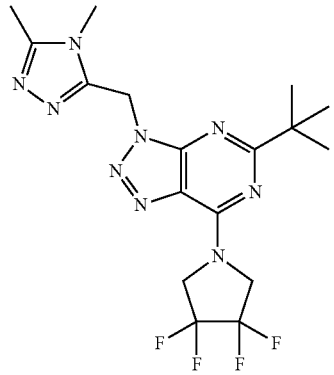 [SMILES: Cc1nnc(Cn2nnc3c(N4CC(F)(F)C(F)(F)C4)nc(C(C)(C)C)nc32)n1C]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(3,3,4,4-tetrafluoro-pyrrolidin-1-yl)-3H-[1,2,3]triazolo[4,5-d]pyrimidine and 3-(chloromethyl)-4,5-dimethyl-4H-1,2,4-triazole hydrochloride and isolated as white solid. MS(m/e): 428.3 (MH⁺).

Example 178

5-tert-Butyl-3-(3-methyl-3H-[1,2,3]triazol-4-ylmethyl)-7-(3,3,4,4-tetrafluoro-pyrrolidin-1-yl)-3H-[1,2,3]triazolo[4,5-d]pyrimidine

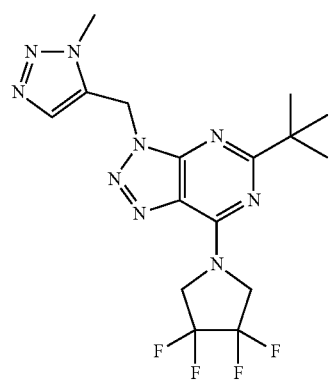 [SMILES: Cn1nncc1Cn1nnc2c(N3CC(F)(F)C(F)(F)C3)nc(C(C)(C)C)nc21]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(3,3,4,4-tetrafluoro-pyrrolidin-1-yl)-3H-[1,2,3]triazolo[4,5-d]pyrimidine and 5-(chloromethyl)-1-methyl-1H-1,2,3-triazole hydrochloride and isolated as light-yellow gum. MS(m/e): 414.3 (MH+).

Example 179

5-tert-Butyl-3-(4-methyl-furazan-3-ylmethyl)-7-(2-oxa-6-aza-spiro[3.3]hept-6-yl)-3H-[1,2,3]triazolo[4,5-d]pyrimidine

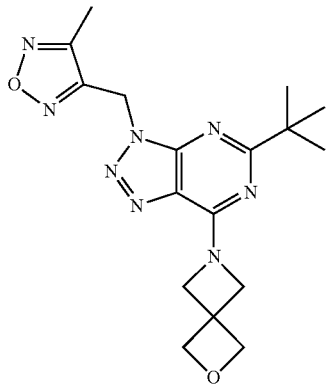 [SMILES: Cc1nonc1Cn1nnc2c(N3CC4(COC4)C3)nc(C(C)(C)C)nc21]

Step 1

5-tert-Butyl-3-(4-methoxy-benzyl)-7-(2-oxa-6-aza-spiro[3.3]hept-6-yl)-3H-[1,2,3]triazolo[4,5-d]pyrimidine

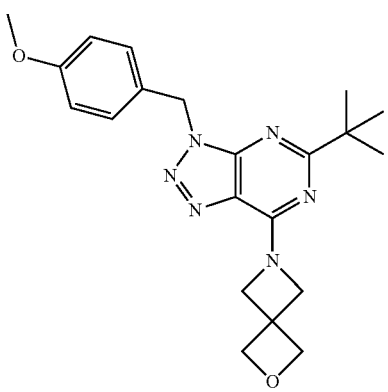 [SMILES: COc1ccc(Cn2nnc3c(N4CC5(COC5)C4)nc(C(C)(C)C)nc32)cc1]

In analogy to the procedure described for the synthesis of 4-(5-tert-butyl-3-(4-methoxy benzyl)-3H-[1,2,3]triazolo[4,5-d]pyrimidin-7-yl)morpholine (example 58, step c), the title compound was prepared from 5-tert-butyl-7-chloro-3-(4-methoxybenzyl)-3H-[1,2,3]triazolo[4,5-d]pyrimidine and 2-oxa-6-azaspiro[3.3]heptane oxalate and used without further purification in the consecutive step.

Step 2

[1-(5-tert-Butyl-3H-[1,2,3]triazolo[4,5-d]pyrimidin-7-yl)-3-chloromethyl-azetidin-3-yl]-methanol

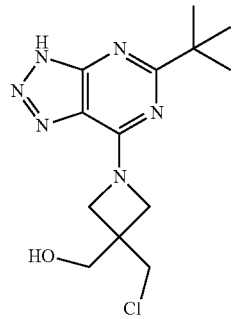 [SMILES: CC(C)(C)c1nc(N2CC(CO)(CCl)C2)c2nn[nH]c2n1]

A mixture of crude 6-(5-tert-butyl-3-(4-methoxybenzyl)-3H-[1,2,3]triazolo[4,5-d]pyrimidin-7-yl)-2-oxa-6-azaspiro[3.3]heptane (example 179, step 1) (361 mg, 915 µmol) and palladium (II) chloride (81.1 mg, 458 µmol) in MeOH (3.00 mL) was stirred at room temperature for 9 h under $H_2$ (1 atm) atmosphere. The mixture was filtered through cotton and concentrated in vacuo. The residue was used without further purification in the consecutive step.

Step 3

5-tert-Butyl-7-(2-oxa-6-aza-spiro[3.3]hept-6-yl)-3H-[1,2,3]triazolo[4,5-d]pyrimidine

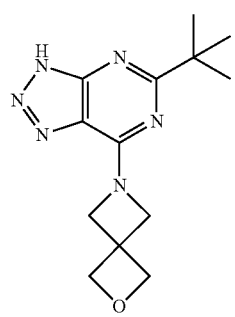 [SMILES: CC(C)(C)c1nc(N2CC3(COC3)C2)c2nn[nH]c2n1]

A mixture of (1-(5-tert-butyl-3H-[1,2,3]triazolo[4,5-d]pyrimidin-7-yl)-3-(chloromethyl)azetidin-3-yl)methanol (284 mg, 915 µmol) (example 179, step 2) and potassium tert-butoxide (205 mg, 1.83 mmol) in THF (3 mL) at 0° C. was stirred to room temperature and stirred for 20 h. The mixture was filtered, concentrated in vacuo and used without further purification in the consecutive step.

Step 4

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(2-oxa-6-aza-spiro[3.3]hept-6-yl)-3H-[1,2,3]triazolo[4,5-d]pyrimidine and 3-(bromomethyl)-4-methyl-1,2,5-oxadiazole and isolated as white solid. MS(m/e): 371.3 (MH+).

Example 180

5-tert-Butyl-3-(3-methyl-[1,2,4]oxadiazol-5-ylmethyl)-7-(2-oxa-6-aza-spiro[3.3]hept-6-yl)-3H-[1,2,3]triazolo[4,5-d]pyrimidine

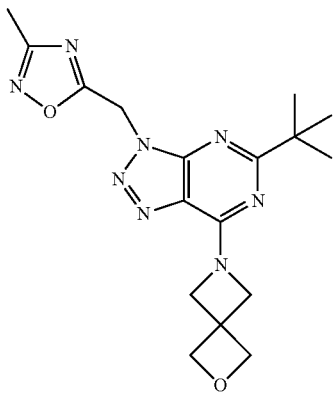 [SMILES: Cc1noc(Cn2nnc3c(N4CC5(COC5)C4)nc(C(C)(C)C)nc32)n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(2-oxa-6-aza-spiro[3.3]hept-6-yl)-3H-[1,2,3]triazolo[4,5-d]pyrimidine and 5-(chloromethyl)-3-methyl-1,2,4-oxadiazole and isolated as light-red solid. MS(m/e): 371.2 (MH+).

Example 181

5-tert-Butyl-3-(5-methyl-[1,3,4]oxadiazol-2-ylmethyl)-7-(2-oxa-6-aza-spiro[3.3]hept-6-yl)-3H-[1,2,3]triazolo[4,5-d]pyrimidine

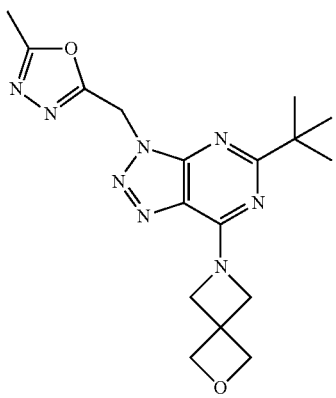 [SMILES: Cc1nnc(Cn2nnc3c(N4CC5(COC5)C4)nc(C(C)(C)C)nc32)o1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(2-oxa-6-aza-spiro[3.3]hept-6-yl)-3H-[1,2,3]triazolo[4,5-d]pyrimidine and 2-(chloromethyl)-5-methyl-1,3,4-oxadiazole and isolated as white solid. MS(m/e): 371.2 (MH+).

Example 182

5-tert-Butyl-3-(1-methyl-1H-tetrazol-5-ylmethyl)-7-(2-oxa-6-aza-spiro[3.3]hept-6-yl)-3H-[1,2,3]triazolo[4,5-d]pyrimidine

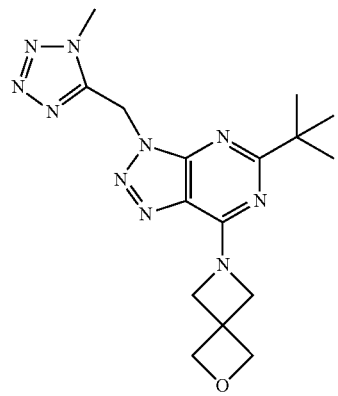 [SMILES: Cn1nnnc1Cn1nnc2c(N3CC4(COC4)C3)nc(C(C)(C)C)nc21]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(2-oxa-6-aza-spiro[3.3]hept-6-yl)-3H-[1,2,3]triazolo[4,5-d]pyrimidine and 5-(chloromethyl)-1-methyl-1H-tetrazole and isolated as white solid. MS(m/e): 371.3 (MH+).

Example 183

5-tert-Butyl-3-(1-cyclopropyl-1H-tetrazol-5-ylmethyl)-7-(2-oxa-6-aza-spiro[3.3]hept-6-yl)-3H-[1,2,3]triazolo[4,5-d]pyrimidine

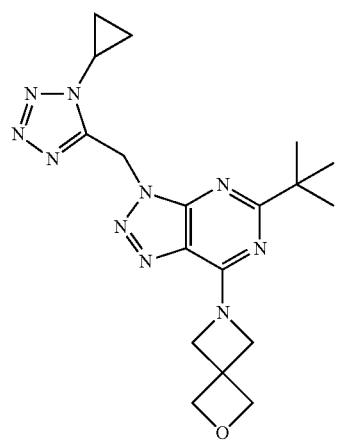 [SMILES: CC(C)(C)c1nc(N2CC3(COC3)C2)c2nnn(Cc3nnnn3C3CC3)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(2-oxa-6-aza-spiro[3.3]hept-6-yl)-3H-[1,2,3]triazolo[4,5-d]pyrimidine and 5-(chloromethyl)-1-cyclopropyl-1H-tetrazole and isolated as white solid. MS(m/e): 397.3 (MH⁺).

Example 184

5-tert-Butyl-3-(4,5-dimethyl-4H-[1,2,4]triazol-3-ylmethyl)-7-(2-oxa-6-aza-spiro[3.3]hept-6-yl)-3H-[1,2,3]triazolo[4,5-d]pyrimidine

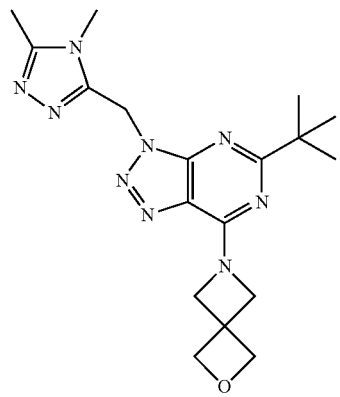 [SMILES: Cc1nnc(Cn2nnc3c(N4CC5(COC5)C4)nc(C(C)(C)C)nc32)n1C]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(2-oxa-6-aza-spiro[3.3]hept-6-yl)-3H-[1,2,3]triazolo[4,5-d]pyrimidine and 3-(chloromethyl)-4,5-dimethyl-4H-1,2,4-triazole hydrochloride and isolated as white solid. MS(m/e): 384.3 (MH⁺).

Example 185

5-tert-Butyl-3-(3-methyl-3H-[1,2,3]triazol-4-ylmethyl)-7-(2-oxa-6-aza-spiro[3.3]hept-6-yl)-3H-[1,2,3]triazolo[4,5-d]pyrimidine

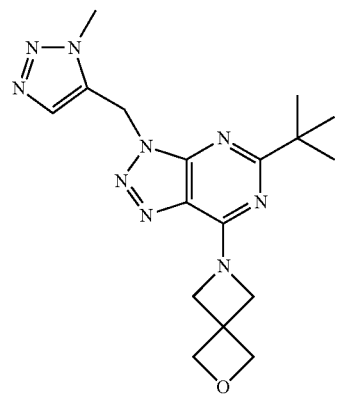 [SMILES: Cn1nncc1Cn1nnc2c(N3CC4(COC4)C3)nc(C(C)(C)C)nc21]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(2-oxa-6-aza-spiro[3.3]hept-6-yl)-3H-[1,2,3]triazolo[4,5-d]pyrimidine and 5-(chloromethyl)-1-methyl-1H-1,2,3-triazole hydrochloride and isolated as white solid. MS(m/e): 370.2 (MH⁺).

Example 186

5-tert-Butyl-3-(2-methanesulfonyl-benzyl)-7-(2-oxa-6-aza-spiro[3.3]hept-6-yl)-3H-[1,2,3]triazolo[4,5-d]pyrimidine

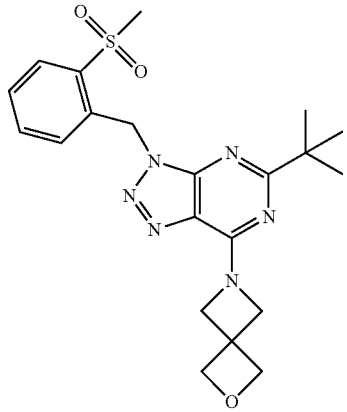 [SMILES: CC(C)(C)c1nc(N2CC3(COC3)C2)c2nnn(Cc3ccccc3S(C)(=O)=O)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(2-oxa-6-aza-spiro[3.3]hept-6-yl)-3H-[1,2,3]triazolo[4,5-d]pyrimidine and 1-(bromomethyl)-2-(methylsulfonyl)benzene and isolated as white solid. MS(m/e): 443.3 (MH⁺).

Example 187

5-tert-Butyl-3-(3-chloro-pyridin-2-ylmethyl)-7-(2-oxa-6-aza-spiro[3.3]hept-6-yl)-3H-[1,2,3]triazolo[4,5-d]pyrimidine

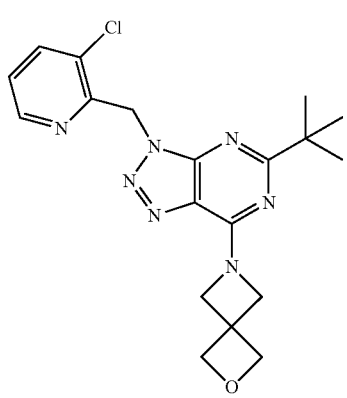 [SMILES: CC(C)(C)c1nc(N2CC3(COC3)C2)c2nnn(Cc3ncccc3Cl)c2n1]

In analogy to the procedure described for the synthesis of 5-tert-butyl-7-(3,3-difluoropyrrolidin-1-yl)-3-ethyl-3H-[1,2,3]triazolo[4,5-d]pyrimidine (example 61), the title compound was prepared from 5-tert-Butyl-7-(2-oxa-6-aza-spiro[3.3]hept-6-yl)-3H-[1,2,3]triazolo[4,5-d]pyrimidine and 3-chloro-2-(chloromethyl)pyridine and isolated as light-brown gum. MS(m/e): 400.3 (MH⁺).

Example 188

1-[5-tert-Butyl-3-(2-chloro-benzyl)-3H-[1,2,3]tria-zolo[4,5-d]pyrimidin-7-yl]-pyrrolidin-3-one

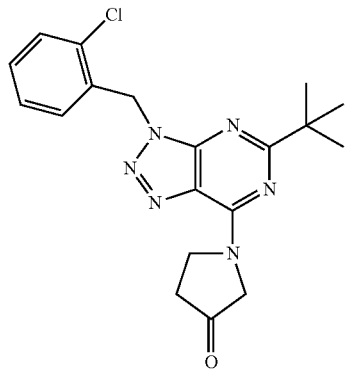 [SMILES: CC(C)(C)c1nc(N2CCC(=O)C2)c2nnn(Cc3ccccc3Cl)c2n1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and pyrrolidin-3-one. MS(m/e): 385.3 (MH⁺).

Example 189

5-tert-Butyl-3-(2-chloro-benzyl)-7-(3,3-dimethyl-pyrrolidin-1-yl)-3H-[1,2,3]triazolo[4,5-d]pyrimidine

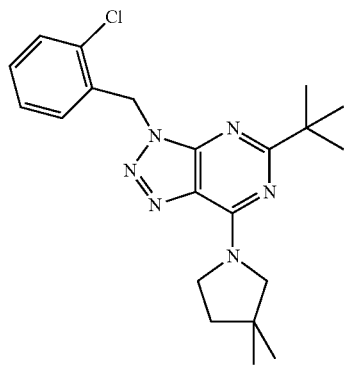 [SMILES: CC1(C)CCN(c2nc(C(C)(C)C)nc3c2nnn3Cc2ccccc2Cl)C1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3,3-dimethylpyrrolidine. MS(m/e): 399.4 (MH⁺).

Example 190

{1-[5-tert-Butyl-3-(2-chloro-benzyl)-3H-[1,2,3]tria-zolo[4,5-d]pyrimidin-7-yl]-pyrrolidin-3-yl}-methyl-amine

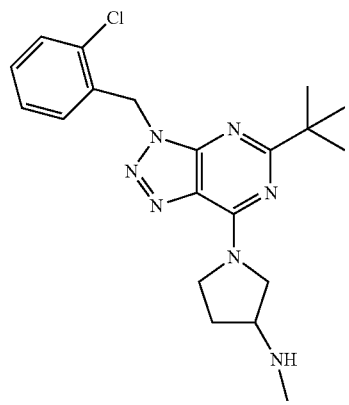 [SMILES: CNC1CCN(c2nc(C(C)(C)C)nc3c2nnn3Cc2ccccc2Cl)C1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and N-methylpyrrolidin-3-amine. MS(m/e): 400.3 (MH⁺).

Example 191

{1-[5-tert-Butyl-3-(2-chloro-benzyl)-3H-[1,2,3]tria-zolo[4,5-d]pyrimidin-7-yl]-pyrrolidin-3-yl}-dim-ethyl-amine

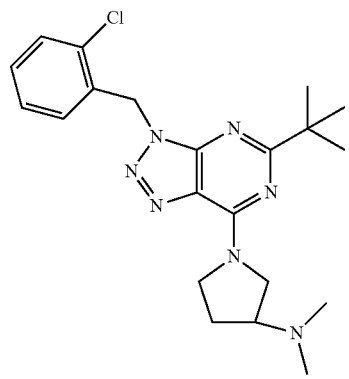 [SMILES: CN(C)C1CCN(c2nc(C(C)(C)C)nc3c2nnn3Cc2ccccc2Cl)C1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and N,N-dimethylpyrrolidin-3-amine. MS(m/e): 414.3 (MH+).

Example 192

N-{(S)-[5-tert-Butyl-3-(2-chloro-benzyl)-3H-[1,2,3]triazolo[4,5-d]pyrimidin-7-yl]-pyrrolidin-3-yl}-acetamide

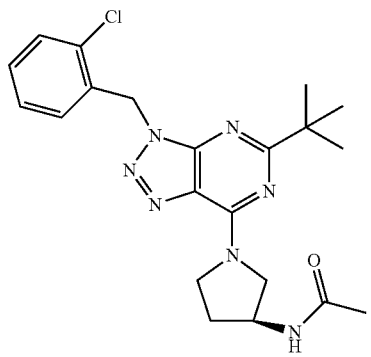 [SMILES: CC(=O)N[C@H]1CCN(c2nc(C(C)(C)C)nc3c2nnn3Cc2ccccc2Cl)C1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (S)-N-(pyrrolidin-3-yl)acetamide. MS(m/e): 428.3 (MH+).

Example 193

N-{(R)-1-[5-tert-Butyl-3-(2-chloro-benzyl)-3H-[1,2,3]triazolo[4,5-d]pyrimidin-7-yl]-pyrrolidin-3-yl}-acetamide

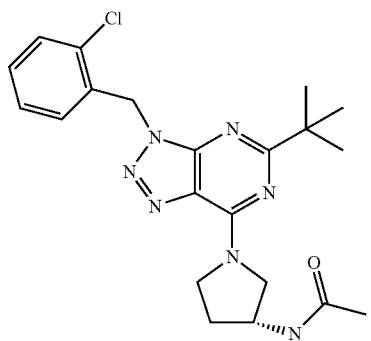

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (R)-N-(pyrrolidin-3-yl)acetamide. MS(m/e): 428.3 (MH+).

Example 194

N-{-[5-tert-Butyl-3-(2-chloro-benzyl)-3H-[1,2,3]triazolo[4,5-d]pyrimidin-7-yl]-pyrrolidin-3-yl}-N-methyl-acetamide

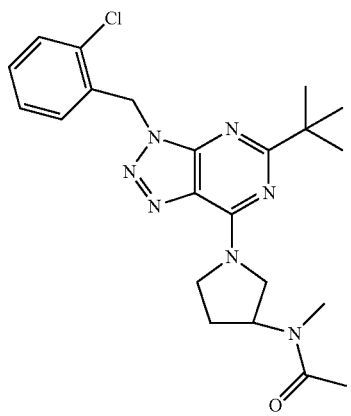 [SMILES: CC(=O)N(C)C1CCN(c2nc(C(C)(C)C)nc3c2nnn3Cc2ccccc2Cl)C1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and N-methyl-N-(pyrrolidin-3-yl)acetamide. MS(m/e): 442.4 (MH+).

Example 195

5-tert-Butyl-3-(2-chloro-benzyl)-7-(3-phenyl-pyrrolidin-1-yl)-3H-[1,2,3]triazolo[4,5-d]pyrimidine

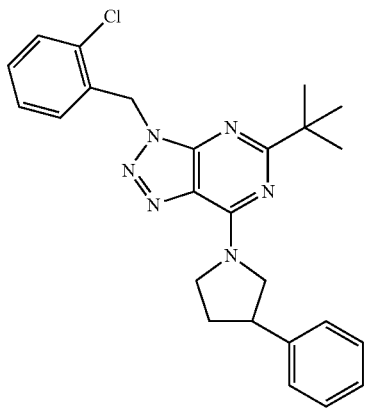 [SMILES: CC(C)(C)c1nc(N2CCC(c3ccccc3)C2)c2nnn(Cc3ccccc3Cl)c2n1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3-phenylpyrrolidine. MS(m/e): 447.4 (MH+).

Example 196

N-{1-[5-tert-Butyl-3-(2-chloro-benzyl)-3H-[1,2,3]triazolo[4,5-d]pyrimidin-7-yl]-pyrrolidin-3-yl}-N-ethyl-acetamide

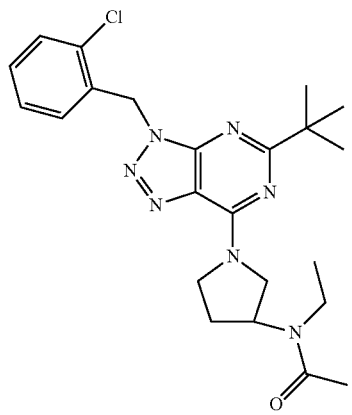 [SMILES: CCN(C(C)=O)C1CCN(c2nc(C(C)(C)C)nc3c2nnn3Cc2ccccc2Cl)C1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and N-ethyl-N-(pyrrolidin-3-yl)acetamide. MS(m/e): 456.5 (MH+).

Example 197

1-[5-tert-Butyl-3-(2-chloro-benzyl)-3H-[1,2,3]triazolo[4,5-d]pyrimidin-7-yl]-azetidine-3-carboxylic acid methyl ester

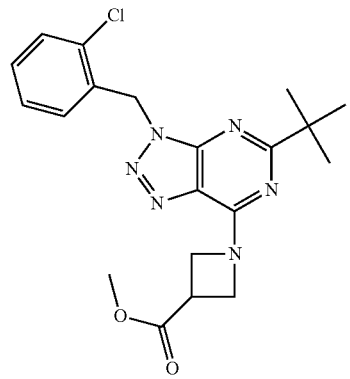 [SMILES: COC(=O)C1CN(c2nc(C(C)(C)C)nc3c2nnn3Cc2ccccc2Cl)C1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and methyl azetidine-3-carboxylate. MS(m/e): 415.3 (MH+).

Example 198

5-tert-Butyl-3-(2-chloro-benzyl)-7-(3-methyl-pyrrolidin-1-yl)-3H-[1,2,3]triazolo[4,5-d]pyrimidine

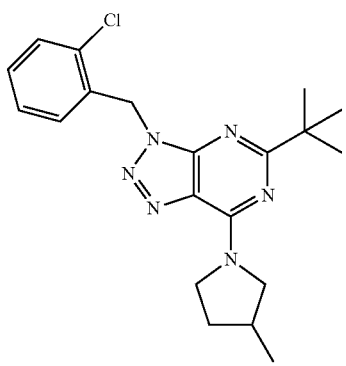 [SMILES: CC1CCN(c2nc(C(C)(C)C)nc3c2nnn3Cc2ccccc2Cl)C1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3-methylpyrrolidine hydrochloride. MS(m/e): 385.3 (MH+).

Example 199

C-{(S)-1-[5-tert-Butyl-3-(2-chloro-benzyl)-3H-[1,2,3]triazolo[4,5-d]pyrimidin-7-yl]-pyrrolidin-2-yl}-methylamine

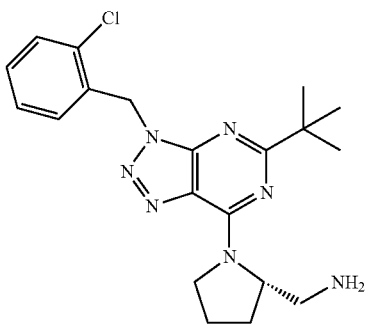 [SMILES: CC(C)(C)c1nc(N2CCC[C@H]2CN)c2nnn(Cc3ccccc3Cl)c2n1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and (S)-pyrrolidin-2-ylmethanamine. MS(m/e): 400.4 (MH+).

Example 200

5-tert-Butyl-3-(2-chloro-benzyl)-7-[2-(1-methyl-1H-pyrazol-3-yl)-pyrrolidin-1-yl]-3H-[1,2,3]triazolo[4,5-d]pyrimidine

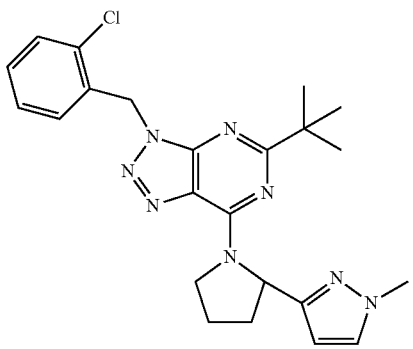 [SMILES: Cn1ccc(C2CCCN2c2nc(C(C)(C)C)nc3c2nnn3Cc2ccccc2Cl)n1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 1-methyl-3-(pyrrolidin-2-yl)-1H-pyrazole. MS(m/e): 451.4

Example 201

5-tert-Butyl-3-(2-chloro-benzyl)-7-[2-(2-methyl-2H-pyrazol-3-yl)-pyrrolidin-1-yl]-3H-[1,2,3]triazolo[4,5-d]pyrimidine

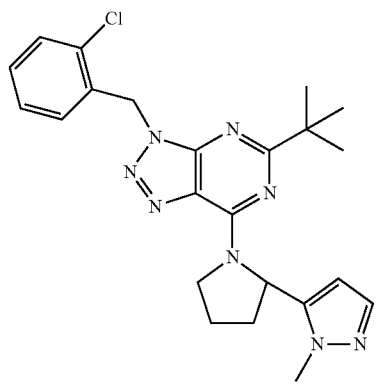 [SMILES: Cn1nccc1C1CCCN1c1nc(C(C)(C)C)nc2c1nnn2Cc1ccccc1Cl]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 1-methyl-5-(pyrrolidin-2-yl)-1H-pyrazole. MS(m/e): 451.4

Example 202

5-tert-Butyl-3-(2-chloro-benzyl)-7-[2-(3-methyl-isoxazol-5-yl)-pyrrolidin-1-yl]-3H-[1,2,3]triazolo[4,5-d]pyrimidine

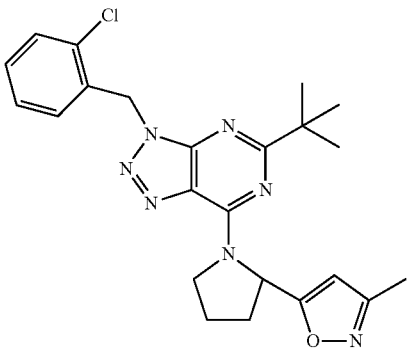 [SMILES: Cc1cc(C2CCCN2c2nc(C(C)(C)C)nc3c2nnn3Cc2ccccc2Cl)on1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3-methyl-5-(pyrrolidin-2-yl)isoxazole. MS(m/e): 452.4

Example 203

5-tert-Butyl-3-(2-chloro-benzyl)-7-[2-(3-methyl-[1,2,4]oxadiazol-5-yl)-pyrrolidin-1-yl]-3H-[1,2,3]triazolo[4,5-d]pyrimidine

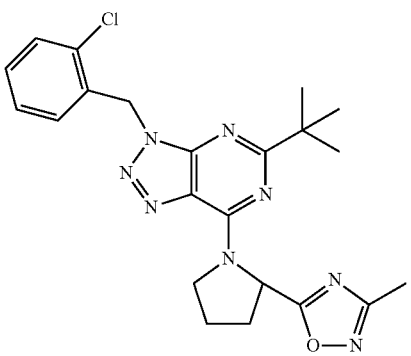 [SMILES: Cc1noc(C2CCCN2c2nc(C(C)(C)C)nc3c2nnn3Cc2ccccc2Cl)n1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and 3-methyl-5-(pyrrolidin-2-yl)-1,2,4-oxadiazole. MS(m/e): 453.4

Example 204

1-[5-tert-Butyl-3-(2-chloro-benzyl)-3H-[1,2,3]triazolo[4,5-d]pyrimidin-7-yl]-pyrrolidin-3-ol

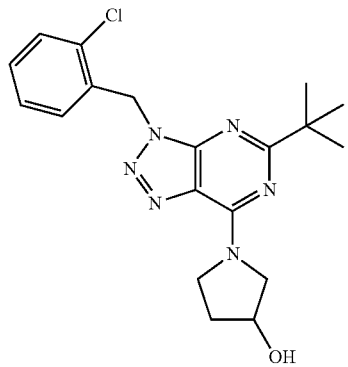 [SMILES: CC(C)(C)c1nc(N2CCC(O)C2)c2nnn(Cc3ccccc3Cl)c2n1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and pyrrolidin-3-ol. MS(m/e): 387.4

Example 205

5-tert-Butyl-3-(2-chloro-benzyl)-7-cyclobutoxy-3H-[1,2,3]triazolo[4,5-d]pyrimidine

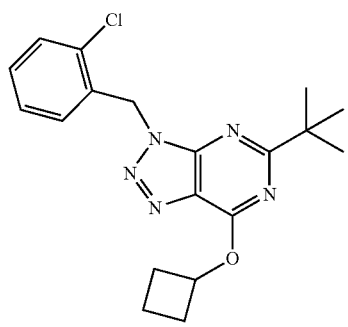 [SMILES: CC(C)(C)c1nc(OC2CCC2)c2nnn(Cc3ccccc3Cl)c2n1]

A mixture of cyclobutanol (173 mg, 2.4 mmol) and NaH (4.8 mg, 0.12 mmol) in DMF (1 mL) was stirred for 30 min at room temperature. 5-tert-butyl-7-chloro-3-(2-chlorobenzyl)-3H-[1,2,3]triazolo[4,5-d]pyrimidine (26.9 mg, 0.08 mmol) was added and the mixture was stirred at room temperature overnight. Formic acid added and the mixture was subjected to preparative HPLC purification on reversed phase eluting with a gradient formed from acetonitrile, water and formic acid. The product containing fractions were evaporated to yield 4 mg (13%) of the title compound. MS(m/e): 372.3.

Example 206

5-tert-Butyl-3-(2-chloro-benzyl)-7-(oxetan-3-yloxy)-3H-[1,2,3]triazolo[4,5-d]pyrimidine

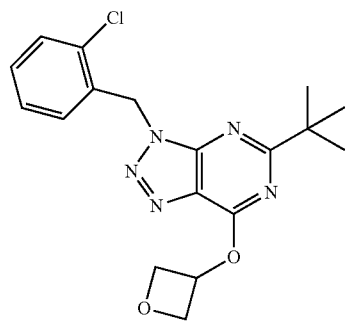 [SMILES: CC(C)(C)c1nc(OC2COC2)c2nnn(Cc3ccccc3Cl)c2n1]

In analogy to the procedure described for the synthesis of 5-tert-Butyl-3-(2-chloro-benzyl)-7-cyclobutoxy-3H-[1,2,3]triazolo[4,5-d]pyrimidine (example 205) the title compound was prepared from 5-tert-butyl-7-chloro-3-(2-chlorobenzyl)-3H-[1,2,3]triazolo[4,5-d]pyrimidine and oxetan-3-ol. MS(m/e): 374.3.

Example 207

5-tert-Butyl-3-(2-chloro-benzyl)-7-methoxy-3H-[1,2,3]triazolo[4,5-d]pyrimidine

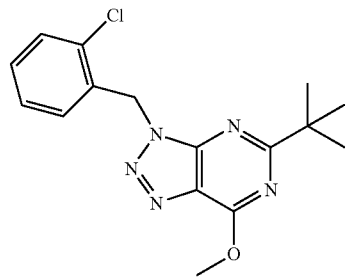 [SMILES: COc1nc(C(C)(C)C)nc2c1nnn2Cc1ccccc1Cl]

In analogy to the procedure described for the synthesis of 5-tert-Butyl-3-(2-chloro-benzyl)-7-cyclobutoxy-3H-[1,2,3]triazolo[4,5-d]pyrimidine (example 205) the title compound was prepared from 5-tert-butyl-7-chloro-3-(2-chlorobenzyl)-3H-[1,2,3]triazolo[4,5-d]pyrimidine and methanol. MS(m/e): 332.2.

Example 208

5-tert-Butyl-3-(2-chloro-benzyl)-7-ethoxy-3H-[1,2,3]triazolo[4,5-d]pyrimidine

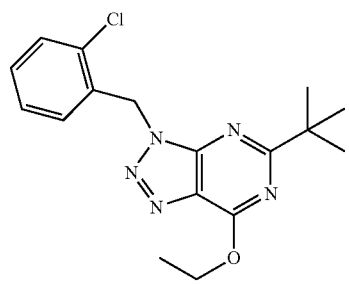 [SMILES: CCOc1nc(C(C)(C)C)nc2c1nnn2Cc1ccccc1Cl]

In analogy to the procedure described for the synthesis of 5-tert-Butyl-3-(2-chloro-benzyl)-7-cyclobutoxy-3H-[1,2,3]triazolo[4,5-d]pyrimidine (example 205) the title compound was prepared from 5-tert-butyl-7-chloro-3-(2-chlorobenzyl)-3H-[1,2,3]triazolo[4,5-d]pyrimidine and ethanol. MS(m/e): 346.2.

Example 209

5-tert-Butyl-3-(2-chloro-benzyl)-7-isopropoxy-3H-[1,2,3]triazolo[4,5-d]pyrimidine

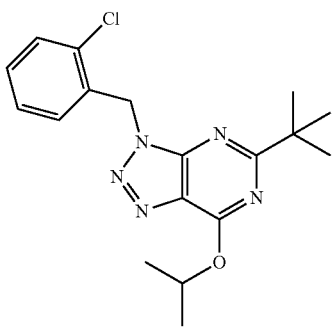 [SMILES: CC(C)Oc1nc(C(C)(C)C)nc2c1nnn2Cc1ccccc1Cl]

In analogy to the procedure described for the synthesis of 5-tert-Butyl-3-(2-chloro-benzyl)-7-cyclobutoxy-3H-[1,2,3]triazolo[4,5-d]pyrimidine (example 205) the title compound was prepared from 5-tert-butyl-7-chloro-3-(2-chlorobenzyl)-3H-[1,2,3]triazolo[4,5-d]pyrimidine and propan-2-ol. MS(m/e): 360.2.

Example 210

5-tert-Butyl-3-(2-chloro-benzyl)-7-cyclopropyl-methoxy-3H-[1,2,3]triazolo[4,5-d]pyrimidine

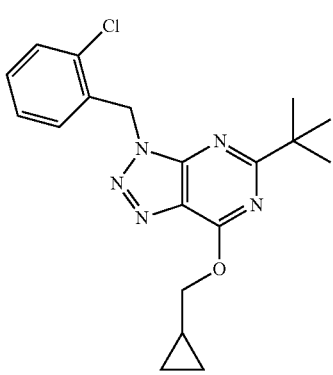 [SMILES: CC(C)(C)c1nc(OCC2CC2)c2nnn(Cc3ccccc3Cl)c2n1]

In analogy to the procedure described for the synthesis of 5-tert-Butyl-3-(2-chloro-benzyl)-7-cyclobutoxy-3H-[1,2,3]triazolo[4,5-d]pyrimidine (example 205) the title compound was prepared from 5-tert-butyl-7-chloro-3-(2-chlorobenzyl)-3H-[1,2,3]triazolo[4,5-d]pyrimidine and cyclopropylmethanol. MS(m/e): 372.3.

Example 211

5-tert-Butyl-3-(2-chloro-benzyl)-7-(1-cyclopropyl-ethoxy)-3H-[1,2,3]triazolo[4,5-d]pyrimidine

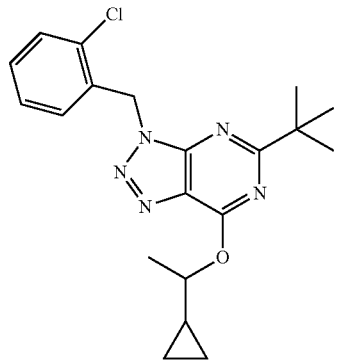 [SMILES: CC(Oc1nc(C(C)(C)C)nc2c1nnn2Cc1ccccc1Cl)C1CC1]

In analogy to the procedure described for the synthesis of 5-tert-Butyl-3-(2-chloro-benzyl)-7-cyclobutoxy-3H-[1,2,3]triazolo[4,5-d]pyrimidine (example 205) the title compound was prepared from 5-tert-butyl-7-chloro-3-(2-chlorobenzyl)-3H-[1,2,3]triazolo[4,5-d]pyrimidine and 1-cyclopropylethanol. MS(m/e): 386.4.

Example 212

5-tert-Butyl-3-(2-chloro-benzyl)-7-cyclopentyloxy-3H-[1,2,3]triazolo[4,5-d]pyrimidine

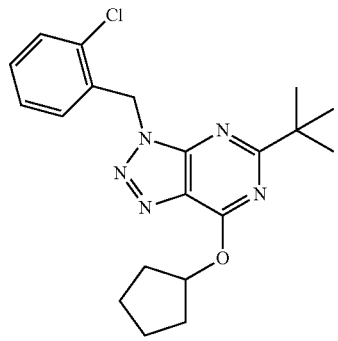 [SMILES: CC(C)(C)c1nc(OC2CCCC2)c2nnn(Cc3ccccc3Cl)c2n1]

In analogy to the procedure described for the synthesis of 5-tert-Butyl-3-(2-chloro-benzyl)-7-cyclobutoxy-3H-[1,2,3]triazolo[4,5-d]pyrimidine (example 205) the title compound was prepared from 5-tert-butyl-7-chloro-3-(2-chlorobenzyl)-3H-[1,2,3]triazolo[4,5-d]pyrimidine and cyclopentanol. MS(m/e): 386.3.

Example 213

5-tert-Butyl-3-(2-chloro-benzyl)-7-(2,2-dimethyl-propoxy)-3H-[1,2,3]triazolo[4,5-d]pyrimidine

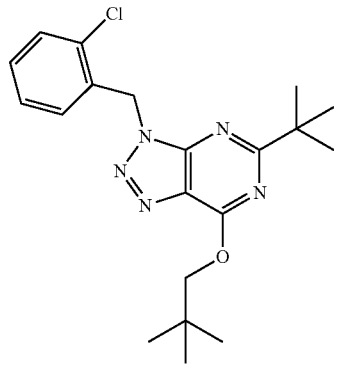 [SMILES: CC(C)(C)COc1nc(C(C)(C)C)nc2c1nnn2Cc1ccccc1Cl]

In analogy to the procedure described for the synthesis of 5-tert-Butyl-3-(2-chloro-benzyl)-7-cyclobutoxy-3H-[1,2,3]triazolo[4,5-d]pyrimidine (example 205) the title compound was prepared from 5-tert-butyl-7-chloro-3-(2-chlorobenzyl)-3H-[1,2,3]triazolo[4,5-d]pyrimidine and 2,2-dimethylpropan-1-ol. MS(m/e): 388.3.

Example 214

5-tert-Butyl-3-(2-chloro-benzyl)-7-(2,2,2-trifluoro-1-methyl-ethoxy)-3H-[1,2,3]triazolo[4,5-d]pyrimidine

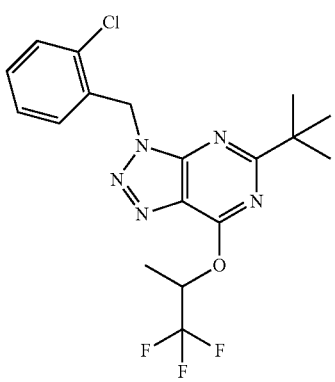 [SMILES: CC(Oc1nc(C(C)(C)C)nc2c1nnn2Cc1ccccc1Cl)C(F)(F)F]

In analogy to the procedure described for the synthesis of 5-tert-Butyl-3-(2-chloro-benzyl)-7-cyclobutoxy-3H-[1,2,3]triazolo[4,5-d]pyrimidine (example 205) the title compound was prepared from 5-tert-butyl-7-chloro-3-(2-chlorobenzyl)-3H-[1,2,3]triazolo[4,5-d]pyrimidine and 1,1,1-trifluoropropan-2-ol. MS(m/e): 414.2.

Example 215

5-tert-Butyl-3-(2-chloro-benzyl)-7-((S)-2,2,2-trifluoro-1-methyl-ethoxy)-3H-[1,2,3]triazolo[4,5-d]pyrimidine

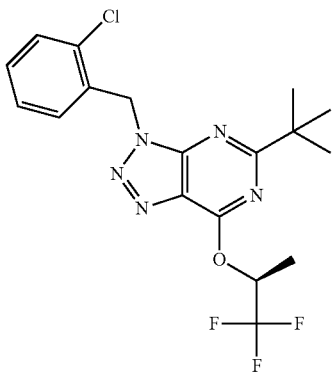 [SMILES: C[C@H](Oc1nc(C(C)(C)C)nc2c1nnn2Cc1ccccc1Cl)C(F)(F)F]

In analogy to the procedure described for the synthesis of 5-tert-Butyl-3-(2-chloro-benzyl)-7-cyclobutoxy-3H-[1,2,3]triazolo[4,5-d]pyrimidine (example 205) the title compound was prepared from 5-tert-butyl-7-chloro-3-(2-chlorobenzyl)-3H-[1,2,3]triazolo[4,5-d]pyrimidine and (S)-1,1,1-trifluoropropan-2-ol. MS(m/e): 414.3.

Example 216

5-tert-Butyl-3-(2-chloro-benzyl)-7-((R)-2,2,2-trifluoro-1-methyl-ethoxy)-3H-[1,2,3]triazolo[4,5-d]pyrimidine

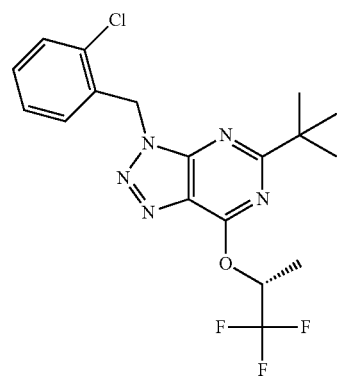 [SMILES: C[C@@H](Oc1nc(C(C)(C)C)nc2c1nnn2Cc1ccccc1Cl)C(F)(F)F]

In analogy to the procedure described for the synthesis of 5-tert-Butyl-3-(2-chloro-benzyl)-7-cyclobutoxy-3H-[1,2,3]triazolo[4,5-d]pyrimidine (example 205) the title compound was prepared from 5-tert-butyl-7-chloro-3-(2-chlorobenzyl)-3H-[1,2,3]triazolo[4,5-d]pyrimidine and (R)-1,1,1-trifluoropropan-2-ol. MS(m/e): 414.3.

Example 217

(3S)-1-(3-benzyl-5-tert-butyl-triazolo[4,5-d]pyrimidin-7-yl)pyrrolidin-3-ol

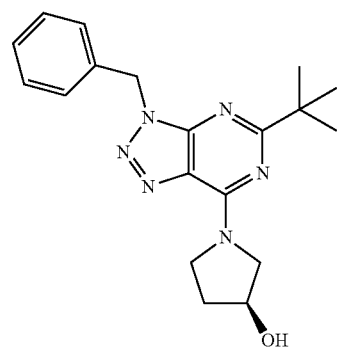 [SMILES: CC(C)(C)c1nc(N2CC[C@H](O)C2)c2nnn(Cc3ccccc3)c2n1]

Step 1 batch process:
5-amino-1-benzyl-triazole-4-carboxamide

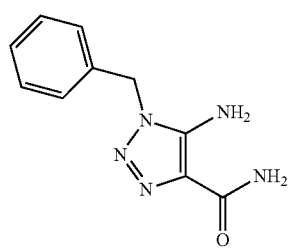 [SMILES: NC(=O)c1nnn(Cc2ccccc2)c1N]

Sodium azide (4.34 g, 66.0 mmol, Eq: 1.05) was charged in the reactor followed by DMSO (44.0 g, 40 ml) and Hunig's base (829 mg, 1.12 ml, 6.29 mmol, Eq: 0.1). The suspension was stirred for 10 min. at 25° C. (Chloromethyl)benzene (8 g, 7.29 ml, 62.9 mmol, Eq: 1.00) was added dropwise over 60 min at 25° C. After 3 h at 25° C., water (1.6 g, 1.6 ml) was added, the reaction mixture was stirred for 30 min and was filtered. The residue was washed with DMSO (17.6 g, 16.0 ml). The obtained benzyl azide solution was used directly in the cycloaddition step.

In a separate reactor, DMSO (17.6 g, 16.0 ml) was charged followed by, 32% aqueous NaOH (7.86 g, 5.82 ml, 62.9 mmol, Eq: 1.0) and water (5.00 g, 5.00 ml). A solution of 2-cyanoacetamide (7.93 g, 94.3 mmol, Eq: 1.50) in DMSO (17.6 g, 16.0 ml) was added dropwise over 15 min at 25° C. The previously prepared benzyl azide solution was added dropwise over 4 h at 25° C. The reaction was stirred overnight at 25° C. and water (120 g, 120 ml) was added dropwise over 30 min at 25° C. (exothermic). The resulting suspension was cooled over 30 min to 0° C., stirred at 0° C. for 30 min and filtered. The filter cake was washed with water (40.0 g, 40.0 ml) and was dried at 50° C./5 mbar to give 12.6 g of the title compound.

Step 2 continuous process:
5-amino-1-benzyl-triazole-4-carboxamide

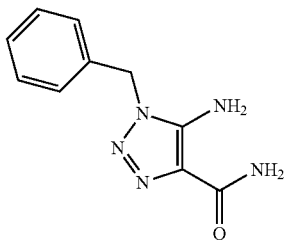 [SMILES: NC(=O)c1nnn(Cc2ccccc2)c1N]

Solution A: Benzyl Azide Solution Preparation:
Sodium azide (54.5 g, 829 mmol, Eq: 1.05) was charged in the reactor followed by DMSO (550 g, 500 ml). Water (37.5 ml) was added and the suspension was stirred at 40° C. for 3-4 h. Hunig's base (10.4 g, 14.1 ml, 79.0 mmol, Eq: 0.1) was added and the suspension was cooled to Tj=30-35° C. Benzyl chloride (100 g, 91.1 ml, 790 mmol, Eq: 1.00) was added dropwise over ca 1 h. The reaction mixture was stirred overnight at 30-35° C. The reaction was cooled to RT and filtered. The filter cake was washed twice with 40 mL DMSO to give 783 g of a light yellow solution (13.4% m/m BnN3 solution, d=1.086, 721 mL solution, 0.146 g/mL BnN3 solution)

Solution B: 2-cyanoacetamide Solution (Prepared in Excess):
120 g cyanoacetamide were dissolved in 327 mL DMSO
d: 1.12
428 mL solution
0.28 g/mL Solution C: 32% Aqueous NaOH Reactor Design:
The two first reactors are microreactor of type XXL from LTF GmbH and are connected in series. The first reactor is used to perform the mixing of the different reagents (the reagent streams are preheated in a ca 1 mL preheater and then combined into a reactor volume of ca 2 mL), the second reactor is used as an additional residence time reactor (ca 5.5 mL volume). The microreactor output stream is then connected to a CSTR cascade to provide additional residence time (a 20 mL then a 40 mL overflow reactor). The microreactors and CSTR overflow reactors are heated at 60-65° C.

Ca 85% conversion is achieved at the exit of the glass microreactor, ca 95% conversion within the first CSTR and >99% conversion at the exit of the second CSTR. Higher conversion can be achieved at the exit of the microreactors by increasing the residence time but to the cost of the throughput.

It is preferable to premix the cyanoacetamide and the base prior to contacting with the BnN3 stream. Indeed the azide can decompose in a runaway manner when contacted with NaOH. The stability also depends on the substitution (the stability decrease dramatically going from p-methoxybenzyl azide to BnN3 to 1-(azidomethyl)-2-chloro-benzene).

NaOH is also preferably used in stoichiometric or slightly sub-stoichiometric amounts. This represents a lab scale solution and other setups are of course possible, using other type of mixers/reactors for example standard static mixers (e.g. Kenics), CSTR cascades, coils, other type of glass or ceramic reactors and combination thereof which can be adapted depending on the desired throughput and scale.

Flows:
A: 3.6 mL/min; B: 1.88 mL/min; C: 0.54 mL/min, which corresponds to a 1:1.5:1.4 equivalent ratio.

Run Summary:
After a standard start-up procedure, the process was run for 3 h07 corresponding to 735 g BnN3 solution (based on flow and gravimetric monitoring). The output stream was discharged in a new collection tank ca every hour. The pumps were switched to a wash solvent and the microreactor exit was switched to waste. Meanwhile, the reaction was continued for ca. 10 min in the overflow reactors which were then emptied in the collection tank. The 3 collected fractions were transferred into a 3 L jacketed reactor and 1.5 L water was added over 5-10 min. The temperature rose from 25 to 43° C. The resulting suspension was stirred overnight at 25° C. then cooled for 2.5 h at 0-5° C. and filtered. The filter cake was washed three times with 100 ml water and dried at 50° C./5-10 mbar to give 154 g of the title compound as a white powder.

Step 2: 3-benzyl-5-tert-butyl-4H-triazolo[4,5-d]pyrimidin-7-one

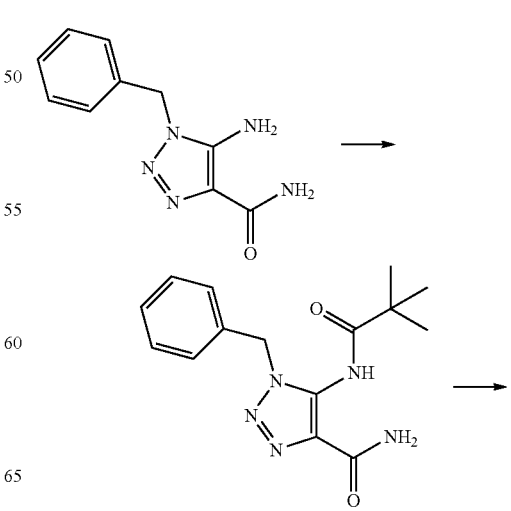

-continued

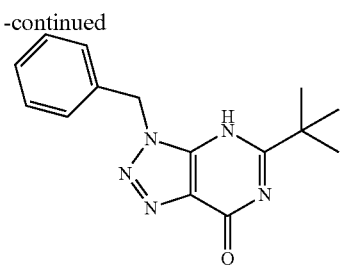

5-amino-1-benzyl-1H-1,2,3-triazole-4-carboxamide (150 g, 691 mmol, Eq: 1.00) was suspended in N,N-dimethylacetamide (512 g, 550 ml). Pyridine (82.1 g, 83.5 ml, 1.04 mol, Eq: 1.5) was added followed by pivaloyl chloride (126 g, 129 ml, 1.04 mol, Eq: 1.5) and the reaction mixture was heated to Tj=80° C. After complete acylation (ca 1 h30), KHCO$_3$ (347 g, 3.45 mol, Eq: 5.00) was added and the suspension was heated to Tj=155° C. to convert the 1-benzyl-5-(2,2-dimethylpropanoylamino)triazole-4-carboxamide intermediate to the product. After 18 h30 at 155° C., the reaction mixture was cooled to RT and water (3.48 kg, 3.48 l) was added dropwise within 30 Min. The light yellow suspension was stirred for 30 min at RT, 2 h at 0° C. and filtered. The filter cake was washed with cold (0-5° C.) water (600 g, 600 ml) and dried at 50° C./5 mbar to give 161.3 g of the title compound as an off-white powder. MS(m/e): 284.0 (MH$^+$).

Step 3: 3-benzyl-5-tert-butyl-7-chloro-triazolo[4,5-d]pyrimidine

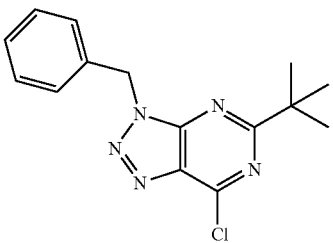 [SMILES: CC(C)(C)c1nc(Cl)c2nnn(Cc3ccccc3)c2n1]

DMF over MS(105 g, 110 ml, 1.43 mol, Eq: 2.56) was charged in the reactor followed by Dichlormethane (1.46 kg, 1.1 l). The solution was heated to 35° C. and oxalylchloride (144 g, 97.6 ml, 1.11 mol, Eq: 2) was added over 1 h. After 45 min, a fine suspension of 3-benzyl-5-tert-butyl-3H-[1,2,3]triazolo[4,5-d]pyrimidin-7(4H)-one (161 g, 557 mmol, Eq: 1.00) in a mixture of dichlormethane (877 g, 662 ml) and DMF (41.8 g, 44.1 ml) was added over of 20 min. After 3 h, the reaction mixture was cooled to RT and slowly added to a cold (0-5° C.) half saturated aqueous NaHCO$_3$ (1.76 l). The organic phase was separated and washed again with half saturated NaHCO$_3$ (662 ml) followed by water (662 g, 662 ml). Then the org. phase was dried over MgSO$_4$ and was concentrated under reduced pressure at 50° C./down to 10 mbar to give 192 g of a crude oil which does crystallize on standing. The crude 3-benzyl-5-tert-butyl-7-chloro-triazolo [4,5-d]pyrimidine was introduced in the next step without further purification.

Step 4: (3S)-1-(3-benzyl-5-tert-butyl-triazolo[4,5-d]pyrimidin-7-yl)pyrrolidin-3-ol 3-benzyl-5-tert-butyl-7-chloro-3H-[1,2,3]triazolo[4,5-d]pyrimidine (192.2 g, 548 mmol, Eq: 1.00) was charged in the reactor followed by Acetonitrile (780 g, 1.0 l) and N-Ethyldiisopropylamine (108 g, 143 ml, 822 mmol, Eq: 1.5). (S)-Pyrrolidin-3-ol (54.1 g, 51.6 ml, 603 mmol, Eq: 1.1) was added dropwise over 30 min at Tr=20 to <30° C. After 2 h at 25° C., the reaction mixture was transferred with Toluene (865 g, 1.0 l) into a 3 l round bottom flask and it was concentrated on a rotary evaporator, to switch solvent to toluene. The toluene solution was washed with a 10% aqueous citric acid solution (1.0 l). The aqueous phase was separated and extracted with toluene (434 g, 500 ml). The org. phases were washed sequentially with half saturated aqueous NaHCO$_3$ (500 ml) and half saturated aqueous NaCl (500 ml). The org. phases were combined, dried over MgSO$_4$ and concentrated at 45° C. to ca 500 mL. Heptane (684 g, 1.0 l) was added under stirring. After 5-10 min the product started to crystallize. The white suspension was stirred for 2 h at RT and was filtered. The white filter cake was washed with heptane (274 g, 400 ml) and dried at 45° C./5 mbar to give 186.9 g of the title compound as a white powder. MS(m/e): 353.1 (MH$^+$).

Example 218

1-(5-tert-butyl-3-(2-chlorobenzyl)-3H-[1,2,3]triazolo[4,5-d]pyrimidin-7-yl)pyrrolidin-3-ol

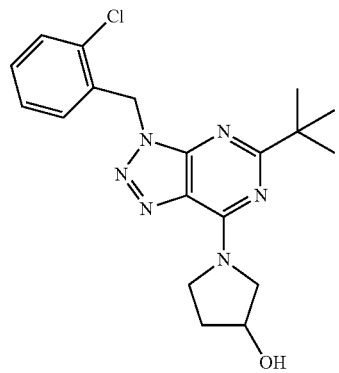

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 5-tert-butyl-7-chloro-3-(2-chlorobenzyl)-3H-[1,2,3]triazolo[4,5-d]pyrimidine and pyrrolidin-3-ol and isolated as colorless foam. MS(m/e): 387.4 (MH$^+$).

Example 219

(R)-1-(5-tert-butyl-3-((1-methyl-1H-tetrazol-5-yl)methyl)-3H-[1,2,3]triazolo[4,5-d]pyrimidin-7-yl)pyrrolidin-3-ol

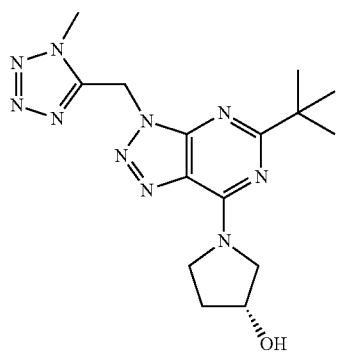 [SMILES: Cn1nnnc1Cn1nnc2c(N3CC[C@@H](O)C3)nc(C(C)(C)C)nc21]

a) (R)-1-(3-Benzyl-5-tert-butyl-3H-[1,2,3]triazolo[4,5-d]pyrimidin-7-yl)-pyrrolidin-3-ol

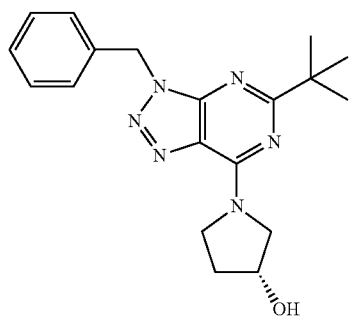 [SMILES: CC(C)(C)c1nc(N2CC[C@@H](O)C2)c2nnn(Cc3ccccc3)c2n1]

In analogy to the procedure described for the synthesis of 5-tert-butyl-3-(2-chlorobenzyl)-7-morpholin-4-yl-3H-[1,2,3]triazolo[4,5-d]pyrimidine (example 1, step c), the title compound was prepared from 3-benzyl-5-tert-butyl-7-chloro-triazolo[4,5-d]pyrimidine and (R)-pyrrolidin-3-ol and isolated as white foam. MS(m/e): 352.4 (MH⁺). b) (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (R)-1-(3-Benzyl-5-tert-butyl-3H-[1,2,3]triazolo[4,5-d]pyrimidin-7-yl)-pyrrolidin-3-ol was hydrogenated over Pd/C and the resulting (R)-1-(5-tert-Butyl-3H-[1,2,3]triazolo[4,5-d]pyrimidin-7-yl)-pyrrolidin-3-ol was reacted in analogy to the procedure described for the synthesis of 5-tert-butyl-7-(3,3-difluoropyrrolidin-1-yl)-3-ethyl-3H-[1,2,3]triazolo[4,5-d]pyrimidine (example 61), with 5-(chloromethyl)-1-methyl-1H-tetrazole and isolated as white solid. MS(m/e): 359.2 (MH⁺).

Example 220

1-(5-tert-butyl-3-((1-methyl-1H-tetrazol-5-yl)methyl)-3H-[1,2,3]triazolo[4,5-d]pyrimidin-7-yl)pyrrolidin-3-ol

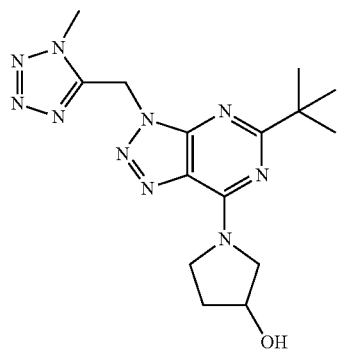 [SMILES: Cn1nnnc1Cn1nnc2c(N3CCC(O)C3)nc(C(C)(C)C)nc21]

a) 1-(3-Benzyl-5-tert-butyl-3H-[1,2,3]triazolo[4,5-d]pyrimidin-7-yl)-pyrrolidin-3-ol

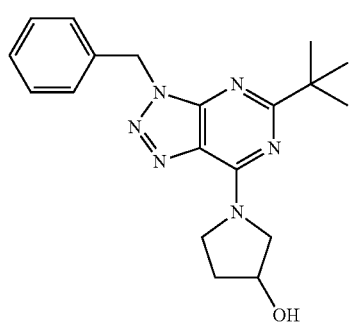 [SMILES: CC(C)(C)c1nc(N2CCC(O)C2)c2nnn(Cc3ccccc3)c2n1]

In analogy to the procedure described for the synthesis of (R)-1-(3-Benzyl-5-tert-butyl-3H-[1,2,3]triazolo[4,5-d]pyrimidin-7-yl)-pyrrolidin-3-ol (example 219, step a) the title compound was prepared from 3-benzyl-5-tert-butyl-7-chloro-triazolo[4,5-d]pyrimidine and pyrrolidin-3-ol and isolated as light yellow oil.

b) 1-(5-tert-butyl-3-((1-methyl-1H-tetrazol-5-yl)methyl)-3H-[1,2,3]triazolo[4,5-d]pyrimidin-7-yl)pyrrolidin-3-ol In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) 1-(3-Benzyl-5-tert-butyl-3H-[1,2,3]triazolo[4,5-d]pyrimidin-7-yl)-pyrrolidin-3-ol was hydrogenated and subsequently reacted with 5-(chloromethyl)-1-methyl-1H-tetrazole and isolated as light yellow oil. MS(m/e): 358.4 (MH⁺).

Example 221-a and Example 221-b (S)-1-(5-tert-butyl-3-(2-chlorobenzyl)-3H-[1,2,3]triazolo[4,5-d]pyrimidin-7-yl)-3-methylpyrrolidin-3-ol and (R)-1-(5-tert-butyl-3-(2-chlorobenzyl)-3H-[1,2,3]triazolo[4,5-d]pyrimidin-7-yl)-3-methylpyrrolidin-3-ol

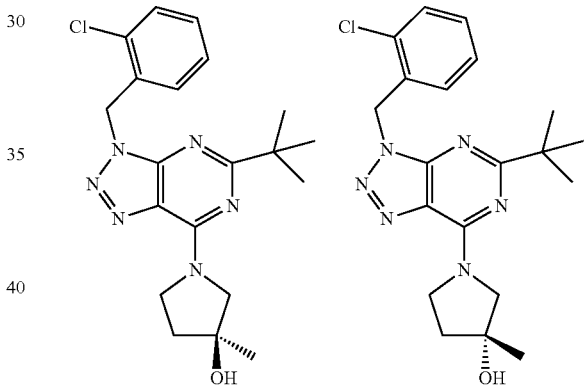

a) 1-(3-Benzyl-5-tert-butyl-3H-[1,2,3]triazolo[4,5-d]pyrimidin-7-yl)-3-methyl-pyrrolidin-3-ol

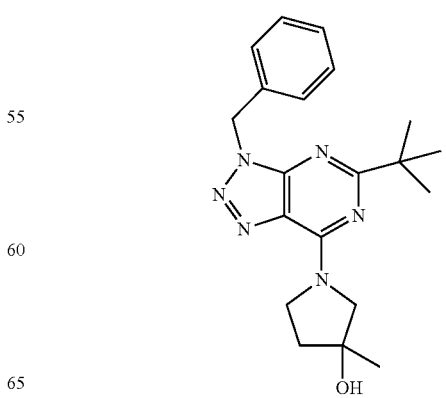

In analogy to the procedure described for the synthesis of (R)-1-(3-Benzyl-5-tert-butyl-3H-[1,2,3]triazolo[4,5-d]pyrimidin-7-yl)-pyrrolidin-3-ol (example 219, step a) the title compound was prepared from 3-benzyl-5-tert-butyl-7-chloro-triazolo[4,5-d]pyrimidine and 3-methyl-pyrrolidin-3 and isolated as white solid and subjected to separation by chiral HPLC to yield (S)-1-(3-benzyl-5-tert-butyl-3H-[1,2,3]triazolo[4,5-d]pyrimidin-7-yl)-3-methylpyrrolidin-3-ol and (R)-1-(3-benzyl-5-tert-butyl-3H-[1,2,3]triazolo[4,5-d]pyrimidin-7-yl)-3-methylpyrrolidin-3-ol. The enantiopure intermediates where isolated with 39% and 36% yield.

b) (S)-1-(5-tert-butyl-3-(2-chlorobenzyl)-3H-[1,2,3]triazolo[4,5-d]pyrimidin-7-yl)-3-methylpyrrolidin-3-ol and (R)-1-(5-tert-butyl-3-(2-chlorobenzyl)-3H-[1,2,3]triazolo[4,5-d]pyrimidin-7-yl)-3-methylpyrrolidin-3-ol In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (R)-1-(3-benzyl-5-tert-butyl-3H-[1,2,3]triazolo[4,5-d]pyrimidin-7-yl)-3-methylpyrrolidin-3-ol through hydrogenation and subsequent reaction with 1-(bromomethyl)-2-chlorobenzene. MS(m/e): 401.4 (MH+).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (S)-1-(3-benzyl-5-tert-butyl-3H-[1,2,3]triazolo[4,5-d]pyrimidin-7-yl)-3-methylpyrrolidin-3-ol through hydrogenation and subsequent reaction with 1-(bromomethyl)-2-chlorobenzene. MS(m/e): 401.4 (MH+).

Example 222-a and Example 222-b (S)-1-(5-tert-butyl-3-(2-(trifluoromethyl)benzyl)-3H-[1,2,3]triazolo[4,5-d]pyrimidin-7-yl)-3-methylpyrrolidin-3-ol and (R)-1-(5-tert-butyl-3-(2-(trifluoromethyl)benzyl)-3H-[1,2,3]triazolo[4,5-d]pyrimidin-7-yl)-3-methylpyrrolidin-3-ol

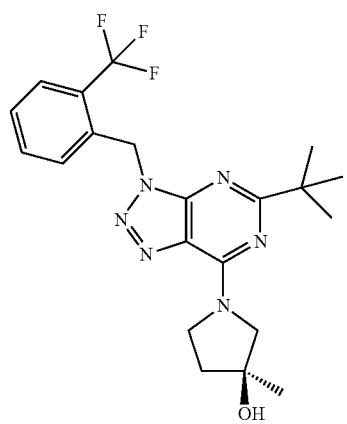

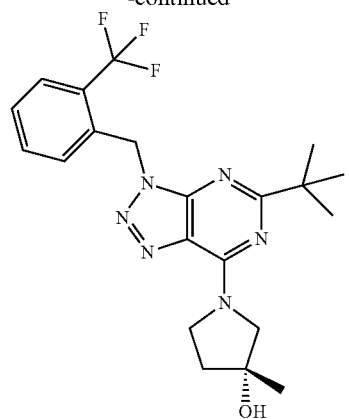

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (S)-1-(3-benzyl-5-tert-butyl-3H-[1,2,3]triazolo[4,5-d]pyrimidin-7-yl)-3-methylpyrrolidin-3-ol through hydrogenation and subsequent reaction with 1-(bromomethyl)-2-(trifluoromethyl)benzene. MS(m/e): 435.4 (MH+).

In analogy to the procedure described for the synthesis of (R)-1-(5-tert-butyl-3-((1-methyl-1H-tetrazol-5-yl)methyl)-3H-[1,23]triazolo[4,5-d]pyrimidin-7-yl)pyrrolidin-3-ol (example 219, step b) the title compound was prepared from (R)-1-(3-benzyl-5-tert-butyl-3H-[1,2,3]triazolo[4,5-d]pyrimidin-7-yl)-3-methylpyrrolidin-3-ol through hydrogenation and subsequent reaction with 1-(bromomethyl)-2-(trifluoromethyl)benzene. MS(m/e): 435.4 (MH+).

Example 223-a and Example 223-b (S)-1-(5-tert-butyl-3-(2-(methylsulfonyl)benzyl)-3H-[1,2,3]triazolo[4,5-d]pyrimidin-7-yl)-3-methylpyrrolidin-3-ol and (R)-1-(5-tert-butyl-3-(2-(methylsulfonyl)benzyl)-3H-[1,2,3]triazolo[4,5-d]pyrimidin-7-yl)-3-methylpyrrolidin-3-ol

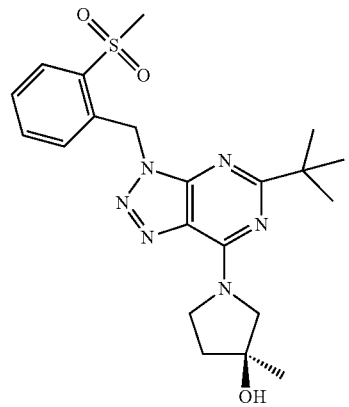

-continued

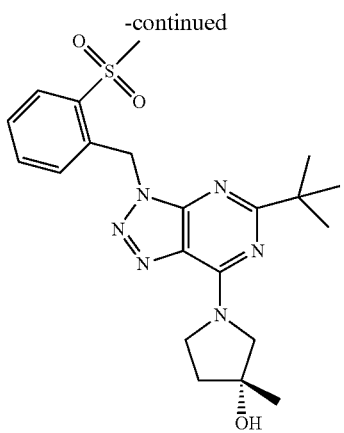

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (S)-1-(3-benzyl-5-tert-butyl-3H-[1,2,3]triazolo[4,5-d]pyrimidin-7-yl)-3-methylpyrrolidin-3-ol through hydrogenation and subsequent reaction with 1-(bromomethyl)-2-(methylsulfonyl)benzene. MS(m/e): 445.4 (MH⁺).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (R)-1-(3-benzyl-5-tert-butyl-3H-[1,2,3]triazolo[4,5-d]pyrimidin-7-yl)-3-methylpyrrolidin-3-ol through hydrogenation and subsequent reaction with 1-(bromomethyl)-2-(methylsulfonyl)benzene. MS(m/e): 445.4 (MH⁺).

Example 224-a and Example 224-b (S)-1-(5-tert-butyl-3-((3-chloropyridin-2-yl)methyl)-3H-[1,2,3]triazolo[4,5-d]pyrimidin-7-yl)-3-methylpyrrolidin-3-ol and (R)-1-(5-tert-butyl-3-((3-chloropyridin-2-yl)methyl)-3H-[1,2,3]triazolo[4,5-d]pyrimidin-7-yl)-3-methylpyrrolidin-3-ol

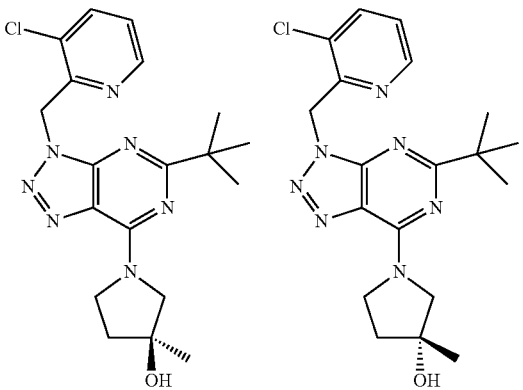

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (S)-1-(3-benzyl-5-tert-butyl-3H-[1,2,3]triazolo[4,5-d]pyrimidin-7-yl)-3-methylpyrrolidin-3-ol through hydrogenation and subsequent reaction with 3-chloro-2-(chloromethyl)pyridine. MS(m/e): 402.4 (MH⁺).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (R)-1-(3-benzyl-5-tert-butyl-3H-[1,2,3]triazolo[4,5-d]pyrimidin-7-yl)-3-methylpyrrolidin-3-ol through hydrogenation and subsequent reaction with 3-chloro-2-(chloromethyl)pyridine. MS(m/e): 402.4 (MH⁺).

Example 225-a and Example 225-b (S)-1-(5-tert-butyl-3-((5-methyl-1,3,4-oxadiazol-2-yl)methyl)-3H-[1,2,3]triazolo[4,5-d]pyrimidin-7-yl)-3-methylpyrrolidin-3-ol and (R)-1-(5-tert-butyl-3-((5-methyl-1,3,4-oxadiazol-2-yl)methyl)-3H-[1,2,3]triazolo[4,5-d]pyrimidin-7-yl)-3-methylpyrrolidin-3-ol

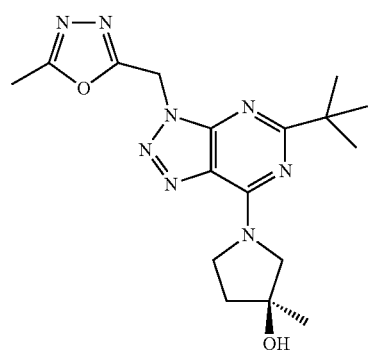

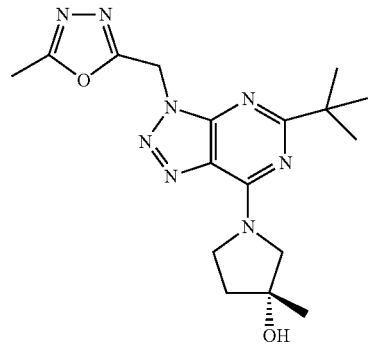

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (S)-1-(3-benzyl-5-tert-butyl-3H-[1,2,3]triazolo[4,5-d]pyrimidin-7-yl)-3-methylpyrrolidin-3-ol through hydrogenation and subsequent reaction with 2-(chloromethyl)-5-methyl-1,3,4-oxadiazole. MS(m/e): 373.4 (MH⁺).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (R)-1-(3-benzyl-5-tert-butyl-3H-[1,2,3]triazolo[4,5-d]pyrimidin-7-yl)-3-methylpyrrolidin-3-ol through hydrogenation and subsequent reaction with 2-(chloromethyl)-5-methyl-1,3,4-oxadiazole. MS(m/e): 373.4 (MH+).

Example 226-a and Example 226-b (S)-1-(5-tert-butyl-3-((3-methyl-1,2,4-oxadiazol-5-yl)methyl)-3H-[1,2,3]triazolo[4,5-d]pyrimidin-7-yl)-3-methylpyrrolidin-3-ol and (R)-1-(5-tert-butyl-3-((3-methyl-1,2,4-oxadiazol-5-yl)methyl)-3H-[1,2,3]triazolo[4,5-d]pyrimidin-7-yl)-3-methylpyrrolidin-3-ol

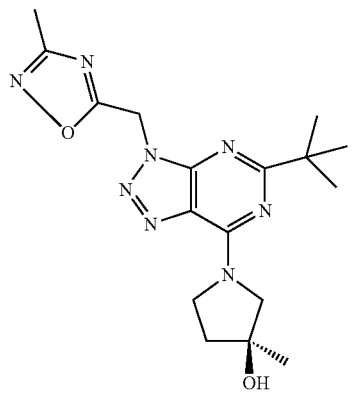

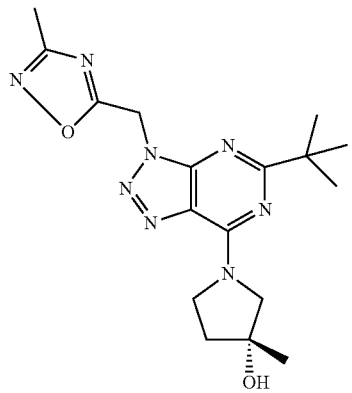

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (S)-1-(3-benzyl-5-tert-butyl-3H-[1,2,3]triazolo[4,5-d]pyrimidin-7-yl)-3-methylpyrrolidin-3-ol through hydrogenation and subsequent reaction with 5-(chloromethyl)-3-methyl-1,2,4-oxadiazole. MS(m/e): 373.4 (MH+).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (R)-1-(3-benzyl-5-tert-butyl-3H-[1,2,3]triazolo[4,5-d]pyrimidin-7-yl)-3-methylpyrrolidin-3-ol through hydrogenation and subsequent reaction with 5-(chloromethyl)-3-methyl-1,2,4-oxadiazole. MS(m/e): 373.4 (MH+).

Example 227-a and Example 227-b (S)-1-(5-tert-butyl-3-((1-methyl-1H-tetrazol-5-yl)methyl)-3H-[1,2,3]triazolo[4,5-d]pyrimidin-7-yl)-3-methylpyrrolidin-3-ol and (R)-1-(5-tert-butyl-3-((1-methyl-1H-tetrazol-5-yl)methyl)-3H-[1,2,3]triazolo[4,5-d]pyrimidin-7-yl)-3-methylpyrrolidin-3-ol

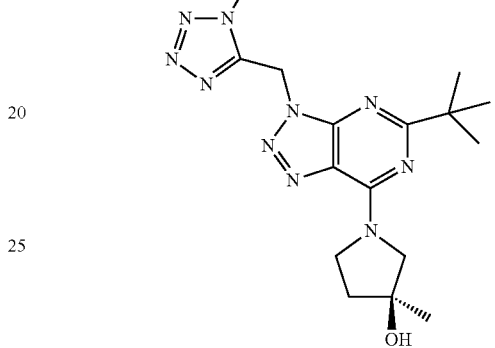

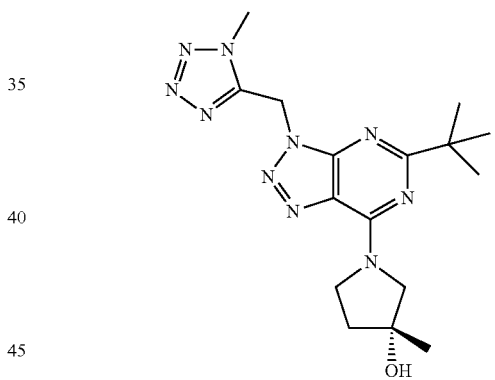

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (S)-1-(3-benzyl-5-tert-butyl-3H-[1,2,3]triazolo[4,5-d]pyrimidin-7-yl)-3-methylpyrrolidin-3-ol through hydrogenation and subsequent reaction with 5-(chloromethyl)-1-methyl-1H-tetrazole. MS(m/e): 373.4 (MH+).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (R)-1-(3-benzyl-5-tert-butyl-3H-[1,2,3]triazolo[4,5-d]pyrimidin-7-yl)-3-methylpyrrolidin-3-ol through hydrogenation and subsequent reaction with 5-(chloromethyl)-1-methyl-1H-tetrazole. MS(m/e): 373.4 (MH+).

Example 228-a and Example 228-b (S)-1-(5-tert-butyl-3-((4-methyl-1,2,5-oxadiazol-3-yl)methyl)-3H-[1,2,3]triazolo[4,5-d]pyrimidin-7-yl)-3-methylpyrrolidin-3-ol and (R)-1-(5-tert-butyl-3-((4-methyl-1,2,5-oxadiazol-3-yl)methyl)-3H-[1,2,3]triazolo[4,5-d]pyrimidin-7-yl)-3-methylpyrrolidin-3-ol

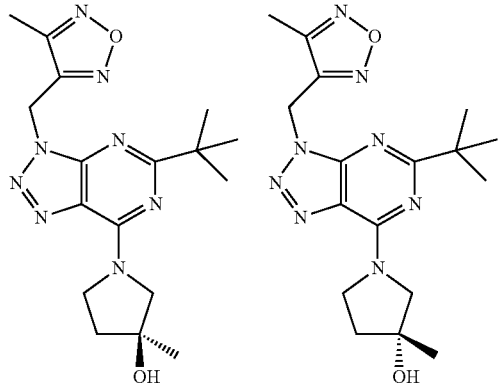

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (S)-1-(3-benzyl-5-tert-butyl-3H-[1,2,3]triazolo[4,5-d]pyrimidin-7-yl)-3-methylpyrrolidin-3-ol through hydrogenation and subsequent reaction with 3-(bromomethyl)-4-methyl-1,2,5-oxadiazole. MS(m/e): 373.4 (MH$^+$).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (R)-1-(3-benzyl-5-tert-butyl-3H-[1,2,3]triazolo[4,5-d]pyrimidin-7-yl)-3-methylpyrrolidin-3-ol through hydrogenation and subsequent reaction with 3-(bromomethyl)-4-methyl-1,2,5-oxadiazole. MS(m/e): 373.4 (MH$^+$).

Example 229-a and Example 229-b (S)-1-(5-tert-butyl-3-(3,3,3-trifluoropropyl)-3H-[1,2,3]triazolo[4,5-d]pyrimidin-7-yl)-3-methylpyrrolidin-3-ol and (R)-1-(5-tert-butyl-3-(3,3,3-trifluoropropyl)-3H-[1,2,3]triazolo[4,5-d]pyrimidin-7-yl)-3-methylpyrrolidin-3-ol

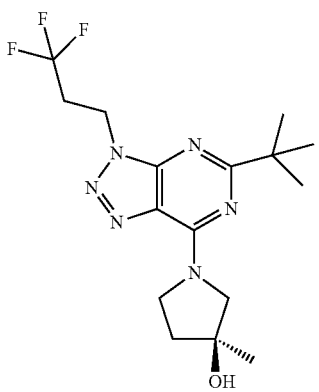

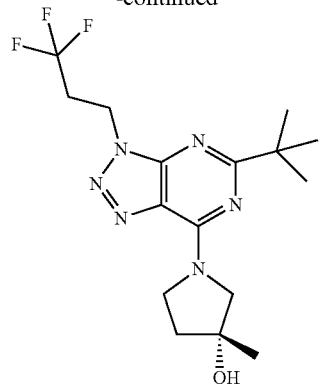

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (S)-1-(3-benzyl-5-tert-butyl-3H-[1,2,3]triazolo[4,5-d]pyrimidin-7-yl)-3-methylpyrrolidin-3-ol through hydrogenation and subsequent reaction with 3-bromo-1,1,1-trifluoropropane. MS(m/e): 373.4 (MH$^+$).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (R)-1-(3-benzyl-5-tert-butyl-3H-[1,2,3]triazolo[4,5-d]pyrimidin-7-yl)-3-methylpyrrolidin-3-ol through hydrogenation and subsequent reaction with 3-bromo-1,1,1-trifluoropropane. MS(m/e): 373.4 (MH$^+$).

Example 230-a and Example 230-b (S)-1-(5-tert-butyl-3-((1-cyclopropyl-1H-tetrazol-5-yl)methyl)-3H-[1,2,3]triazolo[4,5-d]pyrimidin-7-yl)-3-methylpyrrolidin-3-ol and (R)-1-(5-tert-butyl-3-((1-cyclopropyl-1H-tetrazol-5-yl)methyl)-3H-[1,2,3]triazolo[4,5-d]pyrimidin-7-yl)-3-methylpyrrolidin-3-ol

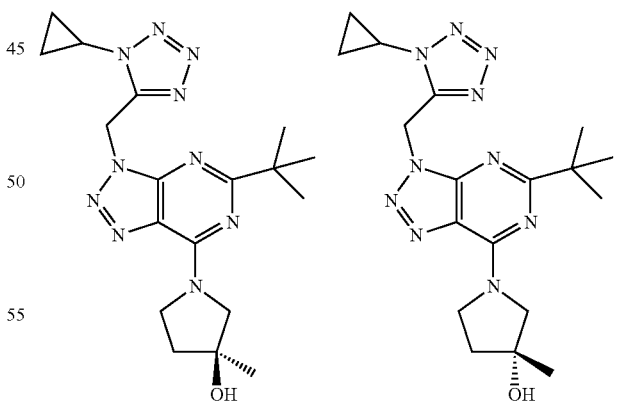

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (S)-1-(3-benzyl-5-tert-butyl-3H-[1,2,3]triazolo[4,5-d]pyrimidin-7-yl)-3-methylpyrrolidin-3-ol through hydrogenation and subsequent reaction with 5-(chloromethyl)-1-cyclopropyl-1H-tetrazole. MS(m/e): 399.4 (MH$^+$).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 219, step b) the title compound was prepared from (R)-1-(3-benzyl-5-tert-butyl-3H-[1,2,3]triazolo[4,5-d]pyrimidin-7-yl)-3-methylpyrrolidin-3-ol through hydrogenation and subsequent reaction with 5-(chloromethyl)-1-cyclopropyl-1H-tetrazole. MS(m/e): 399.4 (MH$^+$).

Example 231

Pharmacological Tests

The following tests were carried out in order to determine the activity of the compounds of formula I:

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM $MgCl_2$, 2.5 mM EDTA, and 0.5% (wt/vol) fatty acid free BSA, pH 7.4 for CB1 receptor and 50 mM Tris, 5 mM $MgCl_2$, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below 10 μM, more particularly of 1 nM to 3 μM and most particularly of 1 nM to 100 nM.

The compounds according to formula (I) have an activity in the above assay (Ki) particularly of 0.5 nM to 10 μM, more particularly of 0.5 nM to 3 μM and most particularly of 0.5 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100l and incubated for 30 min at 30° C. Using the cAMP-Nano-TRF detection kit the assay (Roche Diagnostics) was stopped by the addition of 50 μl lysis reagent (Tris, NaCl, 1.5% Triton X100, 2.5% NP40, 10% $NaN_3$) and 50 μl detection solutions (20 μM mAb Alexa700-cAMP 1:1, and 48 μM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 μM to 0.13 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

All compounds are CB2 agonists with $EC_{50}$ below 3 uM and selectivity versus CB1 in the corresponding assay of at least 10 fold For example, the following compounds showed the following human $EC_{50}$ values in the functional cAMP assay described above:

| Example | human CB2 $EC_{50}$ [μM] | human CB1 $EC_{50}$ [μM] |
| --- | --- | --- |
| 1 | 0.0006 | 1.0641 |
| 2 | 0.0016 | 0.5552 |
| 3 | 0.0013 | 0.1598 |
| 4 | 0.0014 | 0.1902 |
| 5 | 0.0003 | 0.6318 |
| 6 | 0.0002 | 0.1648 |
| 7 | 0.0112 | >10 |
| 8 | 0.6474 | >10 |
| 9 | 0.0176 | >10 |
| 10 | 0.0024 | 0.4039 |
| 11 | 0.0032 | 1.0938 |
| 12 | 0.0016 | 1.1067 |
| 13 | 0.0123 | >10 |
| 14 | 0.0021 | 1.2305 |
| 15 | 0.0032 | 0.9695 |
| 16 | 0.286 | >10 |
| 17 | 0.0087 | >10 |
| 18 | 0.0466 | >10 |
| 19 | 0.0017 | 0.1312 |
| 20 | 0.0017 | 0.3463 |
| 21 | 0.0027 | 0.6011 |
| 22 | 0.0024 | 1.4993 |
| 23 | 0.0754 | >10 |
| 24 | 0.003 | 0.4758 |
| 25 | 0.031 | 0.9191 |
| 26 | 0.0011 | 0.8661 |
| 27 | 0.0051 | >10 |
| 28 | 0.0112 | >10 |
| 29 | 0.0125 | 1.6317 |
| 30 | 0.0269 | >10 |
| 31 | 0.0098 | 1.263 |
| 32 | 0.0207 | >10 |
| 33 | 0.0025 | 0.764 |
| 34 | 0.0275 | 2.2735 |
| 35 | 0.0036 | >10 |
| 36 | 0.0006 | 0.4325 |
| 37 | 0.0003 | 0.4918 |
| 38 | 0.0182 | 0.3611 |
| 39 | 0.0079 | 1.332 |
| 40 | 0.0116 | >10 |
| 41 | 0.0365 | 1.2194 |
| 42 | 0.0003 | 0.9908 |
| 43 | 0.0012 | 0.6261 |
| 44 | 0.001 | >10 |
| 45 | 0.0522 | >10 |
| 46 | 0.0044 | 2.3134 |
| 47 | 0.0202 | >10 |
| 48 | 0.0083 | >10 |
| 49 | 0.0011 | 0.1555 |
| 50 | 0.001 | 0.1394 |
| 51 | 0.0024 | >10 |
| 52 | 0.0208 | >10 |
| 53 | 0.015 | >10 |
| 54 | 0.0028 | >10 |
| 55 | 0.0104 | >10 |
| 56 | 0.0165 | >10 |
| 57 | 0.0123 | >10 |
| 58 | 0.3375 | >10 |
| 59 | 0.0023 | >10 |
| 60 | 0.0025 | >10 |

| Example | human CB2 EC$_{50}$ [μM] | human CB1 EC$_{50}$ [μM] |
|---|---|---|
| 61 | 0.0132 | >10 |
| 62 | 0.0033 | >10 |
| 63 | 0.0182 | >10 |
| 64 | 0.0023 | >10 |
| 65 | 0.0009 | 0.2202 |
| 66 | 0.002 | >10 |
| 67 | 0.0002 | 0.1625 |
| 68 | 0.0007 | >10 |
| 69 | 0.0003 | 0.276 |
| 70 | 0.0001 | 0.0508 |
| 71 | 0.0004 | >10 |
| 72 | 0.0001 | 0.041 |
| 73 | 0.0001 | 0.0609 |
| 74 | 0.0001 | 0.0559 |
| 75 | 0.0002 | 0.0978 |
| 76 | 0.0023 | >10 |
| 77 | 0.0008 | >10 |
| 78 | 0.0001 | 0.1433 |
| 79 | 0.0001 | 0.0823 |
| 80 | 0.0003 | 0.0693 |
| 81 | 0.0001 | 0.0689 |
| 82 | 0.0002 | 0.2523 |
| 83 | 0.0001 | 0.2834 |
| 84 | 0.0012 | 0.451 |
| 85 | 0.0002 | >10 |
| 86 | 0.0004 | 0.371 |
| 87 | 0.001 | 0.2698 |
| 88 | 0.0009 | 0.3907 |
| 89 | 0.0003 | 0.4632 |
| 90 | 0.0005 | 0.3701 |
| 91 | 0.0003 | |
| 92 | 0.3499 | |
| 93 | 0.0045 | >10 |
| 94 | 0.001 | >10 |
| 95 | 0.0015 | |
| 96 | 0.0001 | 0.1667 |
| 97 | 0.0001 | 0.0623 |
| 98 | 0.0001 | 0.098 |
| 99 | 0.0002 | 0.4973 |
| 100 | 0.0001 | 0.11 |
| 101 | 0.0001 | >10 |
| 102 | 0.0006 | >10 |
| 103 | 0.0004 | 0.4147 |
| 104 | 0.0009 | >10 |
| 105 | 0.0065 | >10 |
| 106 | 0.0048 | >10 |
| 107 | 0.2838 | |
| 108 | 0.0003 | >10 |
| 109 | 0.0005 | >10 |
| 110 | 0.0002 | 0.2503 |
| 111 | 0.0002 | 0.1366 |
| 112 | 0.0001 | 0.0047 |
| 113 | 0.0002 | 0.2013 |
| 114 | 0.0004 | >10 |
| 115 | 0.0004 | >10 |
| 116 | 0.003 | >10 |
| 117 | 0.0002 | >10 |
| 118 | 0.0009 | >10 |
| 119 | 0.0003 | 0.091 |
| 120 | 0.0007 | 0.1812 |
| 121 | 0.0003 | >10 |
| 122 | 0.0013 | >10 |
| 123 | 0.0008 | 0.3059 |
| 124 | 0.0003 | 0.2759 |
| 125 | 0.0019 | >10 |
| 126 | 0.0003 | 0.4964 |
| 127 | 0.0004 | >10 |
| 128 | 0.0004 | >10 |
| 129 | 0.0001 | 0.6702 |
| 130 | 0.0005 | 0.5644 |
| 131 | 0.0001 | >10 |
| 132 | 0.0007 | >10 |
| 133 | 0.0044 | >10 |
| 134 | 0.0003 | 0.2341 |
| 135 | 0.0004 | 1.397 |
| 136 | 0.0002 | >10 |
| 137 | 0.0182 | >10 |
| 138 | 0.0004 | >10 |
| 139 | 0.0003 | >10 |
| 140 | 0.0001 | >10 |
| 141 | 0.0005 | >10 |
| 142 | 0.0002 | >10 |
| 143 | 0.0001 | >10 |
| 144 | 0.0004 | 0.1227 |
| 145 | 0.0002 | 2.2486 |
| 146 | 0.0005 | >10 |
| 147 | 0.0003 | 0.209 |
| 148 | 0.0004 | >10 |
| 149 | 0.0174 | >10 |
| 150 | 0.0363 | >10 |
| 151 | 0.0014 | >10 |
| 152 | 0.0105 | >10 |
| 153 | 0.0119 | >10 |
| 154 | 0.0025 | >10 |
| 155 | 0.003 | >10 |
| 156 | 0.0056 | >10 |
| 157 | 0.0001 | >10 |
| 158 | 0.2536 | >10 |
| 159 | 0.0358 | >10 |
| 160 | 0.0007 | >10 |
| 161 | 0.0825 | >10 |
| 162 | 0.0277 | >10 |
| 163 | 0.0055 | >10 |
| 164 | 0.0008 | >10 |
| 165 | 0.0535 | >10 |
| 166 | 0.018 | >10 |
| 167 | 0.0038 | >10 |
| 168 | 0.0094 | >10 |
| 169 | 0.1988 | >10 |
| 170 | 0.1937 | >10 |
| 171 | 0.0542 | >10 |
| 172 | 0.0041 | >10 |
| 173 | 0.0003 | >10 |
| 174 | 0.002 | >10 |
| 175 | 0.0015 | >10 |
| 176 | 0.0005 | 2.0022 |
| 177 | 0.0011 | >10 |
| 178 | 0.0009 | 1.8873 |
| 179 | 0.002 | >10 |
| 180 | 0.0528 | >10 |
| 181 | 0.0594 | >10 |
| 182 | 0.0139 | >10 |
| 183 | 0.0042 | >10 |
| 184 | 0.1124 | >10 |
| 185 | 0.0268 | >10 |
| 186 | 0.0003 | 0.1374 |
| 187 | 0.0008 | 0.1191 |
| 188 | 0.001 | >10 |
| 189 | 0.0332 | >10 |
| 190 | 0.0726 | >10 |
| 191 | 0.1734 | >10 |
| 192 | 0.022 | >10 |
| 193 | 0.5929 | >10 |
| 194 | 0.2846 | >10 |
| 195 | 0.4671 | >10 |
| 196 | 0.1188 | >10 |
| 197 | 0.2574 | >10 |
| 198 | 0.0128 | 1.7086 |
| 199 | 0.183 | >10 |
| 200 | 0.1782 | >10 |
| 201 | 0.0657 | >10 |
| 202 | 0.0868 | >10 |
| 203 | 0.0531 | >10 |
| 204 | 0.0005 | >10 |
| 205 | 0.0122 | >10 |
| 206 | 0.0113 | >10 |
| 207 | 0.068 | >10 |
| 208 | 0.0092 | >10 |
| 209 | 0.016 | >10 |
| 210 | 0.0167 | >10 |
| 211 | 0.0986 | >10 |
| 212 | 0.022 | >10 |

| Example | human CB2 EC$_{50}$ [μM] | human CB1 EC$_{50}$ [μM] |
|---|---|---|
| 213 | 0.0596 | >10 |
| 214 | 0.0094 | >10 |
| 215 | 0.0247 | >10 |
| 216 | 0.0104 | >10 |
| 217 | 0.0033 | >10 |
| 218 | 0.0005 | >10 |
| 219 | 0.0329 | >10 |
| 220 | 0.0047 | >10 |
| 221-a | 0.003 | 1.8045 |
| 221-b | 0.007 | 0.8526 |
| 222-a | 0.0008 | 0.8939 |
| 222-b | 0.0052 | >10 |
| 223-a | 0.0004 | 0.2412 |
| 223-b | 0.003 | 0.2461 |
| 224-a | 0.0011 | 0.8986 |
| 224-b | 0.0064 | >10 |
| 225-a | 0.0291 | >10 |

β-Arrestin Translocation Assay-PathHunter™ (DiscoveRx)

PathHunter™ β-arrestin CHO-K1 CNR1 cell line (catalog number #93-0200C2) and the β-arrestin CHO-K1 CNR2 cell line (catalog number #93-0706C2) were purchased from DiscoveRx Corporation. The cell line was engineered to express the β-galactosidase EA fragment fused to β-arrestin and the ProLink complementary peptide fused to the target receptor. The PathHunter™ protein complementation assay (DiscoveRx Corporation #93-0001) was performed according to the manufacturer's protocol. Assay plates were seeded containing 7500 (CNR1) and 10000 (CNR2) cells in 384 well plates (Corning Costar #3707, white, clear bottom) in 20 μL cell plating reagent 2 (Discoverx #93-0563R2A). After incubation at 37° C. (5% CO$_2$, 95% relative humidity) overnight, 5 μl of test compound was added (1% final DMSO concentration) and the incubation continued at 30° C. for 90 min. Detection reagent (12 μl) was then added and the incubation continued at room temperature for 60 min. Plates were then analyzed for a chemiluminescent signal using a Victor $^3$V reader (Perkin Elmer).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound of formula (I):

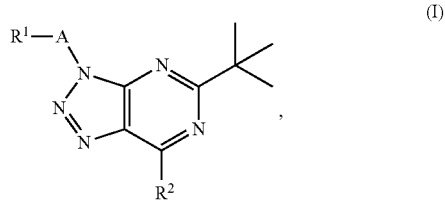

wherein:
A is selected from the group consisting of alkyl, hydroxyalkyl, —CH$_2$C(O)—, —C(O)—, —SO$_2$— and a bond;
R$^1$ is selected from the group consisting of phenyl, halophenyl, alkoxyphenyl, haloalkylphenyl, haloalkoxyphenyl, (halo)(haloalkyl)phenyl, cyanophenyl, hydroxyalkoxyphenyl, alkylsulfonylphenyl, alkylsulfonylaminophenyl, cyano, cycloalkyl, cycloalkylalkoxy, amino, (alkylsulfonyl)(alkyl)[1,2,4]triazolyl, (halo)(dialkylamino)pyridinyl, (alkyl)(oxy)pyridinyl, nitrobenzo[1,2,5]oxadiazolylaminopyridinyl, heterocyclyl, alkylheterocyclyl, hydroxyheterocyclyl, alkylheterocyclyl, heteroaryl, haloheteroaryl, alkylheteroaryl, cycloalkylheteroaryl and haloalkylheteroaryl, wherein said heterocyclyl is a three to eight membered carbocyclic ring comprising at least one nitrogen or oxygen atom, and wherein said heteroaryl is pyridinyl, pyrazolyl, oxadiazolyl, furazanyl, tetrazolyl or triazolyl;

R² is —NR³R⁴; wherein
one of R³ and R⁴ is hydrogen or alkyl and the other one is alkyl or cycloalkyl;
or R³ and R⁴ taken together with the nitrogen atom to which they are attached form heterocyclyl or substituted heterocyclyl, wherein said heterocyclyl is morpholinyl, piperidinyl, piperazinyl, pyrrolidinyl, 2-oxa-6-azaspiro[3.3]heptyl, azetidinyl, thiazolidinyl, thiomorpholinyl, dioxothiomorpholinyl, oxazepanyl, 2-oxa-6-azaspiro[3.4]octyl, 6-oxa-1-azaspiro[3.3]heptyl, 2-oxa-5-azaspiro[3.4]octyl, isoxazolidinyl, aziridinyl, dioxoisothiazolidinyl or oxopyrrolidinyl and wherein said substituted heterocyclyl is heterocyclyl substituted with one to four substituents independently selected from the group consisting of alkyl, halogen, hydroxyl, alkoxy, hydroxyalkyl, carboxyl, alkoxyalkyl, cyano, alkylamino, dialkylamino, alkylcarbonylamino, alkylcarbonyl(alkylamino), phenyl, alkoxycarbonyl, aminoalkyl, alkylpyrazolyl or alkylisoxazolyl;
or a pharmaceutically acceptable salt or ester thereof;
with the proviso that said compound is not 3-[(2-chlorophenyl)methyl]-5-(1,1-dimethylethyl)-7-(4-morpholinyl)-3H-1,2,3-triazolo[4,5-d]pyrimidine or N-cyclopropyl-5-(1,1-dimethylethyl)-3-(phenylmethyl)-3H-1,2,3-triazolo[4,5-d]pyrimidin-7-amine.

2. The compound of claim 1, wherein R¹ is phenyl, halophenyl or alkylheteroaryl.

3. The compound of claim 2, wherein said compound is 5-tert-butyl-3-(2-chloro-benzyl)-7-(4,4-difluoro-piperidin-1-yl)-3H-[1,2,3]triazolo[4,5-d]pyrimidine.

4. The compound of claim 2, wherein said compound is 5-tert-butyl-3-(2-chloro-benzyl)-7-(3,3-difluoro-pyrrolidin-1-yl)-3H-[1,2,3]triazolo[4,5-d]pyrimidine.

5. The compound of claim 2, wherein said compound is 1-[5-tert-butyl-3-(2-chloro-benzyl)-3H-[1,2,3]triazolo[4,5-d]pyrimidin-7-yl]-pyrrolidin-3-ol.

6. The compound of claim 5, wherein said compound is (S)-1-[5-tert-butyl-3-(2-chloro-benzyl)-3H-[1,2,3]triazolo[4,5-d]pyrimidin-7-yl]-pyrrolidin-3-ol.

7. The compound of claim 2, wherein said compound is 5-tert-butyl-3-(2-chloro-benzyl)-7-(3,3,4,4-tetrafluoro-pyrrolidin-1-yl)-3H-[1,2,3]triazolo[4,5-d]pyrimidine.

8. The compound of claim 2, wherein said compound is 5-tert-butyl-3-(2-chloro-3,6-difluoro-benzyl)-7-(3,3-difluoro-pyrrolidin-1-yl)-3H-[1,2,3]triazolo[4,5-d]pyrimidine.

9. The compound of claim 1, wherein R¹ is haloalkylphenyl.

10. The compound of claim 9, wherein said compound is 1-(5-tert-butyl-3-(2-(trifluoromethyl)benzyl)-3H-[1,2,3]triazolo[4,5-d]pyrimidin-7-yl)-3-methylpyrrolidin-3-ol.

11. The compound of claim 10, wherein said compound is (S)-1-(5-tert-butyl-3-(2-(trifluoromethyl)benzyl)-3H-[1,2,3]triazolo[4,5-d]pyrimidin-7-yl)-3-methylpyrrolidin-3-ol.

12. The compound of claim 1, wherein R¹ is alkylsulfonylphenyl.

13. The compound of claim 12, wherein said compound is 1-(5-tert-butyl-3-(2-(methylsulfonyl)benzyl)-3H-[1,2,3]triazolo[4,5-d]pyrimidin-7-yl)-3-methylpyrrolidin-3-ol.

14. The compound of claim 13 wherein said compound is (S)-1-(5-tert-butyl-3-(2-(methylsulfonyl)benzyl)-3H-[1,2,3]triazolo[4,5-d]pyrimidin-7-yl)-3-methylpyrrolidin-3-ol.

15. The compound of claim 2, wherein said compound is 1-[5-tert-butyl-3-(2-methanesulfonyl-benzyl)-3H-[1,2,3]triazolo[4,5-d]pyrimidin-7-yl]-pyrrolidin-3-ol.

16. The compound of claim 15, wherein said compound is (S)-1-[5-tert-butyl-3-(2-methanesulfonyl-benzyl)-3H-[1,2,3]triazolo[4,5-d]pyrimidin-7-yl]-pyrrolidin-3-ol.

17. The compound of claim 1, wherein R¹ is haloheteroaryl or heteroaryl and said heteroaryl is pyridinyl.

18. The compound of claim 17, wherein said compound is 5-tert-butyl-7-(3,3-difluoro-pyrrolidin-1-yl)-3-pyridin-3-ylmethyl-3H-[1,2,3]triazolo[4,5-d]pyrimidine.

19. The compound of claim 17, wherein said compound is 5-tert-butyl-3-(3-chloro-pyridin-2-ylmethyl)-7-(3,3-difluoro-pyrrolidin-1-yl)-3H-[1,2,3]triazolo[4,5-d]pyrimidine.

20. The compound of claim 17, wherein said compound is 1-[5-tert-butyl-3-(2-chloro-pyridin-3-ylmethyl)-3H-[1,2,3]triazolo[4,5-d]pyrimidin-7-yl]-pyrrolidin-3-ol.

21. The compound of claim 20, wherein said compound is (S)-1-[5-tert-butyl-3-(2-chloro-pyridin-3-ylmethyl)-3H-[1,2,3]triazolo[4,5-d]pyrimidin-7-yl]-pyrrolidin-3-ol.

22. The compound of claim 1, wherein R¹ is heteroaryl, alkylheteroaryl or haloheteroaryl and heteroaryl is triazolyl or furazanyl.

23. The compound of claim 22, wherein said compound is 5-tert-butyl-7-(3,3-difluoro-pyrrolidin-1-yl)-3-(1-methyl-1H-tetrazol-5-ylmethyl)-3H-[1,2,3]triazolo[4,5-d]pyrimidine.

24. The compound of claim 22, wherein said compound is 1-[5-tert-butyl-3-(4-methyl-furazan-3-ylmethyl)-3H-[1,2,3]triazolo[4,5-d]pyrimidin-7-yl]-pyrrolidin-3-ol.

25. The compound of claim 24, wherein said compound is (S)-1-[5-tert-butyl-3-(4-methyl-furazan-3-ylmethyl)-3H-[1,2,3]triazolo[4,5-d]pyrimidin-7-yl]-pyrrolidin-3-ol.

26. The compound of claim 22, wherein said compound is 1-[5-tert-butyl-3-(1-methyl-1H-tetrazol-5-ylmethyl)-3H-[1,2,3]triazolo[4,5-d]pyrimidin-7-yl]-pyrrolidin-3-ol.

27. The compound of claim 26, wherein said compound is (S)-1-[5-tert-butyl-3-(1-methyl-1H-tetrazol-5-ylmethyl)-3H-[1,2,3]triazolo[4,5-d]pyrimidin-7-yl]-pyrrolidin-3-ol.

28. The compound according to claim 1, wherein said compound is (S)-1-[5-tert-Butyl-3-(3-chloro-pyridin-2-ylmethyl)-3H-[1,2,3]triazolo[4,5-d]pyrimidin-7-yl]-pyrrolidin-3-ol.

29. The compound according to claim 1, wherein said compound is (R)-1-(5-tert-butyl-3-((1-methyl-1H-tetrazol-5-yl)methyl)-3H-[1,2,3]triazolo[4,5-d]pyrimidin-7-yl)pyrrolidin-3-ol.

30. A pharmaceutical composition, comprising a therapeutically effective amount of a compound according to claim 1 and a pharmaceutically acceptable carrier.

31. The pharmaceutical composition according to claim 30, wherein said compound is 5-tert-butyl-3-(2-chloro-benzyl)-7-(4,4-difluoro-piperidin-1-yl)-3H-[1,2,3]triazolo[4,5-d]pyrimidine.

32. The pharmaceutical composition according to claim 30, wherein said compound is 5-tert-butyl-3-(2-chloro-benzyl)-7-(3,3-difluoro-pyrrolidin-1-yl)-3H-[1,2,3]triazolo[4,5-d]pyrimidine.

33. The pharmaceutical composition according to claim 30, wherein said compound is (S)-1-[5-tert-butyl-3-(2-chloro-benzyl)-3H-[1,2,3]triazolo[4,5-d]pyrimidin-7-yl]-pyrrolidin-3-ol.

34. The pharmaceutical composition according to claim 30, wherein said compound is 5-tert-butyl-3-(2-chloro-benzyl)-7-(3,3,4,4-tetrafluoro-pyrrolidin-1-yl)-3H-[1,2,3]triazolo[4,5-d]pyrimidine.

35. The pharmaceutical composition according to claim 30, wherein said compound is 5-tert-butyl-7-(3,3-difluoro-pyrrolidin-1-yl)-3-pyridin-3-ylmethyl-3H-[1,2,3]triazolo[4,5-d]pyrimidine.

36. The pharmaceutical composition according to claim 30, wherein said compound is 5-tert-butyl-3-(2-chloro-3,6-difluoro-benzyl)-7-(3,3-difluoro-pyrrolidin-1-yl)-3H-[1,2,3]triazolo[4,5-d]pyrimidine.

37. The pharmaceutical composition according to claim 30, wherein said compound is 5-tert-butyl-3-(3-chloro-pyridin-2-ylmethyl)-7-(3,3-difluoro-pyrrolidin-1-yl)-3H-[1,2,3]triazolo[4,5-d]pyrimidine.

38. The pharmaceutical composition according to claim 30, wherein said compound is 5-tert-butyl-7-(3,3-difluoro-pyrrolidin-1-yl)-3-(1-methyl-1H-tetrazol-5-ylmethyl)-3H-[1,2,3]triazolo[4,5-d]pyrimidine.

39. The pharmaceutical composition according to claim 30, wherein said compound is (S)-1-[5-tert-butyl-3-(4-methyl-furazan-3-ylmethyl)-3H-[1,2,3]triazolo[4,5-d]pyrimidin-7-yl]-pyrrolidin-3-ol.

40. The pharmaceutical composition according to claim 30, wherein said compound is (S)-1-[5-tert-butyl-3-(2-chloro-pyridin-3-ylmethyl)-3H-[1,2,3]triazolo[4,5-d]pyrimidin-7-yl]-pyrrolidin-3-ol.

41. The pharmaceutical composition according to claim 30, wherein said compound is (S)-1-[5-tert-butyl-3-(2-methanesulfonyl-benzyl)-3H-[1,2,3]triazolo[4,5-d]pyrimidin-7-yl]-pyrrolidin-3-ol.

42. The pharmaceutical composition according to claim 30, wherein said compound is (S)-1-[5-tert-butyl-3-(1-methyl-1H-tetrazol-5-ylmethyl)-3H-[1,2,3]triazolo[4,5-d]pyrimidin-7-yl]-pyrrolidin-3-ol.

43. The pharmaceutical composition according to claim 30, wherein said compound is (S)-1-(5-tert-butyl-3-(2-(trifluoromethyl)benzyl)-3H-[1,2,3]triazolo[4,5-d]pyrimidin-7-yl)-3-methylpyrrolidin-3-ol.

44. The pharmaceutical composition according to claim 30, wherein said compound is (S)-1-(5-tert-butyl-3-(2-methylsulfonyl)benzyl)-3H-[1,2,3]triazolo[4,5-d]pyrimidin-7-yl)-3-methylpyrrolidin-3-ol.

45. The pharmaceutical composition according to claim 30, wherein said compound is (S)-1-[5-tert-Butyl-3-(3-chloro-pyridin-2-ylmethyl)-3H-[1,2,3]triazolo[4,5-d]pyrimidin-7-yl]-pyrrolidin-3-ol.

46. The pharmaceutical composition according to claim 30, wherein said compound is (R)-1-(5-tert-butyl-3-((1-methyl-1H-tetrazol-5-yl)methyl)-3H-[1,2,3]triazolo[4,5-d]pyrimidin-7-yl)pyrrolidin-3-ol.

* * * * *